US011738082B2

(12) United States Patent
Shenoy

(10) Patent No.: US 11,738,082 B2
(45) Date of Patent: *Aug. 29, 2023

(54) HIGH CONCENTRATION PROTEIN FORMULATIONS WITH REDUCED VISCOSITY

(71) Applicant: Bhami's Research Laboratory, Pvt. Ltd., Karnataka (IN)

(72) Inventor: Bhami Shenoy, Mangalore (IN)

(73) Assignee: Bhami's Research Laboratory, Pvt. Ltd., Karnataka (IN)

(*) Notice: Subject to any disclaimer, the term of this patent is extended or adjusted under 35 U.S.C. 154(b) by 468 days.

This patent is subject to a terminal disclaimer.

(21) Appl. No.: 16/788,218

(22) Filed: Feb. 11, 2020

(65) Prior Publication Data
US 2020/0254094 A1 Aug. 13, 2020

Related U.S. Application Data

(62) Division of application No. 15/542,921, filed as application No. PCT/IN2017/050250 on Jun. 20, 2017, now Pat. No. 10,646,569.

(30) Foreign Application Priority Data

May 16, 2017 (IN) .............................. 201741017199

(51) Int. Cl.
| | | |
|---|---|---|
| *A61K 39/395* | (2006.01) | |
| *A61K 9/00* | (2006.01) | |
| *A61K 9/08* | (2006.01) | |
| *A61K 47/02* | (2006.01) | |
| *A61K 47/18* | (2017.01) | |
| *A61K 47/22* | (2006.01) | |
| *C07K 14/705* | (2006.01) | |
| *C07K 16/00* | (2006.01) | |
| *C07K 16/18* | (2006.01) | |
| *C07K 16/22* | (2006.01) | |
| *C07K 16/28* | (2006.01) | |
| *C07K 16/32* | (2006.01) | |

(52) U.S. Cl.
CPC ...... *A61K 39/39591* (2013.01); *A61K 9/0019* (2013.01); *A61K 9/08* (2013.01); *A61K 47/02* (2013.01); *A61K 47/183* (2013.01); *A61K 47/22* (2013.01); *C07K 14/70578* (2013.01); *C07K 16/00* (2013.01); *C07K 16/18* (2013.01); *C07K 16/22* (2013.01); *C07K 16/2863* (2013.01); *C07K 16/2875* (2013.01); *C07K 16/2887* (2013.01); *C07K 16/32* (2013.01); *C07K 2317/21* (2013.01); *C07K 2317/24* (2013.01); *C07K 2317/30* (2013.01); *C07K 2317/32* (2013.01); *C07K 2317/52* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,031,892 A | 6/1977 | Hurschman |
| 4,538,920 A | 9/1985 | Drake |
| 4,648,532 A | 3/1987 | Green |
| 4,816,567 A | 3/1989 | Cabilly et al. |
| 5,168,062 A | 12/1992 | Stinski |
| 5,330,426 A | 7/1994 | Kriesel et al. |
| 5,385,839 A | 1/1995 | Stinski |
| 5,641,870 A | 6/1997 | Rinderknecht et al. |
| 5,730,978 A | 3/1998 | Wayner |
| 5,736,137 A | 4/1998 | Anderson et al. |
| 5,821,337 A | 10/1998 | Carter et al. |
| 5,840,299 A | 11/1998 | Bendig et al. |
| 5,899,880 A | 5/1999 | Bellhouse et al. |
| 6,033,665 A | 3/2000 | Yednock |
| 6,054,297 A | 4/2000 | Carter et al. |
| 6,217,866 B1 | 4/2001 | Schlessinger et al. |
| 6,235,883 B1 | 5/2001 | Jakobovits et al. |
| 6,252,055 B1 | 6/2001 | Relton |
| 6,267,958 B1 | 7/2001 | Andya et al. |
| 6,300,308 B1 | 10/2001 | Schroit |
| 6,312,694 B1 | 11/2001 | Thorpe et al. |
| 6,406,693 B1 | 6/2002 | Thorpe et al. |
| 6,551,992 B1 | 4/2003 | DeFelippis et al. |
| 6,602,503 B1 | 8/2003 | Lobb et al. |
| 6,730,328 B2 | 5/2004 | Maskiewicz et al. |
| 6,835,187 B2 | 12/2004 | Alexandre et al. |
| 6,875,432 B2 | 4/2005 | Liu et al. |
| 7,132,100 B2 | 11/2006 | Oliver et al. |
| 7,390,786 B2 | 6/2008 | Warne et al. |

(Continued)

FOREIGN PATENT DOCUMENTS

| | | |
|---|---|---|
| CA | 2589632 A1 | 7/2006 |
| CN | 1527724 A | 9/2004 |

(Continued)

OTHER PUBLICATIONS

Adler, M. Challenges in the development of pre-filled syringes for biologies from a formulation scientist's point of view, American Pharmaceutical Review, 15(1) (2012).
Akash, M. S. H. et al., Development of therapeutic proteins: advances and challenges, Turk. J. Biol., 39: 343-358 (2015).
Akers, M., Excipient-drug interactions in parenteral formulations, Journal of Pharmaceutical Sciences, 91(11):2283-2300 (2002).
Arnon, R. et al., Complexes and conjugates of cis-Pt for Immunotargeted Chemotherapy, Adv. Exp. Med. Biol., 303:79-90 (1991).

(Continued)

*Primary Examiner* — Yunsoo Kim

(74) *Attorney, Agent, or Firm* — Choate, Hall & Stewart LLP; Brenda Herschbach Jarrell

(57) ABSTRACT

The present disclosure, among other things, provides low-viscosity, high concentration therapeutic protein agent formulations.

19 Claims, 10 Drawing Sheets

(56) References Cited

U.S. PATENT DOCUMENTS

| | | |
|---|---|---|
| 7,547,292 B2 | 6/2009 | Sheldrake et al. |
| 7,666,413 B2 | 2/2010 | Liu et al. |
| 7,740,842 B2 | 6/2010 | Arvinte et al. |
| 7,758,860 B2 | 7/2010 | Warne et al. |
| 7,790,679 B2 | 9/2010 | Li et al. |
| 8,142,776 B2 | 3/2012 | Liu et al. |
| 8,383,114 B2 | 2/2013 | Sloey et al. |
| 8,647,115 B2 | 2/2014 | Boehm et al. |
| 8,703,126 B2 | 4/2014 | Liu et al. |
| 9,033,261 B2 | 5/2015 | Zhou et al. |
| 9,072,668 B2 | 7/2015 | Dai et al. |
| 9,278,131 B2 | 3/2016 | Dauty et al. |
| 9,320,797 B2 | 4/2016 | Sloey et al. |
| 9,352,043 B2 | 5/2016 | Osslund |
| 9,358,350 B2 | 6/2016 | Bangera et al. |
| 9,364,542 B2 | 6/2016 | Chang |
| 9,428,546 B2 | 8/2016 | Coffman et al. |
| 9,457,089 B2 | 10/2016 | Soula |
| 9,605,051 B2 | 3/2017 | Soane et al. |
| 10,646,569 B2 | 5/2020 | Shenoy |
| 2002/0175186 A1 | 11/2002 | Keller |
| 2007/0072146 A1 | 3/2007 | Pierson |
| 2007/0166660 A1 | 7/2007 | Peuker et al. |
| 2008/0225638 A1 | 9/2008 | Bien et al. |
| 2008/0226689 A1 | 9/2008 | Berry et al. |
| 2009/0268546 A1 | 10/2009 | Reinprecht |
| 2010/0285011 A1 | 11/2010 | Morichika et al. |
| 2011/0027292 A1 | 2/2011 | Warne et al. |
| 2011/0076273 A1 | 3/2011 | Adler et al. |
| 2011/0223208 A1 | 9/2011 | Hill et al. |
| 2012/0230982 A1 | 9/2012 | Zhou et al. |
| 2013/0058958 A1 | 3/2013 | Bowen et al. |
| 2013/0171128 A1 | 7/2013 | Huang et al. |
| 2014/0023655 A1 | 1/2014 | Monck et al. |
| 2014/0044727 A1 | 2/2014 | Monck et al. |
| 2014/0072559 A1 | 3/2014 | Soula |
| 2014/0127227 A1 | 5/2014 | Chang |
| 2014/0255379 A1 | 9/2014 | Davis et al. |
| 2015/0044198 A1 | 2/2015 | Liu et al. |
| 2015/0071920 A1 | 3/2015 | Larson et al. |
| 2015/0071921 A1 | 3/2015 | Larson et al. |
| 2015/0071922 A1 | 3/2015 | Larson et al. |
| 2015/0071925 A1 | 3/2015 | Larson et al. |
| 2015/0150979 A1 | 6/2015 | Yates et al. |
| 2015/0374916 A1 | 12/2015 | Bertolote et al. |
| 2016/0058863 A1 | 3/2016 | Johnston et al. |
| 2016/0074515 A1* | 3/2016 | Soane .................... C07K 16/00 530/387.1 |
| 2016/0096879 A1 | 4/2016 | Soane et al. |
| 2016/0235849 A1 | 8/2016 | Osslund |
| 2016/0271253 A1 | 9/2016 | Chang |
| 2016/0319022 A1 | 11/2016 | Yang et al. |
| 2016/0340431 A1 | 11/2016 | Fox et al. |
| 2016/0367675 A1 | 12/2016 | Liu et al. |
| 2017/0049895 A1 | 2/2017 | Sloey et al. |
| 2018/0333493 A1 | 11/2018 | Shenoy |

FOREIGN PATENT DOCUMENTS

| | | |
|---|---|---|
| EP | 0247989 A2 | 12/1987 |
| EP | 0501179 A1 | 9/1992 |
| EP | 0528437 A1 | 2/1993 |
| EP | 1896100 A2 | 3/2008 |
| EP | 2538973 A2 | 1/2013 |
| EP | 2683403 A1 | 1/2014 |
| EP | 2694708 A2 | 2/2014 |
| EP | 2699286 A2 | 2/2014 |
| EP | 2822590 A1 | 1/2015 |
| EP | 2911693 A1 | 9/2015 |
| EP | 2991678 A1 | 3/2016 |
| EP | 3043775 A2 | 7/2016 |
| WO | WO-99/01556 A2 | 1/1999 |
| WO | WO-2002/030463 A2 | 4/2002 |
| WO | WO-2004/001007 A2 | 12/2003 |
| WO | WO-2004/089335 A2 | 10/2004 |
| WO | WO-2006/044908 A2 | 4/2006 |
| WO | WO-2006/071693 A2 | 7/2006 |
| WO | WO-2007/076062 A2 | 7/2007 |
| WO | WO-2009/043049 A2 | 4/2009 |
| WO | WO-2010/082826 A1 | 7/2010 |
| WO | WO-2011/012637 A2 | 2/2011 |
| WO | WO-2011/084750 A1 | 7/2011 |
| WO | WO-2011/109415 A2 | 9/2011 |
| WO | WO-2011/112669 A1 | 9/2011 |
| WO | WO-2011/121560 A2 | 10/2011 |
| WO | WO-2011/139718 A1 | 11/2011 |
| WO | WO-2011/143307 A1 | 11/2011 |
| WO | WO-2012/014183 A1 | 2/2012 |
| WO | WO-2012/121754 A1 | 9/2012 |
| WO | WO-2012/138958 A1 | 10/2012 |
| WO | WO-2012/141978 A2 | 10/2012 |
| WO | WO-2013/063510 A1 | 5/2013 |
| WO | WO-2013/173687 A1 | 11/2013 |
| WO | WO-2013/190047 A1 | 12/2013 |
| WO | WO-2014/023816 A1 | 2/2014 |
| WO | WO-2014/037680 A1 | 3/2014 |
| WO | WO-2014/141149 A1 | 9/2014 |
| WO | WO-2015/038777 A1 | 3/2015 |
| WO | WO-2015/038782 A1 | 3/2015 |
| WO | WO-2015/038811 A2 | 3/2015 |
| WO | WO-2015/038818 A2 | 3/2015 |
| WO | WO-2015/196091 A1 | 12/2015 |
| WO | WO-2015/196187 A1 | 12/2015 |
| WO | WO-2016/034648 A1 | 3/2016 |
| WO | WO-2016/054259 A1 | 4/2016 |
| WO | WO-2016/065181 A1 | 4/2016 |
| WO | WO-2016/109822 A1 | 7/2016 |
| WO | WO-2017/055966 A1 | 4/2017 |
| WO | WO-2017/070501 A1 | 4/2017 |
| WO | WO-2018/211517 A1 | 11/2018 |

OTHER PUBLICATIONS

Baumann, A., Early development of therapeutic biologics-pharmacokinetics, Curr. Drug Meth., 7:15-21 (2006).

Beck, A., Biosimilar, biobetter and next generation therapeutic antibodies, mAbs, 3(2):107-110 (2011).

Buss, N. et al., Monoclonal antibody therapeutics: history and future, Current Opinion in Pharmacology, 12(5):615-622 (2012).

Cilurzo, F. et al., Injectability evaluation: an open issue, AAPS PharmSci Tech, 12(2):604-609 (2011).

Clackson, T. et al., Making antibody fragments using phage display libraries, Nature, 352:624-628 (1991).

Daugherty, A. & Mrsny, R., Formulation and delivery issues for monoclonal antibody therapeutics, Advanced Drug Delivery Reviews, 58:686-706 (2006).

Dimitrov, D., Therapeutics Proteins, Methods in Molecular Biology, 899:1-26 (2012).

Du, W. & Klibanov, A., Hydrophobic salts markedly diminish viscosity of concentrated protein solutions, Biotechnology and Bioengineering, 108:632-636 (2011).

Ecker, D. et al., The therapeutic monoclonal antibody market, mAbs, 7(1):9-14 (2015).

Federici, M. et al., Analytical lessons learned from selected therapeutic protein drug comparability studies, Biologicals, 41(3):131-147 (2013).

Frokjaer, S. & Otzen, D., Protein drug stability: a formulation challenge, Nature Reviews Drug Discovery, 4:298-306 (2005).

Greenfield, R. et al., Evaluation in Vitro of Adriamycin Immunoconjugates synthesized using an acid-sensitive hydrazone linker, Cancer Research, 50:6600-6607 (1990).

Guo, Z. et al. Structure-activity relationship for hydrophobic salts as viscosity-lowering excipients for concentrated solutions of monoclonal antibodies, Pharmaceutical Research, 29:3102-3109 (2012).

Hoffmann, A. & Stayton, P., Conjugates of stimuli-responsive polymers and proteins, Progress in Polymer Science, 32(8-9):922-932 (2007).

International Search Report for PCT/IN2017/050250, ISA/EPO, 4 pages (dated Nov. 24, 2017).

(56) References Cited

OTHER PUBLICATIONS

Jezek, J., Viscosity of concentrated therapeutic protein compositions, Advanced Drug Delivery Reviews, 63(13):1107-1117 (2011).
Jones, A., Analysis of polypeptides and proteins, Advanced Drug Delivery Reviews, 10(1):29-90 (1993).
Jones, P. et al., Replacing the complementarity-determining regions in a human antibody with those from a mouse, Nature, 321:522-525 (1986).
Kale, T. R. and Momin, M., Needle free injection technology—an overview, Inov. Pharm., 5 (1): Article 143 (2014).
Kiseleva, V.I. et al., [II. Use of antibodies to DNA modified by trans-diaminodichloroplatinum, for identification of specific DNA sequences], Mol. Biol. (Mosk), 25(2):508-514 (1991). [English abstract].
Kohler, G. & Milstein, C., Continuous cultures of fused cells secreting antibody of predefined specificty, Nature, 256:495-497 (1975).
Leader, B. et al., Protein therapeutics: a summary and pharmacological classification, Nature Reviews, 7:21-39 (2008).
Marks, J. et al., By-passing immunization: Human antibodies from V-gene libraries displayed on phage, Journal of Molecular Biology, 222(3):581-597 (1991).
Miller, M. et al., Low viscosity highly concentrated injectable nonaqueous suspensions of lysozyme microparticles, Langmuir, 26(2):1067-1074 (2010).
Morrison, S. et al., Chimeric human antibody molecules: mouse antigen-binding domains with human constant region domains, PNAS, 81(21):6851-6855 (1984).
Pisal, D. et al., Delivery of therapeutic proteins, Journal of Pharmaceutical Sciences, 99(6):2557-2575 (2010).
Presta, L., Antibody engineering, Current Opinion in Biotechnology, 3(4):394-398 (1992).
Ravi, A.D. et.al, Needle free injection technology: A complete insight, Int. Jour. Pharm. Investig., 5(4) : 192-199 (2015).
Reichmann, L. et al., Reshaping human antibodies for therapy, Nature, 332:323-329 (1988).
Satuja, A. and Kalonia, D.S., Nature and consequences of protein-protein interactions in high protein concentration solutions, Int. J Pharm, 1-15 (2008).
Scolnik, P., A business perspective, mAbs, 1(2):179-184 (2009).
Shields, R. L. et al., High Resolution Mapping of the Binding Site on Human IgG1 for FcγRI, FcγRII, FcγRIII, and FcRn and Design of IgG1 Variants with Improved Binding to the FcγR, J. Biol. Chem., 276(9):6591-6604 (2001).
Shire, S. J. at al., Challenges in the development of high protein concentration formulations, J. Pharm. Sci., 93(6): 1390-1402 (2004).
Shire, S. J. Formulation and manufacturability of biologies, Current Opinion in Biotechnology, 20(6): 708-714 (2009).
Srinivasan, C. et al., Non-aqueous suspensions of antibodies are much less viscous than equally concentrated aqueous solutions, Pharm. Res. 30(7):1749-1757 (2013).
Vugmeyster, Y. et al., Pharmacokinetics and toxicology of therapeutic proteins: Advances and challenges, J. Biol. Chem. 3(4): 73-92 (2012).
Wang, W. et al., Antibody structure, instability, and formulation, J. Pharm. Sci., 96(1):1-26 (2007).
Written Opinion for PCT/IN2017/050250, ISA/EPO, 9 pages (dated Nov. 24, 2017).
Zapata, G. et al., Engineering linear F(ab')2 fragments for efficient production in *Escherichia coli* and enhanced antiproliferative activity, Protein Eng., 8:1057-1062 (1995).

\* cited by examiner

HIGH CONCENTRATION PROTEIN FORMULATIONS WITH REDUCED VISCOSITY

BACKGROUND

Protein agent-based therapeutics, including antibody therapeutics, are widely used for a variety of human diseases, and marketing approvals increase every year. Some industry watchers have reported that combined worldwide sales of monoclonal antibody products will be nearly $125 billion by 2020.

SUMMARY

Many protein agent-based therapeutics are administered at doses within a range of about 100 mg to about 1 g of protein agent per injection. The present disclosure recognizes the source of a problem associated with highly concentrated protein-agent formulations, which can present administration challenges due to high viscosity and/or due to aggregation. Among other things, the present disclosure provides low-viscosity, high concentration therapeutic protein agent formulations. Alternatively or additionally, in some embodiments, the present disclosure provides low-aggregation formulations of therapeutic protein agents. In some embodiments, the present disclosure encompasses the recognition that reducing surface adsorption and/or interfacial interaction can have beneficial effects for certain protein formulations. Among other things, in some embodiments, the present disclosure provides formulations of therapeutic protein agents with relatively low surface adsorption and/or interfacial interaction (as compared with that observed for an appropriate reference formulation). In some embodiments, provided formulations can be injected either subcutaneously (SC) or intramuscularly (IM). The present disclosure also provides methods of making and/or using such formulations.

Highly concentrated formulations of macromolecules, such as therapeutic protein agents, including whole antibodies, or fragments thereof, with low-viscosity, are of great value for their ease of storage and delivery in vivo. However, very few techniques exist for the preparation of high concentration, low-viscosity protein agent formulations above 200 mg protein agent per mL solution that are also stable. The present disclosure, among other things, identifies the source of a problem relating to high concentration protein agent compositions. Among other things, the present disclosure appreciates that such compositions can pose a number of challenges such as high viscosity, lower stability, and difficulty in handling and manufacturing. In addition, the present disclosures appreciates that certain viscosity-reducing agents sometimes proposed for use in the art may be required in large amounts in order to reduce viscosity sufficiently, and sometimes these agents can be toxic or not pharmaceutically acceptable.

The present disclosure appreciates that high concentrations of protein agents often must be handled with considerable care, since they can be extremely prone to aggregation and high degrees of protein-protein interactions. Solutions with high protein agent concentrations have a tendency to aggregate and form particulates during processing and/or storage, which makes manipulation during further processing and/or delivery difficult. Concentration-dependent degradation and/or aggregation can present significant challenges for development of high concentration protein agent formulations.

Often, protein agent-based therapeutics are administered through intravenous infusions, which are costly and can require a high level of patient compliance. Some protein agent-based therapeutics may be administered via subcutaneous or intramuscular injection. While these routes can offer clear advantages in ease of administration and cost when compared to intravenous infusions, they can also present challenges that may arise, for example, from limited injection volume tolerance. Typically, it is preferred that injection volumes be under about 2 mL for subcutaneous injections and under about 5 mL for intramuscular injections. Furthermore, it is often preferred that preparations for subcutaneous or intramuscular injections have a viscosity of about 20 centipoise (cP) or lower.

Many protein agent-based therapeutics are administered intravenously (IV); in some instances IV administration is required or useful given the high doses being administered, which can often be in a range of about 100 mg to about 1 g of protein agent per injection. If it is desired to administer a comparable (or identical dose) by a different route—for example by subcutaneous (SC) or intramuscular (IM) injection, then a highly concentrated formulation is required, given that a permitted volume for such routes is so much smaller than that for IV injection. Such high concentration formulations, as discussed herein, can present significant administration challenges, among other things, due to high viscosity. Also, efforts to concentrate protein agents in order achieve smaller volumes for injection can risk damage to protein agents, for example as a result of chemical and/or physical instability. Still further, subjects sometimes report pain at injection sites when viscosity is high. Reported antibody concentrations formulated for SC or IM injections can be up to about 100 mg/mL (Wang et al., J. Pharm. Sci. 96:1-26, 2007) and in some cases, even 150 to 200 mg/mL.

The present disclosure provides, among other things, high concentration formulations (e.g., at concentrations greater than 200 mg/mL) of protein agents with reduced viscosity, including therapeutic agents. In general, provided formulations are suitable for parenteral administration (e.g., by injection), and in many embodiments by parenteral administration that does not involve infusion and/or that is other than intravenous administration. In particular, in many embodiments, the present disclosure provides formulations suitable for administration by subcutaneous (SC) and/or intramuscular (IM) injection. In many embodiments, provided formulations are suitable for administration vial 8-32 gauge needles.

Typically, provided formulations are aqueous formulations. Most commercially available mAb products administered by SC or IM injection are formulated in aqueous buffers, such as a phosphate, succinate or L-histidine buffer, with the addition of excipients and/or surfactants, such as maltose, mannitol, sucrose, lactose, trehalose, lactic acid, proline, methionine, lactic acid, arginine, EDTA, sorbitol, POLOXAMER® or POLYSORBATE® 80 (PEG(80)sorbitan monolaurate). These compounds act to improve overall solution stability.

In some embodiments, the invention relates to a composition of matter comprising a protein agent and a viscosity-reducing agent that reduces viscosity of an aqueous formulation comprising said protein agent. In some embodiments, an aggregation-reducing agent is added to a protein agent formulation. In some embodiments, a protein agent is an antibody. In some embodiments, a protein agent is a fusion protein. In some embodiments, a protein agent is a therapeutic protein. In some embodiments, a protein agent is a pegylated protein.

In some embodiments, the concentration of a protein agent in a high concentration, low-viscosity formulation may be at least about 10 mg/mL, 50 mg/mL, 100 mg/mL, 150 mg/mL, 200 mg/mL, 250 mg/mL, 300 mg/mL, 350 mg/mL, 400 mg/mL, 450 mg/mL, 500 mg/mL or more. In some embodiments, the amount may be within a range bounded by a lower limit and an upper limit, the upper limit being larger than the lower limit. In some embodiments, the lower limit may be about 10 mg/mL, about 25 mg/mL, about 50 mg/mL, about 100 mg/mL, or about 150 mg/mL. In some embodiments, the upper limit may be about 200 mg/mL, about 300 mg/mL, about 400 mg/mL, about 500 mg/mL, about 1000 mg/mL, or about 2000 mg/mL. In some embodiments, the range may be about 10 mg/mL to about 2000 mg/mL. In some embodiments, the range may be about 10 mg/mL to about 1000 mg/mL. In some embodiments, the range may be about 10 mg/mL to about 500 mg/mL. In some embodiments, the range may be about 25 mg/mL to about 2000 mg/mL. In some embodiments, the range may be about 25 mg/mL to about 1000 mg/mL. In some embodiments, the range may be about 25 mg/mL to about 500 mg/mL. In some embodiments, the range may be about 50 mg/mL to about 2000 mg/mL. In some embodiments, the range may be about 50 mg/mL to about 1000 mg/mL. In some embodiments, the range may be about 50 mg/mL to about 500 mg/mL. In some embodiments, the range may be about 100 mg/mL to about 2000 mg/mL. In some embodiments, the range may be about 100 mg/mL to about 1000 mg/mL. In some embodiments, the range may be about 100 mg/mL to about 500 mg/mL. In some embodiments, the range may be about 150 mg/mL to about 2000 mg/mL. In some embodiments, the range may be about 150 mg/mL to about 1000 mg/mL. In some embodiments the range may be about 150 mg/mL to about 500 mg/mL. In some embodiments the range may be about 150 mg/mL to about 450 mg/mL. In some embodiments the range may be about 150 mg/mL to about 400 mg/mL. In some embodiments the range may be about 150 mg/mL to about 350 mg/mL. In some embodiments the range may be about 150 mg/mL to about 300 mg/mL.

In some embodiments, a method is provided for reducing viscosity of a protein agent-containing formulation, wherein a method comprises a step of adding to a formulation a viscosity-reducing amount of a viscosity-reducing agent that reduces viscosity of an aqueous formulation comprising a protein agent.

In some embodiments, a method as described herein comprises preparing a liquid formulation comprising:
 (a) providing protein agent;
 (b) a buffer selected from the group consisting of phosphate buffers, acetate buffers, citrate buffers, histidine buffers, imidazole buffers, and combinations thereof; and
 (c) a viscosity-reducing agent selected from the group consisting of nicotinic acid (acid form), tryptophan, and combinations thereof, so that the protein agent is present in a concentration within a range of about 10 mg/mL to about 2000 mg/mL, the nicotinic acid (acid form), if present, is present in a concentration within a range of about 0.05% w/v to about 2.0% w/v, and the tryptophan, if present, is present at a concentration within a range of greater than 0.21% w/v to about 1% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
 (a) providing protein agent;
 (b) a buffer selected from the group consisting of phosphate buffers, acetate buffers, citrate buffers, histidine buffers, imidazole buffers, and combinations thereof; and
 (c) a viscosity-reducing agent selected from the group consisting of nicotinic acid (acid form), caffeine citrate, and combinations thereof;

so that the protein agent is present in a concentration within a range of about 10 mg/mL to about 2000 mg/mL, the nicotinic acid (acid form), if present, is present in a concentration within a range of about 0.05% w/v to about 2.0% w/v, and the caffeine citrate, if present, is present at a concentration within a range of greater than 0.1% w/v to about 3% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
 (a) providing protein agent;
 (b) a buffer selected from the group consisting of phosphate buffers, acetate buffers, citrate buffers, histidine buffers, imidazole buffers, and combinations thereof; and
 (c) a viscosity-reducing agent selected from the group consisting of nicotinic acid (acid form), aspirin, and combinations thereof;

so that the protein agent is present in a concentration within a range of about 10 mg/mL to about 2000 mg/mL, the nicotinic acid (acid form), if present, is present in a concentration within a range of about 0.05% w/v to about 2.0% w/v, and the aspirin, if present, is present at a concentration within a range of greater than 0.1% w/v to about 0.5% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
 (a) providing protein agent;
 (b) a buffer selected from the group consisting of phosphate buffers, acetate buffers, citrate buffers, histidine buffers, imidazole buffers, and combinations thereof; and
 (c) a viscosity-reducing agent selected from the group consisting of nicotinic acid (acid form), caffeine nicontinate, and combinations thereof;

so that the protein agent is present in a concentration within a range of about 10 mg/mL to about 2000 mg/mL, the nicotinic acid (acid form), if present, is present in a concentration within a range of about 0.05% w/v to about 2.0% w/v, and the caffeine nicontinate, if present, is present at a concentration within a range of greater than 0.05% w/v to about 0.2% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
(a) providing protein agent;
(b) a buffer selected from the group consisting of phosphate buffers, acetate buffers, citrate buffers, histidine buffers, imidazole buffers, and combinations thereof; and
(c) a viscosity-reducing agent selected from the group consisting of nicotinic acid (acid form), acetyl salicyclic acid, and combinations thereof;

so that the protein agent is present in a concentration within a range of about 10 mg/mL to about 2000 mg/mL, the nicotinic acid (acid form), if present, is present in a concentration within a range of about 0.05% w/v to about 2.0% w/v, and the acetyl salicyclic acid, if present, is present at a concentration within a range of greater than 0.02% w/v to about 0.2% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
(a) providing protein agent;
(b) a buffer selected from the group consisting of phosphate buffers, acetate buffers, citrate buffers, histidine buffers, imidazole buffers, and combinations thereof; and
(c) a viscosity-reducing agent selected from the group consisting of tryptophan, caffeine, Thiamine-HCl, nicotinamide, and combinations thereof;

so that the protein agent is present in a concentration within a range of about 10 mg/mL to about 2000 mg/mL, tryptophan, if present, is present in a concentration within a range of about 0.21% w/v to about 1.0% w/v, caffeine, if present, is present at a concentration within a range of about 0.05% w/v to about 3.0% w/v, Thiamine-HCl, if present, is present at a concentration with a range of about 0.05% w/v to about 3.0% w/v, and nicotinaminde, if present, is present at a concentration within a range of about 0.05% w/v to about 3.0% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
(a) providing protein agent;
(b) a buffer selected from the group consisting of phosphate buffers, acetate buffers, citrate buffers, histidine buffers, imidazole buffers, and combinations thereof, and
(c) a viscosity-reducing agent selected from the group consisting of arginine, Thiamine-HCl, and combinations thereof;

so that the protein agent is present in a concentration within a range of about 10 mg/mL to about 2000 mg/mL, arginine, if present, is present in a concentration within a range of about 0.05% w/v to about 3.0% w/v, and Thiamine-HCl, if present, is present at a concentration within a range of about 0.05% w/v to about 3.0% w/v. Typically, a liquid formulation prepared according to this provided method is characterized by a viscosity that is lower than that of an otherwise comparable formulation of the protein agent lacking the viscosity-reducing agent.

In some embodiments, a method as described herein comprises preparing a liquid formulation comprising:
(a) providing protein agent;
(b) a buffer selected from the group consisting of phosphate buffers, acetate buffers, citrate buffers, histidine buffers, imidazole buffers, and combinations thereof; and
(c) a viscosity-reducing agent selected from the group consisting of nicotinic acid (acid form), caffeine citrate, caffeine nicotinate, ascorbic acid, hydroxyproline, tryptophan (>0.2%), theophylline nicotinate, xanthine nicotintate, xanthinol nicotinate, antrallic acid, 4-aminocyclohexane carboxylic acid, 4-aminopyridine-2-carboxylic acid, nicotinyl alcohol, nicametate citrate, nicotinuric acid, ethanol, nicotinyl hydroxamate, ornidazole, piperazine, methylisothiazolinone, methyl nicontinate, aspirin, arginine, and combinations thereof;

so that the protein agent is present in a concentration within a range of about 10 mg/mL to about 2000 mg/mL, the nicotinic acid (acid form), if present, is present in a concentration within a range of about 0.05% w/v to about 2.0% w/v, and caffeine citrate, caffeine nicotinate, ascorbic acid, hydroxyproline, tryptophan (>0.2%), theophylline nicotinate, xanthine nicotintate, xanthinol nicotinate, antrallic acid, 4-aminocyclohexane carboxylic acid, 4-aminopyridine-2-carboxylic acid, nicotinyl alcohol, nicametate citrate, nicotinuric acid, ethanol, nicotinyl hydroxamate, ornidazole, piperazine, methylisothiazolinone, methyl nicontinate, aspirin and arginine, if present, are present at a concentration within a range of greater than 0.01% w/v to about 4.00/% w/v, each, respectively. Typically, a liquid formulation prepared according to this provided method is characterized by a viscosity that is lower than that of an otherwise comparable formulation of the protein agent lacking the viscosity-reducing agent.

In some embodiments, viscosity of a high concentration protein formulation can be reduced using a combination of viscosity-reducing agents. Viscosity-reducing agent combinations that can be added to a high concentration protein agent formulation can include nicotinic acid (acid form) and/or caffeine, nicotinic acid and/or caffeine citrate, nicotinic acid and/or caffeine nicotinate, or nicotinic acid and/or aspirin; in further combination with one or more of nicotinamide (niacinamide), nicotinic acid sodium salt, benzyl nicotinate, inositol hexanicotinate, nicotinyl alcohol (β-pyridyl carbinol), xanthine nicotinate, methyl nicotinate, ethyl nicotinate, propyl nicotinate, isopropyl nicotinate, butyl nicotinate, isoamyl nicotinate, hexyl nicotinate, phenyl nicotinate, gauiacyl nicotinate, xanthinol nicotinate, nicametate citrate, nicotinuric acid, nicotinyl hydroxamate, tocopheryl nicotinate, trigonelline, nicotinoyl-dl-α-alanine, nicotinoyl-L-alanine, nicotinoyl-dl-valine, nicotinoyl-L-leucine, and nicotinoyl-dl-phenylalanine, ethionamide, niceritrol, nicofuranose, Piperocaine, N-ethylpiperidine, Caffeine haematin, ethoxycaffeine, methoxy caffeine, 7-Benzyltheophylline, theophylline, paraxanthine, Theobromine, 7-[(4-methoxyphenyl) methyl]-1,3-dimethyl-2,3,6,7-tetrahydro-1H-purine-2,6-dione, 1,3-dimethyl-7-[(4-methylphenyl) methyl]-2,3,6,7-tetrahydro-1H-purine-2,6-dione, 7-[(4-chlorophenyl) methyl]-1,3-dimethyl-2,3,6,7-tetrahydro-1H-purine-2,6-dione, 7-[(3,5-dimethylphenyl)methyl]-1,3-dimethyl-2,3,6,7-tetrahydro-1H-purine-2,6-dione, 7-benzyl-1,3-dimethyl-2,3,6,7-tetrahydro-1H-purine-2,6-dione, 1,3-dimethyl-7-{[4-(propan-2-yl)phenyl]methyl}-2,3,6,7-tetrahydro-1H-purine-2,6-dione, 1,3-dimethyl-7-[(2-methylphenyl)methyl]-2,3,6,7-tetrahydro-1H-purine-2,6-dione, 4-[(1,3-dimethyl-2,6-dioxo-2,3,6,7-tetrahydro-1H-purin-7-yl)methyl]benzonitrile, 7-[(4-bromophenyl)

methyl]-1,3-dimethyl-2,3,6,7-tetrahydro-1H-purine-2,6-dione, Methyl 4-[(1,3-dimethyl-2,6-dioxo-2,3,6,7-tetra hydro-1H-purin-7-yl)methyl]benzoate, 1,3-dimethyl-7-{[4-(trifluoromethyl)phenyl]methyl}-2,3,6,7-tetrahydro-1H-purine-2,6-dione, 1,3-dimethyl-7-{[4-(methylthio)phenyl] methyl}-2,3,6,7-tetra hydro-1H-purine-2,6-dione, 7-[(3-bromophenyl)methyl]-1,3-dimethyl-2,3,6,7-tetrahydro-1H-purine-2,6-dione, 7-(cyclohexylmethyl)-1,3-dimethyl-2,3,6,7-tetrahydro-1H-purine-2,6-dione; 1,3-dimethyl-7-[(4-nitrophenyl)methyl]-2,3,6,7-tetrahydro-1H-purine-2,6-dione, 1,3-dimethyl-7-[(3-nitrophenyl) methyl]-2,3,6,7-tetrahydro-1H-purine-2,6-dione, 1,3-dimethyl-7-(1-phenylethyl)-2,3,6,9-tetra hydro-1H-purine-2,6-dione, 8-[(pyrrolidin-1-ylcarbonothioyl) sulfanyl]caffeine, 8-hydrazinocaffeine 8-chlorocaffeine, and 8-(3-butyl-4-phenyl-2,3-dihydro thiazol-2-ylidene) hydrazino-3,7-dihydro-1,3,7-trimethyl-1H-purine-2,6-dione, Acetyl salicyclic acid, Salicylic acid, Phenyl acetic acid, 2-amino-cyclohexane-carboxylic acid, Gentisic acid, Pthalic acid, Anthrallic acid, Tetracaine, Proxymetacaine, Metoclopramide, Procaine, Chloroprocaine, Benzocaine, Octisalate, Propylparaben, Thimerosal, Vanillin, Cyclomethylcaine, Mandelic acid, Metoclopramide, L-Pantothenic Acid hemicalcium salt, L-ascorbic acid, Thiamine·HCl, Rutin Hydrate, Riboflavin, Folic Acid, pyridoxine, Biotin, Pantoic acid, S-benzoylthiamine, Pyridoxal, Pyridoxamine, L-Histidine, L-Lysine, L-Arginine, L-2-Amino-3-guanidinopropionic acid hydrochloride, 4-Guanidinobutyric acid, L-Homoarginine·HCl, Aspartame, Glycine, L-Alanine, Proline, trans-4-Hydroxy-L-Proline, L-Valine, L-Leucine, L-Isoleucine, L-Methionine, L-Serine, Tyramine HCl, Histamine, Imidazole, L-phenyl alanine, Tyrosine, Tryptophan, Threonine, L-Glutamic acid, L-Aspartic Acid, L-Valine, 5-fluoro-L-tryptophan, 5-Fluro-DL-Tryptophan, 5-hydroxy-L-tryptophan, 5-methoxy-DL-tryptophan, Tryptamine, Argyrin A and B, Granisetron, Selenomethionine, Carnithine, Asparagine, and Glutamine, arginine-HCl, arginine succinate, arginine dipeptide, arginine tripeptide, polyarginine, 2-amino-3-guanidino-propionic acid, guanidine, ornithine, agmatine, guanidobutyric acid, citrulline, N-hydroxy-L-nor-arginine, nitroarginine methyl ester, argininamide, arginine methyl ester, arginine ethyl ester, lysinamide, lysine methyl ester, histidine methyl ester, alaninamide, alanine methyl ester, putrescine, cadaverine, spermidine, and spermine, Adenine, Guanine, Cytosine, Uracil, Thymine, Adenosine, Guanosine, Cytidine, Uridine, Inosine, Thymidine, Xanthine, Hypoxanthine, 2'-deoxycytidine, 2'-deoxyuridine, Orotic acid, ribothymidine, 1-methyl xanthine, 7-methyl xanthine, and 3-methyl xanthine, D-Sucrose, D-(+)-Trehalose dehydrate, D-(−)-Fructose, D-Mannitol, L-(+)-Arabinose, D-Sorbitol, Lactose, Maltose, D-Ribose, D-Galactose, Glucosamine, Hydroxyalkyl starch, Hyaluronic acid, Pullulane, Chitosan, Dextran, Dextran sulfate, starch, Chondroitin sulfate, carboxymethyl dextran, and hydroxylethyl starch, 2-aminopyrimidine, Sodium acetate, Pyruvate sodium salt, Potassium acetate, α-Ketoglutarate, Oxaloacetic acid, Fumaric acid, DL-Malic Acid, Methyl acetoacetate, DL-Isocitric acid trisodium salt, Succinic acid, Procaine·HCl, Creatinine, Thiazole, Citric Acid, 3-pyridine sulfonic acid, Ethylenediaminetetraacetic acid (EDTA), Ethanolamine, di-ethanolamine, tri-ethanolamine, dimethylcyclohexylamine·HCl, p-Hydroxybenzoic acid, Sodium benzoate, Malonic acid, Maleic acid, Oxalosuccinate, Pyrolline-5-carboxylic acid, Ethanol, DMSO, benzyl alcohol, and 1,5-pentanediol, Sodium chloride, Ammonium chloride, Ammonium acetate, Ammonium sulphate, Calcium chloride, Sodium thiocyanate, Polysorbate 80, Polysorbate 20, n-Dodecyl f-D-maltoside, Octyl β-D-glucopyranoside, Aspirin, calcium carrageenan, calcium cyclamate, calcobutrol, Caloxetic acid, Camphorsulfonic acid, Creatinine, dalfampridine, dehydroacetic acid, diazolidinyl urea, dichlorobenzyl alcohol, dimethyl isosorbide, epitetracycline, ethyl maltol, ethyl vanillin, ornidazole, ethanolamide, HEPES (4-(2-hydroxy ethyl)-1-piperazine ethane sulfonic acid), iodoxamic acid, menthol, medronic acid, m-cresol, glutathione, lactobionic acid, maltitol, oxyquinoline, pentetic acid, piparazine, propenyl guaethol, propylene carbonate, protamine sulfate, QUATERNIUM-15, QUATERNIUM-52, satialgine 11, Sodium 1,2-ethanedisulfonate, sodium cocoyl sarcosinate, sodium lauroyl sarcosinate, sodium polymetaphosphate, sodium pyrophosphate, pyroglutamic acid, sodium trimetaphosphate, sodium tripolyphosphate, sorbitan, tartaric acid, lactic acid, iofetamine, Sucralose, 1-(4-pyridyl)pyridinium chloride, Aminobenzoic acid, Sulfacetamide sodium, Naphthalene 2-sulfonic acid, Tert-butylhydroquinone, Trolamine, Tromantadine, Versetamide, nioxime, methylisothiazolinone, mannose, Lidofenin, Lactitol, isomalt, imidurea, gluconolactone, methanesulfonic acid, xylenesulfonic acid, sulfobutylether-β-cyclodextrin, caffeic acid, Caffeic acid phenethyl ester, Zileuton, inhibitor of leukotrienes, tropane N-heterocycles, atropine, hyoseyamine, scopolamine, tiotropium, ipratropium salts, allithiamine, prosulthiamine, fursulthiamine, benfothiamine, sulbuthiamine, 1-(3-aminopropyl)-2-methyl-1H-imidazole dihydrochloride, cimetidine, piperocaine, cyclomethylcaine, moxifloxacin, chloroquine, mepivacaine, levetriacetam, bupivacaine, cinchocaine, clindamycin, colistin, articane, tetracaine, etidocaine, cyclomethylcaine, piperocaine, phenylephrine, and bupivacaine. Polyethylene glycol, branched PEG, and PolyPEG®, Ethanol, DMSO, lactobionic acid, glucuronic acid, biotin, brocrinat, cyclopentane propionic acid, hydroxynaphthoic acid, phenylpropionic acid, camphoric acid, mandelic acid, sulfosalicyclic acid, hydroxybenzoyl benzoic acid, cinnamic acid, t-butyl acetic acid, phthalic acid, trimethylacetic acid, N-methylglucamine, morpholine, piperidine, isopropylamine, trimethylamine, diethylamine, triethylamine, tripropylamine, 2-diethylaminoethanol, trimethamine, dicyclohexylamine, lidocaine, hydrabamine, cholines, betaines, ethylenediamine, purines, piperazine, N-methylpiperidinepolyamine, 2-amino-2-hydroxymethyl-propane-1,3-diol (TRIS), 4-aminopyridine, aminocyclohexane carboxylic acid, 1-o-tolybiguanide, urea, benzethonium chloride, 5-amino-1-pentanol, 2-(2-aminoethoxy)ethanol, trans-cyclohexane-1,4-diamine, trans-cyclohexane-1R,2R-diamine, propane-1,3-diamine, butane-1,4-diamine, pentane-1,5-diamine, hexane-1,6-diamine, octane-1,8-diamine, 2-(2-aminoethoxy)ethanamine, 2-(2-(2-aminoethoxy)-ethoxy) ethanamine, 3-(4-(3-aminopropoxy)-butoxy)propan-1-amine, 3-(2-(2-(3-aminopropoxy)-ethoxy)-ethoxy)propan-1-amine, N-(2-(2-aminoethylamino)ethyl)ethane-1,2-diamine, N-(2-aminoethyl)ethane-1,2-diamine, N-1-(2-(2-(2-aminoethylamino)ethylamino)-ethyl)ethane-1,2-diamine, N,N-dimethylhexane-1,6-diamine, N,N,N,N-tetramethylbutane-1,4-diamine, phenyltrimethylammonium salts, choline, 1-(3-aminopropyl)-2-methyl-1H-imidazole, 1-(2-aminoethyl)piperazine, 1-[3-(dimethylamino)propyl]piperazine, 1-(2-aminoethyl)piperidine, 2-(2-aminoethyl-1-methylpyrrolidine and combinations thereof.

In some embodiments, viscosity of a high concentration protein formulation can be reduced using a combination of viscosity-reducing agents. Viscosity-reducing agent combinations that can be added to a high concentration protein agent formulation can include nicotinic acid (acid form) and tryptophan, acetyl salicylic acid, caffeine citrate, or leucine.

In some embodiments, viscosity-reducing agent combinations that can be added to a high concentration protein agent formulation can include nicotinic acid and caffeine, arginine, glycine, proline, thiamine-HCl or aspirin. In some embodiments, viscosity-reducing agent combinations that can be added to a high concentration protein agent formulation can include tryptophan and nicotinamide, 2-aminopyrimidine, thiamine-HCl or nicotinic acid sodium salt. In some embodiments, viscosity-reducing agent combinations that can be added to a high concentration protein agent formulation can include caffeine and tryptophan, arginine, thiamine-HCl, nicotinamide or nicotinic acid sodium salt. In some embodiments, a viscosity-reducing agent combination that can be added to a high concentration protein agent formulation can include thiamine-HCl and 2-aminopyrimidine. In some embodiments, a viscosity-reducing agent combination that can be added to a high concentration protein agent formulation can include thiamine-HCl and nicotinamide. In some embodiments, a viscosity-reducing agent combination that can be added to a high concentration protein agent formulation can include thiamine-HCl and nicotinic acid sodium salt. In some embodiments, a viscosity-reducing agent combination that can be added to a high concentration protein agent formulation can include proline and thiamine-HCl. In some embodiments, a viscosity-reducing agent combination that can be added to a high concentration protein agent formulation can include proline and tryptophan. In some embodiments, a viscosity-reducing agent combination that can be added to a high concentration protein agent formulation can include proline and nicotinamide. In some embodiments, a viscosity-reducing agent combination that can be added to a high concentration protein agent formulation can include glycine and thiamine-HCl. In some embodiments, a viscosity-reducing agent combination that can be added to a high concentration protein agent formulation can include glycine and tryptophan. In some embodiments, a viscosity-reducing agent combination that can be added to a high concentration protein agent formulation can include glycine and nicotinamide. In some embodiments, a viscosity-reducing agent combination that can be added to a high concentration protein agent formulation can include arginine and thiamine·HCl. In some embodiments, a viscosity-reducing agent combination that can be added to a high concentration protein agent formulation can include arginine and nicotinamide.

In some embodiments, a viscosity-reducing agent nicotinic acid can be added to a protein agent with another viscosity-reducing agent selected from the group consisting of tryptophan, acetyl salicylic acid, caffeine citrate, leucine, caffeine, arginine, glycine, proline, thiamine-HCl, aspirin, or combinations thereof.

In some embodiments, a viscosity-reducing agent thiamine-HCl can be added to a protein agent with another viscosity-reducing agent selected from the group consisting of 2-aminopyrimadine, nicotinamide, nicotinic acid sodium salt, proline, glycine, and combinations thereof.

In some embodiments, the combinations of viscosity reducing agents are nicotinic acid (acid form) and tryptophan, nicotinic acid and caffeine citrate, nicotinic acid (acid form) and acetyl salicylic acid, nicotinic acid (acid form) and caffeine, caffeine and tryptophan, tryptophan and thiamine-HCl, tryptophan and nicotinamide, tryptophan and glycine, nicotinic acid and aspirin, arginine and thiamine-HCl, proline and thiamine-HCl, tryptophan and proline, proline and nicotinamide, glycine and nicotinamide, and argine and nicotinamide.

A viscosity-reducing agent and other formulation additives like buffering agents, tonicity agents, or solubilizing agents can be included in any amount to achieve a desired viscosity measurement of a liquid protein agent formulation, as long as the amount of a viscosity-reducing agent is not toxic or otherwise harmful to a subject upon administration. In addition, additives or a viscosity-reducing agent added to a protein agent formulation should not substantially interfere with the chemical and/or physical stability of a formulation. In some embodiments, a viscosity-reducing agent can be independently added in an amount that may be, for example, at least about 0.1 mM, 0.5 mM, 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 0.1 mM, about 0.5 mM, about 1 mM, about 5 mM, about 10 mM, about 15 mM, about 25 mM, or about 50 mM. In some embodiments, the upper limit may be about 75 mM, 100 mM, 200 mM, 500 mM, or 1000 mM. In some embodiments, the range may be about 0.1 mM to about 1000 mM. In some embodiments, the range may be about 0.1 mM to about 500 mM. In some embodiments, the range may be about 0.1 mM to about 200 mM. In some embodiments, the range may be about 0.1 mM to about 100 mM. In some embodiments, the range may be about 0.5 mM to about 1000 mM. In some embodiments, the range may be about 0.5 mM to about 500 mM. In some embodiments, the range may be about 0.5 mM to about 200 mM. In some embodiments, the range may be about 0.5 mM to about 100 mM. In some embodiments, the range may be about 1 mM to about 1000 mM. In some embodiments, the range may be about 1 mM to about 500 mM. In some embodiments, the range may be about 1 mM to about 200 mM. In some embodiments, the range may be about 1 mM to about 100 mM. In some embodiments, the range may be about 5 mM to about 1000 mM. In some embodiments, the range may be about 5 mM to about 500 mM. In some embodiments, the range may be about 5 mM to about 200 mM. In some embodiments, the range may be about 10 mM to about 200 mM. In some embodiments, the range may be about 10 mM to about 150 mM. In some embodiments the range may be about 10 mM to about 100 mM. In some embodiments the range may be about 15 mM to about 75 mM. In some embodiments, the range may be about 15 mM to about 25 mM. For some embodiments, with two or more viscosity-reducing agents, the agents are preferably, but not necessarily, present at the same concentration.

In some embodiments, one viscosity-reducing agent is added to a protein agent formulation in a mole ratio to a second viscosity-reducing agent. In some embodiments, a mole ratio of a first viscosity-reducing agent to a second viscosity-reducing agent can be, for example, 1:0.001, 1:0.002, 1:0.004, 1:0.005, 1:0.010, 1:0.050, 1:0.10, 1:0.50, 1:1, 1:2, 1:5, 1:10, 1:25, 1:50, 1:100, 1:500, 1:1000, or higher. In some embodiments, the mole ratio may be bounded by a lower limit and an upper limit, the upper limit being larger than the lower limit. In some embodiments, the lower limit may be about 1:1000, about 1:500, about 1:100, about 1:50, about 1:25, or about 1:10. In some embodiments, the upper limit may be about 1:0.001, about 1:0.002, about 1:0.004, about 1:0.005, about 1:0.010, about 1:0.050, about 1:0.10, about 1:0.050, about 1:1, about 1:2, or about 1:5. In some embodiments, the mole ratio may be in the range of about 1:0.001 to about 1:1000. In some embodiments, the mole ratio may be in the range of about 1:0.002 to about 1:500. In some embodiments, the mole ratio may be in the range of about 1:0.004 to about 1:250. In some embodiments, the mole ratio may be in the range of about 1:0.008 to about 1:125. In some embodiments, the mole ratio may be in the range of about 1:0.01 to about 1:100. In some embodiments, the mole ratio may be in the range of about 1:0.08 to about 1:12.5. In some embodiments, the mole ratio may be in the range of about 1:0.1 to about 1:10.

In some embodiments, one viscosity-reducing agent is added to a protein agent formulation in a mole ratio to a second viscosity-reducing agent. In some embodiments, a mole ratio of a first viscosity-reducing agent to a second viscosity-reducing agent can be, for example, 1000:1, 500:1, 100:1, 50:1, 25:1, 10:1, 5:1, 2:1, 1:1, 0.50:1, 0.10:1, 0.050:1, 0.010:1, 0.005:1, 0.004:1, 0.002:1, 0.001:1, or lower. In some embodiments, the mole ratio may be bounded by a lower limit and an upper limit, the upper limit being larger than the lower limit. In some embodiments, the lower limit may be about 0.001:1, about 0.002:1, about 0.004:1, about 0.005:1, about 0.010:1, about 0.050:1, about 0.10:1, about 0.50:1, or about 1:1. In some embodiments, the upper limit may be about 2:1, about 5:1, about 10:1, about 25:1, about 50:1, about 100:1, about 500:1, or about 1000:1. In some embodiments, the mole ratio may be in the range of about 0.001:1 to about 1000:1. In some embodiments, the mole ratio may be in the range of about 0.002:1 to about 500:1. In some embodiments, the mole ratio may be in the range of about 0.004:1 to about 250:1. In some embodiments, the mole ratio may be in the range of about 0.0125:1 to about 80:1. In some embodiments, the mole ratio may be in the range of about 0.02:1 to about 50:1. In some embodiments, the mole ratio may be in the range of about 0.04:1 to about 25:1. In some embodiments, the mole ratio may be in the range of about 0.08:1 to about 12.5:1. In some embodiments, the mole ratio may be in the range of about 0.01:1 to about 10:1.

In some embodiments, the mole ratio of a protein-agent to a viscosity-reducing agent can be in the range of 0.0005:1 to 200:1. In some embodiments, the mole ratio of a protein-agent to a viscosity-reducing agent can be in the range of 0.0005:1 to 200:1. In some embodiments, the mole ratio of a protein-agent to a viscosity-reducing agent can be in the range of 0.005:1 to 20:1. In some embodiments, the mole ratio of a protein-agent to a viscosity-reducing agent can be in the range of 0.05:1 to 2:1.

In the absence of a viscosity-reducing agent, the viscosity of a protein agent-containing formulation typically increases exponentially as the protein agent concentration increases to accommodate a required lower volume for injection. In some embodiments, such protein agent formulations, in the absence of a viscosity-reducing agent, may have viscosities in the range of 50 cP to 1,500 cP when measured at 25° C. Such formulations are often unsuitable for SC or IM injection due to difficulty in administration by small-bore needles using syringes, and also due to pain at a site of injection. In addition, the chemical and physical stability of a protein agent is at risk at higher concentrations.

In some embodiments, the use of a viscosity-reducing agent reduces the viscosity of a protein agent formulation to a viscosity that, when measured at 25° C., may be, for example, about 100 cP, 75 cP, 50 cP, 45 cP, 40 cP, 35 cP, 30 cP, or lower. In some embodiments, the amount may be within a range bounded by a lower limit and an upper limit, the upper limit being larger than the lower limit. In some embodiments, when measured at 25° C., the lower limit may be about 1 cP, about 5 cP, about 10 cP, or about or 15 cP. In some embodiments, when measured at 25° C., the upper limit may be about 20 cP, about 25 cP, about 30 cP, about 35 cP, about 40 cP, about 45 cP, about 50 cP, about 75 cP, or about 100 cP. In some embodiments, when measured at 25° C., the range may be about 5 cP to about 100 cP. In some embodiments, when measured at 25° C., the range may be about 5 cP to about 75 cP. In some embodiments, when measured at 25° C., the range may be about 5 cP to about 50 cP. In some embodiments, when measured at 25° C., the range may be about 5 cP to about 40 cP. In some embodiments, when measured at 25° C., the range may be about 5 cP to about 35 cP. In some embodiments, when measured at 25° C., the range may be about 5 cP to about 30 cP. In some embodiments, when measured at 25° C., the range may be about 5 cP to about 25 cP. In some embodiments, when measured at 25° C., the range may be about 5 cP to about 20 cP. In some embodiments, when measured at 25° C., the range may be about 5 cP to about 15 cP. In some embodiments, when measured at 25° C., the range may be about 5 cP to about 10 cP.

It is to be understood that a pH can be adjusted as necessary to maximize stability and solubility of a polypeptide in a particular protein agent formulation and as such, a pH outside of physiological ranges yet tolerable to the patient is within the scope of the invention. In some embodiments, the pH of a protein agent formulation may be, for example, at least about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0 or higher. In some embodiments, the pH may be within a range bounded by a lower limit and an upper limit, the upper limit being larger than the lower limit. In some embodiments, the lower limit may be about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In some embodiments, the upper limit may be about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10.0. In some embodiments, the range may be about 3.0 to about 10.0. In some embodiments, the range may be about 4.0 to about 10.0. In some embodiments, the range may be about 4.0 to about 10.0. In some embodiments, the range may be about 5.0 to about 10.0. In some embodiments, the range may be about 5.0 to about 8.0. In some embodiments, the range may be about 5.8 to about 7.4. In some embodiments, the range may be about 6.2 to 7.0.

In some embodiments, a liquid protein agent formulation can be isotonic. In some embodiments, a liquid formulation can be hypertonic. Osmolality of a pharmaceutical composition is regulated to maximize stability of active ingredients, or in this case, of a protein agent, and also to minimize discomfort to a patient upon administration of a therapeutic formulation. Serum has an osmolality of approximately 300±50 milliosmolals per kilogram (mOsm/kg). It is generally preferred that a pharmaceutical composition be isotonic with serum, i.e., having the same or a similar osmolality as serum, which is achieved by addition of a tonicity modifier. Thus, it is contemplated that osmolality typically ranges from about 180 to about 420 mOsm/kg, however, it is to be understood that osmolality may register either higher or lower than the range as specific conditions require.

In some embodiments, a liquid formulation has a physiological osmolality that is hypotonic or isotonic to human blood, for example, about 150 mOsm/kg, 200 mOsm/kg, 225 mOsm/kg, 250 mOsm/kg, 275 mOsm/kg, or 300 mOsm/kg. In some embodiments the amount may be within a range bounded by a lower limit and an upper limit, the upper limit being larger than the lower limit. In some embodiments, the lower limit may be about 150 mOsm/kg, 200 mOsm, about 225 mOsm/kg, or about 250 mOsm/kg. In some embodiments, the upper limit may be about 275 mOsm/kg, or about 300 mOsm/kg. In some embodiments, the range may be about 150 mOsm/kg to about 300 mOsm/kg. In some embodiments the range may be about 200 mOsm/kg to about 300 mOsm/kg. In some embodiments, the range may be about 200 mOsm/kg to about 250 mOsm/kg. In some embodiments the range may be about 250 mOsm/kg to about 300 mOsm/kg.

In some embodiments, a liquid formulation has an osmolality that is hypertonic to human blood, for example, about 350 mOsm/kg, 400 mOsm/kg, 450 mOsm/kg, 500 mOsm/kg, 550 mOsm/kg, 600 mOsm/kg, 650 mOsm/kg, 700 mOsm/kg, 750 mOsm/kg, 800 mOsm/kg, 850 mOsm/kg, 900 mOsm/kg, 950 mOsm/kg, 1000 mOsm/kg, or more. In some embodiments the amount may be within a range bounded by a lower limit and an upper limit, the upper limit being larger than the lower limit. In some embodiments, the lower limit may be about 350 mOsm/kg, about 400 mOsm/kg, about 500 mOsm/kg, about 550 mOsm/kg, about 600 mOsm/kg, or about 650 mOsm/kg. In some embodiments, the upper limit may be about 700 mOsm/kg, about 750 mOsm/kg, about 800 mOsm/kg, about 850 mOsm/kg, about 900 mOsm/kg, about 950 mOsm/kg, or about 1000 mOsm/kg. In some embodiments, the range may be about 350 mOsm/kg to about 1000 mOsm/kg. In some embodiments, the range may be about 400 mOsm/kg to about 1000 mOsm/kg. In some embodiments, the range may be about 400 mOsm/kg to about 800 mOsm/kg. In some embodiments, the range may be about 400 mOsm/kg to about 600 mOsm/kg.

Another aspect of the present invention is directed to an article of manufacture comprising a container holding any of the herein described formulations. In some embodiments, such articles may include a single dose vial, a multi-dose vial, a syringe (e.g. heated, self-mixing, retracting, with or without an attached needle, pre-filled or empty), a bag, or any acceptable, sterile container for storing contents of any pharmaceutically acceptable high concentration, low viscosity protein agent formulation. In some embodiments, a container comprises a single dose of a therapeutic protein agent (e.g., about 1 mg/mL to about 5000 mg/mL of monoclonal antibody).

In some embodiments, a provided formulation, when administered to a subject by intramuscular (IM) or subcutaneous (SC) injection, has decreased incidence and/or intensity of reported injection site pain than is observed with an appropriate comparator reference preparation.

Among other things, the present disclosure identifies a source of one or more problems associated with administration and/or delivery of protein-based agents. The present disclosure also provides solutions to those problems, by providing compositions, formulations, and methodologies as described herein.

This invention relates to methods for making concentrated, low-viscosity liquid formulations of pharmaceutically important protein agents, especially therapeutic protein agents, such as antibodies. This invention further relates to methods of making concentrated low-viscosity liquid formulations of protein agents that are capable of delivering therapeutically effective amounts of such protein agents in volumes useful for SC and IM injections. This invention further relates to methods of making concentrated liquid formulations of protein agents with low viscosities that can improve injectability and/or patient compliance, convenience, and comfort. This invention further relates to providing methods for making and storing concentrated, low-viscosity formulations of protein agents. This invention further relates to providing methods of administering low-viscosity, concentrated liquid formulations of protein agents. The present invention further relates to providing methods for processing reduced-viscosity, high-concentration biologics with concentration and filtration techniques known to those skilled in the art. This invention further relates to therapeutic uses for high concentration, low viscosity protein agent formulations.

Figure 7:
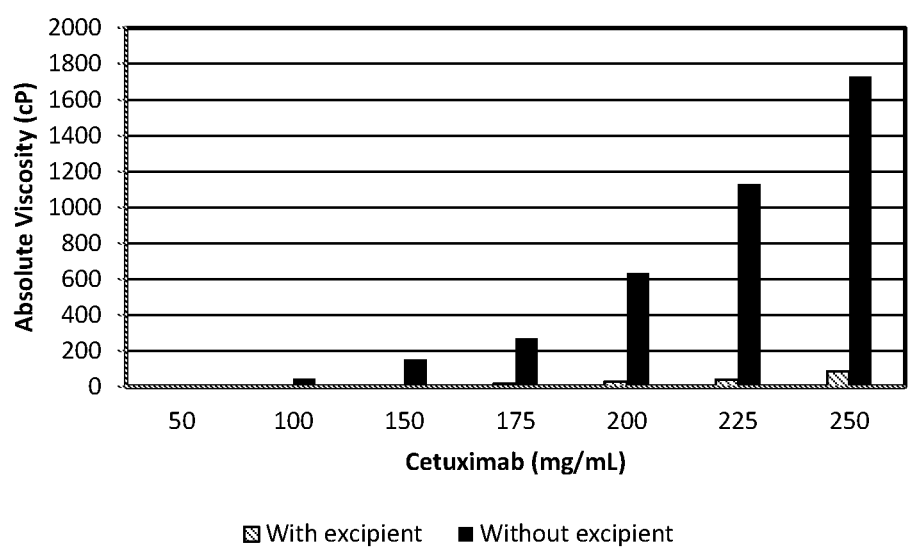

FIG. 7 is a bar graph depicting viscosity (cP) of an aqueous solution in the absence and in the presence of 10 mg/mL of Nicotinic acid (acid form) and 6 mg/mL Tryptophan as a function of cituximab (ERBITUX®) concentration (50 mg/mL, 100 mg/mL, 150 mg/mL, 175 mg/mL, 200 mg/mL, 225 mg/mL, 250 mg/mL) along the X-axis in 25 mM Phosphate buffer, pH 6.0 at 25° C.

Figure 8:
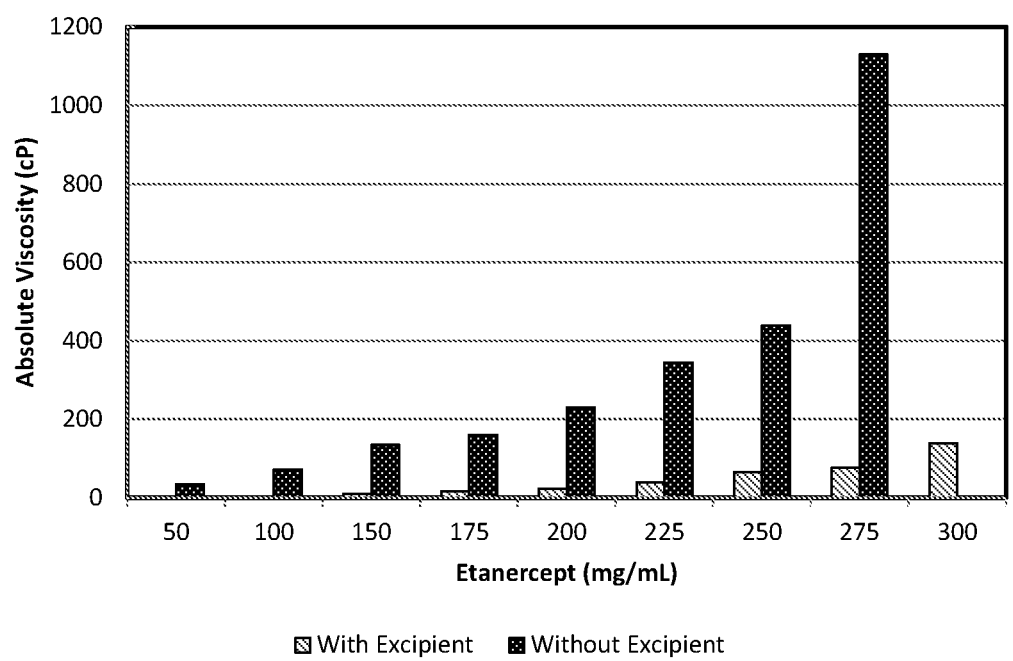

FIG. 8 depicts viscosity (cP) of an aqueous solution in the absence and in the presence of 10 mg/mL of Nicotinic acid (acid form) and 6 mg/mL Tryptophan as a function of etanercept (ENBREL®) concentration (50 mg/mL, 100 mg/mL, 150 mg/mL, 175 mg/mL, 200 mg/mL, 225 mg/mL, 250 mg/mL, 275 mg/mL, 300 mg/mL) along the X-axis in 25 mM Phosphate buffer, pH 6.0 at 25° C.

Figure 9:
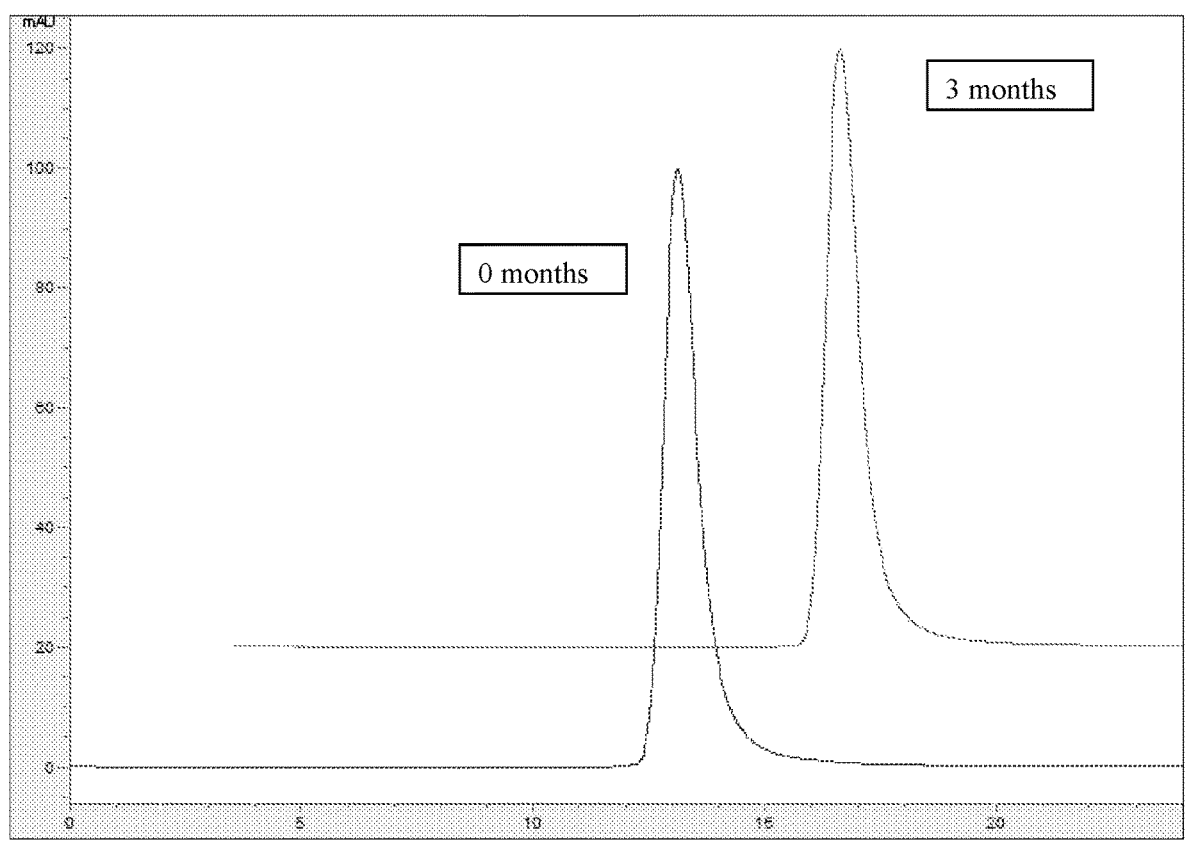

FIG. 9 is a Size-Exclusion Chromatogram trace depicting the absorbance intensity (at 280 nm) as a function of elution time (in minutes) for an aqueous solution of 275 mg/mL Trastuzumab (CANMAB®) stored at 4° C. for up to three months, in the 25 mM Phosphate buffer containing viscosity-reducing agents, 6 mg/mL Tryptophan and 10 mg/mL Nicotinic acid (acid form).

Figure 10:
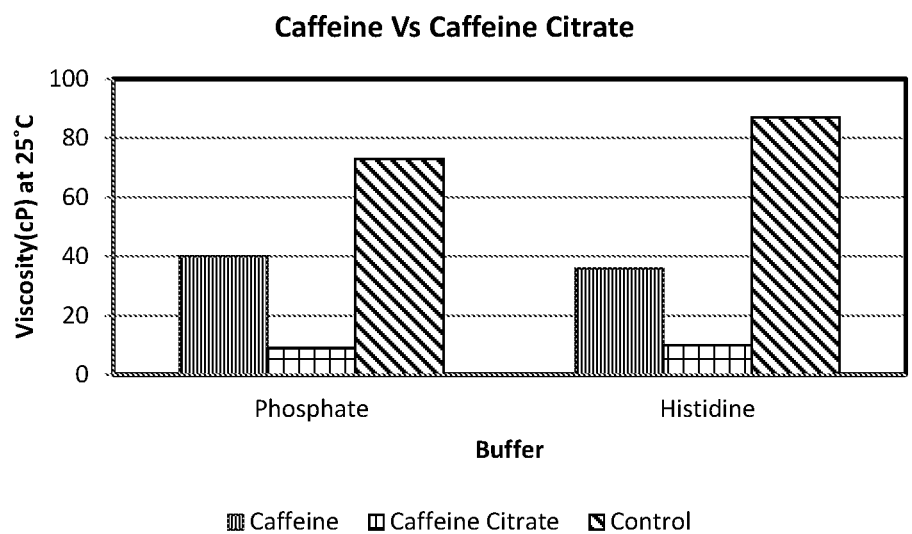

FIG. 10 depicts viscosity (cP) of aqueous solution of Human Gamma Globulin (GLOBUCEL®) at 220 mg/mL in 25 mM Histidine and 25 mM Phosphate buffer systems, pH 6.0 at 25° C. in the presence of viscosity-reducing agents, caffeine (10 mg/mL), caffeine citrate (20 mg/mL), and buffer alone as a control.

DEFINITIONS

In order for the present invention to be more readily understood, certain terms are defined below. Those skilled in the art will appreciate that definitions for certain terms may be provided elsewhere in the specification, and/or will be clear from context.

Alkyl group: As generally used herein, "alkyl group" refers to straight-chain, branched-chain and cyclic hydrocarbon groups. Unless specified otherwise, the term alkyl group embraces hydrocarbon groups containing one or more double or triple bonds. An alkyl group containing at least one ring system is a "cycloalkyl" group. An alkyl group containing at least one double bond is an "alkenyl group," and an alkyl group containing at least one triple bond is an "alkynyl group."

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Absolute viscosity: As generally used herein, the term "absolute viscosity" is sometimes called "dynamic viscosity" or "simple viscosity," is the product of kinematic viscosity and fluid density. Absolute viscosity is expressed in units of centipoise (cP). The SI unit of absolute viscosity is the milliPascal-second (mPa-s), where 1 cP=1 mPa-s.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Aggregation: The term "protein aggregation," as generally used herein, refers to a biological phenomenon in which mis-folded proteins aggregate (i.e., accumulate and clump together) either intra- or extracellularly. These protein aggregates are often correlated with diseases. In fact, protein aggregates have been implicated in a wide variety of disease known as amyloidoses, including ALS, Alzheimers's, Parkinson's and prion disease. This aggregation can be 'native,' in which the protein structure is maintained and the aggregation is largely reversible, or 'non-native,' where denaturation and structural changes mean this effect is largely irreversible. Aggregates may continue to grow and form over a wide size range, including up to and beyond the formation of visible particles, and ultimately this leads to precipitation.

Aggregation preventer/aggregation inhibitor: The term "protein preventer/aggregation inhibitor," as generally used herein, means preventing formation of additional protein aggregate in a protein-containing solution. Thus, inhibiting can encompass preventing the amount of protein aggregate in a protein formulation or solution. Preventing is measured by comparing the amount of aggregate present in a protein-containing solution that comprises at least one inhibitor of insoluble aggregate formation with the amount of aggregate present in a protein-containing solution that does not comprise at least one inhibitor of insoluble aggregate formation and is measured by either using Size-Exclusion chromatography or dynamic light scattering techniques.

Aggregation-reducing agent: The term "aggregation-reducing agent," as generally used herein, means decreasing the amount of protein aggregate in a protein-containing solution. Thus, reducing can encompass decreasing the amount of protein aggregate in a protein formulation or solution. Decreasing is measured by comparing the amount of aggregate present in a protein-containing solution that comprises at least one reducer of insoluble aggregate formation with the amount of aggregate present in a protein-containing solution that does not comprise at least one reducer of insoluble aggregate formation and is measured by either using Size-Exclusion chromatography or dynamic light scattering techniques.

Amino acid: in its broadest sense, as used herein, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc, as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments. F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]

Antibody agent: As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, in some embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody-drug conjugate: As used herein, an "antibody-drug conjugate" refers to a protein that is created by linking an antibody to a biologically active cytotoxic payload or drug. Antibody-drug conjugates (ADC) are generally produced through chemical modification/coupling reactions known to those skilled in the art. ADCs are intended to target and kill only the cancer cells and spare healthy cells. Antibody-drug conjugates are examples of bioconjugates and immunoconjugates.

Antibody fragment: As used herein, an "antibody fragment" refers to a portion of an antibody or antibody agent as described herein, and typically refers to a portion that includes an antigen-binding portion or variable region thereof. An antibody fragment may be produced by any means. For example, in some embodiments, an antibody fragment may be enzymatically or chemically produced by fragmentation of an intact antibody or antibody agent. Alternatively, in some embodiments, an antibody fragment may be recombinantly produced (i.e., by expression of an engineered nucleic acid sequence. In some embodiments, an antibody fragment may be wholly or partially synthetically produced. In some embodiments, an antibody fragment (particularly an antigen-binding antibody fragment) may have a length of at least about 50, 60, 70, 80, 90, 100, 110, 120, 130, 140, 150, 160, 170, 180, 190 amino acids or more, in some embodiments at least about 200 amino acids.

Antigen: As generally used herein, the term "antigen" refers to any substance or material that is specifically recognized and bound by an antibody. Antigens are typically small pieces of proteins (peptides) found on the surfaces of cells or invading microorganisms. Antibodies are thought to specifically recognize antigens as small as four amino acids in length, and the substitution of only one amino acid can abolish antibody recognition of the particular antigen for which it is specific.

Antigenicity: As generally used herein, the term "antigenicity" refers to the ability of an antigen to be specifically recognized and bound by an antibody. An antigen is said to be in its antigenic conformation when it can be specifically recognized and bound by the antibody specific for the antigen. This is different from immunogenicity, which is the ability of an antigen to elicit the production of antibodies specific for the antigen.

Anti-idiotypic antibody: As generally used herein, the term "anti-idiotypic" refers to antibodies having specificity for the antigen-binding sites of other antibody molecules. Anti-idiotypic antibodies are typically generated in the following manner: an antigen elicits the production of antibodies (called Ab-1) that are specific for that antigen. The antigenic determinant (epitopes) of this Ab-1 antibody which usually are called idiotypes are then used as immunogens themselves to elicit a second generation of antibodies that are specific for Ab-1. Such second generation antibodies (Ab-2) are typically called anti-idiotypic antibodies (or anti-idiotypes), and either mimic, or are closely related to, the initial antigen used to generate Ab-1. Without wishing to be bound by any particular theory, we note that it has been postulated that by exploiting this capability, anti-idiotypic antibodies can be used to prevent certain infections, and treat some kinds of cancers and various immune and autoimmune diseases.

Antibody half-life: As generally used herein, the term "antibody half-life" refers to the time in which a given amount of antibody or antibody agent, in vivo, is reduced to 50% of its initial concentration. Those of skill in the art are aware that, for example, IgG typically has a half-life of about 21 days (though IgG3 has a half-life of only 7 days), while IgM, A, D, and E have typical half-lives of 10 days, 6 days, 3 days, and 2 days, respectively.

Antibody loading: As generally used herein, the term "antibody loading" refers to the antibody content of formulations or compositions, typically calculated as a percentage by weight of antibody, a single-chain Fv antibody fragment or Fab antibody fragment, relative to the weight of the dry preparation. A typical range of antibody loading is from 1-80%.

Amorphous solid: As generally used herein, the term "amorphous solid" refers to a non-crystalline solid form of protein, sometimes referred to as "amorphous precipitate", which typically has no molecular lattice structure characteristic of the crystalline solid state.

Aqueous-organic solvent mixture: As generally used herein, the term "aqueous-organic solvent mixture" refers to—a mixture comprising n % organic solvent, where n is between 1 and 99 and m % aqueous, where m is 100−n.

Bioavailability: As generally used herein. The term "bioavailability" refers to the degree to which a substance, e.g., an active antibody or antibody fragment thereof, administered in vivo, becomes available to the tissue to which the substance is targeted. According to this invention, bioavailability also refers to the degree to which a whole antibody, or fragment thereof, that has been administered in vivo as a liquid formulation or a composition or formulation thereof, becomes available in the blood. According to this invention, bioavailability also refers to the ability of the substance, e.g., an active antibody or antibody fragment, to perform a function, e.g., direct cytotoxicity, at the target tissue once the substance has been delivered. Bioavailability may be measured in a number of ways, e.g., as the concentration of the substance, such as an active antibody or antibody fragment, measured as a function of time in the bloodstream. In some embodiments, bioavailability may be assessed, for example, by comparing the "area under the curve" (AUC) in a plot of the plasma concentration as a function of time. The AUC can be calculated, for example, using the linear trapezoidal rule. "AUC", as used herein, which refers to the area under the plasma concentration curve from time zero to a time where the plasma concentration returns to baseline levels. "AUC0-t", as used herein, refers to the area under the plasma concentration curve from time zero to a time, t, later, for example to the time of reaching baseline. The time will typically be measured in days, although hours can also be used as will be apparent by context.

Biological macromolecule: As generally used herein the term "biological macromolecule" refers to biological polymers such as proteins, peptides, glycoproteins, therapeutic protein, polysaccharides, lipoprotein, lipopolysaccharides, lipids, deoxyribonucleic acids (DNA) and ribonucleic acids (RNA). Such, biological macromolecules can also be referred to as macromolecules.

Branded: As used herein, the term "branded" (when used in the context of regulatory approval) generally refer to a protein or biologic, are used interchangeably herein, to mean the single biological product licensed under section 351(a) of the U.S. Public Health Service Act (42 U.S.C. § 262).

Biosimilar: The term "biosimilar," as used herein, is generally used interchangeably with "a generic equivalent" or "follow-on." For example, a "biosimilar mAb" refers to a subsequent version of an innovator's mAb typically made by a different company. "Biosimilar" when used in reference to a branded protein or branded biologic can refer to a biological product evaluated against the branded protein or branded biologic and licensed under section 351(k) of the U.S. Public Health Service Act (42 U.S.C. § 262). A biosimilar mAb can be one that satisfies one or more guidelines adopted May 30, 2012 by the Committee for Medicinal Products for Human Use (CHMP) of the European Medicines Agency and published by the European Union as "Guideline on similar biological medicinal products containing monoclonal antibodies—non-clinical and clinical issues" (Document Reference EMA/CHMP/BMWP/403543/2010). Biosimilars can generally be produced by microbial cells (prokaryotic, eukaryotic), cell lines of human or animal origin (e.g., mammalian, avian, insect), or tissues derived from animals or plants. The expression construct for a proposed biosimilar product will generally encode the same primary amino acid sequence as its reference product. Minor modifications, such as N- or C-terminal truncations that will not have an effect on safety, purity, or potency, may be present.

Bulking agent: As generally used herein, the term "bulking agent" refers to a compound which adds mass to a lyophilized mixture and contributes to the physical structure of the lyophilized cake (e.g. facilitates the production of an essentially uniform lyophilized cake which maintains an open pore structure). Exemplary bulking agents include mannitol, glycine, lactose, modified starch, poly(ethylene glycol), and sorbitol.

Chemical stability: As generally used herein, the term "chemical stability" refers to the ability of the protein components in a formulation to resist degradation via chemical pathways, such as oxidation, deamination, or hydrolysis. A protein formulation is typically considered chemically stable if less than about 5% of the components are degraded after 24 months at 4° C.

Chimeric antibody: As generally used herein, the term "chimeric antibody" refers to an antibody in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass. The term "chimeric antibody" may also refer to forms of non-human (e.g., murine) antibodies, where regions of heavy and light chains are derived from human antibodies and the CDR or variable region is originated from a non-human source.

Composition: As used herein, the term "composition" may be used to refer to a discrete physical entity that comprises one or more specified components. In general, unless otherwise specified, a composition may be of any form—e.g., gas, gel, liquid, solid, etc. In particular, as described herein, are compositions comprising a therapeutic protein, or are prepared using a therapeutic protein. In some embodiments, the composition or formulation comprising of or prepared using a therapeutic protein is prepared such that it is suitable for injection and/or administration to a patient in need thereof. Compositions to be administered for pharmaceutical purposes to patients are typically substantially sterile and do not contain any agents that are unduly toxic or infectious to the recipient.

Derivative: As used herein, when used in connection with antibodies or polypeptides of the invention, refers in general to antibodies or polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some embodiments, derivatives of the invention will retain the original binding properties of the underivatized versions of molecules of the invention.

Diluent or Carrier: As generally used herein, the term "diluent" or "carrier" refers to a pharmaceutically acceptable (i.e., safe and non-toxic for administration to a human or another mammal) ingredient for the preparation of a liquid formulation, such as an aqueous formulation, of a substance after it has been lyophilized. Exemplary diluents include sterile water, bacteriostatic water for injection (BWFI), a pH buffered solution (e.g., phosphate-buffered saline), sterile saline solution, Ringer's solution or dextrose solution, and combinations thereof.

Effective amount: As generally used herein, the term "effective amount" refers to an amount of a therapeutic protein or protein formulation or composition of this invention which is deemed sufficient to potentially treat, immunize, boost, protect, repair or detoxify the subject or the area to which the effective amount is administered over some period of time.

Emulsifier: As generally used herein, refers to a surface active agent which reduces interfacial tension between protein and a solution.

Essentially homogeneous and substantially homogeneous: are used interchangeably herein, and refer to a composition that may, for example, comprise at least about 80%, 85%, 90%, 95% or more by weight of pure protein agent in monomeric and reversible di- and oligo-meric forms. In some embodiments, the amount may be within a range bounded by a lower limit and an upper limit, the upper limit being larger than the lower limit. In some embodiments, the lower limit may be about 80%, about 85%/i, or about 90% pure protein by weight. In some embodiments, the upper limit may be about 95% or about 99% pure protein by weight. In some embodiments, the range may be about 80% to 99% pure protein agent by weight. In some embodiments, the range may be about 85% to about 99% pure protein agent by weight. In some embodiments, the range may be about 90% to about 99% pure protein by weight. In some embodiments, the range may be about 95% to about 99% pure protein by weight.

Essentially pure protein(s) and substantially pure protein(s): are used interchangeably herein and refer to a composition that may, for example, comprise at least about 80%0, 85%, 90%, 95% by weight pure protein agent, or more. In some embodiments, the amount may be within a range bounded by a lower limit and an upper limit, the upper limit being larger than the lower limit. In some embodiments, the lower limit may be about 80%, about 85%, or about 90%. In some embodiments, the upper limit may be about 95% or about 99%. In some embodiments, the range may be about 80% to 99% pure protein agent by weight. In some embodiments, the range may be about 85% to about 99% pure protein agent by weight. In some embodiments, the range may be about 90% to about 99% pure protein by weight. In some embodiments, the range may be about 95% to about 99% pure protein by weight.

Formulation: As generally used herein, the term "formulation" refers to a combination of a therapeutic protein or a combination of therapeutic antibody or antibody fragments thereof, and one or more ingredients or excipients. Examples of excipients are described in the Handbook of Pharmaceutical Excipients, published jointly by the American Pharmaceutical Association and the Pharmaceutical Society of Great Britain. As used herein, "formulations" include "Therapeutic Protein formulations." Furthermore, "formulations" include "Therapeutic High Protein Concentration" and "Antibody or fragments thereof formulations" and "monoclonal antibody formulations."

Fusion protein: As generally used herein, the term "fusion protein" refers to a protein that is created from two different genes encoding for two separate proteins. Fusion proteins are generally produced through recombinant DNA techniques known to those skilled in the art. Two proteins (or protein fragments) are fused together covalently and exhibit properties from both parent proteins.

Glycoprotein: As generally used herein, the term "glycoprotein" refers to a protein or peptide covalently linked to a carbohydrate. The carbohydrate may be monomeric or composed of oligosaccharides.

High-concentration or Concentrated: As generally used herein, the term "high-concentration" or "concentrated" describes liquid formulations having a final concentration of protein that may be at least about 10 mg/mL, 50 mg/mL, 100 mg/mL, 150 mg/mL, 200 mg/mL, 250 mg/mL, 300 mg/mL, 350 mg/mL, 400 mg/mL, 450 mg/mL, 500 mg/mL, 1000 mg/mL, 2000 mg/mL or more. In some embodiments, the amount may be within a range bounded by a lower limit and an upper limit, the upper limit being larger than the lower limit. In some embodiments, the lower limit may be about 10 mg/mL, about 25 mg/mL, about 50 mg/mL, about 100 mg/mL, or about 150 mg/mL. In some embodiments, the upper limit may be about 200 mg/mL, about 300 mg/mL, about 400 mg/mL, about 500 mg/mL, about 1000 mg/mL, or about 2000 mg/mL. In some embodiments, the range may be about 10 mg/mL to about 2000 mg/mL. In some embodiments, the range may be about 10 mg/mL to about 1000 mg/mL. In some embodiments, the range may be about 10 mg/mL to about 500 mg/mL. In some embodiments, the range may be about 50 mg/mL to about 2000 mg/mL. In some embodiments, the range may be about 50 mg/mL to about 1000 mg/mL. In some embodiments, the range may be about 50 mg/mL to about 500 mg/mL. In some embodiments, the range may be about 100 mg/mL to about 500 mg/mL. In some embodiments the range may be about 150 mg/mL to about 500 mg/mL. In some embodiments the range may be about 150 mg/mL to about 450 mg/mL. In some embodiments the range may be about 150 mg/mL to about 400 mg/mL. In some embodiments the range may be about 150 mg/mL to about 350 mg/mL. In some embodiments the range may be about 150 mg/mL to about 300 mg/mL.

Homo-polymer: As generally used herein, the term "homo-polymer" refers to a polymer made with a single monomer species.

Humanized antibody: As generally used herein, the term "humanized antibody" typically refers to an antibody form of non-human (e.g., murine) antibodies that are immunoglobulin chains or fragments thereof (such as Fv, Fab, Fab', F(ab')2, or other antigen-binding subsequences of antibodies) of mostly human sequences, which contain minimal sequences derived from non-human immunoglobulin. (See, e.g., Jones et al., Nature 321:522-525, 1986; Reichmann et al., Nature 332:323-329, 1988; and Presta, Curr. Op. Struct. Biol. 2:593-596, 1992.) Alternatively, a humanized antibody may be derived from a chimeric antibody.

Human antibody: As generally used herein, the term "human antibody" refers to an antibody derived from human sequences, e.g. through screening libraries of human antibody genes through known techniques such as phage display, or produced using transgenic animals that have no endogenous immunoglobulin production and are engineered to contain human immunoglobulin loci.

Hypertonic: As generally used herein, the term "hypertonic" refers to a solution with a higher concentration of solutes than is present on the inside of the cell. When a cell is immersed into a hypertonic solution, the tendency is for water to flow out of the cell in order to balance the concentration of the solutes outside of the cell.

Hypotonic: As generally used herein, the term "hypotonic" refers to a solution with a lower concentration of solutes than is present on the inside of the cell. When a cell is immersed into a hypotonic solution, water typically flows into the cell in order to balance the concentration of the solutes found outside of the cell.

"Improve," "increase", "inhibit", "decrease" or "reduce": As used herein, the terms "improve", "increase", "inhibit', "decrease", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Immunotherapeutic: As generally used herein, is an antibody or single-chain Fv antibody fragment or Fab antibody fragment that has the property of inducing protective immunity to a tumor cell, virus, or bacterium or stimulating the immune system to reduce such tumor cell, virus or bacterium.

Injectability or syringeability: As generally used herein, the term "injectability" or "syringeability" refers to the injection performance of a pharmaceutical formulation through a syringe equipped with an 18-32 gauge needle, optionally a thin walled needle. Injectability generally depends upon factors such as pressure or force required for injection, evenness of flow, aspiration qualities, and freedom from clogging the needle. Injectability of the liquid pharmaceutical formulations may be assessed by comparing the injection force of a reduced-viscosity formulation to a standard formulation without added viscosity-reducing agents. The reduction in the injection force of the formulation containing a viscosity-reducing agent reflects improved injectability of that formulation. The reduced viscosity formulations have improved injectability when the injection force is reduced by 10%, 30%, 50%, 75% or more when compared to a standard formulation with the same concentration of protein under otherwise the same conditions, except for replacement of a viscosity-reducing agent with an appropriate buffer of about the same concentration. In some embodiments, the amount may be within a range bounded by a lower limit and an upper limit, the upper limit being larger than the lower limit. In some embodiments, the lower limit may be about 5%, about 10%, or about 15%. In some embodiments, the upper limit may be about 50%, or about 75%. In some embodiments, the range may be about 10% to about 30%. In some embodiments, the range may be about 10% to about 50%. In some embodiments, the range may be about 10% to about 75%. Alternatively, injectability of liquid pharmaceutical formulations may be assessed by comparing the time required to inject the same volume, such as 0.5 mL to about 1 mL, of different liquid protein formulations when the syringe is depressed with the same force.

Injection force: As generally used herein, the term "injection force" refers to the force required to push a given liquid formulation through a given syringe equipped with a given needle gauge at a given injection speed. The injection force is typically reported in Newtons. For example, the injection force may be measured as the force required to push a liquid formulation through a 1 mL plastic syringe with a 0.25 inch inside diameter that is equipped with a 0.50 inch, 27 gauge needle at a 250 mm/min injection speed. Testing equipment can be used to measure the injection force. When measured under the same conditions, a formulation with lower viscosity will generally require an overall lower injection force.

Isolated antibody: As generally used herein, the term "isolated antibody" refers to an antibody that has been identified and separated from a component of its natural environment. Contaminant components of its natural environment are materials that would interfere with diagnostic or therapeutic uses for the antibody, and may include enzymes, hormones, and other proteinaceous or non-proteinaceous solutes. In certain embodiments, the antibody will be purified (1) to greater than a range of 95% to 99% by weight of antibody, or (2) to homogeneity by use of SDS-PAGE under reducing or non-reducing conditions using Coomassie blue or silver stain to visualize the antibody. Isolated, naturally occurring antibodies include an antibody in-situ within recombinant cells, since at least one component of the antibody's natural environment will not be present. Ordinarily, however, isolated antibodies will typically be prepared by at least one purification step.

Isotonic: As generally used herein, the term "isotonic" refers to a solution wherein the osmotic pressure gradient across the cell membrane is essentially balanced. An isotonic formulation is one which has essentially the same osmotic pressure as human blood.

Kinematic viscosity: As used herein, the term "kinematic viscosity" refers to a measure of the rate at which momentum is transferred through a fluid. It is measured in Stokes (St). The kinematic viscosity is a measure of the resistive flow of a fluid under the influence of gravity. When two fluids of equal volume and differing viscosity are placed in identical capillary viscometers and allowed to flow by gravity, the more viscous fluid typically takes longer than the less viscous fluid to flow through the capillary. The dimension of kinematic viscosity is $length^2/time$. Commonly, kinematic viscosity is expressed in centiStokes (cSt). The SI unit of kinematic viscosity is mm2/s, which is equal to 1 cSt.

Liquid polymer: As generally used herein, the term "liquid polymer" refers to a pure liquid phase synthetic polymer, such as poly-ethylene glycol (PEG), in the absence of aqueous or organic solvents.

Liquid formulation: As used herein, the term "liquid formulation" refers to a protein that is either supplied in an acceptable pharmaceutical diluent or one that is reconstituted in an acceptable pharmaceutical diluent prior to administration to the patient.

Loss of shelf stability: As generally used herein, the term "loss of shelf stability" refers to a loss of specifically defined activity (as with enzymes) or a decrease in binding affinity (as with antibodies) and/or changes in secondary structure of a therapeutic protein stored in formulations with viscosity-reducing agents as compared to the control (i.e., formulation without viscosity lowering agent(s)) over time, when incubated under corresponding conditions.

Loss of stability: As generally used herein, the term "loss of stability" refers to a loss of specifically defined activity (as with enzymes) or a decrease in binding affinity (as with antibodies) and/or changes in secondary structure of a therapeutic protein in formulations with viscosity-reducing agents as compared to the control (i.e., formulation without viscosity lowering agent(s)) over time, while in solution, under corresponding conditions.

Lyoprotectant: As used herein, the term "lyoprotectant" refers to a compound that when added to the formulation containing a viscosity-reducing compound, is capable of reducing the self-association of proteins in addition to contributing to the reduction of the viscosity of an aqueous formulation comprising said protein. In a specific aspect, the self-association to be prevented is that induced or exacerbated by the presence of sugars that are commonly used as lyoprotectants. Accordingly, this method can be particularly useful for preventing self-association of reconstituted lyophilized formulations.

Modification: As used herein, when used in connection with antibodies or polypeptides described herein, includes but is not limited to, one or more amino acid change (including substitutions, insertions or deletions); chemical modifications that do not interfere with antigen binding activity; covalent modification by conjugation to therapeutic or diagnostic agents; labeling (e.g., with radionuclides or various enzymes); covalent polymer attachment such as pegylation (derivatization with polyethylene glycol) and insertion or substitution by chemical synthesis of non-natural amino acids. In some embodiments, modified polypeptides (including antibodies) of the invention will retain the binding properties of unmodified molecules of the invention.

Monoclonal antibody or mAb: As generally used herein, the term "monoclonal; antibody" refers to an antibody obtained from a population of substantially homogeneous antibodies, i.e., individual antibodies comprising the population are identical, except for possible naturally occurring mutations that may be present in minor amounts. Monoclonal antibodies are highly specific, and are directed against a single epitope. These, for example, are typically synthesized by culturing hybridoma cells, as described by Kohler et al. (Nature 256: 495, 1975), or may be made by recombinant DNA methods (see, e.g., U.S. Pat. No. 4,816,567), or isolated from phage antibody libraries using the techniques described in Clackson et al. (Nature 352: 624-628, 1991) and Marks et al. (J. Mol. Biol. 222: 581-597, 1991). As used herein, "mAbs" specifically include derivatized antibodies, antibody-drug conjugates, and "chimeric" antibodies as well as fragments of such antibodies, so long as they exhibit the desired biological activity (U.S. Pat. No. 4,816,567; Morrison et al., Proc. Natl. Acad. Sci. USA 81:6851-6855, 1984).

Newtonian fluids: As generally used herein, the term "newtonian fluids" refers to fluids with a viscosity that is essentially independent of shear rate.

Non-Newtonian fluids: As generally used herein, the term "non-newtonian fluids" refers to fluids with a viscosity that either decreases or increases with increasing shear rate, e.g., the fluids are "shear thinning" or "shear thickening", respectively. In the case of concentrated (i.e., high-concentration) protein solutions, this may manifest as pseudoplastic shear-thinning behavior, i.e., a decrease in viscosity with shear rate.

Organic solvent: As generally used herein, the term "organic solvent" refers to any solvent of non-aqueous origin, including liquid polymers and mixtures thereof. Organic solvents suitable for the present invention include: acetone, methyl alcohol, methyl isobutyl ketone, chloroform, 1-propanol, isopropanol, 2-propanol, acetonitrile, 1-butanol, 2-butanol, ethyl alcohol, cyclohexane, N-methylpyrrolidinone (NMP), dioxane, ethyl acetate, dimethylformamide, dichloroethane, hexane, isooctane, methylene chloride, tert-butyl alcohol, toluene, carbon tetrachloride, or combinations thereof.

Osmolarity: As generally used herein, the term "osmolarity" refers to the total number of dissolved components per liter. Osmolarity is similar to molarity but includes the total number of moles of dissolved species in solution. An osmolarity of 1 Osm/L means there is 1 mole of dissolved components per L of solution. Some solutes, such as ionic solutes that dissociate in solution, will contribute more than 1 mole of dissolved components per mole of solute in the solution. For example, NaCl dissociates into $Na^+$ and $Cl^-$ in solution and thus provides 2 moles of dissolved components per 1 mole of dissolved NaCl in solution. Physiological osmolarity is typically in the range of about 280 mOsm/L to about 310 mOsm/L.

Particle size of protein: As generally used herein, the term "particle size of protein" refers to the average diameter of the predominant population of bioactive molecule particulates, or particle size distributions thereof, in a formulation as determined by using well known particle sizing instruments. For example, dynamic light scattering, SLS (Static Light Scattering), or other methods known to one ordinarily skilled in the art may be used to measure the particle size.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions.

PEGylation: As used herein, the term "PEGylated proteins" refers to protein agents having one or more polymers covalently attached randomly at non-specific site(s) on the protein agent, or in a site-specific manner by covalently attaching the polymer to specific site(s) on the protein agent (Hoffman et al., Progress in Polymer Science, 32:922-932, 2007). The term "PEGylated protein," as used herein, refers to a protein with one or more poly(ethylene glycol) or other stealth polymer groups covalently attached to the protein. PEGylated proteins have prolonged half-lives and enhanced bioavailability due to typically reduced renal filtration, decreased uptake by the reticuloendothelial system, and diminished enzymatic degradation. Exemplary polymers include poly(ethylene glycol); poly(propylene glycol); poly (amino acid) polymers such as poly(glutamic acid), poly (hydroxyethyl-L-asparagine), and poly(hydroxyethyl-L-glutamine); poly(glycerol); poly(2-oxazoline) polymers such as poly(2-methyl-2-oxazoline) and poly(2-ethyl-2-oxazoline); poly(acrylamide); poly(vinylpyrrolidone); poly(N-(2-hydroxypropyl)methacrylamide); and copolymers and mixtures thereof. In preferred embodiments the polymer in a PEGylated protein is poly(ethylene glycol) or a copolymer thereof.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Percent bioavailability: As generally used herein, the term "percent bioavailability" refers to the fraction of the administered dose of the bioactive species which enters circulation, as determined with respect to an intravenously administered dose.

Pharmaceutically effective amount: As generally used herein, the term "pharmaceutically effective amount" refers to an amount of a therapeutic protein, or high concentration of protein formulation or composition thereof, which is effective to treat a condition in a living organism to whom it is administered over some period of time.

Pharmaceutically acceptable salts: As generally used herein, the term "pharmaceutically acceptable salts" refers to salts prepared from pharmaceutically acceptable non-toxic acids and bases, including inorganic acids and bases, and organic acids and bases. Suitable non-toxic acids include inorganic and organic acids such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Suitable positively charged counterions include sodium, potassium, lithium, calcium and magnesium.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Physical stability: As generally used herein, the term "physical stability" refers to the ability of a protein formulation to resist physical deterioration, such as aggregation. A formulation that is physically stable forms only an acceptable percentage of irreversible aggregates (e.g., dimers, trimers, or other aggregates) of the bioactive protein agent. The presence of aggregates may be assessed in a number of ways, including by measuring the average particle size of the proteins in the formulation by means of dynamic light scattering. A formulation is considered physically stable if less than about 5% irreversible aggregates are formed after 24 months at 4° C. Acceptable levels of aggregated contaminants ideally would be less than about 2%. Level as low as about 0.2% is achievable, although approximately 1% is more typical.

Plasticizing: As generally used herein, the term "plasticizing" refers to the use of a plasticizer, e.g., lanolin, ethanol, to make a formulation comprising a therapeutic protein in a solution that becomes viscous after it is injected subcutaneously, forming a matrix. The resulting high viscosity matrix is adhesive, biodegradable and biocompatible. The therapeutic protein is then released in a controlled manner from the matrix.

Polyclonal Antibody: As generally used herein, the term "polyclonal antibody" refers to a mixed population of antibodies of diverse sequences produced by different B-cell lineages that bind to diverse epitopes.

Polyethylene glycol (PEG) size: As generally used herein, the term "polyethylene glycol size" refers to the size of the PEG moieties used according to this invention (e.g., inter alia, PEG 100, PEG 200, PEG 400, PEG 10,000, PEG 80,000) refers to the chain length, i.e., number of ethylene glycol residues in the PEG chain. For example, PEG 200 has 200 ethylene glycol residues in the PEG polymer; PEG 80,000 has 80,000 ethylene glycol residues in the PEG polymer, etc.

Polymer: As generally used herein, the term "polymer" refers to a large molecule built up by the repetition of small, simple chemical units. The repeating units may be linear or branched to form interconnected networks. The repeat unit is usually equivalent or nearly equivalent to the monomer.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Preservative: as generally used herein, refers to a compound which can be added to the formulations herein to reduce contamination by and/or action of bacteria, fungi, or another infectious agent. The addition of a preservative may, for example, facilitate the production of a multi-use (multiple-dose) formulation. Examples of potential preservatives include octadecyl dimethyl benzyl ammonium chloride, hexamethonium chloride, benzalkonium chloride (a mixture of alkylbenzyldimethylammonium chlorides in which the alkyl groups are long-chained), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

Prophylactically effective amount: As generally used herein, the term "prophylactically effective amount" refers to an amount of a therapeutic protein, or high concentration of protein formulation or composition thereof, which is effective to prevent a condition in a living organism to which it is administered over some period of time.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof. Proteins having a molecular weight (expressed in kDa wherein "Da" stands for "Daltons" and 1 kDa=1,000 Da) greater than about 100 kDa may be designated "high-molecular-weight proteins," whereas proteins having a molecular weight less than about 100 kDa may be designated "low-molecular-weight proteins." The term "low-molecular-weight protein" generally excludes small peptides lacking the requisite of at least tertiary structure necessary to be classified as a protein. In some embodiments, the protein has a molecular weight that may be, for example, at least about 25 kDa, 50 kDa, 100 kDa, 150 kDa, 200 kDa, 250 kDa, 300 kDa, 400 kDa, 500 kDa, 1000 kDa, or greater. In some embodiments, the lower limit may be about 25 kDa, about 50 kDa, about 100 kDa, or about 150 kDa. In some embodiments, the upper limit may be about 200 kDa, about 250 kDa, about 300 kDa, about 400 kDa, about 450 kDa, about 500 kDa, or about 1000 kDa. In some embodiments, the amount may be within a range bounded by a lower limit and an upper limit, the upper limit being larger than the lower limit. In some embodiments, the range may be about 25 kDa to about 1000 kDa. In some embodiments, the range may be about 25 kDa to about 500 kDa. In some embodiments, the range may be about 50 kDa to about 1000 kDa. In some embodiments, the range may be about 50 kDa to about 500 kDa. In some embodiments, the range may be about 100 kDa to about 500 kDa. In some embodiments, the range may be about 150 kDa to about 500 kDa. In some embodiments, the range may be about 150 kDa to about 400 kDa. In some embodiments, the range may be about 150 kDa to about 300 kDa. In some embodiments, the range may be about 150 kDa to about 250 kDa. Protein molecular weight may be determined using standard methods known to one skilled in the art, including, but not limited to, mass spectrometry (e.g., ESI, MALDI) or calculation from known amino acid sequences and glycosylation. Proteins can be naturally occurring or non-naturally occurring, synthetic, or semi-synthetic. The final concentration of protein may be at least about 10 mg/mL, 50 mg/mL, 100 mg/mL, 150 mg/mL, 200 mg/mL, 250 mg/mL, 300 mg/mL, 350 mg/mL, 400 mg/mL, 450 mg/mL, 500 mg/mL or more. In some embodiments, the amount may be within a range bounded by a lower limit and an upper limit, the upper limit being larger than the lower limit. In some embodiments, the lower limit may be about 10 mg/mL, about 25 mg/mL, about 50 mg/mL, about 100 mg/mL, or about 150 mg/mL. In some embodiments, the upper limit may be about 200 mg/mL, about 300 mg/mL, about 400 mg/mL, about 500 mg/mL, about 1000 mg/mL, or about 2000 mg/mL. In some embodiments, the range may be about 10 mg/mL to about 2000 mg/mL. In some embodiments, the range may be about 10 mg/mL to about 1000 mg/mL. In some embodiments, the range may be about 10 mg/mL to about 500 mg/mL. In some embodiments, the range may be about 25 mg/mL to about 2000 mg/mL. In some embodiments, the range may be about 25 mg/mL to about 1000 mg/mL. In some embodiments, the range may be about 25 mg/mL to about 500 mg/mL. In some embodiments, the range may be about 50 mg/mL to about 2000 mg/mL. In some embodiments, the range may be about 50 mg/mL to about 1000 mg/mL. In some embodiments, the range may be about 50 mg/mL to about 500 mg/mL. In some embodiments, the range may be about 100 mg/mL to about 2000 mg/mL. In some embodiments, the range may be about 100 mg/mL to about 1000 mg/mL. In some embodiments, the range may be about 100 mg/mL to about 500 mg/mL. In some embodiments, the range may be about 150 mg/mL to about 2000 mg/mL. In some embodiments, the range may be about 150 mg/mL to about 1000 mg/mL. In some embodiments the range may be about 150 mg/mL to about 500 mg/mL. In some embodiments the range may be about 150 mg/mL to about 450 mg/mL. In some embodiments the range may be about 150 mg/mL to about 400 mg/mL. In some embodiments the range may be about 150 mg/mL to about 350 mg/mL. In some embodiments the range may be about 150 mg/mL to about 300 mg/mL.

Protein delivery system: As generally used herein, the term "protein delivery system" refers to a method or means for administering one or more of a protein, such as a therapeutic protein, or high concentration of protein formulation or composition comprising such therapeutic proteins, to a biological entity.

Radiolabel: As generally used herein, the term "radiolabel" refers to the incorporation of a radiolabel to a protein, such as a therapeutic protein, or an antibody. In situations where the radiolabel has a short half-life, as with 131I or 90Y, the radiolabel can also be therapeutic, e.g., used in radio immunotherapies against cancers. Various methods of labeling polypeptides and glycoproteins are known in the art and may be used. Examples of labels include, but are not limited to, the following radioisotopes or radionucleotides: 3H, 14C, 15N, 35S, 90Y, 99Tc, 111In, 125I, and 131I.

Reconstitution: As generally used herein, the term "reconstitution" refers to the dissolution of a dry powder, spray-dried or solvent precipitate, lyophilized therapeutic protein, or lyophilized cake into a high concentration protein formulation or compositions comprising such therapeutic proteins, in an appropriate buffer or pharmaceutical preparation such that the protein is dissolved or dispersed in aqueous solution for administration.

Reduced-viscosity formulation: As generally used herein, the term "reduced-viscosity formulation" refers to a liquid formulation with a high concentration of a high-molecular-weight protein, such as a mAb, or a low-molecular-weight protein that is modified by the presence of one or more additives to lower the viscosity, as compared to a corresponding formulation that does not contain the viscosity-reducing additive(s).

Reference: As generally used herein, describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Rheology: As generally used herein, the term "rheology" refers to the study of the deformation and flow of matter.

Room Temperature: As generally used herein, the term "room temperature," for purposes of this invention, will be understood by those of skill in the art that room temperature can be any temperature from about 20° C. to about 26° C.

Shear rate: as generally used herein, refers to the rate of change of velocity at which one layer of fluid passes over an adjacent layer. The velocity gradient is the rate of change of velocity with distance from the plates. This simple case shows the uniform velocity gradient with shear rate (v1−v2)/h in units of (cm/sec)/(cm)=1/sec. Hence, shear rate units are reciprocal seconds or, in general, reciprocal time. For a microfluidic viscometer, changes in pressure and flow rate are related to shear rate. Shear rate also refers to speed with which a material is deformed. Formulations containing proteins and viscosity-reducing agents are typically measured at shear rates ranging from about 0.5 $s^{-1}$ to about 200 $s^{-1}$ when measured using a cone and plate viscometer and a spindle appropriately chosen by one skilled in the art to accurately measure viscosities in the viscosity range of the sample of interest.

Stabilization: As generally used herein, the term "stabilization" refers to the process of preventing the loss of specific activity and/or changes in secondary structure of a therapeutic protein, antibody, single-chain antibody Fv fragment, or a Fab antibody fragment as compared with the non-formulated aqueous therapeutic protein, antibody, single-chain Fv antibody fragment counterpart, or Fab antibody fragment counterpart, by preparing formulations or compositions of the above to include viscosity-reducing reagents.

Stable formulation: As generally used herein, the term "stable formulation" refers to a formulation that is both chemically stable and physically stable. A stable formulation may be one in which more than about 95% of the bioactive protein molecules retain bioactivity in a formulation after 24 months of storage at 4° C., or equivalent solution conditions at an elevated temperature, such as one month storage at 40° C. Various analytical techniques for measuring protein stability are available in the art and are reviewed, for example, in Peptide and Protein Drug Delivery, 247-301, Vincent Lee, Ed., Marcel Dekker, Inc., New York, N.Y. (1991) and Jones, A., Adv. Drug Delivery Revs. 10:29-90, 1993. Stability can be measured at a selected temperature for a certain time period. For rapid screening, for example, the formulation may be kept at 40° C., for 2 weeks to one month, at which time residual biological activity is measured and compared to the initial condition to assess stability. When the formulation is to be stored at 2° C.-8° C., the formulation should generally be stable at 30° C. or 40° C. for at least one month and/or stable at 2° C.-8° C. for at least 2 years. When the formulation is to be stored at room temperature, or about 25° C., the formulation should generally be stable for at least 2 years at about 25° C. and/or stable at 40° C. for at least about 6 months. The extent of aggregation following lyophilization and storage can be used as an indicator of protein stability. In some embodiments, the stability is assessed by measuring the particle size of the proteins in the formulation. In some embodiments, stability may be assessed by measuring the activity of a formulation using standard biological activity or binding assays well within the abilities of one ordinarily skilled in the art.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically effective amount: As generally used herein, the term "therapeutically effective amount" refers to the lowest concentration of a substance required to elicit a measurable improvement or prevention of any symptom of a particular condition or disorder, to elicit a measurable enhancement of life expectancy, or to generally improve patient quality of life. The therapeutically effective amount is dependent upon the specific biologically active molecule and the specific condition or disorder to be treated. Therapeutically effective amounts of many proteins, such as the mAbs described herein, are well known in the art. The therapeutically effective amounts for treating specific disorders with known proteins, such as mAbs, if to be clinically applied to treat additional disorders, may be determined by standard techniques which are well within the craft of a skilled artisan, such as a physician.

Tonicity: As generally used herein, the term "tonicity" refers to the osmotic pressure gradient resulting from the separation of two solutions by a semi-permeable membrane. In particular, tonicity is used to describe the osmotic pressure created across a cell membrane when a cell is exposed to an external solution. Solutes that can cross the cellular membrane do not contribute to the final osmotic pressure gradient. Only those dissolved species that do not cross the cell membrane will contribute to osmotic pressure differences and thus tonicity.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide. The term "variant" when used in connection with antibodies, refers to a polypeptide sequence of an antibody that contains at least one amino acid substitution, deletion, or insertion in the variable region, or a portion equivalent to the variable region, provided that the variant retains the desired binding affinity or biological activity. In addition, the antibodies as described herein may have amino acid modifications in the invariable region to modify effector function of the antibody, including half-life or clearance, ADCC and/or CDC activity. Such modifications can typically enhance pharmacokinetics or enhance the effectiveness of the antibody in treating cancer, for example. See Shields et al., J. Biol. Chem., 276(9):6591-6604 (2001), incorporated by reference herein in its entirety. In the case of IgG1, modifications to the invariable region, particularly the hinge or CH2 region, may increase or decrease effector function, including ADCC and/or CDC activity. In other embodiments, an IgG2 constant region is modified to decrease antibody-antigen aggregate formation. In the case of IgG4, modifications to the constant region, particularly the hinge region, may reduce the formation of half-antibodies.

Viscosity: The term "viscosity," as generally used herein, refers to the resistance of a substance (typically a liquid) to flow. Viscosity is related to the concept of shear force; it can be understood as the effect of different layers of the fluid exerting shearing force on each other, or on other surfaces, as they move against each other. Viscosity can be "kinematic" or "absolute". There are several measures of viscosity. The units of viscosity are $Ns/m^2$, known as Pascal-seconds (Pa-s). Viscosity may be measured by using, for example, a viscometer at a given shear rate or multiple shear rates. An "extrapolated zero-shear" viscosity can be determined by creating a best fit line of the four highest-shear points on a plot of absolute viscosity versus shear rate, and linearly extrapolating viscosity back to zero-shear. Alternatively, for a Newtonian fluid, viscosity can be determined by averaging viscosity values at multiple shear rates. Viscosity can also be measured using a microfluidic viscometer at single or multiple shear rates (also called flow rates), wherein absolute viscosity is derived from a change in pressure as a liquid flows through a channel. Viscosity equals shear stress over shear rate. Viscosities measured with microfluidic viscometers can, in some embodiments, be directly compared to extrapolated zero-shear viscosities, for example those extrapolated from viscosities measured at multiple shear rates using a cone and plate viscometer. The composition herein may be in either aqueous or lyophilized form. In aqueous form, the composition of matter may have a viscosity, that when measured at 25° C., that may be, for example, about 100 cP, 75 cP, 50 cP, 45 cP, 40 cP, 35 cP, 30 cP, or lower. In some embodiments, the amount may be within a range bounded by a lower limit and an upper limit, the upper limit being larger than the lower limit. In some embodiments, when measured at 25° C., the lower limit may be about 1 cP, about 5 cP, about 10 cP, or about or 15 cP. In some embodiments, when measured at 25° C., the upper limit may be about 20 cP, about 25 cP, about 30 cP, about 35 cP, about 40 cP, about 45 cP, about 50 cP, about 75 cP, or about 100 cP. In some embodiments, when measured at 25° C., the range may be about 5 cP to about 100 cP. In some embodiments, when measured at 25° C., the range may be about 5 cP to about 75 cP. In some embodiments, when measured at 25° C., the range may be about 5 cP to about 50 cP. In some embodiments, when measured at 25° C., the range may be about 5 cP to about 40 cP. In some embodiments, when measured at 25° C., the range may be about 5 cP to about 35 cP. In some embodiments, when measured at 25° C., the range may be about 5 cP to about 30 cP. In some embodiments, when measured at 25° C., the range may be about 5 cP to about 25 cP. In some embodiments, when measured at 25° C., the range may be about 5 cP to about 20 cP. In some embodiments, when measured at 25° C., the range may be about 5 cP to about 15 cP. In some embodiments, when measured at 25° C., the range may be about 5 cP to about 10 cP.

Viscosity gradient: As used herein, the term "viscosity gradient" refers to the rate of change of the viscosity of a protein solution as protein concentration increases. The viscosity gradient can be approximated from a plot of the viscosity as a function of the protein concentration for a series of formulations that are otherwise the same but have different protein concentrations. The viscosity increases approximately exponentially with increasing protein concentration. The viscosity gradient at a specific protein concentration can be approximated from the slope of a line tangent to the plot of viscosity as a function of protein concentration. The viscosity gradient can be approximated from a linear approximation to the plot of viscosity as a function of any protein concentration or over a narrow window of protein concentrations. In some embodiments a formulation is said to have a decreased viscosity gradient if, when the viscosity as a function of protein concentration is approximated as an exponential function, the exponent of the exponential function is smaller than the exponent obtained for the otherwise same formulation without the viscosity-reducing agent. In a similar manner, a formulation can be said to have a lower/higher viscosity gradient when compared to a second formulation if the exponent for the formulation is lower/higher than the exponent for the second formulation. The viscosity gradient can be numerically approximated from a plot of the viscosity as a function of protein concentration by other methods known to the skilled formulation researchers.

Viscosity-reducing agent: As used herein, the term "viscosity-reducing agent" refers to a compound which acts to reduce the viscosity of a solution relative to the viscosity of a solution absent of a viscosity-reducing agent. The viscosity-reducing agent may be a single compound, or may be a mixture of one or more compounds. When the viscosity-reducing agent is a mixture of two or more compounds, the listed concentration refers to each individual agent, unless otherwise specified.

DETAILED DESCRIPTION OF CERTAIN EMBODIMENTS

The present disclosure, among other things, identifies viscosity-reducing additive agents that are capable of lowering viscosity of high concentration protein agent formulations, particularly of aqueous formulations. In some embodiments, inclusion of such additive agents also avoids and/or reduces protein agent aggregation within provided preparations.

Prior efforts to identify useful viscosity-reducing additive agents have often relied on agents with safety and/or toxicity profiles that are uncertain and/or problematic. Preparations including such additives would therefore face a higher regulatory burden prior to approval than would preparations containing compounds demonstrated and/or accepted to be safe. The present disclosure provides, in many embodiments, preparations that utilize only safe additives. Indeed, even if a compound were to be shown to substantially reduce viscosity, the compound may ultimately be unsuitable for use in a formulation intended for injection into a human.

In order to provide therapeutically effective amounts of many high-molecular-weight protein agents, such as mAbs, protein agent concentrations greater than 150 mg/mL for SC/IM injection are often required in volumes less than 2 mL. Due to problems with high viscosity and other properties characteristic of concentrated solutions of large proteins, many therapeutically important mAbs are currently administered via IV infusions in order to deliver therapeutically effective amounts of mAb/protein agent.

The present pharmaceutical formulation is prepared by combining, in addition to therapeutic protein agents as described, one or more of the following types of liquid media, viscosity-reducing agents, surfactants, lyoprotectants, or other ingredients or excipients listed in the paragraphs below. It will be understood by one of ordinary skill in the art that combining the various components to be included in the formulation can be done in any appropriate order, namely, the buffer can be added first, middle or last and the other additive agents can also be added first, middle or last. It is also to be understood by one of ordinary skill in the art that some of these chemicals can be incompatible in certain combinations, and accordingly, can be easily substituted with different chemicals that have similar properties but are compatible in the relevant mixture.

Protein Agents

A therapeutic protein agents is the pharmaceutically active substance of a protein agent formulation.

In some embodiments, a protein agent may include recombinant proteins, isolated or synthetic proteins, cytoskeletal proteins, extracellular matrix proteins, plasma proteins, coagulation factors, acute phase proteins, hemoproteins, cell adhesion proteins, transmembrane transport proteins, synport/antiport proteins, hormones, growth factors, receptors, transmembrane receptors, intracellular receptors, DNA-binding proteins, transcription regulation proteins, RNA-binding proteins, immune system proteins, nutrient storage and transport proteins, chaperone proteins, enzymes, glycoproteins, phosphoproteins, membrane proteins, transport proteins, or lipoproteins, antibodies, recombinant antibodies, antibody fragments, monoclonal antibodies, modified enzymes, pegylated proteins, therapeutic proteins, storage proteins, enzymes, growth factors or hormones, immunomodifiers, anti-infectives, antiproliferatives, vaccines or other therapeutics, prophylactic, diagnostic proteins, and combinations thereof.

In some embodiments a protein agent may include antibodies, recombinant antibodies, antibody fragments, monoclonal antibodies, modified enzymes, pegylated proteins, therapeutic proteins, storage proteins, enzymes, growth factors or hormones, immunomodifiers, anti-infectives, antiproliferatives, vaccines or other therapeutics, prophylactic, diagnostic proteins, and combinations thereof.

In some embodiments, a protein agent is an antibody. Those of ordinary skill in the art are aware that, typically, an antibody as produced in nature is a glycoprotein, typically with an approximate MW of 150 kD. Generally, antibodies are produced by the humoral arm of the immune system of vertebrates in response to the presence of foreign (non-self) or self-identified as non-self-molecules in the body. Antibodies are essential for the prevention and resolution of infection by microorganisms, e.g. parasites, bacteria and viruses. Antibodies perform this function by recognizing and binding, in a highly specific manner, proteins (or, sometimes, other organic molecules including polysaccharides, glycoproteins, lipids, or nucleic acids) called antigens (or epitopes), including those presented on the surface of invading microorganisms and their products. Antibodies bind their target antigens through highly specific interactions between hypervariable domains, called antigen-binding sites, that appear on the antibody and on the epitope itself. Upon binding to the antigen, antibodies activate one or more of the many effector systems of the immune system that contribute to the potential neutralization, destruction and elimination of the infecting microorganism or other antigen-containing entity, e.g. a cancer cell.

Antibodies can also generally be used for the treatment of cancer, inflammation, cardiovascular disease, and transplant rejection, by virtue of their specific binding properties and subsequent potential neutralization of the cellular targets, which are typically involved in disease states. For example, the monoclonal antibody Infliximab binds to tumor necrosis factor and neutralizes its role in inflammation by blocking its interaction with a cell surface receptor; while Rituximab targets malignant B lymphocytes by binding to their cell surface CD20 antigen.

In some embodiments, a protein agent is an immunoglobulin. An "immunoglobulin" or "native antibody" is a tetrameric glycoprotein. In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a "variable" ("V") region of about 100 to 110 or more amino acids which are primarily responsible for antigen recognition. The carboxy-terminal portion of each chain defines an invariable region primarily responsible for effector function. The four chains are arranged in a classic "Y" model. The bottom "leg" of the "Y" is called the Fc region ("c" stands for "crystallizable" or, alternatively, "complement-binding") and is used to anchor the antibody within cell membranes, and is also used to bind macrophage cells and thus activate complementation. The two "arms" at the top of the "Y" are called Fab regions (the "ab" stands for "antigen-binding"). Each Fab region contains an invariable region (at the junction of the Fab and the Fc regions) and a variable region (which extends to the tip of the "Y" or Fc region). Each variable region contains identical antigen-binding sites (at regions within the variable regions called "hypervariable" regions) at each tip of the "Y". The term "hypervariable" region refers to amino acid residues from a complementarity-determining region or CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)). "Framework" or FR residues are the remaining variable region residues other than the hypervariable region residues. Each Fab region has one antigen-binding site, and the complete antibody molecule therefore has two antigen-binding sites (i.e., is "bivalent"). The two antigen-binding sites on a naturally occurring antibody are identical to each other, and therefore the antibody is specific for one antigen (i.e., is "monospecific").

Immunoglobulins can be assigned to different classes depending on the amino acid sequence of the invariable domain of their heavy chains. Heavy chains are classified as mu (μ), delta (Δ), gamma (γ), alpha (α), and epsilon (ε), and define the antibody's isotype as IgM, IgD, IgG, IgA, and IgE, respectively. Typically, IgG, IgE and IgD occur as monomers, while IgA can occur as not only a monomer, but also a dimer or trimer, and IgM can occur as a pentamer. Several of the above may be further divided into subclasses or isotypes, e.g. IgG1, IgG2, IgG3, IgG4, IgA1 and IgA2. Different isotypes have different effector functions; for example, IgG1 and IgG3 isotypes have antibody-dependent cellular cytotoxicity (ADCC) activities. Human light chains are classified as kappa (κ) and lambda (λ) light chains. Within light and heavy chains, the variable and invariable regions are joined by a "J" region of about 12 or more amino acids, with the heavy chain additionally encompassing a "D" region of about 10 more amino acids (See generally, Fundamental Immunology, Ch. 7 (Paul, W., ed., 2nd ed. Raven Press, N.Y. (1989)).

In some embodiments, a whole anti-idiotypic antibody is itself the immunogen. In some embodiments, a therapeutic protein elicits a response to the antigen that the anti-idiotype mimics or is closely related to. Therefore, an anti-idiotypic antibody can act as a type of vaccine or therapy against cancers and autoimmune diseases, e.g., allergies, as well as viruses, for example, hepatitis B virus.

In some embodiments, a protein agent is an antibody fragment. A number of molecular fragments of antibody molecules have been isolated to date. These do not occur naturally, but are engineered from one or more complete antibody molecules. These fragments include Fab fragments (a single Fab that is isolated from a complete antibody by digestion with the enzyme papain), and F(ab')2 fragments (two Fabs covalently-bound to each other, produced by digesting the antibody with the enzyme pepsin). Fab fragments are monospecific, while F(ab')2 fragments are bispecific. Recently, a number of engineered antibody fragments have been introduced. These include double-stranded Fv (dsFv) fragments and single-chain Fv (scFv) fragments (the "v" stands for "variable" in both cases). A dsFv fragment consists of a Fab fragment minus the constant regions, i.e., consisting only of the variable regions of a heavy and light chain covalently bound to each other. A scFv fragment is a single polypeptide chain, consisting of the variable region of a heavy chain linked via a peptide linker to the variable region of a light chain. Classically, both dsFv and scFv fragments are monovalent (and thus mono-specific). However, two dsFv fragments or two scFv fragments can themselves be linked to form a bispecific fragment (which would be analogous to a F(ab')2 fragment without the constant regions). Furthermore, it is possible to link two dsFv fragments or scFv fragments with different antigen-binding sites (i.e., different specificities), to form a bi-specific fragment. Such fragments may be used as either research tools or therapeutic or diagnostic reagents.

In some embodiments, a protein agent is an antibody that can be monoclonal (mAb) or polyclonal. Two particular types of antibody preparations, monoclonal and polyclonal, can be distinguished by their specificities: polyclonal antibodies and monoclonal antibodies. Polyclonal antibodies are found in the immunoglobulin fraction of blood, and are essentially a polyclonal mixture of many different types of antibodies specific for different antigens an individual has been exposed to (i.e., they originate from many different clones of B lymphocytes (or B cells).

Monoclonal antibodies are antibodies of a single specificity, i.e., that are derived from a single clone of B lymphocytes (B cells). These antibodies generally have exquisite specificity for their target antigens and can also typically be produced in high amounts (i.e., high titres). They are useful as markers for specific antigens (e.g., cancer antigens), as diagnostic agents (e.g., in assays to detect viruses like HIV-1), and as therapeutic agents. Whole monoclonal antibodies are those that have a classic molecular structure that includes two complete heavy chains and two complete light chains. This is distinguished from antibody fragments, such as Fab, F(ab')2, Fc fragments, dsFv fragments, and scFv fragments.

Traditionally, monoclonal antibodies have been produced by fusing an antibody-producing B cell with an immortal hybridoma cell to generate B cell hybridomas, which continually produce monoclonal antibodies in cell culture. Another method that is traditionally used to generate monoclonal antibodies involves the expression of monoclonal antibodies in a bacterial cell culture using phage-display technology. Currently, however, monoclonal antibodies may be produced in vivo in large quantities in genetically-modified animals, such as cows and goats (Genzyme Transgenics), pigs and rabbits (Medarex, PPL Therapeutics), chickens (Tranxenogen), and in plants, such as tobacco and corn (Epicyte, Integrated Protein Technologies, Meristem Croptech, and others). For example, large amounts of monoclonal antibodies can be found in the milk of genetically-modified goats (Genzyme Transgenics). Furthermore, as a result of transgenics, mice have been modified to contain and express the entire human B cell genome (which encodes human antibodies). Therefore, such transgenic mice (Abgenix) are a source of human antibodies according to this invention. It should be noted that glycosylation is specific to the animal that is producing the antibodies. For example, human antibodies from sources other than humans will have subtly different glycosylation profiles. Therefore, whole antibodies or single-chain Fv antibody fragments or Fab antibody fragments described in this invention may display modified glycosylation patterns or be deglycosylated, depending on the source of isolation. Antibodies, according to the context of this invention, may also include derivatized antibodies. Such antibodies include those derivatized with polyethylene glycol, or at least one carbohydrate moiety, or least one methyl or ethyl group. Clinically relevant antibodies may also be classified according to the therapeutic area in which they are to be employed. In some embodiments, a clinical antibody employed for therapeutic use may include those for treating cancers (e.g., pancreatic cancer), inflammatory diseases (e.g., autoimmune diseases, arthritis), cardiovascular diseases (e.g., strokes), infectious disease (e.g., HIV/AIDS), respiratory diseases (e.g., asthma), tissue transplantation rejection and organ transplantation rejection. In some embodiments, a clinical antibody is employed for radioimmunotherapy. In some embodiments, an antibody can include Abciximab, Palivizumab, Murumonab-CD3, Gemtuzumab, Trastuzumab, Basiliximab, Daclizumab, Etanercept, Ibritumomab Tiuxetan, or combinations thereof.

In some embodiments, a protein agent may be a chimeric antibody. Though naturally occurring antibodies are derived from a single species, engineered antibodies and antibody fragments may be derived from more than one species of animal, i.e., may be chimeric. Mouse (murine)/human chimeric antibodies have been generated, though other combinations are possible. Chimeric antibodies have been further broken down into two subtypes: chimeric and humanized. Chimeric murine/human antibodies typically contain approximately 75% human and 25% mouse amino acid sequences, respectively. The human sequences represent invariable regions of an antibody while the mouse sequences represent variable regions (and thus contain the antigen-binding sites) of an antibody. The general rationale for using such chimeras is to retain antigen specificity of a mouse antibody but reduce the immunogenicity of a mouse antibody (a murine antibody would cause an immune response against it in species other than the mouse) and thus be able to employ a chimera in human therapies. Chimeric antibodies also include those which comprise CDR regions from different human antibodies. CDR regions, also called hypervariable regions, are sequences within variable regions of antibody molecules that generate antigen-binding sites. CDR regions are so-named because the binding site is complementary in shape and charge distribution to the epitope recognized on an antigen. Alternatively, chimeric antibodies comprise framework regions from one antibody and CDR regions from another antibody. Chimeric antibodies also include those which comprise CDR regions from at least two different human antibodies. Humanized antibodies typically contain approximately 90% (or more) human amino acid sequences. In this scenario, the only murine sequences present are those for a hypervariable region (that are the actual antigen-binding sites contained within a variable region). Humanized antibodies have minimal mouse immunogenicity as compared with chimeric antibodies.

In some embodiments, an antibody comprises amino acid sequences obtained by expressing cDNA encoding the heavy and/or light chain, or alternatively the heavy and/or light chain variable region of an antibody in mammalian host cells. The term "antibody" refers to an intact immunoglobulin, e.g. in the case of IgG, a tetrameric immunoglobulin composed of two heavy chains and two light chains (e.g., chimeric, humanized, or human versions preferably with full length heavy and/or light chains, and optionally with mutations within the framework or constant regions that retain the antigen binding properties).

In some embodiments, proteins and non-protein agents may be conjugated to antibodies by methods that are known in the art. Conjugation methods include direct linkage, linkage via covalently attached linkers, and specific binding pair members (e.g., avidin-biotin). Exemplary methods are described by Greenfield et al., Cancer Research 50, 6600-6607 (1990) for the conjugation of doxorubicin, and by Arnon et al., Adv. Exp. Med. Biol. 303, 79-90 (1991) and by Kiseleva et al., Mol. Biol. (USSR) 25, 508-514 (1991) for the conjugation of platinum compounds.

In some embodiments, a protein agent is a biosimilar mAb. A biosimilar mAb is generally similar to the reference mAb either physiochemically or biologically, both in terms of safety and efficacy. The biosimilar mAb can be evaluated against a reference mAb using one or more in vitro studies including assays detailing binding to target antigen(s); binding to isoforms of the Fc gamma receptors (FcγRI, FcγRII, and FcγRIII), FcRn, and complement (C1q); Fab-associated functions (e.g. neutralization of a soluble ligand, receptor activation or blockade); or Fc-associated functions (e.g. antibody-dependent cell-mediated cytotoxicity, complement-dependent cytotoxicity, complement activation). In vitro comparisons may be combined with in vivo data demonstrating similarity of pharmacokinetics, pharmacodynamics, and/or safety. Clinical evaluations of a biosimilar mAb against a reference mAb can include comparisons of pharmacokinetic properties (e.g. AUC0-inf, AUC0-t, Cmax, tmax, Ctrough); pharmacodynamic endpoints; or similarity of clinical efficacy (e.g. using randomized, parallel group comparative clinical trials). The quality comparison between a biosimilar mAb and a reference mAb can be evaluated using established procedures, including those described in the "Guideline on similar biological medicinal products containing biotechnology-derived proteins as active substance: Quality issues" (EMEA/CHMP/BWP/49348/2005), and the "Guideline on development, production, characterization and specifications for monoclonal antibodies and related substances" (EMEA/CHMP/BWP/157653/2007).

Differences between a biosimilar mAb and a reference mAb can include post-translational modification, e.g. by attaching to the mAb other biochemical groups such as a phosphate, various lipids and carbohydrates; by proteolytic cleavage following translation; by changing the chemical nature of an amino acid (e.g., formylation); or by many other mechanisms. Other post-translational modifications can be a consequence of manufacturing process operations—for example, glycation may occur with exposure of the product to reducing sugars. In other cases, storage conditions may be permissive for certain degradation pathways such as oxidation, deamidation, or aggregation.

In some embodiments, a protein agent is an antibody. In some embodiments, a protein agent is a monoclonal antibody (mAb). In some embodiments, a protein agent has a molecular weight that may be, for example, at least about 25 kDa, 50 kDa, 100 kDa, 150 kDa, 200 kDa, 250 kDa, 300 kDa, 400 kDa, 500 kDa, 1000 kDa, or greater. In some embodiments, the lower limit may be about 25 kDa, about 50 kDa, about 100 kDa, or about 150 kDa. In some embodiments, the upper limit may be about 200 kDa, about 250 kDa, about 300 kDa, about 400 kDa, about 450 kDa, about 500 kDa, or about 1000 kDa. In some embodiments, the amount may be within a range bounded by a lower limit and an upper limit, the upper limit being larger than the lower limit. In some embodiments, the range may be about 25 kDa to about 1000 kDa. In some embodiments, the range may be about 25 kDa to about 500 kDa. In some embodiments, the range may be about 50 kDa to about 1000 kDa. In some embodiments, the range may be about 50 kDa to about 500 kDa. In some embodiments, the range may be about 100 kDa to about 500 kDa. In some embodiments, the range may be about 150 kDa to about 500 kDa. In some embodiments, the range may be about 150 kDa to about 400 kDa. In some embodiments, the range may be about 150 kDa to about 300 kDa. In some embodiments, the range may be about 150 kDa to about 250 kDa. High molecular weight proteins may include those described in Baumann, Curr. Drug Meth. 7:15-21, 2006; Scolnik, mAbs 1:179-184, 2009; Beck, mAbs 3:107-110, 2011; Federici, Biologicals 41:131-147, 2013; Dimitrov, Methods Mol. Biol. 899: 1-26, 2012; Pisal et. al., J. Pharm. Sci. 99: 2557-2575, 2010; Vugmeyster, et. al., J. Biol. Chem. 3: 73-92, 2012; Leader, et. al., Nature Reviews Drug Discovery 7: 21-39, 2008; Sajid et. al., Turk. J. Biol. 39: 343-358, 2015. In some embodiments, a protein agent for use in a formulation described herein is essentially pure and essentially homogeneous (i.e., substantially free from contaminating proteins and/or irreversible aggregates thereof).

In some embodiments, a protein agent may be an antibody. In some embodiment an antibody can include anti-cytokine antibodies, anti-CD antigen antibodies (e.g. anti-CD3, -CD20 (Rituximab), anti-CD25, anti-CD52, anti-CD33, and anti-CD11a), anti-TNF-α (e.g., Infliximab), anti-rattlesnake venom, anti-ICAM (e.g., anti-ICAM-1 and anti-ICAM-3), anti-growth factor antibodies (e.g., anti-VEGF), anti-growth factor receptor antibodies (e.g., anti-HER2/neu (Trastuzumab), and anti-EGFR), anti-immunoglobulin antibodies (e.g., anti-IgE), anti-polyclonal Ab antibodies, anti-viral antibodies (e.g., anti-CMV, anti-HIV (anti-gp120), anti-HBV, anti-RSV (anti-F glycoprotein)), anti-complement antibodies (e.g., anti-C5), anti-clotting factor antibodies (e.g., anti-gpIIb/IIIa and anti-Factor VII), anti-interleukin antibodies (e.g., anti-IL-5, anti-IL-4, and anti-IL-8), antibodies targeted to the Major Histocompatability Complex (e.g., anti-HLA), anti-idiotypic antibodies, anti-integrin antibodies (e.g., anti-β-2-integrin), anti-17-IA cell surface antigen, anti-α4β7, anti-VLA-4, anti-CBL, and combinations thereof.

In some embodiments, a protein agent is an antibody fragment. In some embodiments, and antibody fragments can include inter alia, Fv, and Fab antibody fragments of whole antibodies herein.

In some embodiments, a protein agent is a monoclonal antibody. In some embodiments, a monoclonal antibody can include Idarucizumab (Praxbind®), Raxibacumab (AB-THRAX®), Atezolizumab (TECENTRIQ®, RG7446 (Roche)), Ofatumumab (Arzerra®), Obinutuzumab (GAZYVA®, GA101 (Roche)), Bezlotoxumab (ZINPLAVA™), Necitumumab (Portrazza™), Obiltoxaximab (ANTHIM®), Olaratumab (Lartruvo™), Rituximab (RITUXAN®, ABP 798 (Amgen), MabThera®, GP2013 (Novartis)), Tositumomab (Bexxar®), Trastuzumab (HERCEPTIN®, ABP 980 (Amgen), HERTRAZ™, CANMAB™), Pertuzumab (PERJETA®, RG1273 (Roche)), Tocilizumab (ACTEMRA®), Bevacizumab (AVASTIN®, ABP 215 (Amgen)), Daratumumab (Darzalex®), Elotuzumab (EMPLICITI™), Siltuximab (SYLVANT™), Panitumumab (Vectibix®), Vedolizumab (Entyvio®), Eculizumab (Soliris®), Natalizumab (TYSABRI®), Cetuximab (ERBITUX®), Ipilimumab (YERVOY®), Reslizumab (CINQAIR®), Pembrolizumab (KEYTRUDA®), Nivolumab (OPDIVO®), Infliximab (REMICADE®, ABP 710 (Amgen), FLIXABI®), Abciximab (ReoPro®), Evolocumab (Repatha®), Secukinumab (Cosentyx®), Certolizumab pegol (Cimzia®), Ixekizumab (TALTZ™), Omalizumab (Xolair®), Canakinumab (Ilaris®), Alirocumab (Praluent®), Daclizumab (ZINBRYTA™, ZENAPAX®), Denosumab (XGEVA®), Denosumab (Prolia®), Mepolizumab (Nucala), Ustekinumab (Stelara®), Golimumab (Simponi®), Adalimumab (HUMIRA®, ABP501 (Amgen), GP2017 (Novartis)), Ramucirumab (CYRAMZA®), Ranibizumab (LUCENTIS®, RG3645 (Roche & Novartis)), Efalizumab (Raptiva®), Palivizumab (Synagis®), Ado-trastuzumab emtansine (KADCYLA™), Alemtuzumab (Campath®), Alemtuzumab (LEMTRADA™), Basiliximab (Simulect®), Belimumab (Benlysta®), Blinatumomab (BLINCYTO®), Brentuximab vedotin (Adcetris), Capromab pendetide (ProstaScint®), Dinutuximab (Unituxin), Elotuzumab (EMPLICITI™), Gemtuzumab ozogamicin (Mylotarg), Ibritumomab tiuxetan (Zevalin®), Itolizumab (Alzumab™), Muromonab (Orthoclone OKT3®), Nimotuzumab (Theracim®), Nofetumomab (Verluma®), and biosimilars and in combinations thereof.

Many protein agent therapeutics currently on the market, including antibodies as defined herein, have high dosing requirements and are typically administered via IV infusions. In some embodiments, formulations can include one of the protein agent therapeutics currently on the market or a biosimilar thereof, or combinations thereof. Although some protein agent therapeutics are not of high-molecular-weight, they are administered via IV infusion because of high dosage requirements for therapeutic efficacy. In some embodiments, formulations are provided of low-molecular-weight proteins, as defined herein, with concentrations that can deliver therapeutically effective amounts when injected either by SC or IM injections.

In some embodiments, a protein agent can include an enzyme, a fusion protein, a stealth or pegylated protein, a vaccine, a chemically modified protein, an antibody-drug conjugate, a protein-drug conjugate, a biologically active protein (or protein mixture), and combinations thereof. The term "enzyme," as used herein, refers to the protein or functional fragment thereof that catalyzes a biochemical transformation of a target molecule to a desired product.

Examples 29 through 37 describe particular other potential therapeutic protein agents that may be included herein.

Liquid Media

A buffering agent, acts to maintain the pH of a pharmaceutical formulation in a desired range. When the pH of a pharmaceutical composition is set at or near physiological levels, comfort of the patient upon administration can be maximized. In some embodiments, a buffering agent may maintain the pH of a pharmaceutical composition at a pH that may be, for example, at least about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0 or higher. In some embodiments, the pH may be within a range bounded by a lower limit and an upper limit, the upper limit being larger than the lower limit. In some embodiments, the lower limit may be about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In some embodiments, the upper limit may be about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10.0. In some embodiments, the range may be about 3.0 to about 10.0. In some embodiments, the range may be about 4.0 to about 10.0. In some embodiments, the range may be about 4.0 to about 10.0. In some embodiments, the range may be about 5.0 to about 10.0. In some embodiments, the range may be about 5.0 to 8.0. In some embodiments, the range may be about 5.8 to 7.4. In some embodiments, the range may be about 6.2 to 7.0.

In some embodiments, a pH level can be adjusted as necessary to maximize stability and solubility of a protein agent in a formulation and as such, a pH outside of physiological range yet tolerable to the patient is within the scope of the invention. In some embodiments, pH-adjusting agents such as hydrochloric acid, sodium hydroxide, or a salt thereof, may also be included in a protein agent formulation in order to obtain a desired pH of a protein agent formulation.

In some embodiments, a buffer suitable for use in a pharmaceutical formulation of the invention can include histidine, alkali salts (e.g. sodium or potassium phosphate or their hydrogen or dihydrogen salts), sodium citrate/citric acid, sodium acetate/acetic acid, potassium citrate, maleic acid, ammonium acetate, tris-(hydroxymethyl)-aminomethane (TRIS), various forms of acetate and diethanolamine, ammonium carbonate, ammonium phosphate, boric acid, lactic acid, phosphoric acid, potassium metaphosphate, potassium phosphate monobasic, sodium lactate solution, and combinations thereof. In some embodiments, a suitable buffer for maintaining a pharmaceutical formulation at or near pH 6.2 is sodium phosphate. In some embodiments, acetate can be a more efficient buffer at pH 5 than pH 6, so less acetate may be used in a solution at pH 5 than at pH 6. In some embodiments, a buffering agent may be added to a protein agent formulation at a concentration that may be, for example, at least about 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 1 mM, about 10 mM, about 15 mM, about 25 mM, or about 50 mM. In some embodiments, the upper limit may be about 75 mM, about 100 mM, about 150 mM, about 200 mM, about 300 mM, about 400 mM, about 500 mM, about 600 mM, about 700 mM, about 800 mM, about 900 mM, or about 1000 mM. In some embodiments, the range may be about 1 mM to about 1000 mM. In some embodiments, the range may be about 10 mM to about 300 mM. In some embodiments the range may be about 10 mM to about 100 mM. In some embodiments the range may be about 15 mM to about 75 mM. In some embodiments, the range may be about 15 mM to about 25 mM.

Viscosity-Reducing Agents

In some embodiments, a viscosity-reducing agent is a combination of one or more compounds or agents described herein as a viscosity-reducing agent and/or that would be appreciated by those of ordinary skill in the art as being a close chemical relative of (i.e., as sharing significant structural identity with) one or more such compounds or agents, which combination (and/or close chemical relative), when included in an aqueous protein formulation as described herein, reduces viscosity, reduces aggregation, reduces surface adsorption, reduces interfacial interactions, or otherwise improves a characteristic of a formulation as described herein.

The viscosity of a liquid protein agent formulation, which includes low molecular-weight and/or high-molecular-weight protein agents, is reduced by the addition of one or more viscosity-reducing agents. A pharmaceutical formulation may be converted from non-Newtonian to Newtonian fluids by the addition of a viscosity-reducing amount of one or more viscosity-reducing agents. When employed in a formulation intended for administration to a human or other mammal, a viscosity-reducing agent, like a protein agent, must be pharmaceutically acceptable. A viscosity-reducing agent is typically an organic compound.

In some embodiments, a viscosity-reducing agent as described herein is listed as GRAS by the U.S. Food and Drug Administration ("the FDA"), as of Sep. 11, 2014. "GRAS" is an acronym for the phrase "Generally Recognized As Safe." Under sections 201(s) and 409 of the Federal Food, Drug, and Cosmetic Act (the Act), any substance that is intentionally added to food is a food additive and is subject to premarket review and approval by the FDA unless the substance is generally recognized, among qualified experts, as having been adequately shown to be safe under the conditions of its intended use, or unless the use of the substance is otherwise excluded from the definition of a food additive. In some embodiments, a viscosity-reducing agent is included in Inactive Ingredient Guide of the FDA (IIG), and equivalents listed by the International Pharmaceutical Excipients Council (IPEC) and the European Medicines Agency (EMA), as of Sep. 11, 2014. Substances used in a high concentration, low-viscosity protein agent formulation must be safe for injection.

In some embodiments, a viscosity-reducing agent is an FDA- or EMA-approved drug product as of Sep. 11, 2014. Like compounds drawn from the GRAS and IIG lists, the toxicity and safety profiles of FDA- and EMA-approved drug products are well established. In addition to lowering the viscosity of a protein agent formulation, the use of an FDA- or EMA-approved drug product provides an opportunity for combination therapies.

In some embodiments, a viscosity-reducing agent is or comprises one or more of nicotinic acid (acid form), nicotinamide (niacinamide), nicotinic acid sodium salt, benzyl nicotinate, inositol hexanicotinate, nicotinyl alcohol (β-pyridyl carbinol), xanthine nicotinate, methyl nicotinate, ethyl nicotinate, propyl nicotinate, isopropyl nicotinate, butyl nicotinate, isoamyl nicotinate, hexyl nicotinate, phenyl nicotinate, gauiacyl nicotinate, xanthinol nicotinate, nicametate citrate, nicotinuric acid, nicotinyl hydroxamate, tocopheryl nicotinate, trigonelline, nicotinoyl-dl-α-alanine, nicotinoyl-L-alanine, nicotinoyl-dl-valine, nicotinoyl-L-leucine, and nicotinoyl-dl-phenylalanine, ethionamide, niceritrol, nicofuranose, 4-aminopyridine, Piperocaine, N-ethylpiperidine, caffeine nicotinate, and combinations thereof.

In some embodiments, a viscosity-reducing agent is or comprises one or more of caffeine, caffeine citrate, caffeine nicotinate, caffeine haematin, ethoxycaffeine, methoxy caffeine, 7-Benzyltheophylline, theophylline, paraxanthine, theobromine, 7-[(4-methoxyphenyl) methyl]-1,3-dimethyl-2,3,6,7-tetrahydro-1H-purine-2,6-dione, 1,3-dimethyl-7-[(4-methylphenyl) methyl]-2,3,6,7-tetrahydro-1H-purine-2,6-dione, 7-[(4-chlorophenyl) methyl]-1,3-dimethyl-2,3,6,7-tetrahydro-1H-purine-2,6-dione, 7-[(3,5-dimethylphenyl) methyl]-1,3-dimethyl-2,3,6,7-tetrahydro-1H-purine-2,6-dione, 7-benzyl-1,3-dimethyl-2,3,6,7-tetrahydro-1H-purine-2,6-dione, 1,3-dimethyl-7-{[4-(propan-2-yl)phenyl]methyl}-2,3,6,7-tetrahydro-1H-purine-2,6-dione, 1,3-dimethyl-7-[(2-methylphenyl) methyl]-2,3,6,7-tetrahydro-1H-purine-2,6-dione, 4-[(1,3-dimethyl-2,6-dioxo-2,3,6,7-tetrahydro-1H-purin-7-yl)methyl]benzonitrile, 7-[(4-bromophenyl)methyl]-1,3-dimethyl-2,3,6,7-tetrahydro-1H-purine-2,6-dione, Methyl 4-[(1,3-dimethyl-2,6-dioxo-2,3,6,7-tetra hydro-1H-purin-7-yl)methyl]benzoate, 1,3-dimethyl-7-{[4-(trifluoromethyl)phenyl]methyl}-2,3,6,7-tetrahydro-1H-purine-2,6-dione, 1,3-dimethyl-7-{[4-(methylthio)phenyl]methyl}-2,3,6,7-tetra hydro-1H-purine-2,6-dione, 7-[(3-bromophenyl)methyl]-1,3-dimethyl-2,3,6,7-tetra-hydro-1H-purine-2,6-dione, 7-(cyclohexylmethyl)-1,3-dimethyl-2,3,6,7-tetrahydro-1H-purine-2,6-dione; 1,3-dimethyl-7-[(4-nitrophenyl)methyl]-2,3,6,7-tetrahydro-1H-purine-2,6-dione, 1,3-dimethyl-7-[(3-nitrophenyl) methyl]-2,3,6,7-tetrahydro-1H-purine-2,6-dione, 1,3-dimethyl-7-(1-phenylethyl)-2,3,6,9-tetra hydro-1H-purine-2,6-dione. Thio-derivatives of caffeine such as 8-[(pyrrolidin-1-ylcarbonothioyl) sulfanyl]caffeine, 8-hydrazinocaffeine 8-chlorocaffeine, and 8-(3-butyl-4-phenyl-2,3-dihydro thiazol-2-ylidene) hydrazino-3,7-dihydro-1,3,7-trimethyl-1H-purine-2,6-dione, and combinations thereof.

In some embodiments, a viscosity-reducing agent is or comprises one or more of salicylic acid and its salts both organic and inorganic, Phenyl acetic acid, 2-amino-cyclohexane-carboxylic acid, 1-aminocyclohexane carboxylic acid, Gentisic acid, Acetyl salicylic acid, Pthalic acid, Anthrallic acid, Tetracaine, Proxymetacaine, Metoclopramide, Procaine, Chloroprocaine, Benzocaine, Octisalate, Propylparaben, Thimerosal, Vanillin, Cyclomethylcaine, Mandelic acid, Metoclopramide, and combinations thereof.

In some embodiments, a viscosity-reducing is or comprises one or more of a water-soluable vitamin group including L-Pantothenic Acid hemicalcium salt, L-ascorbic acid, Thiamine-HCl, Rutin Hydrate, Riboflavin, Folic Acid, pyridoxine, Biotin, Pantoic acid, S-benzoylthiamine, Pyridoxal, Pyridoxamine, Niacin, and combinations thereof.

In some embodiments, a viscosity-reducing agent is or comprises one or more of L-Histidine, L-Lysine, L-Arginine, L-2-Amino-3-guanidinopropionic acid hydrochloride, 4-Guanidinobutyric acid, L-Homoarginine·HCl, Aspartame, Glycine, L-Alanine, Proline, trans-4-Hydroxy-L-Proline, L-Valine, L-Leucine, L-Isoleucine, L-Methionine, L-Serine, Tyramine HCl, Histamine, Imidazole, L-phenyl alanine, Tyrosine, Tryptophan, Threonine, L-Glutamic acid, L-Aspartic Acid, L-Valine, 5-fluoro-L-tryptophan, 5-Fluro-DL-Tryptophan, 5-hydroxy-L-tryptophan, 5-methoxy-DL-tryptophan, Tryptamine, Argyrin A and B, Granisetron, Selenomethionine, Carnithine, Asparagine, and Glutamine. arginine-HCl, arginine succinate, arginine dipeptide, arginine tripeptide, polyarginine, homoarginine, 2-amino-3-guanidino-propionic acid, guanidine, ornithine, agmatine, guanidobutyric acid, urea, citrulline, N-hydroxy-L-nor-arginine, nitroarginine methyl ester, argininamide, arginine methyl ester, arginine ethyl ester, lysinamide, lysine methyl ester, histidine methyl ester, alaninamide, alanine methyl ester, putrescine, cadaverine, spermidine, spermine, and combinations thereof.

In some embodiments, a viscosity-reducing agent is or comprises one or more of Adenine, Guanine, Cytosine, Uracil, Thymine, Adenosine, Guanosine, Cytidine, Uridine, Inosine, Thymidine, Caffeine, Caffeine citrate, Xanthine, Hypoxanthine, 2'-deoxycytidine, 2'-deoxyuridine, Orotic acid, ribothymidine, 1-methyl xanthine, 7-methyl xanthine, 3-methyl xanthine, and combinations thereof.

In some embodiments, a viscosity-reducing agent is or comprises one or more of D-Sucrose, D-(+)-Trehalose dehydrate, D-(−)-Fructose, D-Mannitol, L-(+)-Arabinose, D-Sorbitol, Lactose, Maltose, D-Ribose, D-Galactose, Glucosamine, Hydroxyalkyl starch, Hyaluronic acid, Pullulane, Chitosan, Dextran, Dextran sulfate, starch, Chondroitin sulfate, carboxymethyl dextran, hydroxyethyl starch, and combinations thereof.

In some embodiments, a viscosity-reducing agent is or comprises one or more of 2-aminopyrimidine, Sodium acetate, Pyruvate sodium salt, Potassium acetate, α-Ketoglutarate, Oxaloacetic acid, Fumaric acid, DL-Malic Acid, Methyl acetoacetate, DL-Isocitric acid trisodium salt, Succinic acid, Procaine·HCl, Creatinine, Thiazole, Citric Acid, 3-pyridine sulfonic acid, Ethylenediaminetetraacetic acid (EDTA), Ethanolamine, di-ethanolamine, tri-ethanolamine, dimethylcyclohexylamine·HCl, p-Hydroxybenzoic acid, Sodium benzoate, Malonic acid, Maleic acid, Oxalosuccinate, Pyrolline-5-carboxylic acid, Ethanol, DMSO, benzyl alcohol, 1,5-pentanediol, and combinations thereof.

In some embodiments, a viscosity-reducing agent is or comprises one or more of Sodium chloride, Ammonium chloride, Ammonium acetate, Ammonium sulphate, Calcium chloride, Sodium thiocyanate, and combinations thereof.

In some embodiments, a viscosity-reducing agent is or comprises one or more of Polysorbate 80, Polysorbate 20, n-Dodecyl β-D-maltoside, Octyl β-D-glucopyranoside, and combinations thereof.

In some embodiments, a viscosity-reducing is or comprises one or more of aspirin, calcium carrageenan, calcium cyclamate, calcobutrol, Caloxetic acid, Camphorsulfonic acid, Creatinine, dalfampridine, dehydroacetic acid, diazolidinyl urea, dichlorobenzyl alcohol, dimethyl isosorbide, epitetracycline, ethyl maltol, ethyl vanillin, ornidazole, ethanolamide, HEPES (4-(2-hydroxy ethyl)-1-piperazine ethane sulfonic acid), iodoxamic acid, menthol, medronic acid, m-cresol, glutathione, lactobionic acid, maltitol, oxyquinoline, pentetic acid, piparazine, propenyl guaethol, propylene carbonate, protamine sulfate, QUATERNIUM-15, QUATERNIUM-52, satialgine 11, Sodium 1,2-ethanedisulfonate, sodium cocoyl sarcosinate, sodium lauroyl sarcosinate, sodium polymetaphosphate, sodium pyrophosphate, pyroglutamic acid, sodium trimetaphosphate, sodium tripolyphosphate, sorbitan, tartaric acid, lactic acid, iofetamine, Sucralose, 1-(4-pyridyl)pyridinium chloride, Aminobenzoic acid, Sulfacetamide sodium, Naphthalene 2-sulfonic acid, Tert-butylhydroquinone, Trolamine, Tromantadine, Versetamide, nioxime, methylisothiazolinone, mannose, Lidofenin, Lactitol, isomalt, imidurea, gluconolactone, methanesulfonic acid, xylenesulfonic acid, sulfobutylether-β-cyclodextrin, caffeic acid, Caffeic acid phenethyl ester, Zileuton, inhibitor of leukotrienes, tropane N-heterocycles, atropine, hyoseyamine, scopolamine, tiotropium, ipratropium salts, allithiamine, prosulthiamine, fursulthiamine, benfothiamine, sulbuthiamine, 1-(3-aminopropyl)-2-methyl-1H-imidazole dihydrochloride, cimetidine, piperocaine, cyclomethylcaine, moxifloxacin, chloroquine, mepivacaine, levetriacetam, bupivacaine, cinchocaine, clindamycin, colistin, articane, tetracaine, etidocaine, cyclomethylcaine, piperocaine, phenylephrine, bupivacaine, and combinations thereof.

In some embodiments, a viscosity-reducing agent is or comprises one or more of Polyethylene glycol, branched PEG, PolyPEG®, and combinations thereof.

In some embodiments, a viscosity-reducing agent is or comprises one or more of Hydroxy Proline, Homoarginine, Proline, Arginine, Aspartame, Alanine, Glycine, Lysine, Methionine, Serine, Tryptophan, Tyramine HCl, Adenine, Guanine, Adenosine, Guanosine, Cytosine, Thymine, Thymidine, Uridine, Cytidine, Caffeine, Uracil, Caffeine citrate, caffeine nicotinate, L-Pantothenic Acid hemicalcium salt, Nicotinic acid sodium salt, Methylnicotinate, L-ascorbic acid, Thiamine HCl, Nicotinamide, Nicotinic acid (acid form), 2-aminopyrimidine, Sodium acetate, Pyruvate sodium salt, Acetyl salicylic Acid, Potassium acetate, Sodium Chloride, Ammonium Chloride, Ethanol, DMSO, and combinations thereof.

In some embodiments, a viscosity-reducing agent includes at least one carboxylic acid. In some embodiments, a carboxylic acid may be in the form of an alkaline or alkaline earth metal salt, such as lithium, sodium, potassium, magnesium, and calcium salt. In some embodiments, a viscosity-reducing agent may include lactobionic acid, glucuronic acid, 1-aminocyclohexane carboxylic acid, biotin, brocrinat, cyclopentane propionic acid, hydroxynaphthoic acid, phenylpropionic acid, gentisic acid, salicylic acid, camphoric acid, mandelic acid, sulfosalicyclic acid, hydroxybenzoyl benzoic acid, phenyl acetic acid, acetyl salicylic acid, cinnamic acid, t-butyl acetic acid, phthalic acid, trimethylacetic acid, anthrallic acid (and pharmaceutically acceptable salts), and combinations thereof. In some embodiments, a carboxylic acid (or salt thereof) may be combined with one or more compounds of Formula (2) or Formula (3).

In some embodiments, a viscosity-reducing agent is or comprises one or more of an organic base. In some embodiments, a viscosity-reducing agent is or comprises one or more of N-methylglucamine, morpholine, piperidine, and primary, secondary, tertiary, and quaternary amines, substituted amines, cyclic amines, and combinations thereof. In some embodiments, a viscosity-reducing agent is or comprises one or more of isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, lidocaine, hydrabamine, cholines, betaines, choline, betaine, ethylenediamine, theobromine, purines, piperazine, N-ethylpiperidine, N-methylpiperidinepolyamine. Particularly preferred organic bases are arginine, histidine, lysine, ethanolamine, thiamine, 2-amino-2-hydroxymethyl-propane-1,3-diol (TRIS), 4-aminopyridine, aminocyclohexane carboxylic acid, 1-o-tolybiguanide, ornidazole, urea, nictoinamide, benzethonium chloride, 5-amino-1-pentanol, 2-(2-aminoethoxy)ethanol, trans-cyclohexane-1,4-diamine, trans-cyclohexane-1R,2R-diamine, ethylenediamine, propane-1,3-diamine, butane-1,4-diamine, pentane-1,5-diamine, hexane-1,6-diamine, octane-1,8-diamine, 5-amino-1-pentanol, 2-(2-aminoethoxy)ethanamine, 2-(2-(2-aminoethoxy)-ethoxy)ethanamine, 3-(4-(3-aminopropoxy)-butoxy)propan-1-amine, 3-(2-(2-(3-aminopropoxy)-ethoxy)-ethoxy)propan-1-amine, N-(2-(2-aminoethylamino)ethyl)ethane-1,2-diamine, N-(2-aminoethyl)ethane-1,2-diamine, N-1-(2-(2-(2-aminoethylamino)ethylamino)-ethyl)ethane-1,2-diamine, N,N-dimethylhexane-1,6-diamine, N,N,N,N-tetramethylbutane-1,4-diamine, phenyltrimethylammonium salts, isopropylamine, diethylamine, ethanolamine, trimethamine, choline, 1-(3-aminopropyl)-2-methyl-1H-imidazole, piperazine, 1-(2-aminoethyl)piperazine, 1-[3-(dimethylamino)propyl]piperazine, 1-(2-aminoethyl)piperidine, 2-(2-aminoethyl-1-methylpyrrolidine, mixtures thereof, pharmaceutically acceptable salts, and combinations thereof.

In some embodiments, a viscosity-reducing agent can include at least one compound of the structure of Formula (I) or pharmaceutically acceptable salts thereof. In some embodiments, a viscosity-reducing agent can include at least one compound of the structure of Formula (2) or pharmaceutically acceptable salts thereof. In some embodiments, a viscosity-reducing agent can include at least one compound of the structure of Formula (3) or pharmaceutically acceptable salts thereof. In some embodiments, a viscosity-reducing agent can include at least one compound of the structure of Formula (4) or pharmaceutically acceptable salts thereof. In some embodiments, in formulas 1 through 4, R is selected from the group consisting of: hydrogen, =O, —OH, NH$_2$, —F, —Cl, —Br, —I, —NO$_2$, —CN, —C(=O)R, —C(=NR)R, —C(=O)OH, —C(=O)OR, —OC(=O)R, —OC(=O)OR, —SO$_3$H, —SO$_2$N(R)$_2$, —SO$_2$R, —SO$_2$NRC(=O)R, —PO$_3$H$_2$, —RC(=NR)N(R)$_2$, —NHC(=NR)NH—CN, —NRC(=O)R, —NRSO$_2$R, —NRC(=NR)NRC(=NR)N(R)$_2$, —NRC(=O)N(R)$_2$, —C(=O)NH$_2$, —C(=O)N(R)$_2$, —SR, —N(R)$_2$, R1, R2, R3, R4 and R5; wherein R1 is C$_{1-12}$ alkyl, R2 C$_{3-12}$ cycloalkyl, R3 C$_{6-12}$ aryl, R4 C$_{6-12}$ heteroaryl and R5 is C$_{2-12}$ heterocyclyl; wherein each R1, R2, R3. R4 and R5 may be substituted one or more times with R; wherein any two or more of R1, R2, R3, R4 and R5 groups may together form a ring; wherein when two R groups are bonded to the same carbon atom, the two R groups may together form an (=O), (=NR), or (=C(R)$_2$), and combinations thereof. In some embodiments, a viscosity-reducing agent is a mixture of two or more compounds selected from compounds of Formula (1), Formula (2), Formula (3) and Formula (4).

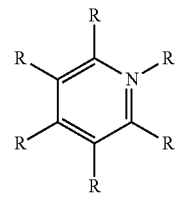

Formula 1

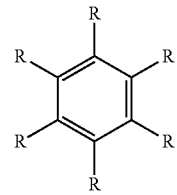

Formula 2

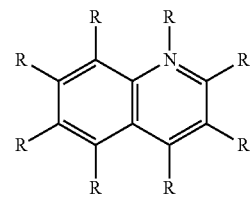

Formula 3

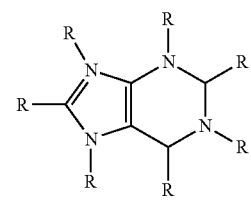

Formula 4

In some embodiments, a viscosity-reducing agent can contain acidic or basic functional groups. Whether or not these functional groups are fully or partially ionized depends on the pH of the formulations they are in. Unless otherwise specified, reference to formulations containing a viscosity-reducing agent with an ionizable functional group includes both the parent compound and any possible ionized states.

In some embodiments, a viscosity-reducing agent is selected from a first set of viscosity-reducing agents, which first set includes each of Nicotinic acid (acid form), Nicotinamide, Nicotinic Acid Sodium Salt, Caffeine, Caffeine Citrate, Caffeine Nicotinate, Uridine, Acetyl Salicylic Acid, Aspirin, Ascorbic Acid, Thiamine-HCl, Pantothenic Acid, Proline. Hydroxyproline, Homo-Arginine, Arginine, Histidine, or Tryptophan (>0.2%), Glycine, and combinations thereof.

In some embodiments, a viscosity-reducing agent is selected from a second set of viscosity-reducing agents, which second set includes each of Theophylline Nicotinate, Xanthine Nicotintate, Xanthinol Nicotinate, Creatinine, Antrallic Acid, 4-Aminocyclohexane Carboxylic Acid, Procaine, 4-Aminopyridine-2-Carboxylic Acid, Morpholine, Piperidine, Paraxanthine, Theobromine, Xanthine, Theophylline, Imidazole, or Nicotinyl Alcohol, and combinations thereof.

In some embodiments, a viscosity-reducing agent is selected from a third set of viscosity-reducing agents, which third set includes each of Nicametate Citrate, Nicotinuric Acid, Ethanol, Nicotinyl Hydroxamate, Ornidazole, Piperazine, or Methylisothiazolinone, and combinations thereof.

In some embodiments, a formulation as described herein includes a plurality of viscosity-reducing agents. In some embodiments, such a plurality is or comprises two or more viscosity-reducing agents found in any of the first, second, or third sets above. In some embodiments, such a plurality is or comprises two or more viscosity-reducing agents from the first set, two or more viscosity-reducing agents from the second set, or two or more viscosity-reducing agents from the third set. In some embodiments, such a plurality comprises at least one viscosity-reducing agent from the first set and at least one viscosity-reducing agent from the second set or at least one viscosity-reducing agent from the third set.

In some embodiments, viscosity of a high concentration protein formulation can be reduced using a combination of viscosity-reducing agents. Viscosity-reducing agent combinations that can be added to a high concentration protein agent formulation can include nicotinic acid (acid form) and/or caffeine, nicotinic acid and/or caffeine citrate, nicotinic acid and/or caffeine nicotinate, or nicotinic acid and/or acetyl salicylic acid; in further combination with one or more of nicotinamide (niacinamide), nicotinic acid sodium salt, benzyl nicotinate, inositol hexanicotinate, nicotinyl alcohol (β-pyridyl carbinol), xanthine nicotinate, methyl nicotinate, ethyl nicotinate, propyl nicotinate, isopropyl nicotinate, butyl nicotinate, isoamyl nicotinate, hexyl nicotinate, phenyl nicotinate, gauiacyl nicotinate, xanthinol nicotinate, nicametate citrate, nicotinuric acid, nicotinyl hydroxamate, tocopheryl nicotinate, trigonelline, nicotinoyl-dl-α-alanine, nicotinoyl-L-alanine, nicotinoyl-dl-valine, nicotinoyl-L-leucine, and nicotinoyl-dl-phenylalanine, ethionamide, niceritrol, nicofuranose, Piperocaine, N-ethylpiperidine, Caffeine haematin, ethoxycaffeine, methoxy caffeine, 7-Benzyltheophylline, theophylline, paraxanthine, Theobromine, 7-[(4-methoxyphenyl) methyl]-1,3-dimethyl-2,3,6,7-tetrahydro-1H-purine-2,6-dione, 1,3-dimethyl-7-[(4-methylphenyl) methyl]-2,3,6,7-tetrahydro-1H-purine-2,6-dione, 7-[(4-chlorophenyl) methyl]-1,3-dimethyl-2,3,6,7-tetrahydro-1H-purine-2,6-dione, 7-[(3,5-dimethylphenyl) methyl]-1,3-dimethyl-2,3,6,7-tetrahydro-1H-purine-2,6-dione, 7-benzyl-1,3-dimethyl-2,3,6,7-tetrahydro-1H-purine-2,6-dione, 1,3-dimethyl-7-{[4-(propan-2-yl)phenyl] methyl}-2,3,6,7-tetrahydro-1H-purine-2,6-dione, 1,3-dimethyl-7-[(2-methylphenyl) methyl]-2,3,6,7-tetrahydro-1H-purine-2,6-dione, 4-[(1,3-dimethyl-2,6-dioxo-2,3,6,7-tetrahydro-1H-purin-7-yl)methyl]benzonitrile, 7-[(4-bromophenyl)methyl]-1,3-dimethyl-2,3,6,7-tetrahydro-1H-purine-2,6-dione, Methyl 4-[(1,3-dimethyl-2,6-dioxo-2,3,6,7-tetra hydro-1H-purin-7-yl)methyl]benzoate, 1,3-dimethyl-7-{[4-(trifluoromethyl)phenyl]methyl}-2,3,6,7-tetrahydro-1H-purine-2,6-dione, 1,3-dimethyl-7-{[4-(methylthio) phenyl]methyl}-2,3,6,7-tetra hydro-1H-purine-2,6-dione, 7-[(3-bromophenyl)methyl]-1,3-dimethyl-2,3,6,7-tetrahydro-1H-purine-2,6-dione, 7-(cyclohexylmethyl)-1,3-dimethyl-2,3,6,7-tetrahydro-1H-purine-2,6-dione; 1,3-dimethyl-7-[(4-nitrophenyl)methyl]-2,3,6,7-tetrahydro-1H-purine-2,6-dione, 1,3-dimethyl-7-[(3-nitrophenyl) methyl]-2,3,6,7-tetrahydro-1H-purine-2,6-dione, 1,3-dimethyl-7-(1-phenylethyl)-2,3,6,9-tetra hydro-1H-purine-2,6-dione, 8-[(pyrrolidin-1-ylcarbonothioyl) sulfanyl]caffeine, 8-hydrazinocaffeine 8-chlorocaffeine, and 8-(3-butyl-4-phenyl-2,3-dihydro thiazol-2-ylidene) hydrazino-3,7-dihydro-1,3,7-trimethyl-1H-purine-2,6-dione, Salicylic acid, Phenyl acetic acid, 2-amino-cyclohexane-carboxylic acid, Gentisic acid, Pthalic acid, Anthrallic acid, Tetracaine, Proxymetacaine, Metoclopramide, Procaine, Chloroprocaine, Benzocaine, Octisalate, Propylparaben, Thimerosal, Vanillin, Cyclomethylcaine, Mandelic acid, Metoclopramide, L-Pantothenic Acid hemicalcium salt, L-ascorbic acid, Thiamine·HCl, Rutin Hydrate, Riboflavin, Folic Acid, pyridoxine, Biotin, Pantoic acid, S-benzoylthiamine, Pyridoxal, Pyridoxamine, L-Histidine, L-Lysine, L-Arginine, L-2-Amino-3-guanidinopropionic acid hydrochloride, 4-Guanidinobutyric acid, L-Homoarginine·HCl, Aspartame, Glycine, L-Alanine, Proline, trans-4-Hydroxy-L-Proline, L-Valine, L-Leucine, L-Isoleucine, L-Methionine, L-Serine, Tyramine HCl, Histamine, Imidazole, L-phenyl alanine, Tyrosine, Tryptophan, Threonine, L-Glutamic acid, L-Aspartic Acid, L-Valine, 5-fluoro-L-tryptophan, 5-Fluro-DL-Tryptophan, 5-hydroxy-L-tryptophan, 5-methoxy-DL-tryptophan, Tryptamine, Argyrin A and B, Granisetron, Selenomethionine, Carnithine, Asparagine, and Glutamine. arginine-HCl, arginine succinate, arginine dipeptide, arginine tripeptide, polyarginine, 2-amino-3-guanidino-propionic acid, guanidine, ornithine, agmatine, guanidobutyric acid, citrulline, N-hydroxy-L-norarginine, nitroarginine methyl ester, argininamide, arginine methyl ester, arginine ethyl ester, lysinamide, lysine methyl ester, histidine methyl ester, alaninamide, alanine methyl ester, putrescine, cadaverine, spermidine, and spermine, Adenine, Guanine, Cytosine, Uracil, Thymine, Adenosine, Guanosine, Cytidine, Uridine, Inosine, Thymidine, Xanthine, Hypoxanthine, 2'-deoxycytidine, 2'-deoxyuridine, Orotic acid, ribothymidine, 1-methyl xanthine, 7-methyl xanthine, and 3-methyl xanthine, D-Sucrose, D-(+)-Trehalose dehydrate, D-(−)-Fructose, D-Mannitol, L-(+)-Arabinose, D-Sorbitol, Lactose, Maltose, D-Ribose, D-Galactose, Glucosamine, Hydroxyalkyl starch, Hyaluronic acid, Pullulane, Chitosan, Dextran, Dextran sulfate, starch, Chondroitin sulfate, carboxymethyl dextran, and hydroxylethyl starch, 2-aminopyrimidine, Sodium acetate, Pyruvate sodium salt, Potassium acetate, α-Ketoglutarate, Oxaloacetic acid, Fumaric acid, DL-Malic Acid, Methyl acetoacetate, DL-Isocitric acid trisodium salt, Succinic acid, Procaine·HCl, Creatinine, Thiazole, Citric Acid, 3-pyridine sulfonic acid, Ethylenediaminetetraacetic acid (EDTA), Ethanolamine, di-ethanolamine, tri-ethanolamine, dimethylcyclohexylamine·HCl, p-Hydroxybenzoic acid, Sodium benzoate, Malonic acid, Maleic acid, Oxalosuccinate, Pyrolline-5-carboxylic acid, Ethanol, DMSO, benzyl alcohol, and 1,5-pentanediol, Sodium chloride, Ammonium chloride, Ammonium acetate, Ammonium sulphate, Calcium chloride, Sodium thiocyanate, Polysorbate 80, Polysorbate 20, n-Dodecyl β-D-maltoside, Octyl β-D-glucopyranoside, Aspirin, calcium carrageenan, calcium cyclamate, calcobutrol, Caloxetic acid, Camphorsulfonic acid, Creatinine, dalfampridine, dehydroacetic acid, diazolidinyl urea, dichlorobenzyl alcohol, dimethyl isosorbide, epitetracycline, ethyl maltol, ethyl vanillin, ornidazole, ethanolamide, HEPES (4-(2-hydroxy ethyl)-1-piperazine ethane sulfonic acid), iodoxamic acid, menthol, medronic acid, m-cresol, glutathione, lactobionic acid, maltitol, oxyquinoline, pentetic acid, piparazine, propenyl guaethol, propylene carbonate, protamine sulfate, QUATERNIUM-15, QUATERNIUM-52, satialgine 11, Sodium 1,2-ethanedisulfonate, sodium cocoyl sarcosinate, sodium lauroyl sarcosinate, sodium polymetaphosphate, sodium pyrophosphate, pyroglutamic acid, sodium trimetaphosphate, sodium tripolyphosphate, sorbitan, tartaric acid, lactic acid, iofetamine, Sucralose, 1-(4-pyridyl)pyridinium chloride, Aminobenzoic acid, Sulfacetamide sodium, Naphthalene 2-sulfonic acid, Tert-butylhydroquinone, Trolamine, Tromantadine, Versetamide, nioxime, methylisothiazolinone, mannose, Lidofenin, Lactitol, isomalt, imidurea, gluconolactone, methanesulfonic acid, xylenesulfonic acid, sulfobutylether-β-cyclodextrin, caffeic acid, Caffeic acid phenethyl ester, Zileuton, inhibitor of leukotrienes, tropane N-heterocycles, atropine, hyoseyamine, scopolamine, tiotropium, ipratropium salts, allithiamine, prosulthiamine, fursulthiamine, benfothiamine, sulbuthiamine, 1-(3-aminopropyl)-2-methyl-1H-imidazole dihydrochloride, cimetidine, piperocaine, cyclomethylcaine, moxifloxacin, chloroquine, mepivacaine, levetriacetam, bupivacaine, cinchocaine, clindamycin, colistin, articane, tetracaine, etidocaine, cyclomethylcaine, piperocaine, phenylephrine, and bupivacaine. Polyethylene glycol, branched PEG, and PolyPEG®, Ethanol, DMSO, lactobionic acid, glucuronic acid, biotin, brocrinat, cyclopentane propionic acid, hydroxynaphthoic acid, phenylpropionic acid, camphoric acid, mandelic acid, sulfosalicyclic acid, hydroxybenzoyl benzoic acid, cinnamic acid, t-butyl acetic acid, phthalic acid, trimethylacetic acid, N-methylglucamine, morpholine, piperidine, isopropylamine, trimethylamine, diethylamine, triethylamine, tripropylamine, 2-diethylaminoethanol, trimethamine, dicyclohexylamine, lidocaine, hydrabamine, cholines, betaines, ethylenediamine, purines, piperazine, N-methylpiperidinepolyamine, 2-amino-2-hydroxymethyl-propane-1,3-diol (TRIS), 4-aminopyridine, aminocyclohexane carboxylic acid, 1-o-tolybiguanide, urea, benzethonium chloride, 5-amino-1-pentanol, 2-(2-aminoethoxy)ethanol, trans-cyclohexane-1,4-diamine, trans-cyclohexane-1R,2R-diamine, propane-1,3-diamine, butane-1,4-diamine, pentane-1,5-diamine, hexane-1,6-diamine, octane-1,8-diamine, 2-(2-aminoethoxy)ethanamine, 2-(2-(2-aminoethoxy)-ethoxy)ethanamine, 3-(4-(3-aminopropoxy)-butoxy)propan-1-amine, 3-(2-(2-(3-aminopropoxy)-ethoxy)-ethoxy)propan-1-amine, N-(2-(2-aminoethylamino)ethyl)ethane-1,2-diamine, N-(2-aminoethyl)ethane-1,2-diamine, N-1-(2-(2-(2-aminoethylamino)ethylamino)-ethyl)ethane-1,2-diamine, N,N-dimethylhexane-1,6-diamine, N,N,N,N-tetramethylbutane-1,4-diamine, phenyltrimethylammonium salts, choline, 1-(3-aminopropyl)-2-methyl-1H-imidazole, 1-(2-aminoethyl)piperazine, 1-[3-(dimethylamino)propyl]piperazine, 1-(2-aminoethyl)piperidine, 2-(2-aminoethyl-1-methylpyrrolidine, and combinations thereof.

In some embodiments, a viscosity-reducing agent nicotinic acid can be added to a protein agent with another viscosity-reducing agent selected from the group consisting of tryptophan, Acetyl salicylic Acid, Caffeine Citrate, leucine, caffeine, arginine, glycine, proline, thiamine-HCl, aspirin, or combinations thereof.

In some embodiments, a viscosity-reducing agent thiamine-HCl can be added to a protein agent with another viscosity-reducing agent selected from the group consisting of 2-aminopyrimadine, nicotinamide, nicotinic acid sodium salt, proline, glycine, and combinations thereof.

In some embodiments, the combinations of viscosity reducing agents are nicotinic acid (acid form) and tryptophan, nicotinic acid and caffeine citrate, nicotinic acid (acid form) and acetyl salicylic acid, nicotinic acid (acid form) and caffeine, caffeine and tryptophan, tryptophan and thiamine-HCl, tryptophan and nicotinamide, tryptophan and glycine, nicotinic acid and aspirin, arginine and thiamine-HCl, proline and thiamine-HCl, tryptophan and proline, proline and nicotinamide, glycine and nicotinamide, and argine and nicotinamide.

In some embodiments, one viscosity-reducing agent is added to a protein agent formulation in a mole ratio to a second viscosity-reducing agent. In some embodiments, a mole ratio of a first viscosity-reducing agent to a second viscosity-reducing agent can be, for example, 1:0.001, 1:0.002, 1:0.004, 1:0.005, 1:0.010, 1:0.050, 1:0.10, 1:0.50, 1:1, 1:2, 1:5, 1:10, 1:25, 1:50, 1:100, 1:500, 1:1000, or higher. In some embodiments, the mole ratio may be bounded by a lower limit and an upper limit, the upper limit being larger than the lower limit. In some embodiments, the lower limit may be about 1:1000, about 1:500, about 1:100, about 1:50, about 1:25, or about 1:10. In some embodiments, the upper limit may be about 1:0.001, about 1:0.002, about 1:0.004, about 1:0.005, about 1:0.010, about 1:0.050, about 1:0.10, about 1:0.050, about 1:1, about 1:2, or about 1:5. In some embodiments, the mole ratio may be in the range of about 1:0.001 to about 1:1000. In some embodiments, the mole ratio may be in the range of about 1:0.002 to about 1:500. In some embodiments, the mole ratio may be in the range of about 1:0.004 to about 1:250. In some embodiments, the mole ratio may be in the range of about 1:0.008 to about 1:125. In some embodiments, the mole ratio may be in the range of about 1:0.01 to about 1:100. In some embodiments, the mole ratio may be in the range of about 1:0.08 to about 1:12.5. In some embodiments, the mole ratio may be in the range of about 1:0.1 to about 1:10.

In some embodiments, one viscosity-reducing agent is added to a protein agent formulation in a mole ratio to a second viscosity-reducing agent. In some embodiments, a mole ratio of a first viscosity-reducing agent to a second viscosity-reducing agent can be, for example, 1000:1, 500:1, 100:1, 50:1, 25:1, 10:1, 5:1, 2:1, 1:1, 0.50:1, 0.10:1, 0.050:1, 0.010:1, 0.005:1, 0.004:1, 0.002:1, 0.001:1, or lower. In some embodiments, the mole ratio may be bounded by a lower limit and an upper limit, the upper limit being larger than the lower limit. In some embodiments, the lower limit may be about 0.001:1, about 0.002:1, about 0.004:1, about 0.005:1, about 0.010:1, about 0.050:1, about 0.10:1, about 0.50:1, or about 1:1. In some embodiments, the upper limit may be about 2:1, about 5:1, about 10:1, about 25:1, about 50:1, about 100:1, about 500:1, or about 1000:1. In some embodiments, the mole ratio may be in the range of about 0.001:1 to about 1000:1. In some embodiments, the mole ratio may be in the range of about 0.002:1 to about 500:1. In some embodiments, the mole ratio may be in the range of about 0.004:1 to about 250:1. In some embodiments, the mole ratio may be in the range of about 0.0125:1 to about 80:1. In some embodiments, the mole ratio may be in the range of about 0.02:1 to about 50:1. In some embodiments, the mole ratio may be in the range of about 0.04:1 to about 25:1. In some embodiments, the mole ratio may be in the range of about 0.08:1 to about 12.5:1. In some embodiments, the mole ratio may be in the range of about 0.01:1 to about 10:1.

In some embodiments, the mole ratio of a protein-agent to a viscosity-reducing agent can be in the range of 0.0005:1 to 200:1. In some embodiments, the mole ratio of a protein-agent to a viscosity-reducing agent can be in the range of 0.0005:1 to 200:1. In some embodiments, the mole ratio of a protein-agent to a viscosity-reducing agent can be in the range of 0.005:1 to 20:1. In some embodiments, the mole ratio of a protein-agent to a viscosity-reducing agent can be in the range of 0.05:1 to 2:1.

A viscosity-reducing agent may be added to a protein agent formulation at a concentration that may be, for example, at least about 0.1 mM, 0.5 mM, 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 0.1 mM, about 0.5 mM, about 1 mM, about 5 mM, about 10 mM, about 15 mM, about 25 mM, or about 50 mM. In some embodiments, the upper limit may be about 75 mM, 100 mM, 200 mM, 500 mM, or 1000 mM. In some embodiments, the range may be about 0.1 mM to about 1000 mM.

In some embodiments, the range may be about 0.1 mM to about 500 mM. In some embodiments, the range may be about 0.1 mM to about 200 mM. In some embodiments, the range may be about 0.1 mM to about 100 mM. In some embodiments, the range may be about 0.5 mM to about 1000 mM. In some embodiments, the range may be about 0.5 mM to about 500 mM. In some embodiments, the range may be about 0.5 mM to about 200 mM. In some embodiments, the range may be about 0.5 mM to about 100 mM. In some embodiments, the range may be about 1 mM to about 1000 mM. In some embodiments, the range may be about 1 mM to about 500 mM. In some embodiments, the range may be about 1 mM to about 200 mM. In some embodiments, the range may be about 1 mM to about 100 mM. In some embodiments, the range may be about 5 mM to about 1000 mM. In some embodiments, the range may bea bout 5 mM to about 500 mM. In some embodiments, the range may be about 5 mM to about 200 mM. In some embodiments, the range may be about 10 mM to about 200 mM. In some embodiments, the range may be about 10 mM to about 150 mM. In some embodiments the range may be about 10 mM to about 100 mM. In some embodiments the range may be about 15 mM to about 75 mM. In some embodiments, the range may be about 15 mM to about 25 mM.

In some embodiments, a viscosity-reducing agent is or comprises one or more of Acetyl Salicylic Acid, 4-Aminocyclohexane Carboxylic Acid, 4-Aminopyridine-2-Carboxylic Acid, Antrallic Acid, Arginine, Ascorbic Acid, Aspirin, Caffeine, Caffeine Citrate, Caffeine Nicotinate, Creatinine, Ethanol, Glycine, Histidine, Homo-arginine, Hydroxyproline, Imidazole, Methylisothiazolinone, Methyl Nicotinate, Morpholine, Nicametate Citrate, Nicotinamide, Nicotinic acid (acid form). Nicotinic Acid (sodium salt), Nicotinuric Acid, Nicotinyl Alcohol, Nicotinyl Hydroxamate, Ornidazole, Pantothenic Acid, Paraxanthine, Piperazine, Procaine, Proline, Thiamine-HCl, Theobromine, Theophylline Nicotinate, Tryptophan (>0.2%), Uridine, Xanthine Nicotintate, Xanthinol Nicotinate. In some embodiments, a viscosity-reducing agent is or comprises one or more of 4-Aminocyclohexane Carboxylic Acid, 4-Aminopyridine-2-Carboxylic Acid, Ascorbic Acid, Aspirin, Caffeine Citrate. Caffeine Nicotinate, Ethanol, Hydroxyproline, Methylisothiazolinone, Nicametate Citrate, Nicotinic acid (acid form), Nicotinuric Acid, Nicotinyl Alcohol, Nicotinyl Hydroxamate, Theophylline Nicotinate, Tryptophan (>0.2%), Xanthine Nicotintate, Xanthinol Nicotinate, optionally in combination with one or more of Acetyl Salicyclic Acid, Antrallic Acid, Arginine, Caffeine, Creatinine, Glycine, Histidine, Homo-Arginine, Imidazole, Morpholine, Nicotinamide, Nicotinic Acid (sodium salt), Ornidazole, Pantothenoic Acid, Paraxanthine, Procaine, Piperazine, Theobromine, Thiamine-HCl, Uridine, and Xanthine Theophylline.

In some embodiments, a viscosity-reducing agent is or comprises one or more of 4-Aminocyclohexane Carboxylic Acid, 4-Aminopyridine-2-Carboxylic Acid, Ascorbic Acid, Aspirin, Caffeine Citrate. Caffeine Nicotinate, Ethanol, Hydroxyproline, Methylisothiazolinone, Nicametate Citrate, Nicotinic acid (acid form), Nicotinuric Acid, Nicotinyl Alcohol, Nicotinyl Hydroxamate, Theophylline Nicotinate, Tryptophan (>0.2%), Xanthine Nicotintate, Xanthinol Nicotinate.

In some embodiments, a viscosity-reducing agent is or comprises one or more of Caffeine Citrate, Caffeine Nicontinate, Nicotinic acid (acid form), and Tryptophan (>0.2%), aspirin, optionally in combination with one or more of nicotinamide, nicotinic acid sodium salt, caffeine, uridine, ascorbic acid, thiamine-HCl, pantothenic acid, proline, hydroxyproline, homo-arginine, arginine, histidine, acetyl salicyclic acid, and glycine. In some embodiments, a viscosity-reducing agent is or comprises one or more of Caffeine Citrate, Caffeine Nicontinate, Nicotinic acid (acid form), aspirin, and Tryptophan (>0.2%). In some embodiments, a viscosity-reducing agent is one of Caffeine Citrate, Caffeine Nicontinate, Nicotinic acid (acid form), and Tryptophan (>0.2%).

Aggregation-Reducing Agents

An aggregation-reducing agent reduces a polypeptide's tendency to associate in inappropriate or unwanted ternary or quaternary complexes. In some embodiments, an aggregation inhibitor is or comprises one or more of amino acids L-arginine, L-cysteine, and combinations thereof. In some embodiments, an aggregation-reducing agent may be added to a protein agent formulation in a concentration that may be, for example, at least about 0.1 mM, 0.5 mM, 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 0.1 mM, about 0.5 mM, about 1 mM, about 5 mM, about 10 mM, about 15 mM, about 25 mM, or about 50 mM. In some embodiments, the upper limit may be about 75 mM, 100 mM, 200 mM, 500 mM, or 1000 mM. In some embodiments, the range may be about 0.1 mM to about 1000 mM. In some embodiments, the range may be about 0.1 mM to about 500 mM. In some embodiments, the range may be about 0.1 mM to about 200 mM. In some embodiments, the range may be about 0.1 mM to about 100 mM. In some embodiments, the range may be about 0.5 mM to about 1000 mM. In some embodiments, the range may be about 0.5 mM to about 500 mM. In some embodiments, the range may be about 0.5 mM to about 200 mM. In some embodiments, the range may be about 0.5 mM to about 100 mM. In some embodiments, the range may be about 1 mM to about 1000 mM. In some embodiments, the range may be about 1 mM to about 500 mM. In some embodiments, the range may be about 1 mM to about 200 mM. In some embodiments, the range may be about 1 mM to about 100 mM. In some embodiments, the range may be about 5 mM to about 1000 mM. In some embodiments, the range may be about 5 mM to about 500 mM. In some embodiments, the range may be about 5 mM to about 200 mM. In some embodiments, the range may be about 10 mM to about 200 mM. In some embodiments, the range may be about 10 mM to about 150 mM. In some embodiments the range may be about 10 mM to about 100 mM. In some embodiments the range may be about 15 mM to about 75 mM. In some embodiments, the range may be about 15 mM to about 25 mM.

In some embodiments, a protein agent formulation with an aggregation-reducing agent can have a decreased aggregation that is at least about 5% less than the analogous control or reference formulation without an aggregation-reducing agent, when measured under the same conditions. In some embodiments, a protein agent formulation may have an aggregation measurement that may be, for example, at least 10%, 20%, 30%, 40%, 50%, 60%, 70%, 80%, 90%, or even more than 90% less than the analogous control protein agent formulation without an aggregation-reducing agent. In some embodiments, the percentage decrease in aggregation once the aggregation-reducing agent is incorporated maybe be within a range bound by a lower limit and an upper limit, the upper limit being larger than the lower limit. In some embodiments, the lower limit may be about 0%, 5%, 10%, 20%, 30%, about 35%, about 40%, about 45%, or about 50% less aggregation than the control formulation. In some embodiments, the upper limit may be about 55%, about 60%, about 65%, about 70%, about 75%, about 80%, about 85%, about 90%, about 95%, or about 99% or about 100%. In some embodiments, the range may be about 30% to about 99% decrease in aggregation. In some embodiments, the range maybe be about 35% to about 99% decrease in aggregation. In some embodiments, the range maybe be about 40% to about 99% decrease in aggregation. In some embodiments, the range maybe be about 45% to about 99% decrease in aggregation. In some embodiments, the range maybe be about 50% to about 99% decrease in aggregation. In some embodiments, the range maybe be about 60% to about 99% decrease in aggregation. In some embodiments, the range maybe be about 70% to about 99% decrease in aggregation. In some embodiments, the range maybe be about 80% to about 99% decrease in aggregation. In some embodiments, the range maybe be about 90% to about 99% decrease in aggregation.

In some embodiments, an aggregation preventer can be used in combination with an aggregation-reducing agent (e.g. nicotinic acid, caffeine citrate, caffeine nicotinate or aspirin). In some embodiments, an aggregation preventer is or comprises one or more of amino acids (e.g. arginine, tryptophan, caffeine, histidine, proline, cysteine, methionine, β-alanine, Potassium Glutamate, Arginine Ethylester, lysine, aspartic acid, glutamic acid, and glycine), metal chelators (e.g. DTPA (diethylenetriaminepentaacetic acid), EGTA (aminopolycarboxylic acid), EDTA (Ethylenediaminetetraacetic acid)), cylclodextrins (e.g. hydroxy propyl beta (HP-Beta), hydroxy propyl gamma (HP-Gamma) and sulfo-butyl ether (SBE) cyclodextrins), sugars (e.g. sucrose, mannitol, dextrose, glycerol, TMAO (trimethylamine N-oxide), trehalose, ethylene glycol, glycine betaine, xylitol, sorbitol), multiple-charge anion (e.g. 6-(N-(7-nitrobenz-2-oxa-1,3-diazol-4-yl)amino)hexanoic acid (NBD-X), methyl acetyl phosphate (MAP)), citraconic anhydride, pyrophosphate or citrate.

In some embodiments, an aggregation preventer can used in combination with an aggregation-reducing agent (e.g., nicotinic acid, caffeine citrate, caffeine nicotinate or aspirin) to enhance the efficiency a viscosity-reducing agent in reducing viscosity, reducing and preventing aggregation and surface adsorption of a high concentration protein agent formulation. In some embodiments, an aggregation preventers is or comprises one or more of surfactants (e.g. polysorbate 20 and polysorbate 80), Brij 56 (e.g. Polyoxyethylene cetyl ether, Poloxamer 188, Triton X-100, NP-40, octyl-β-D-glucopyranoside and n-dodecyl-β-D-maltoside), zwitterion detergents (e.g. NDSB (Non-detergent Sulfo Betaine), CHAPS, Zwittergent 3-14, and LDAO (Lauryldimethylamine N-oxide)), ionic detergents (e.g. CTAB (cetyltrimethylammonium bromide), Sarkosyl (Sodium lauroyl sarcosinate), and SDS), chaotropes (e.g. Urea, Guanidine HCl, N-Methylurea, N-Ethylurea, N-Methylformamide, NaI, $CaCl_2$, $MgCl_2$, NaCl, KCl, $MgSO_4$, $(NH_4)_2SO_4$, $Na_2SO_4$, $Cs_2SO_4$, Potassium citrate, and Citric Acid), alcohols, polyols, polyamines, polymer, ethanol, n-Penthanol, n-Hexanol, Cyclohexanol, Polyethylene glycol (PEG 3350) Polyvinylpyrrolidone 40 (PVP40), Alpha-Cyclodextrin, Beta-cyclodextrin, Putrescine, spermidine, spermine, formamide, and combinations thereof.

In some embodiments, an aggregation-reducing agent is or comprises one or more of uridine, thiamine HCl, pantothenic acid, homo-arginine, caffeine, tryptophan, imidazole, nicotinic acid sodium salt, nicotinamide. In some embodiments, an aggregation-reducing agent is or comprises one or more of creatinine, antrallic acid, morpholine, piperidine, paraxanthine, theobromine, xanthine, theophylline, or ornidazole.

In some embodiments, an aggregation-reducing agent is or comprises one or more of nicotinic acid, caffeine citrate, caffeine nicotinate, arginine, tryptophan, caffeine, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA (aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfo-butyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino)hexanoic acid (NBD-X), methyl acetyl phosphate (MAP), citraconic anhydride, pyrophosphate, octyl-β-D-glucopyranoside, n-dodecyl-β-D-maltoside and citrate.

In some embodiments, an aggregation-reducing agent is or comprises one or more of nicotinic acid, caffeine citrate, caffeine nicotinate, caffeine, methionine, β-alanine, hydroxy propyl beta (HP-Beta) cyclodextrins, octyl-β-D-glucopyranoside, and n-dodecyl-β-D-maltoside.

In some embodiments, an aggregation-reducing agent is or comprises one or more of nicotinic acid, caffeine citrate, caffeine nicotinate, caffeine, octyl-β-D-glucopyranoside, and n-dodecyl-β-D-maltoside and optionally in combination with one or more of arginine, tryptophan, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA (aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfo-butyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino) hexanoic acid (NBD-X), methyl acetyl phosphate (MAP), citraconic anhydride, pyrophosphate and citrate.

Other Components

A wide variety of pharmaceutical excipients useful for liquid protein agent formulations are known to those skilled in the art.

In some embodiments, one or more additives may be included in a protein agent formulation. In some embodiments, an additive is or comprises one or more of liquid solvents, liquid co-solvents, sugars, sugar alcohols (e.g. mannitol, trehalose, sucrose, sorbitol, fructose, maltose, lactose, and dextrans); surfactants, (e.g. TWEEN® 20, 60, or 80 (polysorbate 20, 60, and 80)); buffering agents, preservatives (e.g. benzalkonium chloride, benzethonium chloride, tertiary ammonium salts, and chlorhexidinediacetate); carriers (e.g. poly(ethylene glycol) (PEG)); antioxidants (e.g. ascorbic acid, sodium metabisulfite, and methionine); chelating agents (e.g. EDTA, citric acid, and biodegradable polymers such as water soluble polyesters); cryoprotectants, lyoprotectants, bulking agents, stabilizing agents, and combinations thereof. Other pharmaceutically acceptable carriers, excipients, or stabilizers, are exemplified in Remington: "The Science and Practice of Pharmacy", 20th edition, Alfonso R. Gennaro, Ed., Lippincott Williams & Wilkins (2000) may also be included in a protein formulation described herein, provided that they do not adversely affect the desired characteristics of the formulations.

In some embodiments, an antioxidant may be included in a protein agent formulation described herein. In some embodiments, an antioxidant that may be added to a protein agent formulation can include ascorbic acid, ascorbyl palmitate, butylated hydroxyanisole, butylated hydroxytoluene, DTPA, EDTA, glycine, hypophosphorous acid, lysine, mannitol, monothioglycerol, propyl gallate, sodium bisulfite, sodium formaldehyde sulfoxylate, sodium metabisulfite, sodium thiosulfate, sorbitol, sufur dioxide, tocopherol, tocopherols and combinations thereof. In some embodiments, an antioxidant is added to a protein agent formulation in an amount that may be, for example, at least about 0%, 0.1%, 0.2%, 0.3%, 0.4%, 0.5%, 1%, 1.5%, 2%, 3%, 5%, 10%, 15%, 20% (w/v) or more. In some embodiments, the amount may be within a range bounded by a lower limit and an upper limit, the upper limit being larger than the lower limit. In some embodiments, the lower limit may be about 0%, about 0.1%, about 0.2%, about 0.3%, about 0.4%, about 0.5%, or about 1% (w/v). In some embodiments, the upper limit may be about 1.5%, about 2%, about 2.5%, about 5%, about 10%, or about 15.0%.

In some embodiments, a nitrogen or carbon dioxide overlay may be used to inhibit oxidation of a protein agent formulation. In some embodiments, nitrogen or carbon dioxide overlays can be introduced to the headspace of a vial or prefilled syringe during the filling process.

In some embodiments, a preservative that may be added to a protein agent formulation can include benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol, and combinations thereof. In some embodiments, a preservative is added to a protein agent formulation in an amount that may be, for example, at least about 0%, 0.1%, 0.2%, 0.3%, 0.4%, 0.5%, 1%, 1.5%, 2% (w/v) or more. In some embodiments, the amount may be within a range bounded by a lower limit and an upper limit, the upper limit being larger than the lower limit. In some embodiments, the lower limit may be about 0%, about 0.1%, about 0.2%, about 0.3%, about 0.4%, about 0.5%, or about 1% (w/v). In some embodiments, the upper limit may be about 1.5%, about 2%, about 2.5%, or about 3.0%. In some embodiments, the range may be about 0% to about 3% (w/v). In some embodiments the range may be about 0% to about 2.5% (w/v). In some embodiments the range may be about 0% to about 2% (w/v). In some embodiments the range may be about 0% to about 1.5% (w/v). In some embodiments the range may be about 0% to about 1% (w/v). In some embodiments the range may be about 0% to about 0.5% (w/v). In some embodiments, the range may be about 0% to about 0.4%. In some embodiments, the range may be about 0% to about 0.3%. In some embodiments, the range may be about 0% to about 0.2%. In some embodiments, the range may be about 0% to about 0.1%.

Solubilizing agents and stabilizers (also referred to as emulsifying agents, co-solutes, co-solvents, or surfactants) can increase the solubility and/or stability of a protein agent while in solution or in dried or frozen forms. In some embodiments, a solubilizing or stabilizing is or comprises one or more of sugars/polyols such (e.g. sucrose, lactose, glycerol, xylitol, sorbitol, mannitol, maltose, inositol, trehalose, and glucose), polymers (e.g. serum albumin (bovine serum albumin (BSA), human SA (HSA), and recombinant HA), dextran, PVA, hydroxypropyl methylcellulose (HPMC), polyethyleneimine, gelatin, polyvinylpyrrolidone (PVP), hydroxyethylcellulose (HEC), polyhydric alcohols (e.g., PEG, ethylene glycol, and glycerol, dimethysulfoxide (DMSO), dimethylformamide (DMF); amino acids (e.g. proline, L-methionine, L-serine, sodium glutamic acid, alanine, glycine, lysine hydrochloride, sarcosine, and gamma-aminobutyric acid), potassium phosphate, sodium acetate, ammonium sulfate, magnesium sulfate, sodium sulfate, trimethylamine N-oxide, betaine, metal ions (e.g., zinc, copper, calcium, manganese, and magnesium), CHAPS, monolaurate, 2-O-beta-mannoglycerate, acacia, cholesterol, diethanolamine (adjunct), glyceryl monostearate, lanolin alcohols, lecithin, mono-glycerides, di-glycerides, mono-ethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax, wetting and/or solubilizing agents (e.g. benzalkonium chloride, benzethonium chloride, cetylpyridinium chloride, docusate sodium, nonoxynol 9, nonoxynol 10, octoxynol 9, polyoxyl 50 stearate, tyloxapol); and combinations thereof.

In some embodiments, a stabilizer is or comprises one or more of sorbitan mono-9-octadecenoate poly(oxy-1,2-ethanediyl) derivatives polysorbate 80, polysorbate 20, and combinations thereof. Polysorbate 20 and/or polysorbate 80 can be added to a protein agent solution in the range of 0.001% to 1.0% (w/v), such as 0.005% (w/v), in single use or in multi-dose formulations. In some embodiments, free L-methionine is added to a formulation in the range of 0.05 mM to 50 mM. In some embodiments, the amount of free L-methionine added to a protein agent formulation is 0.05 mM to 5 mM for a single use formulation, and 1 mM to 10 mM for a multi-dose formulation.

In some embodiments, a solubilizing agent or stabilizer is added to a protein agent formulation at a concentration may be, for example, at least 0.001, 0.01, 0.1, 1.0, 1.5, 2.0, 2.5, 3.0, 3.5, 4.0, 4.5, 5.0 weight percent or higher. In some embodiments, the amount may be within a range bounded by a lower limit and an upper limit, the upper limit being larger than the lower limit. In some embodiments, the lower limit may be about 0.001, about 0.01, about 0.1, about 1.0, about 1.5, or about 2.0 weight percent. In some embodiments, the upper limit may be about 3.5, about 3.0, about 4.0, about 4.5, or about 5.0 weight percent. In some embodiments, the range may be about 0.001 to about 5.0 weight percent. In some embodiments, the range may be about 0.01 to about 5.0 weight percent. In some embodiments, the range may be about 0.1 to about 4.0. In some embodiments, the range may be about 0.1 to about 3.0 weight percent. In some embodiments, the range may be about 0.1 to about 2.0 weight percent.

In some embodiments, a surfactant to be added to a protein agent formulation is or comprises one or more of Polysorbate 80, Polysorbate 20, n-Dodecyl β-D-maltoside, Octyl β-D-glucopyranoside, Tween-80, Tween-20, alkyl glycoside, octyl glucoside, SDS, polyoxyethylene copolymer, and combinations thereof.

A tonicity modifier may also be included in a protein agent formulation as described herein. Tonicity modifiers are understood to be molecules that contribute to the osmolality of a solution. The osmolality of a pharmaceutical composition is regulated to maximize the stability of the active ingredients, or in this case, protein agents, and also to minimize discomfort to the patient upon administration of therapeutic formulations. Serum is approximately 300±50 milliosmolals per kilogram (mOsm/kg). It is generally preferred that a pharmaceutical composition be isotonic with serum, i.e., having the same or similar osmolality as serum, which is achieved by addition of a tonicity modifier. Thus, it is contemplated that osmolality will range from about 180 to about 420 mOsm/kg, however, it is to be understood that osmolality can register either higher or lower than the range, as specific conditions require. In some embodiments, a tonicity modifier is or comprises one or more of amino acids (e.g., arginine, cysteine, histidine and glycine), salts (e.g., sodium chloride, potassium chloride and sodium citrate), saccharides (e.g., sucrose, glucose, dextrose, glycerin, sorbitol, trehalose, mannitol), and combinations thereof. A tonicity modifier may be added to a protein agent formulation at an amount that may be, for example, at least about 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 1 mM, about 10 mM, about 15 mM, about 25 mM. In some embodiments, the upper limit may be about 75 mM, about 100 mM, about 200 mM, about 500 mM, or about 1000 mM. In some embodiments, the range may be about 1 mM to about 1000 mM. In some embodiments, the range may be about 10 mM to about 200 mM. In some embodiments, the tonicity modifier is sodium chloride within a concentration range of 0 mM to 200 mM.

Lyoprotectants may also be included in formulations herein. In some embodiments, a lyoprotectant is or comprises one or more of sugars and their corresponding sugar alcohols (e.g. sucrose, lactose, trehalose, dextran, erythritol, arabitol, xylitol, sorbitol, and mannitol), amino acids (e.g. arginine, and histidine), lyotropic salts (e.g. magnesium sulfate), polyols (e.g. propylene glycol, glycerol, poly(ethylene glycol), and polypropylene glycol), and combinations thereof. In some embodiments, a lyoprotectant is is or comprises one or more of selected from the group consisting of gelatin, dextrins, modified starch, carboxymethyl cellulose, and combinations thereof. In some embodiments, a lyoprotectant is or comprises one or more of selected from the group consisting of sugar alcohols lactose, trehalose, maltose, lactulose, and maltulose, glucitol, maltitol, lactitol and isomaltulose, and combinations thereof. In some embodiments, lyoprotectants are generally added to a pre-lyophilized formulation in a "lyoprotecting amount." This means that, following lyophilization of a protein agent in the presence of a lyoprotecting amount, the protein agent essentially retains physical and chemical stability and integrity, as a lyoprotectant is present in the dry form (e.g. in the cake). In some embodiments, a lyoprotectant may be added, or more may be additionally added, when a dried protein agent formulation is reconstituted.

In some embodiments, a lyoprotectant is a sugar. In some embodiments, a lyoprotecant is or comprises one or more of D-Sucrose, D-(+)-Trehalose, D-(−)-Fructose, D-Mannitol, L-(+)-Arabinose, D-sorbitol, Lactose, Maltose and combinations thereof. In some embodiments, a lyoprotectant may be added to a protein agent formulation at a concentration that may be, for example, at least about 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 1mM, about 10 mM, about 15 mM, about 25 mM, or about 50 mM. In some embodiments, the upper limit may be about 75 mM, about 100 mM, about 200 mM, about 500 mM, or about 1000 mM. In some embodiments, the range may be about 1 mM to about 1000 mM. In some embodiments, the range may be about 10 mM to about 500 mM. In some embodiments, the range may be about 10 mM to about 300 mM.

In some embodiments, an is or comprises one or more of salts of amino acids (e.g. glycine, arginine, aspartic acid, glutamic acid, lysine, asparagine, glutamine, proline, and histidine), monosaccharides (e.g. glucose, fructose, galactose, mannose, arabinose, xylose, and ribose), disaccharides (e.g. lactose, trehalose, maltose, and sucrose), polysaccharides (e.g maltodextrins, dextrans, starch, and glycogen), alditols (e.g. mannitol, xylitol, lactitol, and sorbitol), glucuronic acid, galacturonic acid, cyclodextrins (e.g. methyl cyclodextrin and hydroxypropyl-β-cyclodextrin), inorganic salts (e.g. sodium chloride, potassium chloride, magnesium chloride, phosphates of sodium and potassium, boric acid ammonium carbonate and ammonium phosphate), organic salts (e.g. acetates, citrate, ascorbate, and lactate), emulsifying or solubilizing agents (e.g. acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, and sorbitan derivatives), viscosity-increasing reagents (e.g. agar, alginic acid and its salts, guar gum, pectin, polyvinyl alcohol, polyethylene oxide, cellulose and its derivatives, propylene carbonate, polyethylene glycol, hexylene glycol and tyloxapol), and combinations thereof.

In some embodiments, an additive is or comprises one or more of is selected from the group consisting of sucrose, trehalose, lactose, sorbitol, lactitol, inositol, acetates, phosphates, citrates, borates, glycine, arginine, polyethylene oxide, polyvinyl alcohol, polyethylene glycol, hexylene glycol, methoxy polyethylene glycol, gelatin, hydroxypropyl-β-cyclodextrin, and combinations thereof.

In some embodiments, a non-limiting additive agent that may be included in a protein agent formulation can include acidifying agents (e.g. acetic acid, glacial acetic acid, citric acid, fumaric acid, hydrochloric acid, diluted hydrochloric acid, malic acid, nitric acid, phosphoric acid, diluted phosphoric acid, sulfuric acid, and tartaric acid), active ingredients (e.g. ingredients to reduce injection site discomfort), non-steroidal anti-inflammatory drugs (e.g. tromethamine in an appropriate dosage), aerosol propellants (e.g. butane, dichlorodifluoromethane, dichlorotetrafluoroethane, isobutane, propane, and trichloromonofluoromethane), alcohol denaturants (e.g. denatonium benzoate, methyl isobutyl ketone, and sucrose octacetate), alkalizing agents (e.g. strong ammonia solution, ammonium carbonate, diethanolamine, diisopropanolamine, potassium hydroxide, sodium bicarbonate, sodium borate, sodium carbonate, sodium hydroxide, and trolamine), anticaking agents (e.g. calcium silicate, magnesium silicate, colloidal silicon dioxide, and talc), antifoaming agents (e.g. dimethicone and simethicone), chelating agents (e.g. edetate disodium, ethylenediaminetetraacetic acid and salts, and edetic acid), coating agents (e.g. sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, and zein), colors (e.g. caramel, erythrosine (FD&C Red No. 3), FD&C Red No. 40, FD&C Yellow No. 5, FD&C Yellow No. 6, FD&C Blue No. 1, red, yellow, black, blue, color blends, and ferric oxide), complexing agents (e.g. ethylenediaminetetraacetic acid (EDTA) and salts thereof, edetic acid, gentisic acid ethanolmaide and oxyquinoline sulfate), desiccants (e.g. calcium chloride, calcium sulfate and silicon dioxide), filtering aids (e.g. powdered cellulose and purified siliceous earth), flavors and perfumes (e.g. anethole, anise oil, benzaldehyde, cinnamon oil, cocoa, ethyl vanillin, menthol, methyl salicylate, monosodium glutamate, orange flower oil, orange oil, peppermint, peppermint oil, peppermint spirit, rose oil, stronger rose water, thymol, tolu balsam tincture, vanilla, vanilla tincture and vanillin), humectants (e.g. glycerin, hexylene glycol, propylene glycol and sorbitol), ointment bases (e.g. lanolin, anhydrous lanolin, hydrophilic ointment, white ointment, yellow ointment, polyethylene glycol ointment, petrolatum, hydrophilic petrolatum, white petrolatum, rose water ointment and squalane), plasticizers (e.g. castor oil, diacetylated monoglycerides, diethyl phthalate, glycerin, mono- and diacetylated monoglycerides, polyethylene glycol, propylene glycol, triacetin and triethyl citrate), polymer membranes (e.g. cellulose acetate), solvents (e.g. acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation and purified water), sorbents (e.g. powdered cellulose, charcoal, purified siliceous earth, and carbon dioxide sorbents barium hydroxide lime and soda lime), stiffening agents (e.g. hydrogenated castor oil, cetostearyl alcohol, cetyl alcohol, cetyl esters wax, hard fat, paraffin, polyethylene excipient, stearyl alcohol, emulsifying wax, white wax and yellow wax), suppository bases (e.g. cocoa butter, hard fat and polyethylene glycol), suspending and/or viscosity-increasing agents (e.g. acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth and xanthan gum), sweetening agents (e.g. aspartame, dextrates, dextrose, excipient dextrose, fructose, mannitol, saccharin, calcium saccharin, sodium saccharin, sorbitol, solution sorbitol, sucrose, compressible sugar, confectioner's sugar and syrup), tablet binders (e.g. acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch and syrup), tablet and/or capsule diluents (e.g. calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar and confectioner's sugar), tablet disintegrants (e.g. alginic acid, microcrystalline cellulose, croscarmellose sodium, corspovidone, polacrilin potassium, sodium starch glycolate, starch and pregelatinized starch), tablet and/or capsule lubricants (e.g. calcium stearate, glyceryl behenate, magnesium stearate, light mineral oil, polyethylene glycol, sodium stearyl fumarate, stearic acid, purified stearic acid, talc, hydrogenated vegetable oil and zinc stearate), vehicles (e.g. flavors and/or sweeteners (aromatic elixir, compound benzaldehyde elixir, iso-alcoholic elixir, peppermint water, sorbitol solution, syrup, and tolu balsam syrup), oleaginous (e.g. almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, and squalane), solid carriers (e.g. sugar spheres), sterile vehicles (e.g. bacteriostatic water for injection, bacteriostatic sodium chloride injection); water-repelling agents (e.g. cyclomethicone, dimethicone and simethicone), and combinations thereof.

Characteristics

Viscosity

Low-viscosity protein agent formulations can allow for greater flexibility in formulation development. Low-viscosity formulations can exhibit changes in viscosity that are less dependent upon protein agent concentration as compared to an otherwise same formulation control or reference without a viscosity-reducing agent. A low-viscosity protein agent formulation can allow for an increased concentration and a decreased dosage frequency of a protein agent. In some embodiments, a low-viscosity protein agent formulation contains 2 or more, 3 or more, or 4 or more different protein agents. For example, a combination of 2 or more mAbs can be provided in a single low-viscosity protein agent formulation. A low-viscosity protein agent formulation can be used to deliver a therapeutically effective amount of a protein agent in a volume appropriate for subcutaneous (SC) and intramuscular (IM) injections.

A viscosity-reducing agent and other additives like buffering agents, tonicity agents, and solubilizing agents, can be included in any amount to achieve a desired viscosity measurement of a liquid protein agent formulation, as long as the amounts are not toxic or otherwise harmful to the subject upon administration. In addition, additives or a viscosity-reducing agent added to a protein agent formulation should not substantially interfere with the chemical and/or physical stability of the formulation. In some embodiments, a viscosity-reducing agent can be independently added in an amount that may be, for example, at least about 0.1 mM, 0.5 mM, 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 0.1 mM, about 0.5 mM, about 1 mM, about 5 mM, about 10 mM, about 15 mM, about 25 mM, or about 50 mM. In some embodiments, the upper limit may be about 75 mM, 100 mM, 200 mM, 500 mM, or 1000 mM. In some embodiments, the range may be about 0.1 mM to about 1000 mM. In some embodiments, the range may be about 0.1 mM to about 500 mM. In some embodiments, the range may be about 0.1 mM to about 200 mM. In some embodiments, the range may be about 0.1 mM to about 100 mM. In some embodiments, the range may be about 0.5 mM to about 1000 mM. In some embodiments, the range may be about 0.5 mM to about 500 mM. In some embodiments, the range may be about 0.5 mM to about 200 mM. In some embodiments, the range may be about 0.5 mM to about 100 mM. In some embodiments, the range may be about 1 mM to about 1000 mM. In some embodiments, the range may be about 1 mM to about 500 mM. In some embodiments, the range may be about 1 mM to about 200 mM. In some embodiments, the range may be about 1 mM to about 100 mM. In some embodiments, the range may be about 5 mM to about 1000 mM. In some embodiments, the range may be about 5 mM to about 500 mM. In some embodiments, the range may be about 5 mM to about 200 mM. In some embodiments, the range may be about 10 mM to about 200 mM. In some embodiments, the range may be about 10 mM to about 150 mM. In some embodiments the range may be about 10 mM to about 100 mM. In some embodiments the range may be about 15 mM to about 75 mM. In some embodiments, the range may be about 15 mM to about 25 mM. In some embodiments, with two or more viscosity-reducing agents, the agents are preferably, but not necessarily, present at the same concentration.

In the absence of a viscosity-reducing agent, the viscosity of a protein agent-containing formulation increases exponentially as the concentration is increased to accommodate a required lower volume for injection. Such a protein formulation, in the absence of a viscosity-reducing agent, may have a viscosity in the range of 50 cP to 1,500 cP when measured at 25° C. Such formulations are often unsuitable for SC or IM injection due to difficulty in administration by small-bore needles using syringes, and due to pain at the site of injection. In addition, the chemical and physical stability of a protein agent is at risk at higher concentrations. The use of one or more viscosity-reducing agents permits the preparation of formulations with a viscosity, that when measured at 25° C., may be, for example, about 100 cP, 75 cP, 50 cP, 45 cP, 40 cP, 35 cP, 30 cP, or lower. In some embodiments, the amount may be within a range bounded by a lower limit and an upper limit, the upper limit being larger than the lower limit. In some embodiments, when measured at 25° C., the lower limit may be about 1 cP, about 5 cP, about 10 cP, or about or 15 cP. In some embodiments, when measured at 25° C., the upper limit may be about 20 cP, about 25 cP, about 30 cP, about 35 cP, about 40 cP, about 45 cP, about 50 cP, about 75 cP, or about 100 cP. In some embodiments, when measured at 25° C., the range may be about 5 cP to about 100 cP. In some embodiments, when measured at 25° C., the range may be about 5 cP to about 75 cP. In some embodiments, when measured at 25° C., the range may be about 5 cP to about 50 cP. In some embodiments, when measured at 25° C., the range may be about 5 cP to about 40 cP. In some embodiments, when measured at 25° C., the range may be about 5 cP to about 35 cP. In some embodiments, when measured at 25° C., the range may be about 5 cP to about 30 cP. In some embodiments, when measured at 25° C., the range may be about 5 cP to about 25 cP. In some embodiments, when measured at 25° C., the range may be about 5 cP to about 20 cP. In some embodiments, when measured at 25° C., the range may be about 5 cP to about 15 cP. In some embodiments, when measured at 25° C., the range may be about 5 cP to about 10 cP.

In some embodiments, an aqueous protein agent formulation has a viscosity that is at least about 30% less than the analogous control or reference formulation without a viscosity-reducing agent, when measured under the same conditions. In some embodiments, a protein agent formulation has a viscosity that may be, for example, at least 35%, 40%, 50%, 60%, 70%, 80%, 90%, or even more than 90% less than the analogous control protein agent formulation without the viscosity-reducing agent(s). In some embodiments, the percentage decrease in viscosity once the viscosity-reducing agent is incorporated maybe be within a range bound by a lower limit and an upper limit, the upper limit being larger than the lower limit. In some embodiments, the lower limit may be about 30%, about 35%, about 40%, about 45%, or about 50% less viscosity than the control formulation. In some embodiments, the upper limit may be about 55%, about 600, about 65%, about 70%, about 75%, about 80%, about 85%, about 90%, about 95%, or about 99%. In some embodiments, the range may be about 30% to about 99% decrease in viscosity. In some embodiments, the range maybe be about 35% to about 99% decrease in viscosity. In some embodiments, the range maybe be about 40% to about 99% decrease in viscosity. In some embodiments, the range maybe be about 45% to about 99% decrease in viscosity. In some embodiments, the range maybe be about 50% to about 99% decrease in viscosity. In some embodiments, the range maybe be about 60% to about 99% decrease in viscosity. In some embodiments, the range maybe be about 70% to about 99% decrease in viscosity. In some embodiments, the range maybe be about 80% to about 99% decrease in viscosity. In some embodiments, the range maybe be about 90% to about 99% decrease in viscosity.

In some embodiments, a protein agent formulation contains a therapeutically effective amount of one or more high molecular weight protein agents, in a volume appropriate for SC or IM injection, that may be, for example, about 5.0 mL, 4.8 mL, 4.6 mL, 4.4 mL, 4.2 mL, 4.0 mL, 3.8 mL, 3.6 mL, 3.4 mL, 3.2 mL, 3.0 mL, 2.8 mL, 2.6 mL, 2.4 mL, 2.2 mL, 2.0 mL, 1.8 mL, 1.6 mL, 1.4 mL, 1.2 mL, 1.0 mL, 0.75 mL, 0.50 mL, 0.25 mL, 0.10 mL, or less. In some embodiments, the amount may be within a range bounded by a lower limit and an upper limit, the upper limit being larger than the lower limit. The lower limit may be about 0.10 mL, about 0.25 mL, about 0.50 mL, about 0.75 mL, or about 1.0 mL. The upper limit may be about, about 1.2 mL, about 1.4 mL, about 1.6 mL, about 1.8 mL, about 2.0 mL, about 2.2 mL, about 2.4 mL, about 2.6 mL, about 2.8 mL, about 3.0 mL, about 3.2 mL, about 3.4 mL, about 3.6 mL, about 3.8 mL, about 4.0 mL, about 4.2 mL, about 4.4 mL, about 4.6 mL, about 4.8 mL, or about 5.0 mL. In some embodiments, the range may be about 0.10 mL to about 2.0 mL. In some embodiments, the range may be about 0.10 mL to about 1.8 mL. In some embodiments, the range may be about 0.10 mL to about 1.6 mL. In some embodiments, the range may be about 0.10 mL to about 1.4 mL. In some embodiments, the range may be about 0.10 mL to about 1.2 mL. In some embodiments, the range may be about 0.10 mL to about 1.0 mL. In some embodiments, the range may be about 0.10 mL to about 0.75 mL. In some embodiments, the range may be about 0.10 mL to about 0.50 mL. In some embodiments, the range may be about 0.10 mL to about 0.25 mL. In some embodiments, the range may be about 0.10 mL to about 5.0 mL. In some embodiments, the range may be about 1.0 mL to about 5.0 mL. In some embodiments, the range may be about 1.4 mL to about 5.0 mL. In some embodiments, the range may be about 1.8 mL to about 5.0 mL. In some embodiments, the range may be about 2.0 mL to about 5.0 mL. In some embodiments, the range may be about 2.6 mL to about 5.0 mL. In some embodiments, the range may be about 3.0 mL to about 5.0 mL. In some embodiments, the range may be about 3.6 mL to about 5.0 mL. In some embodiments, the range may be about 4.0 mL to about 5.0 mL. In some embodiments, the range may be about 4.6 mL to about 5.0 mL. A formulation appropriate for SC or IM injection may have a protein agent concentration that may be, for example, at least about 10 mg/mL, 50 mg/mL, 100 mg/mL, 150 mg/mL, 200 mg/mL, 250 mg/mL, 300 mg/mL, 350 mg/mL, 400 mg/mL, 450 mg/mL, 500 mg/mL or more. In some embodiments, the amount may be within a range bounded by a lower limit and an upper limit, the upper limit being larger than the lower limit. In some embodiments, the lower limit may be about 10 mg/mL, about 25 mg/mL, about 50 mg/mL, about 100 mg/mL, or about 150 mg/mL. In some embodiments, the upper limit may be about 200 mg/mL, about 300 mg/mL, about 400 mg/mL, about 500 mg/mL, about 1000 mg/mL, or about 2000 mg/mL. In some embodiments, the range may be about 10 mg/mL to about 2000 mg/mL. In some embodiments, the range may be about 10 mg/mL to about 1000 mg/mL. In some embodiments, the range may be about 10 mg/mL to about 500 mg/mL. In some embodiments, the range may be about 25 mg/mL to about 2000 mg/mL. In some embodiments, the range may be about 25 mg/mL to about 1000 mg/mL. In some embodiments, the range may be about 25 mg/mL to about 500 mg/mL. In some embodiments, the range may be about 50 mg/mL to about 2000 mg/mL. In some embodiments, the range may be about 50 mg/mL to about 1000 mg/mL. In some embodiments, the range may be about 50 mg/mL to about 500 mg/mL. In some embodiments, the range may be about 100 mg/mL to about 2000 mg/mL. In some embodiments, the range may be about 100 mg/mL to about 1000 mg/mL. In some embodiments, the range may be about 100 mg/mL to about 500 mg/mL. In some embodiments, the range may be about 150 mg/mL to about 2000 mg/mL. In some embodiments, the range may be about 150 mg/mL to about 1000 mg/mL. In some embodiments the range may be about 150 mg/mL to about 500 mg/mL. In some embodiments the range may be about 150 mg/mL to about 450 mg/mL. In some embodiments the range may be about 150 mg/mL to about 400 mg/mL. In some embodiments the range may be about 150 mg/mL to about 350 mg/mL. In some embodiments the range may be about 150 mg/mL to about 300 mg/mL.

Addition of a viscosity-reducing agent allows for greater flexibility in formulation development. By making a low-viscosity protein agent formulation, the viscosity changes less with increasing protein agent concentration as compared to the otherwise same formulation control without a viscosity-reducing agent. Also, a low-viscosity protein agent formulation exhibits a decreased viscosity gradient. In some embodiments, a viscosity gradient of a protein formulation may be about 2-fold less, 3-fold less, or even more than 3-fold less than a viscosity gradient of an otherwise same protein agent formulation without a viscosity-reducing agent. In some embodiments, a viscosity gradient of a protein agent formulation may be, for example, less than about 5.0 cP mL/mg, 3.0 cP mL/mg, 2.0 cP mL/mg, 1.5 cP mL/mg, 1.0 cP mL/mg, 0.8 cP mL/mg, 0.6 cP ml/mg, 0.5 cP mL/mg, 0.1 cP mL/mg, 0.05 cP mL/mg, 0.02 cP mL/mg, or lower for a protein agent formulation with a protein concentration between 10 mg/mL and 5,000 mg/mL. In some embodiments, a viscosity gradient may be within a range bounded by a lower limit and an upper limit, the upper limit being larger than the lower limit. In some embodiments, the lower limit may be about 0.01 Cp mL/mg, about 0.02 cP mL/mg, or about 0.04 cP mL/mg. In some embodiments, the upper limit may be about 0.05 cP mL/mg, about 0.1 cP mL/mg, about 0.5 cP mg/mL, about 0.6 cP mg/mL, about 0.8 cP mg/mL, about 1.0 cP mL/mg, about 1.5 cp mL/mg, about 2.0 cP mL/mg, about 3.0 cP mL/mg, or about 5.0 cP mL/mg. In some embodiments, the range may be about 0.01 cP mg/mL to about 5.0 cP mg/mL. In some embodiments, the range may be about 0.01 cP mg/mL to about 3.0 cP mg/mL. In some embodiments, the range may be about 0.01 cP mg/mL to about 2.0 cP mg/mL. In some embodiments, the range may be about 0.01 cP mL/mg to about 1.5 cP mL/mg. In some embodiments, the range may be about 0.01 cP mL/mg to about 1.0 cP mL/mg. In some embodiments, the range may be about 0.02 cP mg/mL to about 5.0 cP mg/mL. In some embodiments, the range may be about 0.02 cP mg/mL to about 3.0 cP mg/mL. In some embodiments, the range may be about 0.02 cP mg/mL to about 2.0 cP mg/mL. In some embodiments, the range may be about 0.02 cP mL/mg to about 1.5 cP mL/mg. In some embodiments, the range may be about 0.02 cP mL/mg to about 1.0 cP mL/mg. In some embodiments, the range may be about 0.02 cP mL/mg to about 0.5 cP mL/mg. In some embodiments, the range may be about 0.02 cP mL/mg to about 0.1 cP mL/mg. In some embodiments, the range may be about 0.02 cP mL/mg to about 0.05 cP mL/mg.

In some embodiments, a viscosity-reducing agent may also affect pharmacokinetics when a protein agent formulation is administered subcutaneously or intramuscularly, when compared to administration through an intravenous route, especially with regard to CMAX. As used herein, "CMAX" refers to the maximum plasma concentration after a dose administration, and before administration of a subsequent dose. For example, the CMAX after SC or IM injection may be at least 10% to at least 20% less than the CMAX of an approximately equivalent pharmaceutically effective intravenously administered dose.

In some embodiments, a protein agent formulation with a viscosity-reducing agent does not cause any significant signs of toxicity and/or no irreversible signs of toxicity when administered via subcutaneous, intramuscular, or other types of injection. As used herein, "significant signs of toxicity" includes intoxication, lethargy, and behavioral modifications such as those that occur with damage to the central nervous system, infertility, signs of serious cardiotoxicity such as cardiac arrhythmia, cardiomyopathy, myocardial infarctions, and cardiac or congestive heart failure, kidney failure, liver failure, difficulty breathing, and death.

Osmolarity

In some embodiments, a liquid protein agent formulation has a physiological osmolarity that may be, for example, at least 200 mOsm/L, 220 mOsm/L, 240 mOsm/L, 260 mOsm/L, 280 mOsm/L, 300 mOsm/L, or more. In some embodiments, the amount may be within a range bounded by a lower limit and an upper limit, the upper limit being larger than the lower limit. In some embodiments, the lower limit may be about 200 mOsm/L, about 220 mOsm/L, about 240 mOsm/L, about 260 mOsm/L, about 280 mOsm/L, or about 300 mOsm/L. In some embodiments, the upper limit may be about 310 mOsm/L, about 320 mOsm/L, about 340 mOsm/L, about 360 mOsm/L, about 380 mOsm/L, about 400 mOsm/L, about 425 mOsm/L, about 450 mOsm/L, about 475 mOsm/L, about 500 mOsm/L, about 1000 mOsm/L, or about 2000 mOsm/L. In some embodiments, the range may be between 200 mOsm/L to about 2000 mOsm/L. In some embodiments, the range may be between 200 mOsm/L to about 1000 mOsm/L. In some embodiments, the range may be between 200 mOsm/L to about 500 mOsm/L. In some embodiments, the range may be between 200 mOsm/L to about 400 mOsm/L. In some embodiments, the range may be between 200 mOsm/L to about 380 mOsm/L. In some embodiments, the range may be about 280 mOsm/L to about 310 mOsm/L.

Osmolality and Tonicity

In some embodiments, a liquid protein agent formulation is essentially isotonic to human blood. In some embodiments, a liquid protein agent formulation can be hypertonic.

A tonicity modifier may also be included in a protein agent formulation as described herein. A tonicity modifier is understood to be molecule that contributes to an osmolality of a solution. Osmolality of a pharmaceutical composition is regulated to maximize the stability of an active ingredient, or, in this case, of a protein agent, and also to minimize discomfort to a patient upon administration of a therapeutic protein agent formulation. Serum is approximately 300±50 milliosmolals per kilogram (mOsm/kg). It is generally preferred that a pharmaceutical composition be isotonic with serum, i.e., having the same or similar osmolality as serum, which is achieved by an addition of a tonicity modifier. Thus, it is contemplated that osmolality of a protein agent formulation will range from about 180 to about 420 mOsm/kg, however, it is to be understood that osmolality can register either higher or lower than the range as specific conditions require. In some embodiments, a tonicity modifier is or comprises one or more of amino acids (e.g., arginine, cysteine, histidine and glycine), salts (e.g., sodium chloride, potassium chloride and sodium citrate) and/or saccharides (e.g., sucrose, glucose, dextrose, glycerin, sorbitol, trehalose, and mannitol). A tonicity modifier can be added to a protein agent formulation in an amount that may be, for example, at least about 1 mM, 10 mM, 15 mM, 25 mM, 50 mM, 75 mM, 100 mM, 200 mM, 500 mM, 1000 mM, or more. In some embodiments, the amount may be within a range bounded by a lower limit and an upper limit, the upper limit being larger than the lower limit. In some embodiments, the lower limit may be about 1 mM, about 10 mM, about 15 mM, about 25 mM, or about 50 mM. In some embodiments, the upper limit may be about 75 mM, about 100 mM, about 150 mM, about 200 mM, about 300 mM, about 400 mM, about 500 mM, about 600 mM, about 700 mM, about 800 mM, about 900 mM, or about 1000 mM. In some embodiments, the range may be about 1 mM to about 1000 mM. In some embodiments, the range may be about 10 mM to about 200 mM. In some embodiments, a tonicity modifier is sodium chloride within a concentration range of 0 mM to 200 mM.

In some embodiments, a liquid formulation has a physiological osmolality that is hypotonic or isotonic to human blood, for example, about 150 mOsm/kg, 200 mOsm/kg, 225 mOsm/kg, 250 mOsm/kg, 275 mOsm/kg, or 300 mOsm/kg. In some embodiments the amount may be within a range bounded by a lower limit and an upper limit, the upper limit being larger than the lower limit. In some embodiments, the lower limit may be about 150 mOsm/kg, 200 mOsm, about 225 mOsm/kg, or about 250 mOsm/kg. In some embodiments, the upper limit may be about 275 mOsm/kg, or about 300 mOsm/kg. In some embodiments, the range may be about 150 mOsm/kg to about 300 mOsm/kg. In some embodiments the range may be about 200 mOsm/kg to about 300 mOsm/kg. In some embodiments, the range may be about 200 mOsm/kg to about 250 mOsm/kg. In some embodiments the range may be about 250 mOsm/kg to about 300 mOsm/kg.

In some embodiments, a liquid formulation has an osmolality that is hypertonic to human blood, for example, about 350 mOsm/kg, 400 mOsm/kg, 450 mOsm/kg, 500 mOsm/kg, 550 mOsm/kg, 600 mOsm/kg, 650 mOsm/kg, 700 mOsm/kg, 750 mOsm/kg, 800 mOsm/kg, 850 mOsm/kg, 900 mOsm/kg, 950 mOsm/kg, 1000 mOsm/kg, or more. In some embodiments the amount may be within a range bounded by a lower limit and an upper limit, the upper limit being larger than the lower limit. In some embodiments, the lower limit may be about 350 mOsm/kg, about 400 mOsm/kg, about 500 mOsm/kg, about 550 mOsm/kg, about 600 mOsm/kg, or about 650 mOsm/kg. In some embodiments, the upper limit may be about 700 mOsm/kg, about 750 mOsm/kg, about 800 mOsm/kg, about 850 mOsm/kg, about 900 mOsm/kg, about 950 mOsm/kg, or about 1000 mOsm/kg. In some embodiments, the range may be about 350 mOsm/kg to about 1000 mOsm/kg. In some embodiments, the range may be about 400 mOsm/kg to about 1000 mOsm/kg. In some embodiments, the range may be about 400 mOsm/kg to about 800 mOsm/kg. In some embodiments, the range may be about 400 mOsm/kg to about 600 mOsm/kg.

pH

In some embodiments, the pH of a high concentration, low viscosity protein agent pharmaceutical formulation may be, for example, at least about 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0 or higher. In some embodiments, the pH may be within a range bounded by a lower limit and an upper limit, the upper limit being larger than the lower limit. In some embodiments, the lower limit may be about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, or about 6.0. In some embodiments, the upper limit may be about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, or about 10.0. In some embodiments, the range may be about 3.0 to about 10.0. In some embodiments, the range may be about 4.0 to about 10.0. In some embodiments, the range may be about 4.0 to about 10.0. In some embodiments, the range may be about 5.0 to about 10.0. In some embodiments, the range may be about 5.0 to 8.0. In some embodiments, the range may be about 5.8 to 7.4. In some embodiments, the range may be about 6.2 to 7.0. It is to be understood that a pH can be adjusted as necessary to maximize stability and solubility of a protein agent in a particular formulation and as such, a pH reading outside of physiological ranges, yet tolerable to a patient, are within the scope of the invention.

Stability

Those of skill in the art will appreciate that protein agent stability is one of the most important obstacles to the successful preparation of polymer microparticulate delivery systems that control the release of a protein agent. The stability of high concentration protein agents, such as a therapeutic protein agent (e.g whole antibodies or antibody fragments) encapsulated in polymeric carriers may be challenged at three separate stages: 1) manufacture of a therapeutic protein agent composition, 2) protein agent release from the resulting composition and 3) in vivo stability after protein agent release. During preparation of microparticles or microspheres containing a soluble or amorphous protein agent, the use of lyophilization is especially detrimental to protein agent stability. Subsequently, a released protein agent is susceptible to moisture-induced aggregation, thus resulting in permanent inactivation. In some embodiments, a viscosity-reducing agent and other excipients used for the preparation of a high protein agent concentration formulation reduce aggregation and minimize protein-protein interactions.

In order to achieve high protein agent stability in a high concentration, low-viscosity protein agent formulation, it is necessary to restrict the mobility of individual therapeutic protein agents, which is best achieved in the lyophilized solid state in the presence of excipients.

Bioavailability

Bioavailability may be affected by using a low-viscosity formulation of a therapeutic protein agent. The overall bioavailability can be increased for SC or IM injections as compared to the otherwise same formulation without a viscosity-reducing agent.

In some embodiments, when administered, the percent bioavailability of a protein agent may be at least 1.1 to 1.2 times the percent bioavailability of the otherwise same formulation without a viscosity-reducing agent. In certain terms, the area under the curve, (AUC) value may be at least 10% to 20% or larger than the same value computed for the otherwise same formulation but without a viscosity-reducing agent.

Pharmaceutical Compositions

Formulations for Therapeutic Administration

In some embodiments, a provided formulation may be a pharmaceutical formulation in that all of its components are pharmaceutically acceptable.

In some embodiments, a pharmaceutical formulation may be formulated and/or packaged for a particular route of administration.

In some embodiments, a provided pharmaceutical formulation may be formulated and/or packaged for parenteral administration.

In some embodiments, the route of administration of a protein agent formulation is subcutaneous (SC) and/or intramuscular (IM) injection.

In some embodiments, a therapeutic protein agent is administered in the form of a physiologically acceptable formulation (also referred to herein as a composition, a pharmaceutical composition, or as a pharmaceutical formulation) comprising a therapeutic protein agent that is formulated with one or more physiologically acceptable carriers, excipients, or diluents. Such carriers, excipients, or diluents are nontoxic to recipients at the dosages and concentrations employed. In some embodiments, the preparation of such compositions entails combining a therapeutic protein agent with one or more additives that can include buffers, antioxidants (e.g. ascorbic acid), low molecular weight polypeptides (e.g. those having fewer than 10 amino acids), amino acids (e.g. Leucine, Proline, Alanine, Valine, Glycine, Serine, Asparagine, Glutamine, Aspartic acid, Glutamic acid, Methionine, Tryotophan, Phenylalanine, Isoleucine, Threonine, Cysteine, Tyrosine, Histidine, Lysine and Arginine), carbohydrates (e.g. glucose, sucrose or dextrins), chelating agents (e.g. EDTA), glutathione and combinations thereof. In some embodiments, in a liquid formulation, neutral buffered saline or saline mixed with nonspecific serum albumin are exemplary appropriate diluents. In accordance with appropriate industry standards, preservatives (e.g. benzyl alcohol) may also be added to a protein agent formulation. Further examples of components that may be employed in a pharmaceutical formulation are presented in Remington's Pharmaceutical Sciences, $16^{th}$ Ed., Mack Publishing Company, Easton, Pa., 1980, and in the Handbook of Pharmaceutical Excipients, published jointly by the American Pharmaceutical Association and the Pharmaceutical Society of Great Britain.

In some embodiments, a protein agent formulation is prepared in a bulk formulations and, as such, components of a pharmaceutical formulation are adjusted so that they are higher than would be required for administration, and are later diluted appropriately with a pharmaceutically acceptable diuent prior to administration.

A protein agent formulation can be formulated as lyophilized crystalline or amorphous powder formulation, a form suitable for storage and handling, and in a form suitable for inhalation or pulmonary administration, for example in the form of powders made for the preparation of aerosol formulations. In some embodiments, a protein agent can be formulated in a slurry of crystals or precipitates. In some embodiments, a therapeutic protein agent is used to prepare a liquid formulation, such as an aqueous formulation or a non-aqueous formulation, for therapeutic administration.

In some embodiments, a high concentration protein agent formulation is suitable for parenteral administration, e.g. is sterile, has endotoxin levels acceptable for parenteral administration, e.g. <0.25 EU/mL or 0.008 EU/mg, and comprises a pharmaceutically acceptable excipient.

Aqueous Liquid Formulations

In some embodiments, a therapeutic protein agent formulation is an aqueous formulation that allows for stable, long-term storage. These formulations are useful, in part, because they are more convenient for the patient to use, as these formulations do not require any extra steps such as rehydrating. As used herein, a "solution" or "liquid formulation" is meant to mean a liquid preparation that contains one or more chemical substances dissolved in a suitable solvent or mixture of mutually miscible solvents. Reconstitution is the dissolution of lyophilized therapeutic protein agent formulations or compositions in appropriate buffers or pharmaceutical formulations.

Lyophilized Formulations

A lyophilized therapeutic protein formulation includes a therapeutic protein agent that has been dried and is present as particles in, for example, powder form. In the present context the expression "powder" refers to a collection of essentially dry particles, i.e. the moisture content being at least below about 10% by weight, 6% by weight, 4% by weight, or lower. In some embodiments, the amount may be within a range bounded by a lower limit and an upper limit, the upper limit being larger than the lower limit. In some embodiments, the lower limit may be about 0.1%, about 0.5%, about 1%, about 1.5%, about 2%, about 2.5%, about 3%, about 3.5%, or about 4% by weight. In some embodiments, the upper limit may be about 4.5%, about 5%, about 5.5%, about 6%, about 7%, about 8%, about 9%, or about 10% by weight. In some embodiments, the range of moisture content after lyophilization may be about 0.1% to about 10% by weight. In some embodiments, the range of moisture content after lyophilization may be about 0.1% to about 8% by weight. In some embodiments, the range of moisture content after lyophilization may be about 0.1% to about 6% by weight. In some embodiments, the range of moisture content after lyophilization may be about 0.1% to about 4% by weight. In some embodiments, the range of moisture content after lyophilization may be about 0.1% to about 2.5% by weight. In some embodiments, the range of moisture content after lyophilization may be about 0.1% to about 2% by weight. In some embodiments, the range of moisture content after lyophilization may be about 0.1% to about 1.5% by weight. In some embodiments, the range of moisture content after lyophilization may be about 0.1% to about 1% by weight. In some embodiments, the range of moisture content after lyophilization may be about 0.1% to about 0.5% by weight.

A therapeutic protein agent powder can be optionally combined with carriers or surfactants. A suitable carrier agent is can include carbohydrates (e.g. monosaccharides such as fructose, galactose, glucose, and sorbose), disaccharides (e.g. lactose and trehalose), polysaccharides (e.g. raffinose, maltodextrins, and dextrans), alditols (e.g., mannitol, and xylitol), inorganic salts (e.g. sodium chloride), organic salts (e.g. sodium citrate and sodium ascorbate), and combinations therein. In some embodiments, a carrier is selected from the group consisting of trehalose, raffinose, mannitol, sorbitol, xylitol, inositol, sucrose, sodium chloride, sodium citrate, and combinations thereof. In some embodiments, a surfactant is selected from the group consisting of salts of fatty acids, bile salts and phospholipids. Fatty acids salts include salts of $C_{10-14}$ fatty acids, such as sodium caprate, sodium laurate, and sodium myristate. Bile salts include salts of ursodeoxycholate, taurocholate, glycocholate, taurodihydrofusidate, and combinations thereof. In some embodiments, a surfactant is a salt of taurocholate, such as sodium taurocholate. In some embodiments, a phospholipid that can be used as a surfactant includes lysophosphatidylcholine. The molar ratio of a therapeutic protein agent to a carrier/surfactant in a powder formulation may be, for example, 1:0.01, 1:0.05, 1:0.1, 1:0.5, 1:1, 1:3, 1:5, 1:7, 1:9; 0.01:1, 0.05:1, 0.1:1, 0.5:1, 1:1, 3:1, 5:1, 7:1, or 9:1. In some embodiments, the amount may be within a range bounded by a lower limit and an upper limit, the upper limit being larger than the lower limit. In some embodiments, the lower limit is about 0.01:1, about 0.05:1, about 0.1:1, about 0.5:1, about 1:3, about 1:5, about 1:7, or about 1:9. In some embodiments, the upper limit is about 1:1, about 1:0.5, about 3:1, about 5:1, about 7:1, about 9:1, or about 1:0.1 or about 0.05:1. In some embodiments, the range may be about 9:1 to about 1:9. In some embodiments, the range may be about 5:1 to about 1:5. In some embodiments, the range may be about 3:1 to about 1:3. In some embodiments, the range may be about 0.5:1 to about 1:0.5. In some embodiments, the range may be about 0.05:1 to about 1:0.05.

Therapeutic Protein Agent Concentration in a Provided Formulation

In some embodiments, a therapeutic protein agent in a formulation is present at a concentration that may be, for example, of at least about 50 mg/mL, 51 mg/mL, 52 mg/mL, 53 mg/mL, 54 mg/mL, 55 mg/mL, 56 mg/mL, 57 mg/mL, 58 mg/mL, 59 mg/mL, 60 mg/mL, 61 mg/mL, 62 mg/mL, 63 mg/mL, 64 mg/mL, 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, 90 mg/mL, 91 mg/mL, 92 mg/mL, 93 mg/mL, 94 mg/mL, 95 mg/mL, 96 mg/mL, 97 mg/mL, 98 mg/mL, 99 mg/mL, 100 mg/mL, 101 mg/mL, 102 mg/mL, 103 mg/mL, 104 mg/mL, 105 mg/mL, 106 mg/mL, 107 mg/mL, 108 mg/mL, 109 mg/mL, 110 mg/mL, 111 mg/mL, 112 mg/mL, 113 mg/mL, 114 mg/mL, 115 mg/mL, 116 mg/mL, 117 mg/mL, 118 mg/mL, 119 mg/mL, 120 mg/mL, 121 mg/mL, 122 mg/mL, 123 mg/mL, 124 mg/mL, 125 mg/mL, 126 mg/mL, 127 mg/mL, 128 mg/mL, 129 mg/mL, 130 mg/mL, 131 mg/mL, 132 mg/mL, 133 mg/mL, 134 mg/mL, 135 mg/mL, 136 mg/mL, 137 mg/mL, 138 mg/mL, 139 mg/mL, 140 mg/mL, 141 mg/mL, 142 mg/mL, 143 mg/mL, 144 mg/mL, 145 mg/mL, 146 mg/mL, 147 mg/mL, 148 mg/mL, 149 mg/mL, 150 mg/mL, 151 mg/mL, 152 mg/mL, 153 mg/mL, 154 mg/mL, 155 mg/mL, 156 mg/mL, 157 mg/mL, 158 mg/mL, 159 mg/mL, 160 mg/mL, 161 mg/mL, 162 mg/mL, 163 mg/mL, 164 mg/mL, 165 mg/mL, 166 mg/mL, 167 mg/mL, 168 mg/mL, 169 mg/mL, 170 mg/mL, 171 mg/mL, 172 mg/mL, 173 mg/mL, 174 mg/mL, 175 mg/mL, 176 mg/mL, 177 mg/mL, 178 mg/mL, 179 mg/mL, 180 mg/mL, 181 mg/mL, 182 mg/mL, 183 mg/mL, 184 mg/mL, 185 mg/mL, 186 mg/mL, 187 mg/mL, 188 mg/mL, 189 mg/mL, 190 mg/mL, 191 mg/mL, 192 mg/mL, 193 mg/mL, 194 mg/mL, 195 mg/mL, 196 mg/mL, 197 mg/mL, 198 mg/mL, 199 mg/mL, 200 mg/mL, or more. In some embodiments, the amount may be within a range bounded by a lower limit and an upper limit, the upper limit being larger than the lower limit. In some embodiments, the lower limit may be about about 100 mg/mL, about 101 mg/mL, about 102 mg/mL, about 103 mg/mL, about 104 mg/mL, about 105 mg/mL, about 106 mg/mL, about 107 mg/mL, about 108 mg/mL, about 109 mg/mL, about 110 mg/mL, about 111 mg/mL, about 112 mg/mL, about 113 mg/mL, about 114 mg/mL, about 115 mg/mL, about 116 mg/mL, about 117 mg/mL, about 118 mg/mL, about 119 mg/mL, about 120 mg/mL, about 121 mg/mL, about 122 mg/mL, about 123 mg/mL, about 124 mg/mL, about 125 mg/mL, about 126 mg/mL, about 127 mg/mL, about 128 mg/mL, about 129 mg/mL, about 130 mg/mL, about 131 mg/mL, about 132 mg/mL, about 133 mg/mL, about 134 mg/mL, about 135 mg/mL, about 136 mg/mL, about 137 mg/mL, about 138 mg/mL, about 139 mg/mL, about 140 mg/mL, about 141 mg/mL, about 142 mg/mL, about 143 mg/mL, about 144 mg/mL, about 145 mg/mL, about 146 mg/mL, about 147 mg/mL, about 148 mg/mL, about 149 mg/mL, about 150 mg/mL, about 151 mg/mL, about 152 mg/mL, about 153 mg/mL, about 154 mg/mL, about 155 mg/mL, about 156 mg/mL, about 157 mg/mL, about 158 mg/mL, about 159 mg/mL, about 160 mg/mL, about 161 mg/mL, about 162 mg/mL, about 163 mg/mL, about 164 mg/mL, about 165 mg/mL, about 166 mg/mL, about 167 mg/mL, about 168 mg/mL, about 169 mg/mL, about 170 mg/mL, about 171 mg/mL, about 172 mg/mL, about 173 mg/mL, about 174 mg/mL, about 175 mg/mL, about 176 mg/mL, about 177 mg/mL, about 178 mg/mL, about 179 mg/mL, about 180 mg/mL, about 181 mg/mL, about 182 mg/mL, about 183 mg/mL, about 184 mg/mL, about 185 mg/mL, about 186 mg/mL, about 187 mg/mL, about 188 mg/mL, about 189 mg/mL, about 190 mg/mL, about 191 mg/mL, about 192 mg/mL, about 193 mg/mL, about 194 mg/mL, about 195 mg/mL, about 196 mg/mL, about 197 mg/mL, about 198 mg/mL, about 199 mg/mL, or about 200 mg/mL. In some embodiments, the upper limit may be about 250 mg/mL, about 300 mg/mL, about 350 mg/mL, about 400 mg/mL, about 450 mg/mL, about 500 mg/mL, about 1000 mg/mL, or about 2000 mg/mL. In some embodiments, the range may be about 50 mg/mL to about 2000 mg/mL. In some embodiments, the range may be about 50 mg/mL to about 1000 mg/mL. In some embodiments, the range may be about 50 mg/mL to about 500 mg/mL. In some embodiments, the range may be about 100 mg/mL to about 500 mg/mL. In some embodiments, the range may be about 100 mg/mL to about 400 mg/mL. In some embodiments, the range may be about 100 mg/mL to about 350 mg/mL. In some embodiments, the range may be about 100 mg/mL to about 300 mg/mL. In some embodiments, the range may be about 100 mg/mL to about 250 mg/mL. In some embodiments, the range may be about 100 mg/mL to about 200 mg/mL.

Manufacturing

Production and/or Purification of Protein Agent

A protein agent that is to be formulated, may be produced by any known technique, including by culturing cells transformed or transfected with a vector containing one or more nucleic acid sequences encoding a protein agent, as is well known in the art, or through synthetic techniques (such as recombinant techniques and peptide synthesis or a combination of these techniques), or may be isolated from an endogenous source of a protein agent.

Purification of a protein agent to be formulated may be conducted by any suitable technique known in the art that can include ethanol, polyethylene glycol or ammonium sulfate precipitation, ion-exchange chromatography, affinity chromatography, adsorption chromatography, hydrophobic interaction chromatography, size-exclusion chromatography, dialysis, chromato-focusing, other HPLC techniques to remove contaminants, metal chelating columns to bind epitope-tagged forms, and ultrafiltration/diafiltration (non-limiting examples include centrifugal filtration and tangential flow filtration).

A viscosity-reducing agent may be used to assist in a protein agent purification and concentration. A viscosity-reducing agent may be included at viscosity-reducing concentration, that may be, for example, 0.005 M, 0.01 M, 0.1 M, 0.5M, or 1.0 M. In some embodiments, the amount may be within a range bounded by a lower limit and an upper limit, the upper limit being larger than the lower limit. In some embodiments, the lower limit may be about 0.005 M, about 0.01 M, or about 0.1 M. In some embodiments, the upper limit may be about 0.15 M, about 0.20 M, about 0.25 M, about 0.30 M, about 0.5 M, or about 1.0 M. In some embodiments, the range may be about 0.005 M to about 1.0 M. In some embodiments, the range may be about 0.005 M to about 0.5 M. In some embodiments, the range may be about 0.005 M to about 0.3 M. In some embodiments, the range may be about 0.01 M to about 0.15 M. In some embodiments, the range may be about 0.03 M to about 0.10 M. This allows a formulation of a pharmaceutically active protein agent to be purified and/or concentrated at a higher concentration using common methods known to those skilled in the art that can include tangential flow filtration, centrifugal concentration, and, after buffer exchange, using dialysis UF/DF containing viscosity-reducing agents, or even without buffer exchange with viscosity-reducing agents.

In some embodiments, a low-viscosity, high concentration formulation of a therapeutic protein agent consisting of whole antibodies, single-chain Fv antibody fragments, Fab antibody fragments, or a formulation or composition comprising such a protein agent is prepared by the following process:

First, a therapeutic protein agent is buffer exchanged with pharmaceutically acceptable buffers or water. Next, excipients or ingredients selected the group consisting of sugars, sugar alcohols, amino acids, vitamins, viscosity lowering agents, wetting or solubilizing agents, buffer salts, emulsifying agents, antimicrobial agents, chelating agents, antioxidants, and combinations thereof are added directly to a protein agent solution. After adding, a protein agent solution ais incubated with excipients for a minimum of 1 hour to a maximum of 24 hours. Excipient concentrations are typically between about 0.01 and about 10% (w/v). Other ingredient concentrations are between about 0.01 and about 90% (w/v). Protein agent concentrations are between about 0.01 and about 99% (w/v).

A buffer exchanged protein agent solution containing excipients and a viscosity-reducing agent is then concentrated using the TFF system. Alternatively, a protein agent solution containing a viscosity-reducing agents and other excipients can be dried by air drying, spray drying, lyophilization or vacuum drying. Drying is carried out for a minimum of about 1 hour to a maximum of about 72 hours after incubation, until the moisture content of the final product is below about 5% to about 10% by weight. Finally, micromizing (reducing the size) of a cake can be performed if necessary.

Preparation of a Viscosity-Reducing Protein Agent Formulation

In some embodiments, when preparing a low viscosity, high concentration formulation of a protein agent, a viscosity-reducing agent such as amino acids and/or vitamins, or enhancers such as surfactants, are not added during the buffer exchange step. Excipients, ingredients, or a viscosity-reducing agent is added to a low concentration protein agent solution after buffer exchange, but before the concentration step, at a concentration that may be, for example, about 0.01%, 0.05%, 0.1%, 0.5%, 1%, 5%, 10%, 20%, 30%, 40%, 50%, 60% (w/v) or more. In some embodiments, the amount may be within a range bounded by a lower limit and an upper limit, the upper limit being larger than the lower limit. In some embodiments, the lower limit may be about 0.01%, about 0.05%, about 0.1%, about 0.5%, about 1%, or about 5% (w/v). In some embodiments, the upper limit may be about 10%, about 20%, about 300 about 40%, about 50%, or about 60%, (w/v). In some embodiments, the range may be about 0.01% to about 60% (w/v). In some embodiments, the range may be about 0.01% to about 50% (w/v). In some embodiments, the range may be about 0.05% to about 60% (w/v). In some embodiments, the range may be about 0.05% to about 50% (w/v). In some embodiments, the range may be about 0.1% to about 60% (w/v). In some embodiments, the range may be about 0.1% to about 50% (w/v). In some embodiments, the range may be about 0.5% to about 60% (w/v). In some embodiments, the range may be about 0.5% to about 50% (w/v). In some embodiments, the range may be about 1% to about 60% (w/v). In some embodiments, the range may be about 1% to about 50% (w/v). In some embodiments, the range may be about 1% to about 10% (w/v). In some embodiments, the range may be about 0.1% to about 25% (w/v). In some embodiments, the range may be about 0.1% to about 10% (w/v). Excipients, ingredients, or a viscosity-reducing agent are incubated with a therapeutic protein agent in buffer containing excipients for about 0.1 to about 3 hrs. Alternatively, incubation is carried out for about 0.1 to about 12 hrs, or, alternatively, incubation is carried out for about 0.1 to about 24 hrs.

Drying of Protein Agent and/or Protein Agent-Containing Viscosity-Reducing Formulations Disclosed herein are methods of reconstituting any of the foregoing powdered formulations comprising adding a sterile diluent to achieve a high protein concentration such as those described herein. In some embodiments, a protein agent and a viscosity-lowering agent is provided in a lyophilized dosage unit, ready for reconstitution with a sterile aqueous pharmaceutically acceptable vehicle, to yield a concentrated low-viscosity liquid protein agent formulation.

An advantage of the present invention is that a high concentration of therapeutic protein agent or a composition comprising a viscosity-reducing agent and a therapeutic protein agent can be dried by lyophilization. Lyophilization, or freeze-drying, allows water to be separated from a composition. A therapeutic protein agent or composition thereof is first frozen and then placed in a high vacuum. In a vacuum, the crystalline water sublimes, leaving behind solely a therapeutic protein agent or a composition thereof, and only tightly bound water molecules. Such processing further stabilizes a composition and allows for easier storage and transportation at typically encountered ambient temperatures. A lyophilized dosage unit is a lyophilized cake of a protein agent, a viscosity-reducing agent, and other excipients, to which water, saline or another pharmaceutically acceptable fluid can be added. By including a viscosity-reducing agent, a lyophilized dosage unit dissolves/reconstitutes faster than one without a viscosity-reducing agent.

Spray drying also allows water to be separated out from therapeutic high concentration protein agent formulations. It is highly suited for the continuous production of dry solids in either powder, granulate or agglomerate form from liquid feedstocks as solutions, emulsions, and pumpable suspensions. Spray drying involves the atomization of a liquid feedstock into a spray of droplets and contacting droplets with hot air in a drying chamber. Sprays are produced by either rotary (wheel) or nozzle atomizers. Relatively high temperatures are needed for spray drying operations, however, heat damage to products is generally only slight, because of an evaporative cooling effect during the critical drying period and because the subsequent time of exposure to high temperatures of the dry material may be very short. Powder is discharged continuously from the drying chamber. Operating conditions and dryer design are selected according to the drying characteristics of the product and the powder specification. Spray drying is an ideal process where the end product must comply with precise quality standards regarding particle size distribution, residual moisture content, bulk density and particle shape.

Drying of a protein agent or protein agent-containing formulation is especially desirable for a protein agent, which can be dispensed into a single dose sterile container ("ampule") or, alternatively, in any desired increment of a single dose. Ampules containing dispensed formulations can then be capped, batch frozen, and lyophilized under sterile conditions. Such sterile containers can be transported throughout the world and stored at ambient temperatures. Such a system is useful for providing sterile vaccines and therapeutic antibodies to remote and under-developed parts of the world. At the point of use, contents of an ampule is rehydrated with a sterile solvent or a buffer of choice and then dispensed to the patient. For such a preparation, minimal or no refrigeration is required.

Radiolabeling of Protein Agent

In further embodiments of this invention, therapeutic protein agents, specifically whole antibodies, scFv fragments of antibodies, or Fab fragments of antibodies, may be radiolabeled to be used in antibody radiation therapies. In such therapies, for example, radiolabeled anti-cancer antibodies, scFv fragments, Fab antibody fragments, or formulations or compositions comprising such therapeutic protein agents, can be delivered to the site of cancer. After delivery, a protein agent binds to targeted cancer antigens and consequently delivers radioisotopes directly to cancerous cells or tumors. The release of a protein agent may be timed according to this invention. Alternatively, when using crosslinked antibodies in radiation therapies, the crosslinkers themselves may be radiolabeled. In some embodiments, whole antibodies or antibody fragments that are crosslinked serve to target and deliver radioisotopes to cancerous cells. Radioisotopes are carried and released by the crosslinkers. In some embodiments, useful radiolabels can include 3H, 14C, 15N, 35S, 90Y, 99Tc, 111In, 125I, 131I. Practically, however, in vivo use in radiotherapies would limit a radiolabel to 131I, 90Y, or any other radiolabels defined by a short half-life. For example, the monoclonal antibody Rituximab (see Example 1) has been labeled with 90Yttrium (90Y), in order to be used for radioimmunotherapy in patients with non-Hodgkin's lymphomas.

Kits and Articles of Manufacture

Described herein are kits which comprise one or more of a protein agent formulation described herein, packaged in a manner which facilitates use for administration to subjects. In some embodiments, such kits include a formulation described herein (e.g., a composition comprising any therapeutic protein agent described therein), packaged in a container that can include a sealed bottle, vessel, single-use or multi-use vial, prefilled syringe, or prefilled injection device, optionally with a label affixed to a container or included in a package that describes use of compounds or compositions in practicing the method. In one aspect, compounds or compositions are packaged in unit dosage forms. Kits may further include devices suitable for administering compositions according to specific routes of administration. Preferably, kits contain labels that describe uses of a therapeutic protein agent described herein or a viscosity-reducing formulation described herein.

A high concentration, low-viscosity therapeutic protein agent solutions is useful in diagnostic methods and kits. For example, a high concentration formulation may be used in a kit for diagnosing the presence of a target antigen in samples from patients or other specimens. Such kits may comprise a container and, optionally, instructions for use. Protein agents in a kit may be labelled with a detectable label. Methods for detecting target antigens in a sample, such as blood, tumors, cells, or tissue samples, may be carried out by mixing a sample with a therapeutic protein agent according to this invention, and then determining whether a sample binds to an antibody or antibody fragment.

The present invention is also directed to an article of manufacture comprising a container which encompasses a formulation of the present invention. In some embodiments, such articles may include a single dose vial, multi-dose vial, syringe (e.g. heated, self-mixing, retracting, with or without an attached needle, pre-filled or empty), a bag, or any acceptable, sterile container for storing the contents of a pharmaceutically acceptable, high concentration, low viscosity protein agent formulation. In some embodiments, a container comprises a single dose of a therapeutic protein agent or antibody or fusion protein (e.g., about 100 mg to about 1000 mg of monoclonal antibody) as described herein.

In some embodiments, a container may hold an amount of a protein agent formulation that may be, for example, at least about 100 mg, 120 mg, 140 mg, or more of protein agent formulation, and would be suitable for administering a single dose of about 90 to 95% or more of protein agent formulation present in a container. In some embodiments, a container may hold an amount of a protein agent formulation that may be within a range bounded by a lower limit and an upper limit, the upper limit being larger than the lower limit. In some embodiments, the lower limit may be about 50 mg, about 100 mg, about 120 mg, about 140 mg, about 160 mg, about 180 mg, or about 200 mg. In some embodiments, the upper limit may be about 500 mg, about 1000 mg, about 1500 mg, about 2000 mg, about 5000 mg, or about 10000 mg. In some embodiments, the range may be about 50 mg to about 10000 mg. In some embodiments, the range may be about 50 mg to about 5000 mg. In some embodiments, the range may be about 50 mg to about 2000 mg. In some embodiments, the range may be about 100 mg to about 2000 mg. In some embodiments, the range may be about 100 mg to about 1800 mg. In some embodiments, the range may be about 100 mg to about 1600 mg. In some embodiments, the range may be about 100 mg to about 1400 mg. In some embodiments, the range may be about 100 mg to about 1200 mg. In some embodiments, the range may be about 100 mg to about 1000 mg. In some embodiments, the range may be about 100 mg to about 800 mg. In some embodiments, the range may be about 100 mg to about 600 mg. In some embodiments, the range may be about 100 mg to about 400 mg. In some embodiments, the range may be about 100 mg to about 200 mg.

In some embodiments, a container may be suitable for administering a single dose of a protein agent formulation that may be, for example, about 0.1, 0.5, 1, 2, 3, 4, 5 or 6 or more mg/kg body weight. In some embodiments, a container is suitable for administering an amount of a protein agent formulation that may be within a range bounded by a lower limit and an upper limit, the upper limit being larger than the lower limit. In some embodiments, the lower limit may be about 0.1, about 0.5, about 1, about 2, about 3, about 4, about 5, about 6, about 7, about 8, about 9, or about 10 mg/kg body weight. In some embodiments, the upper limit may be about 20 mg/kg, about 30 mg/kg, about 40 mg/kg, about 50 mg/kg, about 60 mg/kg, about 70 mg/kg or about 80 mg/kg body weight. In some embodiments, the range may be about 0.1 to about 80 mg/kg body weight. In some embodiments, the range may be about 0.5 to about 80 mg/kg body weight. In some embodiments, the range may be about 1 mg/kg to about 80 mg/kg body weight. In some embodiments, the range may be about 2 mg/kg to about 80 mg/kg body weight. In some embodiments, the range may be 4 mg/kg up to about 80 mg/kg body weight. In some embodiments, the range may be 6 mg/kg up to about 80 mg/kg body weight. In some embodiments, the range may be 8 mg/kg up to about 80 mg/kg body weight. In some embodiments, the range may be 10 mg/kg up to about 80 mg/kg body weight. In some embodiments, the range may be 20 mg/kg up to about 80 mg/kg body weight. In some embodiments, the range may be 30 mg/kg up to about 80 mg/kg body weight. In some embodiments, the range may be 40 mg/kg up to about 80 mg/kg body weight. In some embodiments, the range may be 50 mg/kg up to about 80 mg/kg body weight. In some embodiments, the range may be 60 mg/kg up to about 80 mg/kg body weight. In some embodiments, the range may be 70 mg/kg up to about 80 mg/kg body weight. In any of these embodiments, the container may comprise antibodies at high concentrations such as those described herein. In any of these embodiments, containers may comprise powdered formulations and may be for reconstituted in a volume of about 0.5-2 mL for SC and 0.5 to 5 mL for IM.

Administration

To date, a therapeutic proteins agent has generally been administered by frequent injection or infusion, due to a characteristic negligible oral bioavailability and a short plasma life. A high concentration, low-viscosity solution of a therapeutic protein has advantageously improved patient compliance and convenience. Furthermore, because of an increased bioavailability and an increased stability of a protein agent in a low-viscosity, high protein agent concentration formulation, more stable blood levels of an administered therapeutic protein agent can be achieved, potentially with lower dosages. Also, the slow and constant release capabilities afforded by the present invention advantageously permit reduced dosages, due to more efficient delivery of an active therapeutic protein agent. Significant cost savings may be achieved by using high concentration, low-viscosity therapeutic protein agents formulations described herein.

Dosing

A dosage regimen involved in a method for treating a condition described herein will be determined by an attending physician, taking into account various factors which modify the action of drugs, including age, condition, body weight, sex and diet of a patient, the severity of any infection, time of administration and other clinical factors. An appropriate dosage ("therapeutically effective amount") of protein agent, will depend on the condition to be treated, the severity and course of the disease or condition, whether a protein agent is administered for preventive or therapeutic purposes, previous therapy, a patient's clinical history and response to a protein agent, the type of protein agent used, and the discretion of an attending physician.

A viscosity-reducing agent may be used to prepare a dosage unit formulation suitable for reconstitution to make a liquid pharmaceutical formulation for subcutaneous or intramuscular injections. A dosage unit may contain a dry powder of one or more protein agents; one or more viscosity-reducing agents; and other excipients. Protein agents that are present in the dosage unit such that after reconstitution in a pharmaceutically acceptable solvent, a resulting formulation has a protein agent concentration that may be at least about 10 mg/mL, 50 mg/mL, 100 mg/mL, 150 mg/mL, 200 mg/mL, 250 mg/mL, 300 mg/mL, 350 mg/mL, 400 mg/mL, 450 mg/mL, 500 mg/mL or more. In some embodiments, the amount may be within a range bounded by a lower limit and an upper limit, the upper limit being larger than the lower limit. In some embodiments, the lower limit may be about 10 mg/mL, about 25 mg/mL, about 50 mg/mL, about 100 mg/mL, or about 150 mg/mL. In some embodiments, the upper limit may be about 200 mg/mL, about 300 mg/mL, about 400 mg/mL, about 500 mg/mL, about 1000 mg/mL, or about 2000 mg/mL. In some embodiments, the range may be about 10 mg/mL to about 2000 mg/mL. In some embodiments, the range may be about 10 mg/mL to about 1000 mg/mL. In some embodiments, the range may be about 10 mg/mL to about 500 mg/mL. In some embodiments, the range may be about 25 mg/mL to about 2000 mg/mL. In some embodiments, the range may be about 25 mg/mL to about 1000 mg/mL. In some embodiments, the range may be about 25 mg/mL to about 500 mg/mL. In some embodiments, the range may be about 50 mg/mL to about 2000 mg/mL. In some embodiments, the range may be about 50 mg/mL to about 1000 mg/mL. In some embodiments, the range may be about 50 mg/mL to about 500 mg/mL. In some embodiments, the range may be about 100 mg/mL to about 2000 mg/mL. In some embodiments, the range may be about 100 mg/mL to about 1000 mg/mL. In some embodiments, the range may be about 100 mg/mL to about 500 mg/mL. In some embodiments, the range may be about 150 mg/mL to about 2000 mg/mL. In some embodiments, the range may be about 150 mg/mL to about 1000 mg/mL. In some embodiments the range may be about 150 mg/mL to about 500 mg/mL. In some embodiments the range may be about 150 mg/mL to about 450 mg/mL. In some embodiments the range may be about 150 mg/mL to about 400 mg/mL. In some embodiments the range may be about 150 mg/mL to about 350 mg/mL. In some embodiments the range may be about 150 mg/mL to about 300 mg/mL.

In some embodiments, a reconstituted formulation may have an absolute viscosity that when measured at 25° C., may be, for example, about 100 cP, 75 cP, 50 cP, 45 cP, 40 cP, 35 cP, 30 cP, or lower. In some embodiments, the amount may be within a range bounded by a lower limit and an upper limit, the upper limit being larger than the lower limit. In some embodiments, when measured at 25° C., the lower limit may be about 1 cP, about 5 cP, about 10 cP, or about or 15 cP. In some embodiments, when measured at 25° C., the upper limit may be about 20 cP, about 25 cP, about 30 cP, about 35 cP, about 40 cP, about 45 cP, about 50 cP, about 75 cP, or about 100 cP. In some embodiments, when measured at 25° C., the range may be about 5 cP to about 100 cP. In some embodiments, when measured at 25° C., the range may be about 5 cP to about 75 cP. In some embodiments, when measured at 25° C., the range may be about 5 cP to about 50 cP. In some embodiments, when measured at 25° C., the range may be about 5 cP to about 40 cP. In some embodiments, when measured at 25° C., the range may be about 5 cP to about 35 cP. In some embodiments, when measured at 25° C., the range may be about 5 cP to about 30 cP. In some embodiments, when measured at 25° C., the range may be about 5 cP to about 25 cP. In some embodiments, when measured at 25° C., the range may be about 5 cP to about 20 cP. In some embodiments, when measured at 25° C., the range may be about 5 cP to about 15 cP. In some embodiments, when measured at 25° C., the range may be about 5 cP to about 10 cP.

In some embodiments, a dosage unit of a therapeutic protein agent may be, for example, at least 50 mg, 100 mg, 120 mg, 140 mg, 160 mg, 180 mg, 200 mg, 220 mg, 240 mg, 260 mg, 280 mg, 300 mg 350 mg, 400 mg, 500 mg, or more. In some embodiments, the amount may be within a range bounded by a lower limit and an upper limit, the upper limit being larger than the lower limit. In some embodiments, the lower limit may be about 50 mg, about 100 mg, about 120 mg, about 140 mg, about 160 mg, about 180 mg, about 200 mg, about 220 mg, about 240 mg, about 260 mg, about 280 mg, or about 300 mg. In some embodiments, the upper limit may be about 400 mg, about 500 mg, about 600 mg, about 700 mg, about 800 mg, about 900 mg, about 1000 mg, about 1500 mg, about 2000 mg, about 3000 mg, about 4000 mg, or about 5000 mg. In some embodiments, the range may be about 50 mg to about 5000 mg. In some embodiments, the range may be about 50 mg to about 4000 mg. In some embodiments, the range may be about 50 mg to about 3000 mg. In some embodiments, the range may be about 50 mg to about 2000 mg. In some embodiments, the range may be about 100 mg to about 2000 mg. In some embodiments, the range may be about 100 mg to about 1800 mg. In some embodiments, the range may be about 100 mg to about 1600 mg. In some embodiments, the range may be about 100 mg to about 1400 mg. In some embodiments, the range may be about 120 mg to about 1200 mg. In some embodiments, the range may be about 120 mg to about 1000 mg. In some embodiments, the range may be about 120 mg to about 800 mg. In some embodiments, the range may be about 120 mg to about 700 mg. In some embodiments, the range may be about 120 mg to about 480 mg. In some embodiments, the range may be about 120 mg to about 480 mg. In some embodiments, the range may be about 100 mg to about 480 mg. In some embodiments, the range may be about 1200 mg to about 480 mg. In some embodiments, the range may be about 140 mg to about 480 mg. In some embodiments, the range may be about 145 mg to about 480 mg. In some embodiments, the range may be about 150 mg to about 480 mg. In some embodiments, the range may be about 160 mg to about 480 mg. In some embodiments, the range may be about 170 mg to about 480 mg. In some embodiments, the range may be about 180 mg to about 480 mg. In some embodiments, the range may be about 190 mg to about 480 mg. In some embodiments, the range may be about 200 mg to about 480 mg. In some embodiments, the range may be about 210 mg to about 480 mg. In some embodiments, the range may be about 220 mg to about 480 mg. In some embodiments, the range may be about 230 mg to about 480 mg. In some embodiments, the range may be about 240 mg to about 480 mg. In some embodiments, the range may be about 250 mg to about 480 mg. In some embodiments, the range may be about 260 mg to about 480 mg. In some embodiments, the range may be about 270 mg to about 480 mg. In some embodiments, the range may be about 280 mg to about 480 mg. In some embodiments, the range may be about 290 mg to about 480 mg. In some embodiments, the range may be about 300 mg to about 480 mg. In some embodiments, the range may be about 310 mg to about 480 mg. In some embodiments, the range may be about 320 mg to about 480 mg. In some embodiments, the range may be about 330 mg to about 480 mg. In some embodiments, the range may be about 340 mg to about 480 mg. In some embodiments, the range may be about 350 mg to about 480 mg. In some embodiments, the range may be about 360 mg to about 480 mg. In some embodiments, the range may be about 370 mg to about 480 mg. In some embodiments, the range may be about 380 mg to about 480 mg. In some embodiments, the range may be about 390 mg to about 480 mg. In some embodiments, the range may be about 400 mg to about 480 mg. In some embodiments, the range may be about 410 mg to about 480 mg. In some embodiments, the range may be about 420 mg to about 480 mg. In some embodiments, the range may be about 430 mg to about 480 mg. In some embodiments, the range may be about 440 mg to about 480 mg. In some embodiments, the range may be about 450 mg to about 480 mg. In some embodiments, the range may be about 460 mg to about 480 mg. In some embodiments, the range may be about 470 mg to about 480 mg. In some embodiments, the range may be about 480 mg to about 490 mg. In some embodiments, the range may be about 490 mg to about 500 mg of a therapeutic protein, e.g., an antibody.

In some embodiments, amounts of a therapeutic protein agent, or formulations or compositions comprising a high concentration protein agent, which provides a single dosage, will vary depending upon a particular mode of administration, a specific high protein agent concentration preparation, formulation or composition, dose level and dose frequency. In some embodiments, a protein agent preparation can contain, for example, about 0.01%, 0.1%, 1%, 10%, 20%, 30%, 40% 50%, 60%, 70%, 80%, 90% or greater of protein agent (w/w). In some embodiments, the amount may be within a range bounded by a lower limit and an upper limit, the upper limit being larger than the lower limit. In some embodiments, the lower limit may be about 0.01%, about 0.1%, about 1%, about 10%, about 20%, or about 30% (w/w). In some embodiments, the upper limit may be about 40%, about 50%, about 60%, about 70%, about 80%, about 90, or about 99% (w/w). In some embodiments, the range may be about 0.01% to about 99%, (w/w). In some embodiments, the range may be about 0.1% to about 99% (w/w). In some embodiments, the range may be about 1% to about 99% (w/w). In some embodiments, the range may be about 10% to about 99% (w/w). In some embodiments, the range may be about 20% to about 99%, (w/w). In some embodiments, the range may be about 30% to about 99% (w/w). In some embodiments, the range may be about 40% to about 99% (w/w). In some embodiments, the range may be about 50% to about 99% (w/w). In some embodiments, the range may be about 60% to about 99% (w/w). In some embodiments, the range may be about 70% to about 99% (w/w). In some embodiments, the range may be about 80% to about 99% (w/w). In some embodiments, the range may be about 90% to about 99% (w/w). In some embodiments, the range may be about 95% to about 99% (w/w).

Doing frequencies of a high concentration, low viscosity protein agent may formulation may be reduced when administered to a patient at a higher protein agent concentration than otherwise similar formulations without a viscosity-reducing agents. For instance, a protein agent previously requiring once daily administration may now be administered once every two days, or every three days, or even less frequently when a protein agents is formulated with a viscosity-reducing agent. A protein agent which currently requires multiple administrations on the same day (either at the same time or at different times of the day) may be administered in fewer injections per day. In some instances, the frequency may be reduced to a single injection once per day. Also, a viscosity-reducing agent in a high protein agent concentration formulation may allow for greater flexibility in dosing including a decreased dosing frequency compared to a protein formulation without a viscosity-reducing agent. In some embodiments, a dosage of a protein agent formulation may be administered for example, at least once every two days, every three days, every five days, every 1 week, 2 weeks, 3 weeks, 4 weeks, 5 weeks, 6 weeks, 7 weeks, 8 weeks, 9 weeks, 10 weeks, 11 weeks, 12 weeks, or more. In some embodiments, the amount of time may be within a range bounded by a lower limit and an upper limit, the upper limit being larger than the lower limit. In some embodiments, the lower limit may be about two days, about three days, about five days, about 1 week, about 2 weeks, about 3 weeks, about 4 weeks, about 5 weeks, about 6 weeks, or about 7 weeks. In some embodiments, the upper limit may be about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, or about 52 weeks. In some embodiments, the range may be about two days to about 52 weeks. In some embodiments, the range may be about two days to about 26 weeks. In some embodiments, the range may be about two days to about 23 weeks. In some embodiments, the range may be about two days to about 22 weeks. In some embodiments, the range may be about two days to about 21 weeks. In some embodiments, the range may be about two days to about 19 weeks. In some embodiments, the range may be about two days to about 18 weeks. In some embodiments, the range may be about two days to about 17 weeks. In some embodiments, the range may be about two days to about 16 weeks. In some embodiments, the range may be about two days to about 15 weeks. In some embodiments, the range may be about two days to about 14 weeks. In some embodiments, the range may be about two days to about 13 weeks. In some embodiments, the range may be about two days to about 12 weeks. In some embodiments, the range may be about two days to about 11 weeks. In some embodiments, the range may be about two days to about 10 weeks. In some embodiments, the range may be about two days to about 9 weeks. In some embodiments, the range may be about two days to about 8 weeks. In some embodiments, the range may be about two days to about 7 weeks. In some embodiments, the range may be about two days to about 6 weeks. In some embodiments, the range may be about two days to about 5 weeks. In some embodiments, the range may be about two days to about 4 weeks. In some embodiments, the range may be about two days to about 3 weeks. In some embodiments, the range may be about two days to about 2 weeks. In some embodiments, the range may be about two days to about 1 week. In some embodiments, the range may be about two days to about five days. In some embodiments, the range may be about two days to about three days.

In some embodiments, a frequency of dosing will take into account pharmacokinetic parameters of a therapeutic protein agent. In some embodiments, a clinician will administer a formulation until a dosage is reached that achieves a desired effect. In some embodiments, a formulation can therefore be administered in an amount that may be, for example, at least as a single dose, two doses, three doses, four doses, or more. In some embodiments, the dose may be within a range bounded by a lower limit and an upper limit, the upper limit being larger than the lower limit. In some embodiments, the lower limit may be about one dose or about two doses. In some embodiments, the upper limit may be about 100 doses, about 200 doses, about 250 doses, about 500 doses, or about 1000 doses. In some embodiments, the range may be about one to about 1,000 doses. In some embodiments, the range may be about one to about 500 doses. In some embodiments, the range may be about one to about 250 doses. In some embodiments, the range may be about one to about 100 doses. In some embodiments, the range may be about one to about 50 doses. In some embodiments, the range may be about one to about 25 doses. In some embodiments, the range may be about one to about 10 doses. In some embodiments, the range may be about one to about 5 doses. In some embodiments, the range may be about one to about two doses.

In some embodiments, doses, which may or may not contain the same amount of desired molecules, may be distributed over time or as a continuous infusion via an implantation device or catheter. A formulation may also be delivered subcutaneously or intravenously with a standard needle and syringe. In addition, with respect to subcutaneous delivery, pen delivery devices as well as autoinjector delivery devices, have applications in delivering a pharmaceutical formulation of the present invention. Further refinement of an appropriate dosage is routinely made by those of ordinary skill in the art and is within the ambit of tasks routinely performed by them. In certain embodiments, an appropriate dosage can be ascertained through use of appropriate dose-response data, which can be obtained by methods that are well known to those of skill in the art.

In some embodiments, a formulation is generally administered parenterally, e.g. intravenously, subcutaneously, intramuscularly, or via aerosol (intrapulmonary or inhalational administration). In some embodiments, a formulation is administered intravenously by an initial bolus followed by a continuous infusion to maintain therapeutic circulating levels of drug product. In some embodiments, a formulation is administered as a one-time dose. Those of ordinary skill in the art will readily optimize effective dosages and administration regimens as determined by good medical practice and clinical condition of an individual patient. Frequency of dosing will depend on pharmacokinetic parameters of a protein agent and a chosen route of administration. An optimal pharmaceutical formulation will be determined by one skilled in the art depending upon a chosen route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference). Such a formulation may influence a physical state, stability, rate of in vivo release, and rate of in vivo clearance of an administered protein agent. Depending on route of administration, a suitable dose may be calculated according to body weight, body surface area or organ size. Further refinement of calculations necessary to determine an appropriate dosage for treatment involving protein agent formulations is routinely made by those of ordinary skill in the art without undue experimentation, especially in light of dosage information and assays disclosed herein, as well as pharmacokinetic data observed in human clinical trials. Appropriate dosages may be ascertained through use of established assays for determining blood level dosages in conjunction with appropriate dose-response data. Final dosage regimens will be determined by an attending physician, considering various factors which modify the action of drugs, e.g. a drug's specific activity, severity of damage and responsiveness of a patient, age, condition, body weight, sex and diet of a patient, severity of any infection, time of administration, and other clinical factors. As studies are conducted, further information will emerge regarding appropriate dosage levels and duration of treatment for various diseases and conditions.

Dosage of a high concentration protein agent formulation containing a viscosity-reducing agent is designed in such a way that injections cause no significant signs of irritation at a site of injection, and a primary irritation index is less than 3 when evaluated using a Draize scoring system. In some embodiments, injections cause macroscopically similar levels of irritation using a viscosity-reducing agent when compared to injections of equivalent volumes of saline solution. A high protein agent concentration, low-viscosity formulation can be administered causing no significant signs of irritation at a site of injection, as measured by a primary irritation index. In some embodiments, a primary irritation index may be, for example, less than 3, 2, 1 or lower when evaluated using a Draize scoring system. In some embodiments, the primary irritation index may be within a range bounded by a lower limit and an upper limit, the upper limit being larger than the lower limit. In some embodiments, the lower limit may be about 0, about 0.5, or about 1. In some embodiments, the upper limit may be about 2 or about 3. In some embodiments, the range may be about 0 to about 3. In some embodiments, the range may be about 0 to about 2. In some embodiments, the range may be about 0 to about 1. In some embodiments, the range may be about 0 to about 0.5.

In some embodiments, a low-viscosity protein agent formulation causes no significant irritation when administered in a frequency that may be, for example, not more than twice daily, once daily, twice weekly, once weekly, twice monthly, or once monthly. In some embodiments, a frequency may be within a range bounded by a lower limit and an upper limit, the upper limit being larger than the lower limit. In some embodiments, the lower limit is about twice daily, about once daily, about twice weekly, or about once weekly. In some embodiments, the upper limit is about twice monthly or about once every month. In some embodiments, the range may be about twice daily to about once monthly. In some embodiments, the range may be about once daily to about once monthly. In some embodiments, the range may be about twice weekly to about once monthly. In some embodiments, the range may be about one weekly to about once monthly. In some embodiments, the range may be about twice monthly to about once monthly.

In some embodiments, as used herein, "significant signs of irritation" includes erythema, redness, and/or swelling at a site of injection that may, for example, have a diameter of greater than about 2.5 cm, 5.0 cm, 10 cm or more necrosis at the site of injection. In some embodiments, the diameter may be within a range bounded by a lower limit and an upper limit, the upper limit being larger than the lower limit. In some embodiments, the lower limit may be about 0 cm, about 0.5 cm, about 1.0 cm, about 1.5 cm, or about 2.0 cm. In some embodiments, the upper limit may be about 5.0 cm, about 10.0 cm, about 20.0 cm, about 25.0 cm, about 50.0 cm, or about 100.0 cm. In some embodiments, the range may be about 0 cm to about 100 cm. In some embodiments, the range may be about 1.0 cm to about 100 cm. In some embodiments, the range may be about 2.0 cm to about 100 cm. In some embodiments, the range may be about 2.5 cm to about 100 cm. In some embodiments, the range may be about 5.0 cm to about 100 cm. In some embodiments, the range may be about 10 cm to about 100 cm. In some embodiments, the range may be about 20 cm to about 100 cm. In some embodiments, the range may be about 50 cm to about 100 cm. In some embodiments, the range may be about 75 cm to about 100 cm. Additional "significant signs of irritation" include exfoliative dermatitis at a site of injection, and severe pain that prevents daily activity and/or requires medical attention or hospitalization. In some embodiments, injections of a protein agent formulation cause macroscopically similar levels of irritation when compared to injections of equivalent volumes of a control saline solution.

A viscosity-reducing formulation can be provided as a solution or in a dosage unit form wherein a protein agent is lyophilized in one vial, with or without a viscosity-reducing agent and other excipients, and a solvent, with or without a viscosity-reducing agent and other excipients, is provided in a second vial. In some embodiments, a solvent is added to a protein agent shortly before or at the time of injection to ensure uniform mixing and dissolution.

According to this invention, any individual, including humans, animals and plants, may be treated in a pharmaceutically acceptable manner with a pharmaceutically effective amount of a therapeutic protein agent, or a formulation comprising thereof, for a period of time sufficient to treat a condition or conditions in an individual to whom the protein agent formulation is administered over some period of time. Alternatively, individuals may receive a prophylactically effective amount of therapeutic protein agent or a formulation thereof, which is effective to treat or prevent a condition or conditions in an individual to whom it is administered over some period of time.

Upon improvement of an individual's condition, maintenance doses of a therapeutic protein agent, including whole antibodies, single-chain Fv antibody fragments, Fab antibody fragments, or a formulation or composition comprising such a protein agent with a viscosity-reducing agent, may be administered, if necessary. Subsequently, a dosage or frequency of administration, or both, may be reduced as a function of symptoms, to a level at which an improved condition is retained. When a condition or conditions have been alleviated to a desired level, treatment should cease. An individuals may, however, require intermittent treatment on a long-term basis upon any recurrence of a condition, conditions, or symptoms thereof.

Effective modes of administration and accompanying dosing regimens of a therapeutic protein agent, or formulations or compositions comprising a high concentration of protein agent with low viscosity, will depend on a desired effect, previous therapy (if any), an individual's health status, status of a condition or conditions, response to a therapeutic protein agent formulations, and judgment of a treating physician or clinician. A therapeutic protein agent formulation may be administered in any dosage form acceptable for pharmaceuticals, immunotherapy, or veterinary preparations, at one time or over a series of treatments.

Enteral Routes of Administration

A low-viscosity protein agent formulation comprising a high concentration protein agent may be delivered to humans, animals, or plants at a desired site of delivery according to this invention. In some embodiments, such delivery may include use of devices, such as implant-capable devices, or may involve other microparticulate protein delivery systems. Such systems may allow for slow or controlled release of a protein agent in the subject.

In some embodiments, a protein agent may be formulated in the presence of plasticizers, which aim to enhance preservation of a native, biologically active, tertiary structure of a protein agent. In some embodiments, a plasticizer also creates reservoirs which can allow for slow release of active whole antibodies, or fragments thereof, to a subject where and when they are needed. A biologically active protein agent, including whole antibodies or fragments thereof, is subsequently released in a controlled manner over a period of time as determined by a particular encapsulation technique, polymer constitution, solubility, and presence and nature of any excipients used.

Formulations and compositions comprising a high concentration, low-viscosity protein agent in a polymeric delivery carrier may also comprise any conventional carrier or adjuvant used in vaccines, pharmaceuticals, personal care formulations and compositions, veterinary preparations, or oral enzyme supplementations. In some embodiments, a carrier ca include Freund's adjuvant, an ion exchanger, alumina, aluminum stearate, lecithin, buffer agents (e.g. phosphates), glycine, sorbic acid, potassium sorbate, partial glyceride mixtures of saturated vegetable fatty acids, water, salts or electrolytes (e.g. protamine sulfate), disodium hydrogen phosphate, sodium chloride, zinc salts, colloidal silica, magnesium, trisilicate, cellulose-based substances, polyethylene glycol, and combinations thereof. In some embodiments, an adjuvant can include sodium carboxymethylcellulose, polyacrylates, polyoxyethylene-polyoxypropylene-block polymers, polyethylene glycol, wood wax alcohols, and combinations thereof.

In some embodiments, a high concentration, low-viscosity therapeutic protein agents may be combined with conventional materials used for controlled release administration, including pharmaceutical controlled release administration. In some embodiments, a material for controlled release administration can include coatings, shells and films (e.g. enteric coatings), polymer coatings and films, and combinations thereof.

According to this invention, any individual, including humans, animals and plants, may be treated in a pharmaceutically acceptable manner with a pharmaceutically effective amount of a low-viscosity, high concentration protein agent formulation, for a period of time sufficient to treat a condition in an individual to whom it is administered. In some embodiments, an individual may receive a prophylactically effective amount of a high concentration, low-viscosity protein agent formulation, which is effective to prevent a condition in an individual to whom it is administered over some period of time.

In some embodiments, a pharmaceutical, veterinary, or prophylactic preparation comprising a high concentration, low viscosity therapeutic protein agent formulation, may also be administered by a vehicle that can include tablets, liposomes, granules, spheres, microparticles, microspheres, capsules, and combinations thereof.

A high concentration, low-viscosity therapeutic protein agent formulation may be administered alone, as part of a pharmaceutical, personal care or veterinary preparation, or as part of a prophylactic preparation, with or without an adjuvant. In some embodiments, a protein agent formulation may be administered by a parenteral or an enteral route. In some embodiments, a protein agent formulation may be administered via a route that can include oral, pulmonary, nasal, aural, anal, dermal, ocular, intravenous, intramuscular, intra-arterial, intraperitoneal, mucosal, sublingual, subcutaneous, transdermal, topical or intracranial routes, or into the buccal cavity, and in combinations thereof.

In some embodiments, in either pharmaceutical, personal care or veterinary applications, a therapeutic protein agent formulation may be topically administered to any epithelial surface. In some embodiments, an epithelial surface can include oral, ocular, aural, anal, nasal surfaces, and combinations thereof, which may be treated, protected, repaired or detoxified by application of a therapeutic protein agent formulations.

In some embodiments, a high concentration, low-viscosity protein agent formulation may be prepared in a tablet form. Such tablets constitute a liquid-free, dust-free form for storage of a therapeutic protein agent, which is then easily handled and allows for retention of an acceptable level of activity or potency.

In some embodiments, a high protein concentration formulation of a therapeutic protein agent may be packaged in a variety of conventional forms employed for administration to provide a reactive therapeutic protein agent at a site where needed. In some embodiments, a package form can include solid, semi-solid and liquid dosage forms that include liquid solutions or suspensions, slurries, gels, creams, emulsions, lotions, powders, sprays, foams, pastes, ointments, salves, balms drops, and combinations thereof.

Parenteral Routes of Administration

In some embodiments, a therapeutic protein agent formulation may be appropriate for a variety of modes of administration, including parenteral administration. In some embodiments, a parenteral route of administration is selected from the group consisting of intramuscular, intraperitoneal, intradermal, intravitreal, epidural, intracerebral, intra-arterial, intraarticular, intra-cavernous, intra-lesional, intraosseous, intraocular, intrathecal, transdermal, trans-mucosal, extra-amniotic administration, and combinations thereof.

In some embodiments, intravenous, intraperitoneal, subcutaneous and intra-cerebrospinal routes of administration are achieved using a 18-32 gauge needle, in a volume that may be, for example, of about 5 mL, 4 mL, 3 mL, 2 mL, 1 mL, 0.5 mL, or less. In some embodiments, the amount may be bounded by a lower limit and an upper limit, the upper limit being larger than the lower limit. In some embodiments, the lower limit may be about 0.01 mL, about 0.1 mL, about 0.5 mL, or about 1.0 mL. In some embodiments, the upper limit may be about 1.5 mL, about 2.0 mL, about 2.5 mL, or about 3.0 mL. In some embodiments, the range may be about 0.01 mL to about 5 mL. In some embodiments, the range may be about 0.01 mL to about 3 mL. In some embodiments, the range may be about 0.01 mL to about 2 mL. In some embodiments, the range may be about 0.01 mL to about 1.5 mL. In some embodiments, the range may be about 0.01 mL to about 1 mL. In some embodiments, the range may be about 0.01 mL to about 0.5 mL. In some embodiments, the range may be about 0.01 mL to about 0.1 mL. In some embodiments, the range may be about 0.1 mL to about 2 mL. In some embodiments, the range may be about 0.1 mL to about 1 mL.

A reduced-viscosity protein agent formulation has improved injectability and requires less injection force compared to an analogous control formulation without a viscosity-reducing agent (e.g., in phosphate buffer alone) under otherwise same conditions. In some embodiments, the force of injection may be, for example, at least 10%, 15%, 20%, 25%, 30%, 35%, 40%, 45%, or even more than 50% less than the analogous control protein agent formulation without viscosity-reducing agents. In some embodiments, the percentage decrease in injection force once viscosity-reducing agents are incorporated maybe be within a range bound by a lower limit and an upper limit, the upper limit being larger than the lower limit. In some embodiments, the lower limit may be about 10%, about 15%, about 20%, or about 25% less force than the control formulation upon injection. In some embodiments, the upper limit may be about 30%, about 35%, about 40%, about 45%, or about 50% less force than the control formulation upon injection. In some embodiments, the range may be about 10% to about 60% decrease in injection force. In some embodiments, the range may be about 10% to about 55% decrease in injection force. In some embodiments, the range may be about 10% to about 50% decrease in injection force. In some embodiments, the range may be about 15% to about 50% decrease in injection force. In some embodiments, the range may be about 20% to about 50% decrease in injection force. In some embodiments, the range may be about 25% to about 50% decrease in injection force. In some embodiments, the range may be about 30% to about 50% decrease in injection force. In some embodiments, the range may be about 35% to about 50% decrease in injection force. In some embodiments, the range may be about 40% to about 50% decrease in injection force. In some embodiments, the range may be about 45% to about 50% decrease in injection force as compared to standard control formulations without the viscosity-reducing agent(s) but otherwise under the same injection conditions. In some embodiments, a protein agent formulation possesses "Newtonian flow characteristics." defined as having a viscosity that is substantially independent of shear rate. A protein agent formulations can be readily injected through a needle of about 22-32 gauge. In some embodiments, an injection is administered via a 27 gauge needle and the injection force is less than 30 N. A formulation can be administered, in most cases, using a very small gauge needle, for example, between 27 and 31 gauge, preferably 29 gauge and more preferably 31 gauge needle.

To increase drug delivery efficiency, patient compliance, and to ease a procedure of administration of a protein agent formulation by a healthcare provider, a variety of syringes are available on the market. In some embodiments, a syringe can include wearable injection devices, self-mixing syringes, needleless syringes, auto injectors, pre-filled syringes retractable syringes, and combinations thereof. In some embodiments, a protein agent formulation can be pre-heated just before a drug administration procedure using a syringe heater or a pre-heated syringe that is heated in a separate warming unit prior to filling a syringe. In some embodiments, a protein agent formulation, including a reconstituted formulation, can be administered using a heated and/or self-mixing syringe or autoinjector. A protein agent formulation can also be pre-heated in a separate warming unit prior to filling a syringe. A syringe heater is a device which often contains one or more slots for holding a syringe filled with a protein agent formulation, and a controlling system to heat, monitor and maintain a temperature range of a formulation-filled syringe at a given specific temperature range.

In some embodiments, a syringe heater can be a separate device where a syringe containing a protein agent formulation is heated, or it can be a built-in device in which a syringe itself contains an integrated heater. In some embodiments, a syringe heater that can be used for any standard thermostable syringe can include pre-filled syringes, retractable syringes, needleless syringes of variable sizes, and combinations thereof. The disadvantage of a separate heating device over a built-in heating device is that once a syringe is heated and taken out, heat dissipates to the environment. An appropriate syringe heater or syringe heater tape device can be obtained from GDPGlobal® precision dispensing systems, Watlow Electric Manufacturing Co., and many others. A stage heater, or heating block of in-line perfusion (Single in-line or multiple in-line) can be procured from Warner Instruments. Any of the heaters described herein are capable of heating a protein agent formulation from ambient temperature to about 90° C. as a higher range, or a further high range of 185° C. Examples of syringe heaters include SW-60, SW-61, SH-27B, SF-28 model supplied by Warner Instruments.

A heated syringe maintains a therapeutic protein agent formulation at a set temperature with precision of ±1° C., ±3° C. or up to ±5° C. from a set temperature. Depending on stability of a liquid protein agent formulation, a heated syringe can maintain a temperature of about 40° C., 50° C., or 80° C. In some embodiments, a temperature of a therapeutic protein agent formulation is maintained at a value that may be, for example, at least 20° C., 25° C., 30° C., 35° C., 40° C., or more. In some embodiments, the amount may be within a range bounded by a lower limit and an upper limit, the upper limit being larger than the lower limit. In some embodiments, the lower limit may be about 20° C., about 25° C., about 30° C., or about 35° C. In some embodiments, the upper limit may be about about 40° C., about 45° C., about 50° C., about 55° C., about 60° C., about 65° C., about 70° C., about 75° C., or about 80° C. In some embodiments, the range may be about 20° C. to about 80° C. In some embodiments, the range may be about 20° C. to about 70° C. In some embodiments, the range may be about 20° C. to about 60° C. In some embodiments, the range may be about 20° C. to about 50° C. In some embodiments, the range may be about 20° C. to about 40° C. In some embodiments, the range may be about 20° C. to about 30° C. In some embodiments, the range may be about 25° C. to about 40° C. This allows a protein agent formulation in a heated syringe to be maintained at a temperature close to body temperature, thereby reducing patient discomfort and also helping to reduce viscosity of adrug formulation, which enables easy injection of fluids with less effort, causing less pain at a site of injection.

Self-Mixing Syringes:

In some embodiments, a self-mixing syringe may be used for reconstitution and administration of a high concentration, low viscosity protein agent formulation, which helps a patient by reducing an inconvenience of visiting a healthcare center. A self-mixing device consists of two or more chambers. In a two chamber self-mixing system, a first component is a fluid (BFWI, saline etc.) and a second component includes a lyophilized drug, or in this case, more specifically, a protein agent. Various mechanisms are present for mixing of two contents at a controlled rate and under sterile conditions to achieve a final injection solution. Application of axial pressure on a vial causes mixing of the contents of the two components. Mixing of the contents in two chambers can be done by using a static mixer or a dynamic mixer. Merlin Packaging Technologies offers micro-sized static mixers for controlled dispensing and minimal waste of the formulations.

Pre-Filled Syringes:

In some embodiments, a therapeutic protein agent in a liquid or lyophilized formulation may be administered in a pre-filled syringe. In some embodiments, a pre-filled syringe can include BD PosiFlush™, BD Hypak™ from Becton Dickinson, SureClick® Single-Use Safety Prefilled Syringe from Amgen, Safety Tip-Lok™ from GlaxoSmithKline, Autoject II®, SnapDragon®, SimpleJect™, Humira® Pen from Owen Mumford, and combinations thereof. In some embodiments, a pre-filled syringe can include an autoinjector, a self-mixing syringe, a retractable syringe, and a syringes in a wearable device.

In some embodiments, a protein agent formulation can be administered using a retractable syringe which can be automatically or manually retracted. In a manually operated syringe, after dispensing a drug, a plunger is pulled back until an obvious stop is felt. This will pull the needle into the barrel of a syringe and then the plunger is disassembled. This technology is mainly used to prevent viral contamination and accidental needlesticks during administration. In some embodiments, a retractable syringes is selected from the group consisting of BD Integra™ Syringe with Retracting PrecisionGlide Needle from Becton Dickinson, Futura® Safety Syringe from Hypoguard USA, Inc., Careo® Retractable Safety Syrine from Life-Shield Products, Inc, and combinations thereof.

A biological therapeutic protein agent formulation is more often than not, a viscous solution that is mostly administered subcutaneously and at at high doses, requiring more than 1 mL of fluid per dose. Administration of such a high volume requires expertise in the field and also often necessitates a patient visit to a healthcare center solely for drug therapy, decreasing patient compliance and satisfaction. For such a bolus injection, which requires a relatively large volume of drug to be administered, wearable injection devices are available on the market. These devices contain a pre-programmed unit which delivers a set volume of drug at a controlled rate and duration. In some embodiments, a wearable injection device can include Precision-Therapy™ from Unilife, Gammagard from Baxter, Gammaked from Talecris Biotherapeutics, Gamunex-C from Grifols Therapeutics, Hizentra from CSL Behring, and combinations thereof. Autoinjection wearable devices contain a syringe which when operated causes a syringe to move forward to project a needle, aiding in administration of a therapeutic agent into a patient's body. Autoinjection wearable devices are typically designed for self-administration of a therapeutic formulation by untrained personnel.

Needleless Syringes:

Delivery of a substance into the body of a mammal or other suitable recipient, which does not involve using a sharp needle for injection, is made possible through needleless injection devices. This device contains a drug chamber pre-filled with drug, a nozzle with an orifice that serves as a skin contacting surface and a pressure source, and compressed gas to propel the drug through the orifice at a very high speed (Tejaswi R. Kale and Munira Momin., *Inov Pharm.* 2014; 5 (1): Article 148). Different types of needleless syringes can include powder injections, liquid injections and depot or projectile injections. In some embodiments, a needleless liquid injection device can include Jetinjector from Becton Dikinson, Medi-jector VISION™ from Antares Pharma. Inc, Biojector 2000®, Vitajet™3, Iject® from Bioject, and combinations thereof. Powder and depot-based needleless systems are available as Powderject system from Powderject Pharmaceuticals and Depixol® Depo Injection from Lundbeck Limited respectively. Needless syringes are used for administering formulations though IM, SC, and ID routes, and involve the use of spring, laser power, or energy propelled (e.g. Lorentz force, air force and shock waves) forces for injecting a protein agent drug into a patient's body as described by Ravi. et. al. (Ravi. et. al, Int. Jour. Pharm. Investig. 2015; 5(4): 192-199). In some embodiments, commercially-available, needle-free injection devices or systems that can be used to administer a high protein agent concentration, low viscosity formulation can include inter alia, Intraject® (Weston Medical, Ltd.), Biojector 2000® (Bioject, Inc.), MadaJet® (MADA Medical Products, Inc.), and J-Tip® (National Medical Products, Inc.), LectraJet® (DCI, Inc.), Mesoflash® (also called Isojet®) (Prolitec), VACCI JET Electrique® (ENDOS Pharma), two-stage fluid medicament jet injector (Avant Drug Delivery Systems, Inc.), and combinations thereof.

In some embodiments, the present invention may utilize a slow release methodology, such as a silicon based ring or a rod which has been preloaded with a therapeutic protein agent formulations, and can therefore act as an implants for delivery. Such a methodology provides a constant level of therapeutic protein agent to the bloodstream over a period of weeks or months. Such implants can be inserted intradermally and can be safely replaced and removed when needed.

Therapeutic Uses

Disclosed herein are methods of reducing pain at an injection site of a therapeutic protein agent in a mammal in need thereof, comprising administration of a liquid therapeutic formulation by injection, wherein a liquid formulation comprises a therapeutically effective amount of a therapeutic protein agent, wherein a formulations further comprises a pharmaceutically acceptable viscosity-reducing agent or an aggregation-reducing agent selected from groups mentioned previously, wherein a pharmaceutically acceptable viscosity-reducing agent or aggregation-inducing agent is added to a formulation in a viscosity-reducing amount; and wherein a mammal experiences less pain with administration of a therapeutic protein agent formulation containing a viscosity-reducing agents or an aggregation-reducing agent in comparison to a protein formulation without such agents.

Further disclosed herein are methods of treating a disease or disorder in mammals, comprising administering to said mammal a liquid therapeutic protein agent formulation, wherein a therapeutic formulation comprises a therapeutically effective amount of a therapeutic protein agent, and wherein a formulations further comprises a pharmaceutically acceptable viscosity-reducing agent, aggregation-reducing agent, or other additive as described above; and wherein a therapeutic formulation is effective for treatment of a diseases or disorder. In some embodiments, a formulations is administered by a subcutaneous injection, or intramuscular injection, or intravenous injection. In some embodiments, a therapeutic formulation has improved stability when compared to a control formulation. In some embodiments, an excipient compound is essentially pure.

In some embodiments, a therapeutic use for a high concentration, low viscosity protein agent formulation can include treatment and/or detection of cancers such as breast cancer, gastric cancer, Non-Hodgkin's Lymphoma, urothelial carcinoma & solid tumors, Metastatic colorectal cancer, Non-squamous non-small cell lung cancer, Metastatic breast cancer, Hodgkin lymphoma, Biliary cancer, Acute myeloid Leukemia, prostate cancer, multiple myeloma, solid tumors of bone, neuroblastoma, pancreatic cancer, acute myelogenous leukemia, metastatic melanoma, metastatic squamous non-small cell cancer, Anaplastic astrocytoma; Brain cancer, Glioblastoma, Glioma, Head and neck cancer, Merkel cell carcinoma, Nasopharyngeal cancer, Oesophageal cancer, Hepatocellular carcinoma, refractory euroblastoma, Osteosarcoma, Peritoneal cancer, Fallopian tube cancer, Mesothelioma, Metastatic Melanoma, Renal Cell Carcinoma, NR-LU-10 for cancer, lupus, Chronic Lymphocytic Leukemia, soft tissue sarcoma, ovarian cancer, bladder cancer, esophageal cancer, gastric nasopharyngeal cancer, adrenocortical carcinoma, HER2-positive breast cancer, adenocarcinoma, Granulomatosis with Polyangiitis (GPA), microscopic polyangiitis, idiopathic pulmonary fibrosis, focal segmental glomerulosclerosis, Prolactinoma, and combinations thereof.

In some embodiments, a therapeutic use for a high concentration, low viscosity protein agent formulation can include treatment and/or dectection of an autoimmune disease such as Rheumatoid Arthritis (RA), Osteoarthritis, Juvenile Idiopathic Arthritis (JIA), Psoriatic Arthritis (PsA), Ankylosing Spondylitis (AS), Crohn's Disease (CD), Ulcerative Colitis (UC), Plaque Psoriasis (Ps), systemic lupus erythematosus, Lupus nephritis, Familial Cold Autoinflammatory Syndrome (FCAS), Sjogren's syndrome, and combinations thereof.

In some embodiments, a therapeutic use for a high concentration, low viscosity protein agent formulation can include treatment and/or dectection of an other immunologically-related disorder such as Leukopaenia, paroxysmal nocturnal hemoglobinuria (PNH), atypical hemolytic uremic syndrome (aHUS), thrombotic microangiopathy (TMA), Inflammatory bowel disease, ulcerative colitis and transplantation rejection, surgery-related, life-threatening, uncontrolled bleeding, and combinations thereof.

In some embodiments, a therapeutic use for a high concentration, low viscosity protein agent formulation can include treatment and/or dectection of an infectious disease like *Clostridium difficile* infection, respiratory syncytial virus (RSV) disease, Anthrax, Flu virus infection, Influenza Virus infection, Hepatitis B virus infection, Rabies virus infection, invasive *Candida* infection, bacterial septic shock, HIV infection, Nosocomial pneumonia, Staphylococcal infections, STEC (Shiga-like toxin-producing *Escherichia coli* or *E. coli* serotype 0121) infection causing diarrhea and HUS (hemolytic-uremic syndrome), Cytomegalovirus, Botulism, Ebola Virus, and combinations thereof.

In some embodiments, a therapeutic use for a high concentration, low viscosity protein agent formulation can include treatment and/or dectection of a cardiovascular disease such as cardiac ischemic complications, percutaneous coronary intervention, Acute myocardial infarction, pulmonary embolism, deep vein thrombosis, arterial thrombosis or embolism, occlusion of arteriovenous cannula, thrombocytopenia with chronic immune (idiopathic) thrombocytopenic purpura (ITP), and combinations thereof.

In some embodiments, a therapeutic use for a high concentration, low viscosity protein agent formulation can include treatment and/or dectection of an opthalmic disorder such as Age-Related Macular Degeneration (AMD), Macular Edema, Retinal Vein Occlusion (RVO), Diabetic Macular Edema, Neuromyelitis optica, and combinations thereof.

In some embodiments, a therapeutic use for a high concentration, low viscosity protein agent formulation can include treatment and/or dectection of a respiratory disorder such as asthma, chronic idiopathic urticaria, acute bronchospasm or status asthmaticus, Chronic obstructive pulmonary disease, and combinations thereof.

In some embodiments, a therapeutic use for a high concentration, low viscosity protein agent formulation can include treatment and/or dectection of a metabolic disorder like hyperlipidemia, Diabetes mellitus type-1 and 2, Hypercholesterolaemia, dyslipidemia, and combinations thereof.

In some embodiments, a therapeutic use for a high concentration, low viscosity protein agent formulation can include treatment and/or dectection of a genetic disorder like Haemophilia A and B, Prader-Willi syndrome, Turner syndrome, Cryopyrin-Associated Periodic Syndromes (CAPS), Muckle-Wells Syndrome (MWS), X-linked hypophosphatemia, Sickle-cell pain crisis, and combinations thereof.

In some embodiments, a therapeutic use for a high concentration, low viscosity protein agent formulation can include treatment and/or dectection of a bone-related ailment like Osteoporosis, aplastic anaemia, and combinations thereof.

In some embodiments, a therapeutic use for a high concentration, low viscosity protein agent formulation can include treatment and/or dectection of other disorders including removal of venom; Alzheimer's disease, Back pain (Sciatic nerve pain), Migraine, Atopic dermatitis, Duchenne muscular dystrophy, Hepatic fibrosis, Cystic Fibrosis, *Pseudomonas aeruginosa* Infections, Ventilator-associated pneumonia, and combinations thereof.

In some embodiments, a solution containing a viscosity-reducing agent and a high concentration of a therapeutic protein agent, and compositions and formulations thereof, may be used alone or in a test kit to diagnose a disease or infection that can include inter alia, osteomyelitis, *salmonellosis*, shigellosis, and the location and extent of disease staging in cancers such as non-Hodgkin's lymphoma and leukemia, and combinations thereof.

In some embodiments, a therapeutic protein agent formulation may be used as an in vivo imaging agent for detection of a disease such as cardiovascular thrombosis.

Storage

A protein agent formulation as described herein may be stored by any suitable method known to one skilled in the art. In some embodiments, a method for storage of a protein agent can include freezing, lyophilizing, spray drying the liquid protein formulation, and combinations thereof. In some embodiments, a lyophilized formulation is frozen for storage at subzero temperatures, such as at about −80° C. In some cases, a lyophilized or aqueous formulation is stored at 2-8° C.

In some embodiments, a lyophilized formulation of a protein agent is provided and/or is used in preparation and manufacture of a low-viscosity, high concentration protein agent formulation. In some embodiments, a pre-lyophilized protein agent in powder form is reconstituted by dissolution in an aqueous solution. In some embodiments, a liquid formulation is filled into a specific dosage unit container such as a vial or pre-filled mixing syringe. Then, a liquid formulation can be lyophilized, optionally with lyoprotectants, preservatives, antioxidants, and other typical pharmaceutically acceptable excipients present in a formulation. Lastly, products are stored under sterile storage conditions until shortly before use, at which time they can be reconstituted with a defined volume of diluent to achieve a desired concentration and viscosity.

In some embodiments, a diluent useful for reconstituting a lyophilized formulation prior to injection are selected from the group consisting of sterile water, bacteriostatic water for injection (e.g. BWFI), pH buffered solutions (e.g., phosphate-buffered saline), sterile saline solution, Ringer's solution, dextrose solution, aqueous solutions of salts and/or buffers, and combinations thereof.

EXEMPLIFICATION

Example 1: Effect of Various Buffer Systems on the Viscosity of Solutions of Human Gamma Globulin The present example describes the effect of various buffer systems on the viscosity of solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, either histidine or phosphate or citrate buffer was added from the stock concentration of 1000 mM for histidine buffer or 1000 mM for citrate buffer or 1000 mM for phosphate buffer, pH 6.0 to get a final concentration of 25 mM each. The HGG solutions in various buffers were concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the respective buffer (which does not contain any HGG). Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

Figure 1:
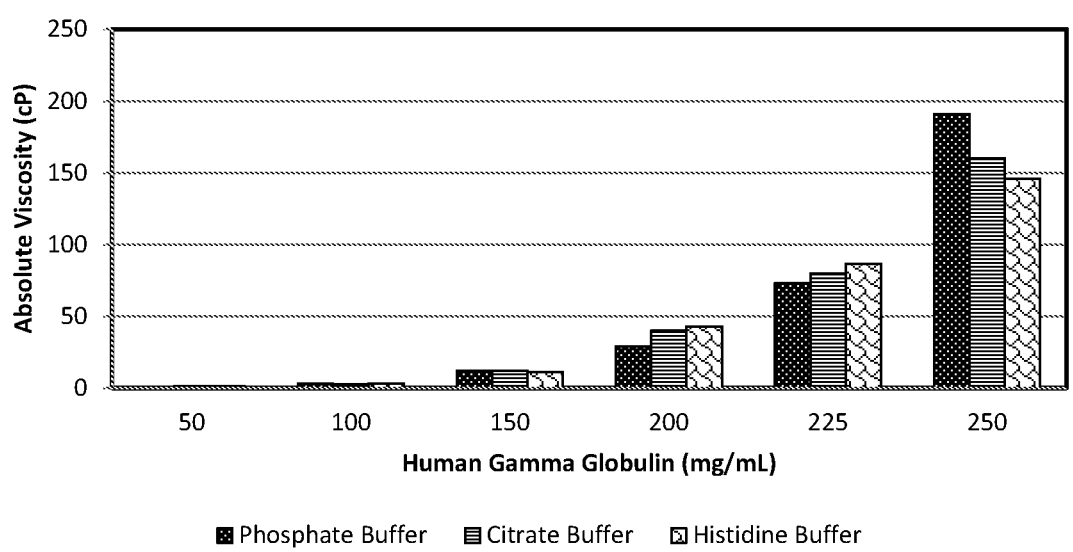
FIG. 1 depicts viscosity (in cP) as a function of protein concentration (in mg/mL) for Human Gamma Globulin (GLOBUCEL®) solution either in 25 mM of Phosphate or Citrate or Histidine Buffer, pH 6.0 at 25° C.

The data in Table 1 demonstrate the viscosity of Human gamma globulin GLOBUCEL® in various buffers at different protein concentrations. The viscosity of HGG in various buffers increases exponentially with increasing HGG concentration. The data in FIG. 1 and Table 1 show that the higher the concentration of HGG, the greater the viscosity.

TABLE 1

Viscosity of Various Concentrations of HGG in Phosphate, Citrate and Histidine Buffer, pH 6.0 at 25° C.

| Buffer | HGG Concentration (mg/mL)* | | | | | |
|---|---|---|---|---|---|---|
| | 50 | 100 | 150 | 200 | 225 | 250 |
| | Viscosity, cP** | | | | | |
| 25 mM Phosphate Buffer, pH 6.0 | 1 | 3 | 12 | 29 | 73 | 191 |
| 25 mM Citrate Buffer, pH 6.0 | 1 | 3 | 12 | 40 | 80 | 160 |
| 25 mM Histidine Buffer, pH 6.0 | 1 | 3 | 11 | 43 | 87 | 146 |

*The protein concentration = Stated Value ± 5 mg/mL
**Viscosity = Stated Value ± 0.2

Example 2: Effect of pH on the Viscosity of Solutions of Human Gamma Globulin The present example describes the effect of pH on the viscosity of solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, either citrate-phosphate buffer pH 5.0 or citrate-phosphate buffer pH 6.0 or citrate-phosphate buffer pH 7.0 was added from the stock concentration of 1000 mM for citrate buffer at pH 5.0 or pH 6.0 or pH 7.0 to get a final concentration of 25 mM each. The HGG solutions in various pH buffers were concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the respective buffer (which does not contain any HGG). Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 2 demonstrate the viscosity of Human gamma globulin GLOBUCEL® in various pHs. The viscosity of HGG decreases as the pH goes down from 7.0 to 5.0.

TABLE 2

Viscosity Dependence of Solutions of HGG at pH 5.0, pH 6.0 and pH 7.0 Citrate-phosphate Buffer at 25° C.

| pH | HGG Concentration (mg/mL)* | |
|---|---|---|
| | 190 | 210 |
| | Viscosity, cP** | |
| 25 mM Citrate-phosphate Buffer, pH 5.0 | 27 | 94 |
| 25 mM Citrate-phosphate Buffer, pH 6.0 | 32 | 143 |
| 25 mM Citrate-phosphate Buffer, pH 7.0 | 39 | 204 |

*The protein concentration = Stated Value ± 5 mg/mL
**Viscosity = Stated Value ± 0.2

Example 3: A Comparative Study on Various Amino Acids or its Derivatives and their Effect on the Viscosity of Aqueous Solutions of Human Gamma Globulin The present example describes the effect of various amino acids or amino acid derivatives on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate/histidine Buffer was added from the stock concentration of 1000 mM phosphate/citrate/histidine buffer, pH 6.0 to get a final concentration of 25 mM. To the buffered HGG different amino acid or its derivative was added individually and mixed until complete dissolution. The excipient containing HGG was concentrated to a final volume of less than 150 μL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate/histidine containing viscosity-reducing agent alone (which does not contain any HGG) for measuring the protein concentration in excipient containing sample; and for HGG without any excipient, buffer alone without any excipient was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left( A \frac{0.1\%}{280 \text{ nm}} = A \frac{1 \text{ mg/mL}}{280 \text{ nm}} = 1.4 \right)$$

at 280 nm. The viscosities of the solution were measured either using a Cambridge Viscometer, VISCOlab5000 using 70 μL of sample at 25° C. or using a DV2T cone and plate viscometer using 1.5 mL of sample at 25° C. at extrapolated zero shear rate.

Results

The data in Table 3, 4 and 5 demonstrate the viscosity reducing effect of various amino acids or its derivatives on Human gamma globulin (GLOBUCEL®) in either phosphate or citrate or histidine buffer. The data in Table 3, 4 and 5 show that the amino acid tryptophan, once added, helps to lower the viscosity of the protein agent solution.

TABLE 3

Effect of Amino Acids and its Derivatives on Viscosity of Aqueous Solutions of HGG in Phosphate buffer System, pH 6.0 at 25° C.

| Excipient | Molecular Weight of Excipient | Concentration of Excipient mg/mL | Concentration of Excipient mM | Phosphate Buffer HGG Concentration (mg/mL)* | Phosphate Buffer Viscosity (cP) @ 25° C.** |
|---|---|---|---|---|---|
| None | — | — | — | 200 | 29 |
| None | — | — | — | 225 | 73 |
| None | — | — | — | 250 | 191 |
| Glycine | 75.07 | 10 | 133 | 228 | 186 |
| | | | | 206 | 63 |
| Proline | 115.13 | 10 | 87 | 201 | 68 |
| Methionine | 149.21 | 10 | 67 | 228 | 170 |
| Lysine | 182.65 | 10 | 55 | 267 | 199 |
| Alanine | 89.09 | 10 | 112 | 222 | 112 |
| Tryptophan | 204.23 | 6 | 29 | 243 | 35 |
| | | | | 200 | 14 |
| Arginine | 174.2 | 10 | 58 | 220 | 197 |
| | | | | 205 | 85 |
| Serine | 105.09 | 10 | 95 | 238 | 135 |
| Histidine | 155.15 | 10 | 65 | 180 | 31 |
| Hydroxy Proline | 131.13 | 10 | 76 | 177 | 30 |
| Homoarginine | 224.69 | 10 | 45 | 188 | 28 |
| Tyramine-HCl | 173.64 | 10 | 58 | 215 | 145 |

*The protein concentration = Stated Value ± 5 mg/mL
**Viscosity = Stated Value ± 0.2

TABLE 4

Effect of Amino Acids on Viscosity of Aqueous Solutions of HGG in Citrate buffer System, pH 6.0 at 25° C.

| Excipient | Molecular Weight of Excipient | Concentration of Excipient mg/mL | Concentration of Excipient mM | Citrate Buffer HGG Concentration (mg/mL)* | Citrate Buffer Viscosity (cP) @ 25° C.** |
|---|---|---|---|---|---|
| None | — | — | — | 200 | 40 |
| None | — | — | — | 225 | 80 |
| None | — | — | — | 250 | 160 |
| Glycine | 75.07 | 10 | 133 | 208 | 73 |
| Proline | 115.13 | 10 | 87 | 201 | 55 |
| Tryptophan | 204.23 | 6 | 29 | 231 | 60 |
| Arginine | 174.2 | 10 | 58 | 247 | 87 |

*The protein concentration = Stated Value ± 5 mg/mL
**Viscosity = Stated Value ± 0.2

TABLE 5

Effect of Tryptophan on Viscosity of Aqueous Solutions of HGG in Histidine buffer System, pH 6.0 at 25° C.

| Excipient | Molecular Weight of Excipient | Concentration of Excipient mg/mL | Concentration of Excipient mM | Histidine Buffer HGG Concentration (mg/mL)* | Histidine Buffer Viscosity (cP) @ 25° C.** |
|---|---|---|---|---|---|
| None | — | — | — | 200 | 43 |
| None | — | — | — | 225 | 87 |

TABLE 5-continued

Effect of Tryptophan on Viscosity of Aqueous Solutions of HGG in Histidine buffer System, pH 6.0 at 25° C.

| Excipient | Molecular Weight of Excipient | Concentration of Excipient mg/mL | Concentration of Excipient mM | Histidine Buffer HGG Concentration (mg/mL)* | Histidine Buffer Viscosity (cP) @ 25° C.** |
|---|---|---|---|---|---|
| None | — | — | — | 250 | 146 |
| Tryptophan | 204.23 | 6 | 29 | 256 | 18 |

*The protein concentration = Stated Value ± 5 mg/mL
**Viscosity = Stated Value ± 0.2

Example 4: A Comparative Study on Various Nucleosides, Nucleotides or its Derivatives and their Effect on the Viscosity of Aqueous Solutions of Human Gamma Globulin The present example describes the effect of various nucleosides, nucleotides or derivatives on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate/histidine Buffer was added from the stock concentration of 1000 mM phosphate/citrate/histidine buffer, pH 6.0 to get a final concentration of 25 mM. To the buffered HGG, different nucleosides or nucleotides or its derivative was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate/histidine containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280\ nm} = A\frac{1\ mg/mL}{280\ nm} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Tables 6, 7 and 8 demonstrate the viscosity reducing effect of various nucleosides or nucleotides or its derivatives on Human gamma globulin (GLOBUCEL®) in either phosphate or citrate or histidine Buffer. The data in Table 6, 7 and 8 show that the caffeine citrate, caffeine and uridine, once added to the protein agent solution, help to lower the viscosity of the solution.

TABLE 6

Effect of Nucleosides/Nucleotides and Its Derivatives on Viscosity of Aqueous Solutions of HGG in Phosphate buffer System, pH 6.0 at 2.5° C.

| Excipient | Molecular Weight of Excipient | Concentration of Excipient mg/mL | Concentration of Excipient mM | Phosphate Buffer HGG Concentration (mg/mL)* | Phosphate Buffer Viscosity (cP) @ 25° C.** |
|---|---|---|---|---|---|
| None | — | — | — | 200 | 29 |
| None | — | — | — | 225 | 73 |
| None | — | — | — | 250 | 191 |
| Thymidine | 242.23 | 10 | 41 | 161 | 60 |
| Uridine | 244.2 | 10 | 41 | 203 | 28 |
| Uracil | 112.09 | 1 | 9 | 235 | 140 |
| Cytidine | 243.33 | 10 | 41 | 218 | 203 |
| Caffeine | 194.19 | 10 | 51 | 219 | 40 |
| Caffeine citrate | 386.31 | 20 | 51 | 394 | 171 |
|  |  |  |  | 373 | 66 |
|  |  |  |  | 271 | 28 |

*The protein concentration = Stated Value ± 5 mg/mL
**Viscosity = Stated Value ± 0.2

TABLE 7

Effect of Nucleosides/Nucleotides and its Derivatives on Viscosity of Aqueous Solutions of HGG in Citrate buffer System, pH 6.0 at 25° C.

| Excipient | Molecular Weight of Excipient | Concentration of Excipient mg/mL | Concentration of Excipient mM | Citrate Buffer HGG Concentration (mg/mL)* | Citrate Buffer Viscosity (cP) @ 25° C.** |
|---|---|---|---|---|---|
| None | — | — | — | 200 | 40 |
| None | — | — | — | 225 | 80 |
| None | — | — | — | 250 | 160 |
| Caffeine | 194.19 | 10 | 51 | 320 | 178 |
|  |  |  |  | 260 | 73 |
|  |  |  |  | 201 | 30 |

*The protein concentration = Stated Value ± 5 mg/mL
**Viscosity = Stated Value ± 0.2

TABLE 8

Effect of Nucleosides/Nucleotides and its Derivatives on Viscosity of Aqueous Solutions of HGG in Histidine buffer System, pH 6.0 at 25° C.

| Excipient | Molecular Weight of Excipient | Concentration of Excipient mg/ML | Concentration of Excipient mM | Histidine Buffer HGG Concentration (mg/mL)* | Histidine Buffer Viscosity (cP) @ 25° C.** |
|---|---|---|---|---|---|
| None | — | — | — | 200 | 43 |
| None | — | — | — | 225 | 87 |
| None | — | — | — | 250 | 146 |

TABLE 8-continued

Effect of Nucleosides/Nucleotides and its Derivatives on Viscosity of Aqueous Solutions of HGG in Histidine buffer System, pH 6.0 at 25° C.

| Excipient | Molecular Weight of Excipient | Concentration of Excipient mg/ML | mM | Histidine Buffer HGG Concentration (mg/mL)* | Viscosity (cP) @ 25° C.** |
|---|---|---|---|---|---|
| Caffeine | 194.19 | 10 | 51 | 220 | 36 |
| Caffeine | 386.31 | 20 | 51 | 391 | 183 |
| Citrate | | | | 358 | 68 |
| | | | | 280 | 27 |
| Caffeine Nicotinate*** | 317.31 | 10 | 31 | 297 | 37 |

*The protein concentration = Stated Value ± 5 mg/mL
**Viscosity = Stated Value ± 0.2
***Contains 0.04% EDTA, 0.1% octyl glucopyranoside, 50 mM NaCl, 10 mg/mL sorbitol

Example 5: A Comparative Study on Various Sugars or Sugar-Alcohols and their Effect on the Viscosity of Aqueous Solutions of Human Gamma Globulin The present example describes the effect of various sugars or sugar-alcohols on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate buffer was added from the stock concentration of 1000 mM phosphate/citrate buffer, pH 6.0 to get a final concentration of 25 mM. To the buffered HGG different sugar or sugar-alcohol or its derivative was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 9 and 10 demonstrate the viscosity-reducing effect of various sugars or sugar-alcohols or its derivatives on Human gamma globulin (GLOBUCEL®) in either phosphate or citrate buffer. The data in Table 9 and 10 show that the neither sugars or sugar-alcohols may have a large viscosity reducing effect as compared to other potential excipients.

TABLE 9

Effect of Sugar or Sugar-alcohol on Viscosity of Aqueous Solutions of HGG in Phosphate buffer System, pH 6.0 at 25° C.

| Excipient | Molecular Weight of Excipient | Concentration of Excipient mg/mL | mM | Phosphate Buffer HGG Concentration (mg/mL)* | Viscosity (cP) @ 25° C.** |
|---|---|---|---|---|---|
| None | — | — | — | 200 | 29 |
| None | — | — | — | 225 | 73 |
| None | — | — | — | 250 | 191 |
| Trehalose dihydrate | 378.33 | 20 | 53 | 246 | 54 |
| Sucrose | 342.3 | 20 | 58 | 204 | 190 |
| D-sorbitol | 182.17 | 10 | 56 | 240 | 176 |

*The protein concentration = Stated Value ± 5 mg/mL
**Viscosity = Stated Value ± 0.2

TABLE 10

Effect of Sugar or Sugar-alcohol on Viscosity of Aqueous Solutions of HGG in Citrate buffer System, pH 6.0 at 25° C.

| Excipient | Molecular Weight of Excipient | Concentration of Excipient mg/mL | mM | Citrate Buffer HGG Concentration (mg/mL)* | Viscosity (cP) @ 25° C.** |
|---|---|---|---|---|---|
| None | — | — | — | 200 | 40 |
| None | — | — | — | 225 | 80 |
| None | — | — | — | 250 | 160 |
| Trehalose dihydrate | 378.33 | 20 | 53 | 217 | 87 |
| Sucrose | 342.3 | 20 | 58 | 192 | 76 |
| D-sorbitol | 182.17 | 10 | 56 | 182 | 45 |
| Fructose | 180.16 | 10 | 56 | 183 | 69 |
| Mannitol | 182.17 | 10 | 55 | 183 | 65 |
| Arabinose | 150.13 | 10 | 67 | 186 | 65 |

*The protein concentration = Stated Value ± 5 mg/mL
**Viscosity = Stated Value ± 0.2

Example 6: A Comparative Study on Various Organic and Inorganic Salts and their Effect on the Viscosity of Aqueous Solutions of Human Gamma Globulin The present example describes the effect of various organic and inorganic salts on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/histidine buffer was added from the stock concentration of 1000 mM phosphate/histidine buffer, pH 6.0 to get a final concentration of 25 mM. To the buffered HGG different organic or inorganic salt was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/histidine containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 11 and 12 demonstrate the viscosity reducing effect of various organic or inorganic salts on Human gamma globulin (GLOBUCEL®) in either phosphate or histidine buffer. The data in Table 11 and 12 show that sodium chloride has a viscosity-reducing effect, as well as ammonium chloride when at high concentrations.

TABLE 11

Effect of organic and inorganic salt on Viscosity of Aqueous Solutions of HGG in Phosphate buffer System, pH 6.0 at 25° C.

| Excipient | Molecular Weight of Excipient | Concentration of Excipient mg/mL | mM | Phosphate Buffer HGG Concentration (mg/mL)* | Viscosity (cP) @ 25° C.** |
|---|---|---|---|---|---|
| None | — | — | — | 200 | 29 |
| None | — | — | — | 225 | 73 |
| None | — | — | — | 250 | 191 |
| Ammonium chloride | 53.49 | 40 | 747 | 205 | 21 |
| | | 5.35 | 100 | 182 | 53 |
| Sodium Chloride | 58.44 | 5.84 | 100 | 209 | 70 |
| Potassium acetate | 98.15 | 40 | 408 | 228 | 172 |
| Pyruvate sodium salt | 110.04 | 10 | 91 | 213 | 171 |
| Sodium Acetate | 82.03 | 8.2 | 100 | 174 | 19 |
| 2-Amino-pyrimidine | 95.1 | 10 | 105 | 120 | 87 |

*The protein concentration = Stated Value ± 5 mg/mL
**Viscosity = Stated Value ± 0.2

TABLE 12

Effect of Sodium Chloride on Viscosity of Aqueous Solutions of HGG in Histidine buffer System, pH 6.0 at 25° C.

| Excipient | Molecular Weight of Excipient | Concentration of Excipient mg/mL | mM | Histidine Buffer HGG Concentration (mg/mL)* | Viscosity (cP) @ 25° C.** |
|---|---|---|---|---|---|
| None | — | — | — | 200 | 43 |
| None | — | — | — | 225 | 87 |
| None | — | — | — | 250 | 146 |
| Sodium Chloride | 58.44 | 5.84 | 100 | 249 | 115 |
| | | | | 227 | 48 |

*The protein concentration = Stated Value ± 5 mg/mL
**Viscosity = Stated Value ± 0.2

Example 7: A Comparative Study on Various Vitamins and its Derivatives and their Effect on the Viscosity of Aqueous Solutions of Human Gamma Globulin The present example describes the effect of various vitamins and its derivatives on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate/histidine buffer was added from the stock concentration of 1000 mM phosphate/citrate/histidine buffer, pH 6.0 to get a final concentration of 25 mM. To the buffered HGG different vitamin or its derivative was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate/histidine containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 13, Table 14 and Table 15 demonstrate the viscosity-reducing effect of various vitamins, salts of vitamins or derivatives of vitamins, on Human gamma globulin (GLOBUCEL®) in either phosphate or citrate or histidine buffer. The data in Table 13, Table 14 and Table 15 show that the nicotinic acid (acid form), when added to a protein agent-containing solution, contributes to significantly reducing the viscosity of the solution.

TABLE 13

Viscosity of Aqueous Solutions of HGG in Phosphate Buffer, pH 6.0 at 25° C. in the presence of Various Vitamins or Its Derivatives.

| Excipient | Molecular Weight of Excipient | Concentration of Excipient mg/mL | mM | Phosphate Buffer HGG Concentration (mg/mL)* | Viscosity (cP) @ 25° C.** |
|---|---|---|---|---|---|
| None | — | — | — | 200 | 29 |
| None | — | — | — | 225 | 73 |
| None | — | — | — | 250 | 191 |
| Thiamine-HCl | 337.27 | 10 | 30 | 248 | 92 |
|  |  |  |  | 179 | 24 |
|  |  | 27.3 | 81 | 246 | 91 |
|  |  |  |  | 200 | 34 |
| Nicotinic acid (acid form) | 123.11 | 10 | 81 | 250 | 30 |
| L-Ascorbic acid | 176.12 | 10 | 57 | 214 | 59 |
| L-Pantothenic Acid hemi-calcium salt | 238.27 | 10 | 42 | 182 | 14 |
| Nicotinamide | 122.12 | 10 | 82 | 250 | 76 |
|  |  |  |  | 191 | 21 |
| Methylnicotinate | 137.14 | 10 | 73 | 216 | 84 |
| Nicotinic acid Sodium Salt | 145.09 | 10 | 69 | 225 | 95 |
|  |  |  |  | 202 | 29 |

*The protein concentration = Stated Value ± 5 mg/mL
**Viscosity = Stated Value ± 0.2

TABLE 14

Viscosity of Aqueous Solutions of HGG in Citrate Buffer, pH 6.0 at 25° C. in the presence of Various Vitamins or Its Derivatives.

| Excipient | Molecular Weight of Excipient | Concentration of Excipient mg/mL | mM | Citrate Buffer HGG Concentration (mg/mL) | Viscosity (cP) @ 25° C.** |
|---|---|---|---|---|---|
| None | — | — | — | 200 | 40 |
| None | — | — | — | 225 | 80 |
| None | — | — | — | 250 | 160 |
| Thiamine•HCl | 337.27 | 10 | 30 | 294 | 185 |
|  |  |  |  | 210 | 102 |
| Nicotinic acid (acid form) | 123.11 | 10 | 81 | 277 | 123 |
|  |  |  |  | 246 | 48 |

TABLE 14-continued

Viscosity of Aqueous Solutions of HGG in Citrate Buffer, pH 6.0 at 25° C. in the presence of Various Vitamins or Its Derivatives.

| Excipient | Molecular Weight of Excipient | Concentration of Excipient mg/mL | mM | Citrate Buffer HGG Concentration (mg/mL) | Viscosity (cP) @ 25° C.** |
|---|---|---|---|---|---|
| Nicotinamide | 122.12 | 10 | 82 | 219 | 72 |
| Nicotinic acid Sodium Salt | 145.09 | 10 | 69 | 242 | 159 |
|  |  |  |  | 201 | 71 |

*The protein concentration = Stated Value ± 5 mg/mL
**Viscosity = Stated Value ± 0.2

TABLE 15

Viscosity of Aqueous Solutions of HGG in Histidine Buffer, pH 6.0 at 25° C. in the presence of Various Vitamins or Its Derivatives.

| Excipient | Molecular Weight of Excipient | Concentration of Excipient mg/mL | mM | Histidine Buffer HGG Concentration (mg/mL)* | Viscosity (cP) @ 25° C.** |
|---|---|---|---|---|---|
| None | — | — | — | 200 | 43 |
| None | — | — | — | 225 | 87 |
| None | — | — | — | 250 | 146 |
| Thiamine•HCl | 337.27 | 10 | 30 | 200 | 29 |
| Nicotinic acid (acid form) | 123.11 | 10 | 81 | 342 | 178 |
|  |  |  |  | 231 | 23 |
| Nicotinamide | 122.12 | 10 | 82 | 224 | 43 |
|  |  |  |  | 105 | 26 |
| Nicotinic acid Sodium Salt | 145.09 | 10 | 69 | 235 | 140 |
|  |  |  |  | 203 | 21 |
|  |  | 11.3 | 81 | 236 | 83 |

*The protein concentration = Stated Value ± 5 mg/mL
**Viscosity = Stated Value ± 0.2

Example 8: A Comparative Study on Various Organic Solvents and Organic Compounds and their Effect Viscosity on Aqueous Solutions of Human Gamma Globulin The present example describes the effect of various organic and organic compounds on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate/histidine buffer was added from the stock concentration of 1000 mM phosphate/citrate/histidine buffer, pH 6.0 to get a final concentration of 25 mM. To the buffered HGG different organic solvent or organic compound was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate/histidine containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left( A \frac{0.1\%}{280 \text{ nm}} = A \frac{1 \text{ mg/mL}}{280 \text{ nm}} = 1.4 \right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Tables 16, 17 and Table 18 demonstrate the viscosity reducing effect of various vitamins on Human gamma globulin (GLOBUCEL®) in either phosphate or citrate or histidine. The data in Table 16, 17 and Table 18 show that polysorbate 80 has a viscosity-reducing effect. The viscosity-reducing effect of Aspirin, (acetyl salicylate), in histidine has a large decrease in viscosity at very high HGG concentrations.

TABLE 16

Viscosity of Aqueous Solutions of HGG in Phosphate Buffer, pH 6.0 at 25° C. in the presence of Various Organic Solvents or Organic Compounds.

| Excipient | Molecular Weight of Excipient | Phosphate Buffer HGG Concentration (mg/mL)* | Viscosity (cP) @ 25° C.** |
|---|---|---|---|
| None | — | 200 | 29 |
| None | — | 225 | 73 |
| None | — | 250 | 191 |
| Polysorbate 80, 0.07% | 1310 | 241 | 84 |
| Aspartame (10 mg/mL; 34 mM) | 294.3 | 218 | 143 |
| DMSO, 5% | 78.13 | 204 | 121 |
| Ethanol, 5% | 46.07 | 182 | 53 |

*The protein concentration = Stated Value ± 5 mg/mL
**Viscosity = Stated Value ± 0.2

TABLE 17

Viscosity of Aqueous Solutions of HGG in Citrate Buffer, pH 6.0 at 25° C. in the presence of Various Organic Solvents or Organic Compounds.

| Excipient | Molecular Weight of Excipient | Citrate Buffer HGG Concentration (mg/mL)* | Viscosity (cP) @ 25° C.** |
|---|---|---|---|
| None | — | 200 | 40 |
| None | — | 225 | 80 |
| None | — | 250 | 160 |
| Polysorbate 80, 0.07% | 1310 | 228 | 78 |
| Aspartame (10 mg/mL; 34 mM) | 294.3 | 140 | 51 |
| DMSO, 5% | 78.13 | 165 | 28 |
| Ethanol, 5% | 46.07 | 113 | 5 |

*The protein concentration = Stated Value ± 5 mg/mL
**Viscosity = Stated Value ± 0.2

TABLE 18

Viscosity of Aqueous Solutions of HGG in Histidine Buffer, pH 6.0 at 25° C. in the presence of Various Organic Solvents or Organic Compounds.

| Excipient | Molecular Weight of Excipient | Histidine Buffer HGG Concentration (mg/mL)* | Viscosity (cP) @ 25° C.** |
|---|---|---|---|
| None | — | 200 | 43 |
| None | — | 225 | 87 |
| None | — | 250 | 146 |
| Acetyl salicylic acid (2.5 mg/mL; 14 mM) | 180.16 | 283 | 43 |

*The protein concentration = Stated Value ± 5 mg/mL
**Viscosity = Stated Value ± 0.2

Example 9: Viscosity-Reducing Effect of Nicotinic Acid (Acid Form), a Viscosity-Reducing Reagent, as a Function of Nicotinic Acid (Acid Form) Concentration on Aqueous Solution of Human Gamma Globulin (HGG)

The present example describes the effect of different concentrations of a viscosity-reducing agent nicotinic acid (acid form) on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, histidine buffer was added from the stock concentration of 1000 mM histidine buffer, pH 6.0 to get a final concentration of 25 mM. To the buffered HGG different concentration of viscosity-reducing agent, nicotinic acid (acid form), was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the histidine buffer containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 μL of sample at 25° C. or using a DV2T cone and plate viscometer using 1.5 mL of sample at 25° C. at extrapolated zero shear rate.

Results

The data in Table 19 demonstrate the viscosity reducing effect of different concentrations of viscosity-reducing agent nicotinic acid (acid form) on Human Gamma Globulin (HGG) in histidine buffer. The viscosity-reducing effect of nicotinic acid (acid form) is seen to rise from 1.7 to 3.5 fold with increasing concentrations of nicotinic acid (acid form). The data in Table 19 show that the higher the concentration of viscosity-reducing agent, the greater the viscosity-reducing effect, at least within the nicotinic acid (acid form) concentration range tested. The solubility of nicotinic acid (acid form) decreases when the concentration of nicotinic acid (acid form) increased above 18 mg/mL.

TABLE 19

Viscosities of aqueous solution of HGG (260 mg/mL ± 5 mg/mL), pH 6.0) in the presence of different concentrations of nicotinic acid (acid form) at 25° C.

| Nicotinic acid (acid form) Concentration (mg/mL) | | | | |
|---|---|---|---|---|
| 0 | 1 | 5 | 10 | 15 |
| Viscosity, cP* | | | | |
| 146$ | 85 | 68 | 52 | 41 |

$Viscosity at 250 mg/mL
*Viscosity = Stated Value ± 0.2

Example 10: The Effect of Temperature on Viscosity of Aqueous Solution of Human Gamma Globulin Formulated with Viscosity-Reducing Agent Nicotinic Acid (Acid Form)

The present example describes the effect of temperature on the viscosity of an aqueous formulation of Human Gamma Globulin with viscosity-reducing agent nicotinic acid (acid form).

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, histidine buffer was added from the stock concentration of 1000 mM histidine buffer, pH 6.0 to get a final concentration of 25 mM. To the buffered HGG viscosity-reducing agent, nicotinic acid (acid form), was added and mixed until complete dissolution. The excipient containing HGG was concentrated to a final volume of less than 150 μL using Vivaspin centrifugal concentrators (Sartorius). The collected protein sample was stored at 4° C. O/N. The final concentration of HGG in solution was determined by measuring absorbance at 280 nm in a UV visible spectrophotometer against the histidine buffer containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 μL of sample either at 20 or 25 or 30° C.; or using a DV2T cone and plate viscometer using 1.5 mL of sample at 20 or 25 or 30° C. at extrapolated zero shear rate.

Results

The data in Table 20 demonstrate the viscosity reducing effect of nicotinic acid (acid form) at all three temperatures tested between 20 to 30° C. In addition, the viscosity of HGG is decreases with increasing temperature from 20 to 30° C.

TABLE 20

Viscosities of aqueous solution of HGG (274 mg/mL ± 5 mg/mL, pH 6.0) in the presence of nicotinic acid (acid form) at different temperatures.

| Temperature (° C.) | | |
|---|---|---|
| 20 | 25 | 30 |
| Viscosity, cP* | | |
| 63 | 41 | 35 |

*Viscosity = Stated Value ± 0.2

Example 11: Removal of Viscosity-Reducing Agent, Nicotinic Acid (Acid Form) Reverses Viscosity-Reducing Effect of Nicotinic Acid (Acid Form)

The present example describes the effect of viscosity-reducing agent nicotinic acid (acid form) on the viscosity of aqueous solutions of Human Gamma Globulin, in comparison with the removal of viscosity-reducing agent nictonic acid (acid form) and the change in viscosity of the formulation.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, histidine buffer was added from the stock concentration of 1000 mM histidine buffer, pH 6.0 to get a final concentration of 25 mM. To the buffered HGG viscosity-reducing agent, nicotinic acid (acid form), was added and mixed until complete dissolution. The excipient containing HGG was concentrated to a final volume of less than 150 µL using Vivaspin centrifugal concentrators (Sartorius). The collected protein sample was stored at 4° C. O/N.

The collected HGG sample was divided into two fractions. One fraction was used as excipient, nicotinic acid (acid form) containing sample; the other fraction was dialysed extensively against 25 mM histidine buffer, pH 6.0 for 24 hr with three changes to remove viscosity-reducing agent, nicotinic acid (acid form) and concentrated using Vivaspin centrifugal concentrators as described above. All three samples, the HGG sample without any nicotinic acid (acid form) (control); the HGG sample containing viscosity-reducing agent, nicotinic acid (acid form); and the dialysed HGG sample where the viscosity-reducing agent had been removed) were then processed for estimating the protein and viscosity.

The final concentration of HGG in solution was determined by measuring absorbance at 280 nm in a UV visible spectrophotometer against the histidine buffer containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample either at 25° C.; or using a DV2T cone and plate viscometer using 1.5 mL of sample at 25° C. at extrapolated zero shear rate.

Results

The three samples generated are as follows: The commercially available HGG with original excipient maltose was either (i) dialysed and concentrated on a centrifugal device (Sartorius) as a control sample (Original Excipient removed by dialysis), (ii) buffer exchanged into histidine buffer containing nicotinic acid (acid form) as mentioned above, and (iii) buffer exchanged as described in (ii), and then further buffer exchanged with 25 mM histidine buffer as described above under Materials and Methods. The data in Table 21 demonstrate the viscosity reducing effect of viscosity-reducing agent nicotinic acid (acid form). But, on removal of nicotinic acid (acid form), the viscosity-reducing agent, the viscosity increased. Furthermore, upon removal of nicotinic acid (acid form), HGG solution viscosity returned to approximately the same level as the original solution, suggesting that nicotinic acid (acid form) is the one which reduces viscosity and does not modify or damage the protein, HGG.

TABLE 21

Viscosities of aqueous solution of HGG (260 mg/mL ± 5 mg/mL, pH 6.0 and 50 mg/mL ± 5 mg/mL, pH 6.0)) in the presence and absence of nicotinic acid (acid form); and after removal of nicotinic acid (acid form).

| Sample | HGG Concentration (mg/mL)* | |
|---|---|---|
| | 260 | 50 |
| | Viscosity, cP** | |
| Original HGG Sample without maltose | 146 | 1.53 |
| HGG Containing Nicotinic acid (acid form) | 52 | 1.3 |
| HGG After removal of Nicotinic acid (acid form) | 138 | 1.6 |

*The protein concentration = Stated Value ± 5 mg/mL
**Viscosity = Stated Value ± 0.2

Example 12: Viscosity-Reducing Agents with UV Absorption do not Interfere in the Estimation of Protein Concentration in Human Gamma Globulin Formulations The present example describes how viscosity-reducing agents do not interfere with the UV absorption measurement that determines protein agent concentration of a formulation of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate buffer was added from the stock concentration of 1000 mM phosphate buffer, pH 6.0 to get a final concentration of 25 mM. To the buffered HGG different viscosity-reducing agent was added individually and mixed until complete dissolution. The excipient/viscosity-reducing reagent containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate containing specific excipient alone (which does not contain HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm.

Results

The data in Table 22 demonstrate that the presence of UV absorbing excipients/viscosity-reducing reagents like nicotinic acid (acid form), tryptophan, caffeine or Thiamine-HCl do not interfere in the estimation of protein/HGG concentration in the samples using a UV-Vis spectrophotometer.

TABLE 22

Formulations Containing UV Absorbing Viscosity-Reducing Agents.

| Formulation | $A_{260\,nm}$ | $A_{280\,nm}$ | $A_{320\,nm}$ | HGG Concentration (mg/mL) |
|---|---|---|---|---|
| HGG | 0.13712 | 0.26319 | 2.42E-03 | 37.6 |
| HGG - Nicotinic acid (acid form) | 0.13942 | 0.26479 | 1.23E-03 | 37.8 |
| HGG - Tryptophan | 0.14064 | 0.26804 | 1.25E-03 | 38.3 |
| HGG - Caffeine | 0.14553 | 0.26941 | 3.33E-03 | 38.5 |
| HGG - Thiamine•HCl | 0.14398 | 0.26355 | 3.78E-03 | 37.7 |

Example 13: A Comparative Study on Viscosity-Reducing Agent Nicotinic Acid (Acid Form) Versus Other Closely Related Viscosity-Reducing Agents and their Effect on Viscosity of Aqueous Solutions of Human Gamma Globulin The present example describes the effect of nicotinic acid (acid form) and other closely related viscosity-reducing agents on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate/histidine buffer was added from the stock concentration of 1000 mM phosphate/citrate/histidine buffer, pH 6.0 to get a final concentration of 25 mM. To the buffered HGG different viscosity-reducing agent(s) was added individually and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate/histidine containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left( A \frac{0.1\%}{280\,nm} = A \frac{1\,mg/mL}{280\,nm} = 1.4 \right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

Figure 2:
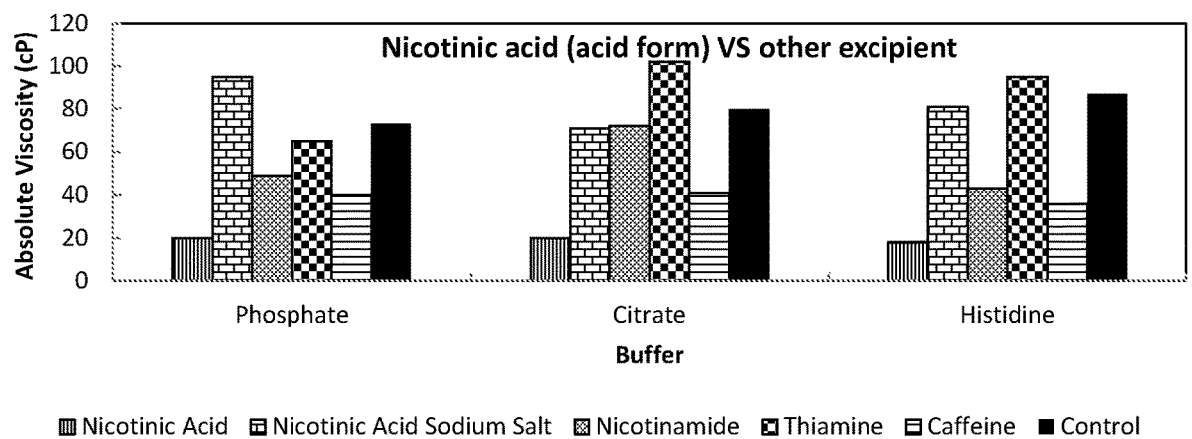
FIG. 2 is a bar graph depicting the comparative data on viscosity (in cP) of an aqueous solution of Human Gamma Globulin (GLOBUCEL®) at 220 mg/mL protein concentration either in 25 mM of Phosphate or Citrate or Histidine Buffer, pH 6.0, buffer systems at 25° C. in the presence of either Nicotinic acid (acid form) (10 mg/mL) or other closely related viscosity-reducing agents such as nicotinamide (10 mg/mL), nicotinic acid sodium salt (10 mg/mL), caffeine (10 mg/mL), thiamine (10 mg/mL) and buffer alone (in the absence any viscosity-reducing agents).

The data in Table 23 demonstrate the viscosity reducing effect of nicotinic acid (acid form), nicotinic acid sodium salt, nicotinamide, thiamine·HCl and caffeine on Human gamma globulin (GLOBUCEL®) in either phosphate or citrate or histidine buffer. The data in FIG. 2 and Table 23 show that in this scenario, nicotinic acid (acid form)>caffeine>nicotinamide>nicotinic acid sodium salt>thiamine-HCl in reducing viscosity in all three buffer systems at 10 mg/mL concentration of viscosity-reducing agent and at HGG concentration of 220 mg/mL.

TABLE 23

Viscosity of Aqueous Solutions of HGG in Various buffer Systems, pH 6.0 at 25° C. in the presence of Viscosity-Reducing Agents (Excipient concentration: 10 mg/mL; HGG Concentration, 220 mg/mL*).

| Viscosity-Reducing Agent | Phosphate Buffer | Citrate Buffer | Histidine Buffer |
|---|---|---|---|
| | | Viscosity, cP** | |
| Nicotinic acid (acid form) | 20 | 20 | 18 |
| Nicotinic acid Sodium Salt | 95 | 71$ | 81 |
| Nicotinamide | 49 | 72 | 43 |
| Thiamine•HCl | 65 | 102 | 95 |
| Caffeine | 40 | 41 | 36 |
| None$ | 73 | 80 | 87 |

$Protein concentration is at 225 mg/mL.
*The protein concentration = Stated Value ± 5 mg/mL
**Viscosity = Stated Value ± 0.2

Example 14: A Comparative Study on Various Combinations of Organic Molecules and their Effect on Viscosity of Aqueous Solutions of Human Gamma Globulin The present example describes the effect of various combinations of organic molecules and their effect on the viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/citrate/histidine buffer was added from the stock concentration of 1000 mM phosphate/citrate/histidine buffer, pH 6.0 to get a final concentration of 25 mM. To the buffered HGG different organic molecules in combination were added and mixed until complete dissolution. The excipient containing HGG was concentrated to a final volume of less than 150 µL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/citrate/histidine containing viscosity-reducing agents alone (which does not contain any HGG) for measuring the protein concentration in excipient containing sample; and for HGG without any excipients, buffer alone (without any excipients) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left( A \frac{0.1\%}{280\,nm} = A \frac{1\,mg/mL}{280\,nm} = 1.4 \right)$$

at 280 nm. The viscosities of the solution were measured either using a Cambridge Viscometer, VISCOlab5000 using 70 μL of sample at 25° C. or using a DV2T cone and plate viscometer using 1.5 mL of sample at 25° C. at extrapolated zero shear rate.

Results

The data in Table 24, 24A and 25 demonstrate the viscosity reducing effect of various combinations of organic compounds on Human gamma globulin (GLOBUCEL®) in either phosphate or citrate or histidine buffer. The data in Table 24, 24A and 25 show that nicotinic acid (acid form) in combinations with aspirin, caffeine citrate, caffeine, tryptophan, glycine or proline had a larger viscosity-reducing effect than other combinations tested.

TABLE 24

Effect of Combinations of Viscosity-Reducing Agents on Viscosity of Aqueous Solutions of HGG in Phosphate buffer System, pH 6.0 at 25° C.

| | Phosphate Buffer | |
|---|---|---|
| Excipient | HGG Concentration (mg/mL)* | Viscosity (cP) @ 25° C.** |
| None | 200 | 29 |
| None | 225 | 73 |
| None | 250 | 191 |
| Tryptophan, Nicotinic acid (acid form) (6 + 10 mg/mL) | 344 | 166 |
| | 303 | 72 |
| | 273 | 32 |
| | 237 | 13 |
| Tryptophan, Nicotinic acid Sodium Salt (6 + 10 mg/mL) | 233 | 68 |
| Tryptophan, Nicotinamide (6 + 10 mg/mL) | 280 | 181 |
| | 251 | 34 |
| Tryptophan, Thiamine (6 + 10 mg/mL) | 235 | 15 |
| Tryptophan, 2-aminopyrimidine (6 + 10 mg/mL) | 236 | 185 |
| Thiamine, Nicotinic acid (acid form) (10 + 10 mg/mL) | 248 | 124 |
| | 234 | 59 |
| Thiamine, Nicotinic acid Sodium Salt (10 + 10 mg/mL) | 240 | 47 |
| Thiamine, Nicotinamide (10 + 10 mg/mL) | 225 | 61 |
| Caffeine, Nicotinic acid (acid form) (10 + 10 mg/mL) | 389 | 166 |
| | 234 | 15 |
| | 207 | 5 |
| Caffeine, Nicotinic acid Sodium Salt (10 + 10 mg/mL) | 274 | 88 |
| | 257 | 78 |
| | 244 | 37 |
| Caffeine, Nicotinamide (10 + 10 mg/mL) | 273 | 97 |
| Caffeine, Thiamine (10 + 10 mg/mL) | 217 | 58 |
| Caffeine, Tryptophan (10 + 6 mg/mL) | 241 | 23 |
| | 203 | 12 |
| Caffeine Citrate, Nicotinic acid (acid form) (20 + 10 mg/mL) | 359 | 39 |
| | 336 | 24 |
| Proline, Nicotinic acid (acid form) (10 + 10 mg/mL) | 272 | 43 |
| | 189 | 13 |
| Proline, Thiamine (10 + 10 mg/mL) | 193 | 20 |
| Proline, Tryptophan (10 + 6 mg/mL) | 222 | 78 |
| | 187 | 14 |
| Glycine, Nicotinic acid (acid form) (10 + 10 mg/mL) | 247 | 33 |
| | 187 | 10 |
| Glycine, Thiamine (10 + 10 mg/mL) | 202 | 35 |
| | 91 | 7 |
| Glycine, Tryptophan (10 + 6 mg/mL) | 250 | 45 |
| | 186 | 11 |
| Arginine, Nicotinic acid (acid form) (10 + 10 mg/mL) | 264 | 100 |
| | 237 | 35 |
| Arginine, Thiamine (10 + 10 mg/mL) | 235 | 89 |
| | 218 | 31 |

*The protein concentration = Stated Value ± 5 mg/mL
**Viscosity = Stated Value ± 0.2

TABLE 24A

Effect of Combinations of Viscosity-Reducing Agents on Viscosity of Aqueous Solutions of HGG in Phosphate buffer System, pH 6.0 at 25° C.

| | Citrate Buffer | |
|---|---|---|
| Excipient | HGG Concentration (mg/mL)* | Viscosity (cP) @ 25° C.** |
| None | 200 | 40 |
| None | 225 | 80 |
| None | 250 | 160 |
| Tryptophan, Nicotinic acid (acid form) (6 + 10 mg/mL) | 270 | 59 |
| | 235 | 33 |
| Tryptophan, Nicotinic acid Sodium Salt (6 + 10 mg/mL) | 276 | 87 |
| Tryptophan, Nicotinamide (6 + 10 mg/mL) | 307 | 198 |
| | 241 | 49 |
| Tryptophan, Thiamine (6 + 10 mg/mL) | 292 | 60 |
| | 269 | 36 |
| | 231 | 15 |
| Thiamine, Nicotinic acid (acid form) (10 + 10 mg/mL) | 255 | 78 |
| | 235 | 47 |
| Thiamine, Nicotinic acid Sodium Salt (10 + 10 mg/mL) | 236 | 68 |
| Thiamine, Nicotinamide (10 + 10 mg/mL) | 232 | 62 |
| Caffeine, Nicotinic acid (acid form) (10 + 10 mg/mL) | 250 | 20 |
| | 231 | 14 |
| Caffeine, Nicotinic acid Sodium Salt (10 + 10 mg/mL) | 232 | 28 |
| | 211 | 15 |
| Caffeine, Nicotinamide (10 + 10 mg/mL) | 220 | 60 |
| Caffeine, Thiamine (10 + 10 mg/mL) | 224 | 61 |
| Caffeine, Tryptophan (10 + 6 mg/mL) | 313 | 76 |
| | 244 | 29 |
| Proline, Nicotinic acid (acid form) (10 + 10 mg/mL) | 302 | 209 |
| | 250 | 31 |
| Proline, Nicotinamide (10 + 10 mg/mL) | 234 | 106 |
| Proline, Thiamine (10 + 10 mg/mL) | 222 | 97 |
| Proline, Tryptophan (10 + 6 mg/mL) | 258 | 94 |
| Glycine, Nicotinic acid (acid form) (10 + 10 mg/mL) | 268 | 150 |
| | 226 | 48 |
| Glycine, Nicotinamide (10 + 10 mg/mL) | 215 | 39 |
| Glycine, Thiamine (10 + 10 mg/mL) | 264 | 140 |
| | 206 | 102 |
| Glycine, Tryptophan (10 + 6 mg/mL) | 232 | 54 |
| Arginine, Nicotinic acid (acid form) (10 + 10 mg/mL) | 245 | 133 |
| | 211 | 77 |
| Arginine, Nicotinamide (10 + 10 mg/mL) | 235 | 131 |
| Arginine, Thiamine (10 + 10 mg/mL) | 232 | 88 |

*The protein concentration = Stated Value ± 5 mg/mL
**Viscosity = Stated Value ± 0.2

TABLE 25

Effect of Combinations of Viscosity-Reducing Agents on Viscosity of Aqueous Solutions of HGG in Histidine buffer System, pH 6.0 at 25° C.

| | Histidine Buffer | |
|---|---|---|
| Excipient | HGG Concentration (mg/mL)* | Viscosity (cP) @ 25° C.** |
| None | 200 | 43 |
| None | 225 | 87 |
| None | 250 | 146 |
| Tryptophan, Nicotinic acid (acid form) (6 + 10 mg/mL) | 270 | 37 |
| Tryptophan, Nicotinic acid Sodium Salt (6 + 10 mg/mL) | 239 | 36 |
| Tryptophan, Nicotinamide (6 + 10 mg/mL) | 250 | 40 |
| Tryptophan, Thiamine (6 + 10 mg/mL) | 238 | 61 |
| Thiamine, Nicotinic acid (acid form) (10 + 10 mg/mL) | 228 | 40 |
| Thiamine, Nicotinic acid Sodium Salt (10 + 10 mg/mL) | 231 | 94 |

TABLE 25-continued

Effect of Combinations of Viscosity-Reducing Agents on Viscosity of Aqueous Solutions of HGG in Histidine buffer System, pH 6.0 at 25° C.

| Excipient | Histidine Buffer | |
|---|---|---|
| | HGG Concentration (mg/mL)* | Viscosity (cP) @ 25° C.** |
| Thiamine, nicotinamide (10 + 10 mg/mL) | 223 | 70 |
| Caffeine, Nicotinic acid (acid form) (10 + 10 mg/mL) | 334 | 83 |
| | 262 | 21 |
| Caffeine, Nicotinic acid Sodium Salt (10 + 10 mg/mL) | 238 | 40 |
| Caffeine, Nicotinamide (10 + 10 mg/mL) | 224 | 39 |
| Caffeine, thiamine (10 + 10 mg/mL) | 221 | 47 |
| Caffeine, Tryptophan (10 + 6 mg/mL) | 290 | 41 |
| Caffeine, Tryptophan (10 + 6 mg/mL)$^\$$ | 289 | 48 |
| Caffeine, Arginine (10 + 10 mg/mL) | 248 | 93 |
| Aspirin, Nicotinic acid (acid form) (2.5 + 10 mg/mL) | 343 | 46 |

$^\$$In 25 mM imidazole buffer, pH 6.0
*The protein concentration = Stated Value ± 5 mg/mL
**Viscosity = Stated Value ± 0.2

Example 15: A Comparison of Different Methods for Measuring Viscosity of Human Gamma Globulin The present example describes the different methods of measuring viscosity yield comparable results.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, citrate-phosphate Buffer was added from the stock concentration of 1000 mM citrate-phosphate buffer, pH 6.0 to get a final concentration of 25 mM. To the buffered HGG different viscosity-reducing agent(s) was added individually or in combination and mixed until complete dissolution. The excipient containing HGG was concentrated to a final volume of less than 150 μL using Vivaspin centrifugal concentrators (Sartorius). The collected protein sample was stored at 4° C. O/N. The final concentration of HGG in solution was determined by measuring absorbance at 280 nm in a UV visible spectrophotometer against the citrate-phosphate buffer containing viscosity-reducing agent alone (which does not contain any HGG). Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, ViscoLab 5000 using 70 μL of sample at 25° C. or using a DV2T cone and plate viscometer using 1.5 mL of sample at 25° C. at extrapolated zero shear rate. The viscosities at 25° C. and pH 6.0 are reported in Table 11 as extrapolated zero-shear viscosities from cone and plate viscometer measurements and as absolute viscosities measured with a ViscoLab viscometer. The cone and plate measurements used a DV2T cone and plate viscometer (Brookfield) equipped with a CPE40 spindle measured at multiple shear rates between 2 and 400 s$^{-1}$. An extrapolated zero-shear viscosity was determined from a plot of absolute viscosity versus shear rate. For measuring absolute viscosity, viscometer ViscoLab 5000 equipped with a piston covering the range from 5-100 cP was used and for viscosities above 100 cP, ViscoLab 4000 equipped with a piston covering the range 50-1000 cP was used.

Results

The data in Table 26 demonstrate that absolute viscosities from the ViscoLab viscometer can be directly compared to extrapolated zero-shear viscosities determined from a cone and plate viscometer. In order to compare a broad range of protein agent concentrations and presence of a number of viscosity-reducing agents, aqueous solutions of a model antibody, human gamma globulin, were prepared with and without viscosity-reducing agents such as nicotinamide, tryptophan and thiamine. The viscosities were measured as described above at protein concentrations ranging from 192 to 243 mg/mL. The data presented in Table 26 demonstrate that the absolute viscosities measured using both instruments are in agreement even in the presence of viscosity-reducing reagents.

TABLE 26

Viscosities of Aqueous Human Gamma Globulin Solutions with and without Viscosity-Reducing Agents at 25° C. and pH 6.0 measured on two different viscometers.

| | ViscoLab 5000 | Cone and Plate Viscometer (C&P) |
|---|---|---|
| | Viscosity, cP** | |
| Without Viscosity-Reducing Agent (HGG, 192 mg/mL*) | 32 | 22 |
| With Tryptophan + Nicotinamide (HGG, 243 mg/mL*) | 25 | 36 |
| With Tryptophan + Thiamine (HGG, 242 mg/mL*) | 10 | 12 |

*The protein concentration = Stated Value ± 5 mg/mL
**Viscosity = Stated Value ± 0.2

Example 16: Effect of Viscosity-Reducing Agents, a Combination of Nicotinic Acid (Acid Form) and Tryptophan, the Viscosity of Human Gamma Globulin Solutions The present example describes the effect of the combination of viscosity-reducing agents nicotinic acid (acid form) and tryptophan on viscosity of aqueous solutions of Human Gamma Globulin.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate buffer was added from the stock concentration of 1000 mM phosphate buffer, pH 6.0 to get a final concentration of 25 mM. To the buffered HGG different viscosity-reducing agent(s) was added individually or in combination and mixed until complete dissolution. The excipient containing HGG was concentrated to a final volume of less than 150 μL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left( A \frac{0.1\%}{280 \text{ nm}} = A \frac{1 \text{ mg/mL}}{280 \text{ nm}} = 1.4 \right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

Figure 3:
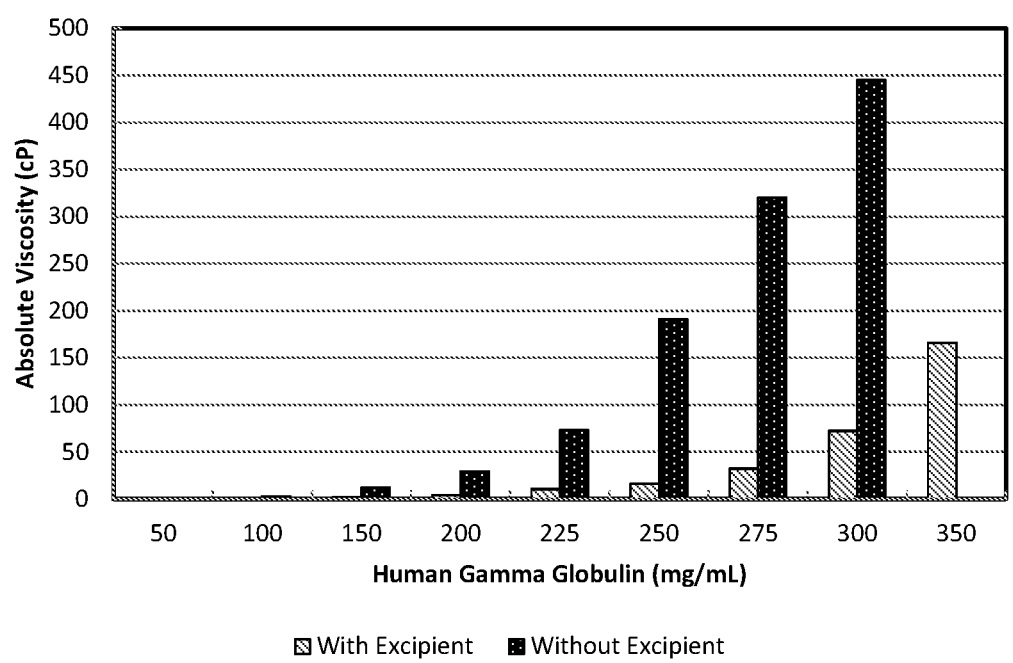
FIG. 3 depicts viscosity of an aqueous solution (cP) in the absence and in the presence of 10 mg/mL of Nicotinic acid (acid form) and 6 mg/mL Tryptophan as a function of Human Gamma Globulin (GLOBUCEL®) concentration (50 mg/mL, 100 mg/mL, 150 mg/mL, 200 mg/mL, 225 mg/mL, 250 mg/mL, 275 mg/mL, 300 mg/mL, 350 mg/mL) along the X-axis in 25 mM Phosphate buffer, pH 6.0 at 25° C.

The data in Table 27 demonstrate the viscosity reducing effect of the combination of viscosity-reducing agents nicotinic acid (acid form) and tryptophan on different concentrations of Human gamma globulin (GLOBUCEL®) in phosphate buffer. The viscosity of HGG in phosphate buffer increases exponentially with increasing HGG concentration. The viscosity of a solution of HGG in the presence of excipients were seen to increase exponentially with increasing HGG concentration, but to a lesser extent than the formulation in phosphate buffer i.e. the viscosity gradient is reduced. The data in FIG. 3 and Table 27 show that the higher the concentration of HGG, the greater the viscosity-reducing effect. The magnitude of viscosity-reducing effects afforded by the addition of viscosity-reducing agents, nicotinic acid (acid form) and tryptophan to the phosphate buffer was 11.2-fold at 250±10 mg/mL.

TABLE 27

Viscosity of Various Concentrations of HGG in Phosphate buffer, pH 6.0 at 25° C. in the absence and presence of excipients (Excipient: 10 mg/mL of Nicotinic acid (acid form) and 6 mg/mL Tryptophan).

| | HGG Concentration (mg/mL)* | | | | | | | | |
|---|---|---|---|---|---|---|---|---|---|
| | 50 | 100 | 150 | 200 | 225 | 250 | 275 | 300 | 350 |
| | Viscosity, cP** | | | | | | | | |
| With Excipient | 1 | 1 | 2 | 4 | 11 | 17 | 32 | 77 | 166 |
| Without Excipient | 1 | 3 | 12 | 79 | 73 | 191 | 320 | 445 | ND |

*The protein concentration = Stated Value ± 5 mg/mL
**Viscosity = Stated Value ± 0.2

Example 17: Effect of Viscosity-Reducing Agents, a Combination of Nicotinic Acid (Acid Form) and Tryptophan, on the Viscosity of Trastuzumab Solutions The present example describes the effect of the combination of viscosity-reducing agents nicotinic acid (acid form) and tryptophan on viscosity of aqueous solutions of Trastuzumab.

Materials and Methods

Commercially obtained Trastuzumab, HERCEPTIN® (lyophilized powder contains 440 mg trastuzumab, 9.9 mg of L-Histidine·HCl, 6.4 mg of L-Histidine, 400 mg of a,a-trehalose dihydrate, and 1.8 mg polysorbate 20, USP; and 20 mL of water for injection for reconstitution) was dialyzed against 25 mM phosphate buffer, pH 6.0 for 24 hr at 4° C. with three changes. To the dialysed Trastuzumab different viscosity-reducing agent(s) was added individually or in combination and mixed until complete dissolution. The excipient containing Trastuzumab was concentrated to a final volume of less than 150 µL using Vivaspin centrifugal concentrators (Sartorius). The collected protein sample was stored at 4° C. O/N. The final concentration of Trastuzumab in solution was determined by measuring absorbance at 280 nm in a UV visible spectrophotometer against the phosphate buffer containing viscosity-reducing agent alone (which does not contain any Trastuzumab) for measuring the protein concentration in excipient containing sample, and for Trastuzumab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.48

$$\left( A \frac{0.1\%}{280 \text{ nm}} = A \frac{1 \text{ mg/mL}}{280 \text{ nm}} = 1.48 \right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

Figure 4:
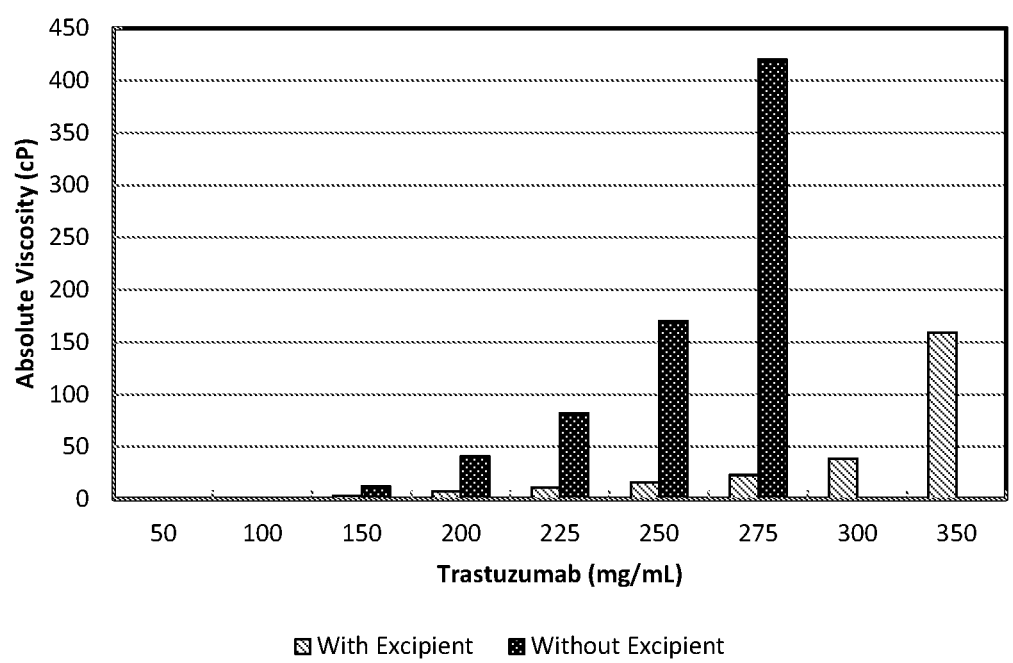
FIG. 4 depicts viscosity (cP) of an aqueous solution in the absence and in the presence of 10 mg/mL of Nicotinic acid (acid form) and 6 mg/mL Tryptophan as a function of Trastuzumab (Herceptin® or CANMAB®) concentration (50 mg/mL, 100 mg/mL, 150 mg/mL, 200 mg/mL, 225 mg/mL, 250 mg/mL, 275 mg/mL, 300 mg/mL, 350 mg/mL) along the X-axis in 25 mM Phosphate buffer, pH 6.0 at 25° C.

The data in Table 28 demonstrate the viscosity reducing effect of the combination of viscosity-reducing agents nicotinic acid (acid form) and tryptophan on different concentrations of Trastuzumab (HERCEPTIN®) in phosphate buffer. The viscosity of Trastuzumab in phosphate buffer increases exponentially with increasing Trastuzumab concentration. The viscosity of a solution of Trastuzumab in the presence of excipients also increases exponentially with increasing Trastuzumab concentration, but to a lesser extent than the formulation in phosphate buffer alone. The data in FIG. 4 and Table 28 show that the higher the concentration of Trastuzumab, the greater the viscosity-reducing effect. The magnitude of viscosity-reducing effects afforded by the addition of viscosity-reducing agents, nicotinic acid (acid form) and tryptophan to the phosphate buffer was 18.3-fold at 275±10 mg/mL.

TABLE 28

Viscosity of Various Concentrations of Trastuzumab in Phosphate buffer, pH 6.0 at 25° C. in the absence and presence of excipients (Excipient: 10 mg/mL of Nicotinic acid (acid form) and 6 mg/mL Tryptophan).

| | Trastuzumab Concentration (mg/mL)* | | | | | | | | |
|---|---|---|---|---|---|---|---|---|---|
| | 50 | 100 | 150 | 200 | 225 | 250 | 275 | 300 | 350 |
| | Viscosity, cP** | | | | | | | | |
| With Excipient | 1 | 2 | 3 | 8 | 11 | 16 | 23 | 39 | 159 |
| Without Excipient | | 12 | 41 | 82 | 170 | 420 | | | |

*The protein concentration = Stated Value ± 5 mg/mL
**Viscosity = Stated Value ± 0.2

Example 18: Effect of Viscosity-Reducing Agents, a Combination of Nicotinic Acid (Acid Form) and Tryptophan, on the Viscosity of Rituximab Solutions The present example describes the effect of the combination of viscosity-reducing agents nicotinic acid (acid form) and tryptophan on viscosity of aqueous solutions of Rituximab.

Materials and Methods

Commercially obtained Rituximab, RITUXAN®, 500 mg in 50 mL (10 mg/mL Rituximab, 9 mg/mL sodium chloride, 7.35 mg/mL of Trisodium citrate Dihydrate, and 0.7 mg/mL polysorbate 80, USP) was dialyzed against 25 mM phosphate buffer, pH 6.0 for 24 hr at 4° C. with three changes. To the dialysed Rituximab different viscosity-reducing agent(s) was added individually or in combination and mixed until complete dissolution. The excipient containing Rituximab was concentrated to a final volume of less than 150 µL using Vivaspin centrifugal concentrators (Sartorius). The collected protein sample was stored at 4° C. O/N. The final concentration of Rituximab in solution was determined by measuring absorbance at 280 nm in a UV visible spectrophotometer against the phosphate buffer containing viscosity-reducing agent alone (which does not contain any Rituximab) for measuring the protein concentration in excipient containing sample; and for Rituximab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.7

$$\left(A\frac{0.1\%}{280 \text{ nm}} = A\frac{1 \text{ mg/mL}}{280 \text{ nm}} = 1.7\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

Figure 5:
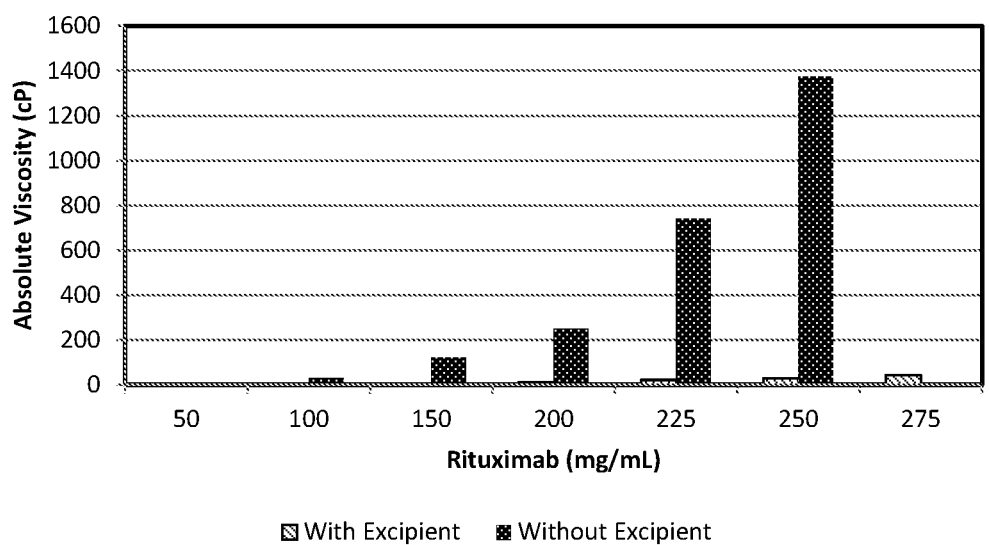
FIG. 5 is a (cP) bar graph depicting viscosity of an aqueous solution in the absence and in the presence of 10 mg/mL of Nicotinic acid (acid form) and 6 mg/mL Tryptophan as a function of Rituximab (RITUXAN®) concentration (50 mg/mL, 100 mg/mL, 150 mg/mL, 200 mg/mL, 225 mg/mL, 250 mg/mL, 275 mg/mL) along the X-axis in 25 mM Phosphate buffer, pH 6.0 at 25° C.

The data in Table 29 demonstrate the viscosity reducing effect of the combination of viscosity-reducing agents nicotinic acid (acid form) and tryptophan on different concentrations of Rituximab (RITUXAN®) in phosphate Buffer. The viscosity of Rituximab in phosphate buffer increases exponentially with increasing Rituximab concentration. The viscosity of a solution of Rituximab in the presence of viscosity-reducing agents also increases exponentially with increasing Rituximab concentration, but to a lesser extent than the formulation in phosphate buffer alone. The data in FIG. 5 and Table 29 show that the higher the concentration of Rituximab, the greater the viscosity-reducing effect. The magnitude of viscosity-reducing effects afforded by the addition of viscosity-reducing agents, nicotinic acid (acid form) and tryptophan to the phosphate buffer was 47.4-fold at 250±10 mg/mL.

TABLE 29

Viscosity of Various Concentrations of Rituximab in Phosphate buffer, pH 6.0 at 25° C. in the absence and presence of excipients (Excipient: 10 mg/mL of Nicotinic acid (acid form) and 6 mg/mL Tryptgphan).

| | Rituximab Concentration (mg/mL)* | | | | | | |
|---|---|---|---|---|---|---|---|
| | 50 | 100 | 150 | 200 | 225 | 250 | 275 |
| | Viscosity, cP** | | | | | | |
| With Excipient | 1 | 2 | 5 | 12 | 22 | 29 | 43 |
| Without Excipient | 3 | 30 | 120 | 251 | 740 | 1375 | |

*The protein concentration = Stated Value ± 5 mg/mL
**Viscosity = Stated Value ± 0.2

Example 19: Effect of Viscosity-Reducing Agents, a Combination of Nicotinic Acid (Acid Form) and Tryptophan, on Bevacizumab The present example describes the effect of the combination of viscosity-reducing agents nicotinic acid (acid form) and tryptophan on viscosity of aqueous solutions of Bevacizumab.

Materials and Methods

Commercially obtained Bevacizumab, AVASTIN®, 400 mg in 16 mL (100 mg/4 mL Bevacizumab, 240 mg/4 mL Trehalose dihydrate, 23.2 mg/4 mL sodium phosphate, monobasic, monohydrate, 4.8 mg/4 mL sodium phosphate dibasic, anhydrous, and 1.6 mg/4 mL polysorbate 20, USP) was dialyzed against 25 mM phosphate buffer, pH 6.0 for 24 hr at 4° C. with three changes. To the dialysed Bevacizumab different viscosity-reducing agent(s) was added individually or in combination and mixed until complete dissolution. The excipient containing Bevacizumab was concentrated to a final volume of less than 150 µL using Vivaspin centrifugal concentrators (Sartorius). The collected protein sample was stored at 4° C. O/N. The final concentration of Bevacizumab in solution was determined by measuring absorbance at 280 nm in a UV visible spectrophotometer against the phosphate buffer containing viscosity-reducing agent alone (which does not contain any Bevacizumab) for measuring the protein concentration in excipient containing sample, and for Bevacizumab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.54

$$\left(A\frac{0.1\%}{280 \text{ nm}} = A\frac{1 \text{ mg/mL}}{280 \text{ nm}} = 1.54\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 30 demonstrate the viscosity-reducing effect of the combination of viscosity-reducing agents nicotinic acid (acid form) and tryptophan on different concentrations of Bevacizumab (AVASTIN®) in phosphate Buffer.

Figure 6:
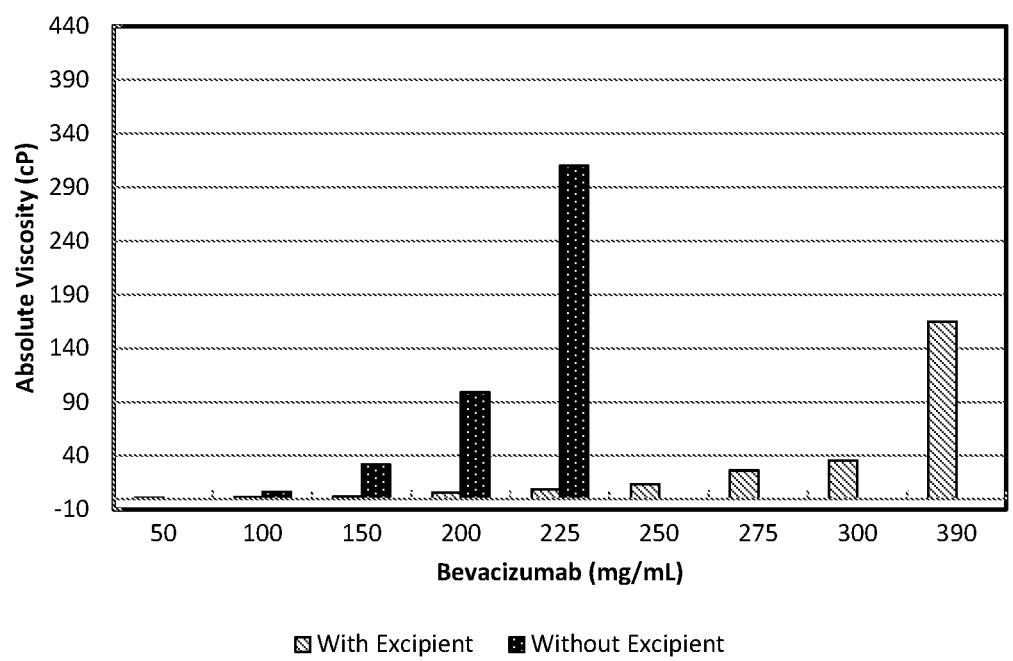
FIG. 6 depicts viscosity (cP) of an aqueous solution in the absence and in the presence of 10 mg/mL of viscosity-reducing agents Nicotinic acid (acid form) and 6 mg/mL Tryptophan as a function of bevacizumab (AVASTIN®) concentration (50 mg/mL, 100 mg/mL, 150 mg/mL, 200 mg/mL, 225 mg/mL, 250 mg/mL, 275 mg/mL, 300 mg/mL, 390 mg/mL) along the X-axis in 25 mM Phosphate buffer, pH 6.0 at 25° C.

The viscosity of Bevacizumab in phosphate buffer increases exponentially with increasing Bevacizumab concentration. The viscosity of a solution of Bevacizumab in the presence of viscosity-reducing agents also increases exponentially with increasing Bevacizumab concentration, but to a lesser extent than the formulation in phosphate buffer alone. The data in FIG. 6 and Table 30 show that the higher the concentration of Bevacizumab, the greater the viscosity-reducing effect. The magnitude of viscosity-reducing effects afforded by the addition of viscosity-reducing agents, nicotinic acid (acid form) and tryptophan to the phosphate buffer was 34.4-fold at 225±10 mg/mL.

TABLE 30

Viscosity of Various Concentrations of Bevacizumab in Phosphate buffer, pH 6.0 at 25° C. in the absence and presence of excipients (Excipient: 10 mg/mL of Nicotinic acid (acid form) and 6 mg/mL Tryptophan).

| | Bevacizumab Concentration (mg/mL)* | | | | | | | | |
|---|---|---|---|---|---|---|---|---|---|
| | 50 | 100 | 150 | 200 | 225 | 250 | 275 | 300 | 390 |
| | Viscosity, cP** | | | | | | | | |
| With Excipient | 1 | 1 | 2 | 6 | 9 | 14 | 26 | 36 | 165 |
| Without Excipient | | 7 | 32 | 99 | 310 | | | | |

*The protein concentration = Stated Value ± 5 mg/mL
**Viscosity = Stated Value ± 0.2

Example 20: Effect of Viscosity-Reducing Agents, a Combination of Nicotinic Acid (Acid Form) and Tryptophan, on Viscosity of Cetuximab Solutions The present example describes the effect of the combination of viscosity-reducing agents nicotinic acid (acid form) and tryptophan on viscosity of aqueous solutions of Cetuximab.

Materials and Methods

Commercially obtained Cetuximab, ERBITUX®, 100 mg in 50 mL (2 mg/1 mL Cetuximab, 8.48 mg/1 mL sodium chloride, 0.41 mg/1 mL sodium phosphate, monobasic, monohydrate, 1.88 mg/1 mL sodium phosphate dibasic, heptahydrate) was dialyzed against 25 mM phosphate buffer, pH 6.0 for 24 hr at 4° C. with three changes. To the dialysed Cetuximab different viscosity-reducing agent(s) was added individually or in combination and mixed until complete dissolution. The excipient containing Cetuximab was concentrated to a final volume of less than 150 μL using Vivaspin centrifugal concentrators (Sartorius). The collected protein sample was stored at 4° C. O/N. The final concentration of Cetuximab in solution was determined by measuring absorbance at 280 nm in a UV visible spectrophotometer against the phosphate buffer containing viscosity-reducing agent alone (which does not contain any Cetuximab) for measuring the protein concentration in excipient containing sample, and for Cetuximab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 μL of sample at 25° C. or using a DV2T cone and plate viscometer using 1.5 mL of sample at 25° C. at extrapolated zero shear rate.

Results

The data in Table 31 demonstrate the viscosity reducing effect of the combination of viscosity-reducing agents nicotinic acid (acid form) and tryptophan on different concentrations of Cetuximab (ERBITUX®) in phosphate Buffer. The viscosity of Cetuximab in phosphate buffer increases exponentially with increasing Cetuximab concentration. The viscosity of a solution of Cetuximab in the presence of viscosity-reducing agents also increases exponentially with increasing Cetuximab concentration, but to a lesser extent than the formulation in phosphate buffer. The data in FIG. 7 and Table 31 show that the higher the concentration of Cetuximab, the greater the viscosity-reducing effect. The magnitude of viscosity-reducing effects afforded by the addition of viscosity-reducing agents, nicotinic acid (acid form) and tryptophan to the phosphate buffer was 20.11-fold at 250±10 mg/mL.

TABLE 31

Viscosity of Various Concentrations of Cetuximab in Phosphate buffer, pH 6.0 at 25° C. in the absence and presence of excipients (Excipient: 10 mg/mL of Nicotinic acid (acid form) and 6 mg/mL Tryptophan).

| | Cetuximab Concentration (mg/mL) | | | | | | |
|---|---|---|---|---|---|---|---|
| | 50 | 100 | 150 | 175 | 200 | 225 | 250 |
| | Viscosity, cP** | | | | | | |
| With Excipient | 2 | 3 | 9 | 17 | 28 | 40 | 86 |
| Without Excipient | 4 | 45 | 152 | 270 | 635 | 1130 | 1730 |

*The protein concentration = Stated Value ± 5 mg/mL
**Viscosity = Stated Value ± 0.2

Example 21: Effect of Viscosity-Reducing Agents, a Combination of Nicotinic Acid (Acid Form) and Tryptophan, on Viscosity of Etanercept Solutions The present example describes the effect of the combination of viscosity-reducing agents nicotinic acid (acid form) and tryptophan on viscosity of aqueous solutions of Etanercept.

Materials and Methods

Commercially obtained Etanercept, ENBREL®, 25 mg as a lyophilized powder (25 mg Etanercept, 40 mg mannitol, 10 mg sucrose, and 1.2 mg Tromethamine and for reconstitution 0.9% benzyl alcohol in water) was dialyzed against 25 mM phosphate buffer, pH 6.0 for 24 hr at 4° C. with three changes. To the dialysed Etanercept different viscosity-reducing agent(s) was added individually or in combination and mixed until complete dissolution. The excipient containing Etanercept was concentrated to a final volume of less than 150 μL using Vivaspin centrifugal concentrators (Sartorius). The collected protein sample was stored at 4° C. O/N. The final concentration of Etanercept in solution was determined by measuring absorbance at 280 nm in a UV visible spectrophotometer against the phosphate buffer containing viscosity-reducing agent alone (which does not contain any Etanercept) for measuring the protein concentration in excipient containing sample; and for Etanercept without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 0.9

$$\left(A\frac{0.1\%}{280\ nm} = A\frac{1\ mg/mL}{280\ nm} = 0.96\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 32 demonstrate the viscosity-reducing effect of the combination of nicotinic acid (acid form) and tryptophan excipients on different concentrations of Etanercept (ENBREL®) in phosphate buffer. The viscosity of Etanercept in phosphate buffer increases exponentially with increasing Etanercept concentration. The viscosity of a solution of Etanercept in the presence of viscosity-reducing agents also increases exponentially with increasing Etanercept concentration, but to a lesser extent than the formulation in phosphate buffer. The data in FIG. 8 and Table 32 show that the higher the concentration of Etanercept, the greater the viscosity-reducing effect. The magnitude of viscosity-reducing effects afforded by the addition of viscosity-reducing agents, nicotinic acid (acid form) and tryptophan to the phosphate buffer was 14.6-fold at 275±10 mg/mL.

TABLE 32

Viscosity of Various Concentrations of Etanercept in Phosphate buffer, pH 6.0 at 25° C. in the absence and presence of excipients (Excipient: 10 mg/mL of Nicotinic acid (acid form) and 6 mg/mL Tryptophan).

| | Etanercept Concentration (mg/mL)* | | | | | | | | |
|---|---|---|---|---|---|---|---|---|---|
| | 50 | 100 | 150 | 175 | 200 | 225 | 250 | 275 | 300 |
| | Viscosity, cP** | | | | | | | | |
| With Excipient | 2 | 3 | 11 | 17 | 23 | 40 | 65 | 77 | 139 |
| Without Excipient | 35 | 72 | 135 | 160 | 230 | 345 | 439 | 1130 | |

*The protein concentration = Stated Value ± 5 mg/mL
**Viscosity = Stated Value ± 0.2

Example 22: Effect of Viscosity-Reducing Agents, a Combination of Nicotinic Acid (Acid Form) and Tryptophan, on Trastuzumab—A Biophysical Characterization The present example describes the effect of the combination of viscosity-reducing agents nicotinic acid (acid form) and tryptophan on aggregation of Human Gamma Globulin in aqueous solutions.

Materials and Methods

Commercially obtained Trastuzumab, HERCEPTIN® (lyophilized powder contains 440 mg Trastuzumab, 9.9 mg of L-Histidine·HCl, 6.4 mg of L-Histidine, 400 mg of a,a-trehalose dihydrate, and 1.8 mg polysorbate 20, USP; and 20 mL of water for injection for reconstitution) was dialyzed against 25 mM phosphate buffer, pH 6.0 for 24 hr at 4° C. with three changes. To the dialysed Trastuzumab different viscosity-reducing agent(s) was added individually or in combination and mixed until complete dissolution. The excipient containing Trastuzumab was concentrated to a final volume of less than 150 µL using Vivaspin centrifugal concentrators (Sartorius). The collected protein sample was stored at 4° C. O/N. The final concentration of Trastuzumab in solution was determined by measuring absorbance at 280 nm in a UV visible spectrophotometer against the phosphate buffer containing viscosity-reducing agent alone (which does not contain any Trastuzumab) for measuring the protein concentration in excipient containing sample; and for Trastuzumab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.48

$$\left(A\frac{0.1\%}{280\ nm} = A\frac{1\ mg/mL}{280\ nm} = 1.48\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 28 demonstrate the viscosity reducing effect of the combination of viscosity-reducing agents nicotinic acid (acid form) and tryptophan on Trastuzumab (HERCEPTIN®) in phosphate buffer. The magnitude of viscosity-reducing effects afforded by the addition of viscosity-reducing agents, nicotinic acid (acid form) and tryptophan to the phosphate buffer was 18.3-fold at 275±10 mg/mL and 10.6-fold at 250±10 mg/mL.

Biophysical characterization of formulated Trastuzumab in aqueous solution with viscosity-reducing agents, tryptophan and nicotinic acid (acid form), was carried out over a three month period. Samples of Trastuzumab were prepared as described above. The data in Table 33 and FIG. 9 demonstrate that the monomer content of concentrated solutions of Trastuzumab at 250-275 mg/mL as determined by Size Exclusion Chromatography (Phenomenex BioSEP SEC-S2000 (7.8 mm×30 cm; 50 mM sodium phosphate buffer, pH 6.5 containing 0.1M sodium chloride; flow rate 0.5 mL/min; isocratic) is similar to the drug product at all time points and no detectable aggregates or degradation is observed after storage for three months at 4° C. The viscosity, as measured using a ViscoLab 5000 viscometer, remained the same or stable after storage for 3 months at 4° C. (Table 34). In addition, antigen binding of the formulated Trastuzumab after storage for 90 days at 4° C., did not alter using Trastuzumab-Specific Sandwich ELISA assay. Moreover, the monomer content (Table 35) of concentrated solution of Trastuzumab are comparable to the drug product after 2 week storage at room temperature.

TABLE 33

No Aggregation after Three Months at 4° C. of Aqueous Solution of Formulated Trastuzumab in the Presence of Viscosity-Reducing Agents – Tryptophan + Nicotinic acid (acid form)

|  | 0 Month | | 1 Month | | 2 Month | | 3 Month* | |
| --- | --- | --- | --- | --- | --- | --- | --- | --- |
|  | Aggregation peak area (%) | Standard peak area (%) | Aggregation peak area (%) | Standard peak area (%) | Aggregation peak area (%) | Standard peak area (%) | Aggregation peak area (%) | Standard peak area (%) |
| Trastuzumab-DP** | 1.09 | 98.93 | Nil | 100 | Nil | 100 | Nil | 100 |
| Trastuzumab-Formulated | Nil | 100 | Nil | 100 | Nil | 100 | Nil | 100 |

*No Degradation of samples even after three months;
**DP-Drug Product. The values are within ±0.2% of the stated numbers

TABLE 34

Reduced Viscosity and Antigen Binding Capacity are Maintained over Time at 4° C. of Aqueous Solution of Formulated Trastuzumab in the Presence of Viscosity-Reducing Agents - Tryptophan + Nicotinic acid (acid form)

| Month | Viscosity (cP)* | % Binding (ELISA Assay)** |
| --- | --- | --- |
| 0 | 23 | — |
| 1 | 24 | 100 |
| 3 | 23 | 100 |

*Viscosity = Stated Value ± 0.2;
The % Binding values are within ± 0.2% of the stated numbers

TABLE 35

No Aggregation after 14 days at Room Temperature of Aqueous Solution of Formulated Trastuzumab in the Presence of Viscosity-Reducing Agents – Tryptophan + Nicotinic acid (acid form)

|  | 0 day | | | 14 days | | |
| --- | --- | --- | --- | --- | --- | --- |
|  | Aggregation peak Area (%) | Standard peak area (%) | Degradation peak area (%) | Aggregation peak area (%) | Standard peak area (%) | Degradation peak area (%) |
| Trastuzumab-Drug Product | 1.09 | 98.93 | Nil | Nil | 100 | Nil |
| Trastuzumab-Formulated | Nil | 100 | Nil | Nil | 100 | Nil |

The % Binding values are within ±0.2% of the stated numbers

Example 23: Effect of Viscosity-Reducing Agents, a Combination of Nicotinic Acid (Acid Form) and Tryptophan on Rituximab—A Biophysical Characterization The present example describes the effect of the combination of viscosity-reducing agents nicotinic acid (acid form) and tryptophan on aggregation of Rituximab in aqueous solutions.

Materials and Methods

Commercially obtained Rituximab, RITUXAN®, 500 mg in 50 mL (10 mg/mL Rituximab, 9 mg/mL sodium chloride, 7.35 mg/mL of Trisodium citrate Dihydrate, and 0.7 mg/mL polysorbate 80, USP) was dialyzed against 25 mM phosphate buffer, pH 6.0 for 24 hr at 4° C. with three changes. To the dialysed Rituximab different viscosity-reducing agent(s) was added individually or in combination and mixed until complete dissolution. The excipient containing Rituximab was concentrated to a final volume of less than 150 μL using Vivaspin centrifugal concentrators (Sartorius). The collected protein sample was stored at 4° C. O/N. The final concentration of Rituximab in solution was determined by measuring absorbance at 280 nm in a UV visible spectrophotometer against the phosphate buffer containing viscosity-reducing agent alone (which does not contain any Rituximab) for measuring the protein concentration in excipient containing sample; and for Rituximab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.7

$$\left(A\frac{0.1\%}{280 \text{ nm}} = A\frac{1 \text{ mg/mL}}{280 \text{ nm}} = 1.7\right)$$

at 280 nm. The viscosities of the solution were measured either using a Cambridge Viscometer, VISCOlab5000 using 70 μL of sample at 25° C. or using a DV2T cone and plate viscometer using 1.5 mL of sample at 25° C. at extrapolated zero shear rate.
Results The data in Table 29 demonstrate the viscosity-reducing effect of the combination of viscosity-reducing agents nicotinic acid (acid form) and tryptophan on Rituximab (RITUXAN®) in phosphate Buffer. The magnitude of viscosity-reducing effects afforded by the addition of viscosity-reducing agents, nicotinic acid (acid form) and tryptophan to the phosphate buffer was 47.4-fold at 250±10 mg/mL.

Biophysical characterization of formulated Rituximab in aqueous solution with viscosity-reducing agents, Tryptophan and nicotinic acid (acid form), were carried out over a seven day period at room temperature. Samples of Rituximab were prepared as described above. The data in Table 36 demonstrated that the monomer content of concentrated solutions of Rituximab at 250 mg/mL as determined by Size Exclusion Chromatography (Phenomenex BioSEP SEC-S2000 (7.8 mm×30 cm; 50 mM sodium phosphate buffer, pH 6.5 containing 0.1M sodium chloride; flow rate 0.5 mL/min; isocratic) is similar to the drug product at all time points and no detectable aggregates or degradation is observed after storage for 7 days at 25° C.

nm in a UV visible spectrophotometer against the phosphate buffer containing viscosity-reducing agent alone (which does not contain any Bevacizumab) for measuring the protein concentration in excipient containing sample, and for Bevacizumab without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.54

$$\left(A\frac{0.1\%}{280\text{ nm}} = A\frac{1\text{ mg/mL}}{280\text{ nm}} = 1.54\right)$$

at 280 nm. The viscosities of the solution were measured either using a Cambridge Viscometer, VISCOlab5000 using 70 μL of sample at 25° C. or using a DV2T cone and plate viscometer using 1.5 mL of sample at 25° C. at extrapolated zero shear rate.

TABLE 36

No Aggregation after 7 days at 25° C. of Aqueous Solution of Formulated Rituximab in the Presence of Viscosity-Reducing Agents – Tryptophan + Nicotinic acid (acid form)

| | 0 day | | | 7 days | | |
|---|---|---|---|---|---|---|
| | Aggregation peak area (%) | Standard peak area (%) | Degradation peak area (%) | Aggregation peak area (%) | Standard peak area (%) | Degradation peak area (%) |
| Rituximab | 1.027 | 98.97 | Nil | 0.96 | 99.04 | Nil |

The values are within ±0.2% of the stated numbers.

Example 24: Effect of Viscosity-Reducing Agents, a Combination of Nicotinic Acid (Acid Form) and Tryptophan, on Bevacizumab—A Biophysical Characterization The present example describes the effect of the combination of viscosity-reducing agents nicotinic acid (acid form) and tryptophan on aggregation of Bevacizumab in aqueous solutions.
Materials and Methods Commercially obtained Bevacizumab, AVASTIN®, 400 mg in 16 mL (100 mg/4 mL Bevacizumab, 240 mg/4 mL Trehalose dihydrate, 23.2 mg/4 mL sodium phosphate, monobasic, monohydrate, 4.8 mg/4 mL sodium phosphate dibasic, anhydrous, and 1.6 mg/4 mL polysorbate 20, USP) was dialyzed against 25 mM phosphate buffer, pH 6.0 for 24 hr at 4° C. with three changes. To the dialysed Bevacizumab different viscosity-reducing agent(s) was added individually or in combination and mixed until complete dissolution. The excipient-containing Bevacizumab was concentrated to a final volume of less than 150 μL using Vivaspin centrifugal concentrators (Sartorius). The collected protein sample was stored at 4° C. O/N. The final concentration of Bevacizumab in solution was determined by measuring absorbance at 280

Results

The data in Table 30 demonstrate the viscosity-reducing effect of the combination of viscosity-reducing agents nicotinic acid (acid form) and tryptophan on Bevacizumab (AVASTIN®) in phosphate Buffer. The magnitude of viscosity-reducing effects afforded by the addition of viscosity-reducing agents, nicotinic acid (acid form) and tryptophan, to the phosphate buffer was 34.4-fold at 225±10 mg/mL.

Biophysical characterization of formulated Bevacizumab in aqueous solution with viscosity-reducing agents, tryptophan and nicotinic acid (acid form), was carried out over a three month period. Samples of Bevacizumab were prepared as described above. The data in Table 37 demonstrate that the monomer content of concentrated solutions of Bevacizumab at 225 mg/mL as determined by Size Exclusion Chromatography (Phenomenex BioSEP SEC-S2000 (7.8 mm×30 cm; 50 mM sodium phosphate buffer, pH 6.5 containing 0.1M sodium chloride; flow rate 0.5 mL/min; isocratic) is similar to the drug product at all time points and no detectable aggregatioin or degradation is observed after storage for three months at 4° C. Moreover, the monomer content (Table 38) of concentrated solution of Bevacizumab are comparable to the drug product after 7 days at 25° C.

TABLE 37

No Aggregation after Three Months at 4° C. of Aqueous Solution of Formulated
Bevacizumab in the Presence of Viscosity-Reducing Agents – Tryptophan + Nicotinic acid (acid form)

|  | 0 day | | 1 month | | 2 month | | 3 month* | |
| --- | --- | --- | --- | --- | --- | --- | --- | --- |
|  | Aggregation peak area (%) | Standard peak area (%) | Aggregation peak area (%) | Standard peak area (%) | Aggregation peak area (%) | Standard peak area (%) | Aggregation peak area (%) | Standard peak area (%) |
| Bevacizumab-Drug Product | 0.601 | 99.39 | 1.099 | 98.90 | Nil | 100 | Nil | 100 |
| Bevacizumab-Formulated | 100 | 100 | Nil | 100 | Nil | 100 | Nil | 100 |

*No Degradation of samples even after three months.

TABLE 38

No Aggregation after 7 days at 25° C. of Aqueous Solution of Formulated Bevacizumab
in the Presence of Viscosity-Reducing Agents – Tryptophan + Nicotinic acid (acid form)

|  | 0 day | | | 7 days | | |
| --- | --- | --- | --- | --- | --- | --- |
|  | Aggregation peak area (%) | Standard peak area (%) | Degradation peak area (%) | Aggregation peak area (%) | Standard peak area (%) | Degradation peak area (%) |
| Bevacizumab | 0.601 | 99.39 | Nil | 0.882 | 99.118 | Nil |

The values are within ±0.2% of the stated numbers.

Example 25: Effect of Aggregation-Reducing Agents on Formulations Containing Nicotinic Acid (Acid Form) and Tryptophan on Human Gamma Globulin and Rituximab The present example describes the effect of the combination of viscosity-reducing and aggregation-reducing agents, nicotinic acid (acid form) and tryptophan on aggregation of Human Gamma Globulin and Rituximab in aqueous solutions.

Materials and Methods

Commercially obtained antibodies, human gamma globulin (HGG), GLOBUCEL® (50 mg/mL) containing pharmaceutical excipients (Maltose) and Rituximab, RITUXAN®, 500 mg in 50 mL (10 mg/mL Rituximab, 9 mg/mL sodium chloride, 7.35 mg/mL of Trisodium citrate Dihydrate, and 0.7 mg/mL polysorbate 80, USP) were dialyzed either against water (HGG) or against 25 mM phosphate buffer, pH 6.0 (rituximab) for 24 hr at 4'C with three changes. To the aqueous solution of HGG (in water), histidine buffer was added from the stock concentration of 1000 mM histidine buffer, pH 6.0 to get a final concentration of 25 mM. To the buffered antibody solutions, different aggregation reducing-agents were added individually or in combination and mixed until complete dissolution. The excipient-containing antibody solutions and antibody in buffer alone (without excipients) were concentrated to a final volume of less than 150 µL using Vivaspin centrifugal concentrators (Sartorius). The collected protein sample was stored at 4° C. O/N. The final concentration of protein (antibody) in solution was determined by measuring absorbance at 280 nm in a UV visible spectrophotometer against the histidine containing aggregation-reducing agent (which does not contain any HGG or rituximab) for measuring the protein concentration in excipient containing sample; and for antibody without any excipient, buffer alone (without any excipient) was used as a blank to determine the protein concentration. The protein concentrations were experimentally determined using the extinction coefficient of 1.4

$$\left( A \frac{0.1\%}{280 \text{ nm}} = A \frac{1 \text{ mg/mL}}{280 \text{ nm}} = 1.4 \right)$$

at 280 nm.

Percent reduction in aggregation of formulated HGG and rituximab in aqueous solution with aggregation-reducing agents, tryptophan and nicotinic acid (acid form), was carried out at different time points. Samples of HGG and rituximab were prepared as described above. The data in Table 39 demonstrate the percent reduction in aggregation of HGG and rituximab at 250-275 mg/mL as determined by Size Exclusion Chromatography (Phenomenex BioSEP SEC-S2000 (7.8 mm×30 cm; 50 mM sodium phosphate buffer, pH 6.5 containing 0.1M sodium chloride; flow rate 0.5 mL/min; isocratic). The amount of reduction in aggregation is calculated setting the values at 0 time point equal to 100% in control (without any aggregation-reducing agent) and the reduction in aggregation in test samples (with aggregation-reducing agent) is expressed as percent reduction when compared to control at 0 time point.

Results

The data in Table 39 demonstrate that nicotinic acid (acid form) and tryptophan in combination reduced the amount of aggregation in the high concentration formulations of both HGG and rituximab when compared to the control without any aggregation-reducing agent. The amount of aggregated species remaining after 48 hours is almost 0 when compared to the control (buffer alone without any aggregation-reducing agent). The amount of aggregated species in the initial sample before adding aggregation-reducing agents was 3 to 10% in HGG and 1 to 5% in rituximab samples (these values are considered as 100%). The data in Table 39 show the percent reduction in aggregation of HGG and Rituximab over a time period of 24-48 hours.

TABLE 39

Effect of aggregation-reducing agents, nicotinic acid and tryptophan on the aggregated HGG and Rituximab species.

| | Percent reduction in aggregation | |
|---|---|---|
| | After 24 hours | After 48 hours |
| HGG | 75 | 100 |
| Rituximab | 90 | 100 |

Example 26: An Exemplary Protein Agent Formulation Containing Viscosity-Reducing Agents Lowers the Viscosity of Many Therapeutic Proteins Significantly, Even in the Presence of Very High Protein Concentrations The present example describes an exemplary protein agent formulation containing viscosity-reducing agents nicotinic and (acid form) and tryptophan plus added excipients, and the effect of these additives on solutions of a wide span of protein agents.

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate buffer was added from the stock concentration of 1000 mM phosphate buffer, pH 6.0 to get a final concentration of 25 mM.

Commercially obtained Trastuzumab, HERCEPTIN® (lyophilized powder contains 440 mg Trastuzumab, 9.9 mg of L-Histidine·HCl, 6.4 mg of L-Histidine, 400 mg of a,a-trehalose dihydrate, and 1.8 mg polysorbate 20, USP; and 20 mL of water for injection for reconstitution) was dialyzed against 25 mM phosphate buffer, pH 6.0 for 24 hr at 4° C. with three changes.

Commercially obtained Rituximab, RITUXAN®, 500 mg in 50 mL (10 mg/mL Rituximab, 9 mg/mL sodium chloride, 7.35 mg/mL of Trisodium citrate Dihydrate, and 0.7 mg/mL polysorbate 80, USP) was dialyzed against 25 mM phosphate buffer, pH 6.0 for 24 hr at 4° C. with three changes.

Commercially obtained Bevacizumab, AVASTIN®, 400 mg in 16 mL (100 mg/4 mL Bevacizumab, 240 mg/4 mL Trehalose dihydrate, 23.2 mg/4 mL sodium phosphate, monobasic, monohydrate, 4.8 mg/4 mL sodium phosphate dibasic, anhydrous, and 1.6 mg/4 mL polysorbate 20, USP) was dialyzed against 25 mM phosphate buffer, pH 6.0 for 24 hr at 4° C. with three changes.

Commercially obtained Cetuximab, ERBITUX®, 100 mg in 50 mL (2 mg/1 mL Cetuximab, 8.48 mg/1 mL sodium chloride, 0.41 mg/1 mL sodium phosphate, monobasic, monohydrate, 1.88 mg/1 mL sodium phosphate dibasic, heptahydrate) was dialyzed against 25 mM phosphate buffer, pH 6.0 for 24 hr at 4° C. with three changes.

Commercially obtained Etanercept, ENBREL®, 25 mg as a lyophilized powder (25 mg Etanercept, 40 mg mannitol, 10 mg sucrose, and 1.2 mg Tromethamine and for reconstitution 0.9% benzyl alcohol in water) was dialyzed against 25 mM phosphate buffer, pH 6.0 for 24 hr at 4° C. with three changes.

To the dialysed samples of above protein agents, a combination of viscosity-reducing agents nicotinic acid (acid form) and tryptophan were added and mixed until complete dissolution. The excipient-containing samples as described above were concentrated to a final volume of less than 150 µL using Vivaspin centrifugal concentrators (Sartorius). The collected protein samples were stored at 4° C. O/N. The final concentration of proteins in each solutions were determined by measuring absorbance at 280 nm in a UV visible spectrophotometer against the phosphate buffer containing viscosity-reducing agent alone (which does not contain any protein) for measuring the protein concentration in excipient containing sample; and for protein without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4 for HGG; 1.48 for Trastuzumab; 1.7 for Rituximab; 1.54 for Bevacizumab; 1.4 for Cetuximab; 1.4 for Infliximab and 0.96 for Etanercept $$\left(A\frac{0.1\%}{280\ nm} = A\frac{1\ mg/mL}{280\ nm}\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 40 demonstrate the viscosity reducing effect of a combination of viscosity-reducing agents nicotinic acid (acid form) and tryptophan on an array of different proteins such as human gamma globulin, monoclonal antibodies such as Trastuzumab, Rituximab, Bevacizumab, Cetuximab and a fusion protein like Etanercept. The combination formulation can lower the viscosity not only of monoclonal antibodies but also of other proteins like fusion proteins at very high concentrations, and is thus can be applied to a wide span of protein agents.

TABLE 40

Viscosities of Various Therapeutic Proteins in Phosphate buffer, pH 6.0 at 25° C. in the absence and presence of a Universal Formulation

| | Protein | Viscosity, cP** | |
|---|---|---|---|
| Protein | Concentration, mg/mL* | With Excipient | Without Excipient |
| HGG | 275 | 32 | 320 |
| Trastuzumab | 275 | 23 | 420 |
| Rituximab | 275 | 43 | 1375$$ |
| Bevacizumab | 275 | 26 | 310$ |
| Cetuximab | 225 | 40 | 1130 |
| Etanercept | 225 | 40 | 345 |
| Infliximab | 275 | 15 | 1560$ |

$Protein concentration is at 225 mg/mL.
$$Protein concentration is at 250 mg/mL.
*The protein concentration = Stated Value ± 5 mg/mL
**Viscosity = Stated Value ± 0.2

Example 27: Isotonic Solutions of Viscosity-Reducing Excipients Reduce the Viscosity of Highly Concentrated Solutions of Human Gamma Globulin The present example describes the effect of viscosity-reducing agents on tonicity of Human Gamma Globulin aqueous solutions.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate buffer was added from the stock concentration of 1000 mM phosphate buffer, pH 6.0 to get a final concentration of 25 mM. To the buffered HGG different viscosity-reducing agent(s) was added individually or in combination and mixed until complete dissolution. The excipient containing HGG was concentrated to a final volume of less than 150 μL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate containing viscosity-reducing agents alone (which does not contain any HGG). Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, ViscoLab 5000 using 70 μL of sample at 25° C. or using a DV2T cone and plate viscometer using 1.5 mL of sample at 25° C. at extrapolated zero shear rate.

Results

The data in Table 41 demonstrate that the isotonic formulations of viscosity-reducing reagents in the presence of a buffering reagent like phosphate, a tonicity reagent like sodium chloride, a solubilizing reagent like polysorbate 80 and a lyoprotectant like sorbitol are capable of reducing the viscosities at very high protein concentration. The osmolarity of the solution of formulated HGG can be in the range of 250 to 360 mOsm/L, isotonic region, with protein concentrations up to 288 mg/mL and the viscosities in the range of 30 to 35 cP.

TABLE 41

Viscosities of Aqueous Human Gamma Globulin Solutions with Various Viscosity-Reducing Reagents in the Isotonic Formulation.

| Formulation | Osmolarity (mOsm/L) | HGG Concentration (mg/mL)$ | Viscosity (cP)$$ |
|---|---|---|---|
| None | 50 | 250 | 191 |
| Base buffer: 25 mM Phosphate Buffer, pH 6.0; 50 mM NaCl; 0.07% polysorbate 80; 10 mg/mL sorbitol | 197 | 245 | 120 |

TABLE 41-continued

Viscosities of Aqueous Human Gamma Globulin Solutions with Various Viscosity-Reducing Reagents in the Isotonic Formulation.

| Formulation | Osmolarity (mOsm/L) | HGG Concentration (mg/mL)$ | Viscosity (cP)$$ |
|---|---|---|---|
| 25 mM Phosphate Buffer, pH 6.0; 50 mM NaCl; 0.07% polysorbate 80; 10 mg/mL sorbitol, 10 mg/mL Caffiene; 10 mg/mL Nicotinic acid (acid form) | 360 | 292 | 70 |
|  |  | 245 | 30 |
| 25 mM Phosphate Buffer, pH 6.0; 50 mg NaCl; 0.07% polysorbate 80; 10 mg/mL sorbitol; 10 mg/mL Nicotinic acid (acid form); 6 mg/mL tryptophan | 291 | 288 | 35 |

*The protein concentration = Stated Value ± 5 mg/mL
**Viscosity = Stated Value ± 0.2

Example 28: A Comparative Study on Viscosity-Reducing Agents Caffeine Versus Caffeine Citrate (Cafcit) and their Effect on Viscosity of Aqueous Solutions of Human Gamma Globulin The present example describes the effect of viscosity-reducing agents caffeine and caffeine citrate on viscosity of Human Gamma Globulin in aqueous solutions.

Materials and Methods

Commercially obtained human gamma globulin (HGG), GLOBUCEL® (50 mg/mL) containing pharmaceutical excipients (Maltose) was dialyzed against water for 24 hr at 4° C. with three changes. To the aqueous solution of HGG, phosphate/histidine buffer was added from the stock concentration of 1000 mM phosphate/histidine buffer, pH 6.0 to get a final concentration of 25 mM. To the buffered HGG different viscosity-reducing agent was added individually and mixed until complete dissolution. The excipient containing HGG was concentrated to a final volume of less than 150 μL using Vivaspin centrifugal concentrators (Sartorius). The collected protein sample was stored at 4° C. O/N. The final concentration of HGG in solution was determined by measuring absorbance at 280 nm in a UV visible spectrophotometer against the phosphate/histidine containing viscosity-reducing agent alone (which does not contain any HGG) for measuring the protein concentration in excipient containing sample; and for HGG without any excipient, buffer alone (without any excipient) was used as a blank to determine the protein concentration. Reported protein concentrations represent the range of all protein samples in each Table or Figure. Specifically, reported values are the median plus or minus half the range. The protein concentrations were experimentally determined using the extinction coefficient of 1.4

$$\left(A\frac{0.1\%}{280 \text{ nm}} = A\frac{1 \text{ mg/mL}}{280 \text{ nm}} = 1.4\right)$$

at 280 nm. The viscosities of the solution were measured either using a Cambridge Viscometer, VISCOlab5000 using 70 µL of sample at 25° C. or using a DV2T cone and plate viscometer using 1.5 mL of sample at 25° C. at extrapolated zero shear rate.

Results

The data in Table 42 demonstrate the viscosity-reducing effect of caffeine and caffeine citrate (cafcit) on Human gamma globulin (GLOBUCEL®) in either phosphate or histidine buffer. The data in FIG. 10 and Table 42 show that the Cafcit lowers the viscosity to a greater extent than caffeine in both buffer systems at 51 mM concentration of viscosity-reducing agent and at HGG concentration of 220 mg/mL.

TABLE 42

Viscosity of Aqueous Solutions of HGG in Various buffer Systems, pH 6.0 at 25° C. in the presence of Viscosity-Reducing Agents (Excipient concentration: 10 mg/mL; HGG Concentration, 220 mg/mL*).

| Viscosity-Reducing Agent | Phosphate buffer | Histidine buffer |
|---|---|---|
| | Viscosity, cP** | |
| Caffeine | 40 | 36 |
| Caffeine Citrate | 9 | 10 |
| Control (Buffer alone) | 73 | 87 |

*The protein concentration = Stated Value ± 5 mg/mL
**Viscosity = Stated Value ± 0.2

Example 29: FDA Approved Therapeutic Proteins

The present example describes known FDA-approved therapeutic proteins that may be used in low viscosity formulations described herein.

Protein agent therapeutics currently on the market that can be formulated with viscosity-reducing agents include:

Abobotulinum toxinA (DYSPORT®) developed Medicis and Ipsen Biopharmaceuticals, Inc. is used in treatment of cervical dystonia which targets acetylcholine release inhibitor and a neuromuscular blocking agent (Dose/Dosage: 500 Units).

Agalsidase alfa (REPLAGAL™) developed by Shire Plc. is used in treatment of Fabry Disease which targets human α-galactosidase A (Dose/Dosage: 10 mg every other week).

Agalsidase beta (FABRAZYME®) developed by Genzyme is used in treatment of Fabry disease which targets globotriaosylceramide (GL-3) deposition in capillary endothelium of the kidney (Dose/Dosage: 50 mg every two week).

Albiglutide (TANZEUM®) developed by GlaxoSmithKline is used in treatment of improve glycemic control in adults with type 2 diabetes mellitus which targets GLP-1 receptor (Dose/Dosage: 50 mg once weekly).

Alglucosidase alfa (LUMIZYME®, MYOZYME®) developed by Genzyme is used in treatment of late (non-infantile) onset Pompe disease (GAA deficiency) which targets lysosomal glycogen-specific enzyme (Dose/Dosage: 100 mg every 2 weeks).

Alpha1-Proteinase Inhibitor (Human) (Aralast™) developed by Alpha Therapeutic Corporation is used in treatment of Congenital Alpha1-Proteinase Inhibitor deficiency which targets purified human alpha1-proteinase (α1-PI) or alpha1-antitrypsin (Dose/Dosage: 300 mg once weekly).

Alteplase (ACTIVASE®) developed by Genentech is used in treatment of Acute Ischemic Stroke (AIS), Myocardial Infarction (AMI), and Massive Pulmonary Embolism (PE) which targets tissue plasminogen activator (tPA) (Dose/Dosage: 100 mg).

Anakinra (Kineret®) developed by Amgen is used in treatment of Rheumatoid Arthritis (RA), Cryopyrin-Associated Periodic Syndromes (CAPS) which targets interleukin-1 receptor (Dose/Dosage: 100 mg/day daily).

Anistreplase (Eminase®) developed by Beecham is used in treatment of Thrombolysis which targets Thrombolytic Agents: anisoylated plasminogen streptokinase activator complex; APSAC) (Dose/Dosage: 100 mg over a period of two hours).

Antifolate (ALIMTA®) developed by Eli Lilly and Company is used in treatment of malignant pleural mesothelioma, NSCLC which targets an antifolate antineoplastic agent (Dose/Dosage: 500 mg).

Antihemophilic Factor (ADVATE®) developed by Baxalta is used in treatment of congenital factor VIII deficiency or classic hemophilia (Dose/Dosage: 200 IU every other day).

Antihemophilic Factor (Recombinant) (ADYNOVATE®) developed by Baxalta US is used in treatment of hemophilia A (congenital factor VIII deficiency) (Dose/Dosage: 1 U/kg 2 times a week).

Antihemophilic Factor (Recombinant) (AFSTYLA®) developed by CSL Behring Pharmacovigilance is used in treatment of hemophilia A (congenital Factor VIII deficiency) (Dose/Dosage: 2500 IU 2 to 3 times weekly).

Antihemophilic Factor (Recombinant) (NUWIQ®) developed by Octapharma USA Inc is used in treatment of Hemophilia A, control of bleeding which targets blood coagulation factor VIII (Factor VIII) (Dose/Dosage: 2500 IU three times per week).

Anti-Rhesus (Rh) immunoglobulin G (Rhophylac®) developed by CSL Behring AG is used in treatment of routine antepartum and postpartum prevention of Rh (D) immunization in Rh (D)-negative women; suppression of Rh immunization in Rh (D)-negative individuals transfused with Rh(D)-positive red blood cells by Neutralizing Rh antigens that could otherwise elicit anti-Rh antibodies in an Rh-negative individual (Dose/Dosage: 2500 mcg).

Antithrombin III (Human) (Thrombate III®) developed by Talecris Biotherapeutics, Inc. is used in treatment of hereditary antithrombin III deficiency, thromboembolism (Dose/Dosage: 2250 IU).

Asfotase alfa (STRENSIQ™) developed by Alexion is used in treatment of (Dose/Dosage: 100 mg three times per week).

Asparaginase (ELSPAR®) developed by Merck is used in treatment of acute lymphoblastic leukemia (ALL) which targets asparagine specific enzyme (Dose/Dosage: 6,000 IU three times a week).

Asparaginase *Erwinia chrysanthem* (ERWINAZE™) developed by EUSA Pharma (USA), Inc is used in treatment of acute lymphoblastic leukemia (ALL) who have developed hypersensitivity to *E. coli*-derived asparaginase which targets asparagine specific enzyme (Dose/Dosage: 25,000 IU three times a week).

Bivalirudin (ANGIOMAX®) developed by The Medicines Company is used in treatment of Reduce blood-clotting risk in coronary angioplasty and heparin-induced thrombocytopenia which targets direct thrombin inhibitor, anticoagulant (Dose/Dosage: 87.5 mg per hour).

BMN 110 (Vimizim®) developed by BioMarin is used in treatment of (Dose/Dosage: 100 mg/week).

Botulinum toxin type A (BOTOX®) developed by Allergan is used in treatment of dystonia cervical; cosmetic uses, Chronic Migraine, Spasticity, Primary Axillary Hyperhidrosis (Dose/Dosage: 100 Units).

Botulinum toxin type B2 (Myobloc®) developed by Elan Pharmaceuticals, Inc. is used in treatment of cervical dystonia divided among affected muscles which targets rimabotulinum toxinB (Dose/Dosage: 5,000 Units).

C1 Esterase Inhibitor [Human] (CINRYZE®) developed by Lev Pharmaceuticals is used in treatment of Hereditary Angioedema (HAE) which targets C1 esterase inhibitor (Dose/Dosage: 1,000 Units every 4 days).

COAGULATION FACTOR IX (RECOMBINANT) (BENEFIX®) developed by Wyeth Pharmaceuticals Inc. is used in treatment of factor IX deficiency, hemophilia B or Christmas disease (Dose/Dosage: 50-100 (IU/dL).

Coagulation Factor VIIa (Recombinant) (NovoSeven®) developed by Novo Nordisk is used in treatment of Hemophilia A or B, Congenital Factor VII deficiency (Dose/Dosage: 4.5 mg/kg).

Collagenase *Clostridium histolyticum* (XIAFLEX®) developed by BioSpecific Technologies Corp. is used in treatment of Dupuytren's contracture, Peyronie's disease which targets combination of bacterial collagenases (Dose/Dosage: 0.58 mg 4-week intervals).

Darbepoetin alfa (Aranesp®) developed by Amgen is used in treatment of Chronic Kidney Disease (CKD) which targets Erythropoiesis-stimulating agent (ESA) (Dose/Dosage: 500 mcg every 3 weeks).

Denileukin diftitox (ONTAK®) developed by Eisai Medical Research Inc. is used in treatment of Persistent or recurrent cutaneous T-cell lymphoma whose malignant cells express the CD25 component of the IL2 receptor which targets Directs the cytocidal action of diphtheria toxin to cells expressing the IL2 receptor (Dose/Dosage: 900 mcg).

Desirudin (Iprivask™) developed by Aventis Pharmaceuticals North America LLC is used in treatment of deep vein thrombosis which targets direct inhibitor of human thrombin (Dose/Dosage: 15 mg every 12 hours).

Digoxin immune serum Fab (ovine) (DigiFab®) developed by Protherics Inc is used in treatment of Digoxin toxicity which targets Monovalent Fab immunoglobulin fragment obtained from sheep immunized with a digoxin derivative (Dose/Dosage: 0.5 mg).

Drotrecogin-α5 (Xigris™) developed by Eli lilly is used in treatment of severe sepsis with a high risk of death which targets Activated protein C, Antithrombotic (inhibits coagulation factors Va and VIIIa), anti-inflammatory (Dose/Dosage: 1200 mcg per hr based on infusion rate).

Elosufase alfa (VIMIZIM®) developed by BioMarin is used in treatment of Mucopolysaccharidosis type IVA (MPS IVA; Morquio A syndrome) which targets hydrolytic lysosomal glycosaminoglycan (GAG)-specific enzyme (Dose/Dosage: 100 mg every week).

Epoetin alfa (PROCRIT®, EPOGEN®) developed by Amgen is used in treatment of Anemia of Chronic Renal Failure, Zidovudine-treated HIV-infected which targets division and differentiation of committed erythroid progenitors in the bone marrow (Dose/Dosage: 5000 units).

Exenatide (BYETTA®) developed by Amylin Pharmaceuticals, Inc. and Eli Lilly is used in treatment of Type 2 diabetes resistant to treatment with metformin and a sulphonylurea which targets glucagon-like peptide-1 (GLP-1) receptor agonist (Dose/Dosage: 10 mcg twice daily).

Filgrastim (NEUPOGEN®) developed by Amgen Inc. is used in treatment of Neutropaenia in AIDS or post-chemotherapy or bone-marrow transplantation, severe chronic neutropaenia which targets human granulocyte colony stimulating factor (G-CSF) recombinant (Dose/Dosage: 500 mcg per day).

Follitropin beta (FOLLISTIM® AQ) developed by Organon USA, Inc. is used in treatment of Augments ovulation in Assisted reproduction, Hypogonadotropic, Hypogonadism) which targets gonadotropin (Dose/Dosage: 50 IU.

Galsulfase (NAGLAZYME®) developed by BioMarin Pharmaceutical Inc is used in treatment of Mucopolysaccharidosis VI (MPS VI), improve walking and stair-climbing capacity which targets variant form of N-acetylgalactosamine 4-sulfatase (Dose/Dosage: 50 mg once every week).

Glucarpidase (VORAXAZE®) developed by BTG International, Inc is used in treatment of delayed methotrexate clearance due to impaired renal function which targets carboxypeptidase enzyme (Dose/Dosage: 2500 U).

Hepatitis B surface antigen (HBsAg) (Engerix®B) developed by GlaxoSmithKline, (Recombivax HB) by MERCK Elovac B (Human Biologicals Institute), Genevac B (Serum Institute), (Shanvac B) by Shanta Biotechnics is used in treatment of Hepatitis B vaccination which targets Non-infectious protein on surface of hepatitis B virus (Dose/Dosage: 20 mcg/mL).

Histrelin acetate (Supprelin® LA) developed by Indevus Pharmaceuticals is used in treatment of central precocious puberty (CPP) which targets gonadotropin releasing hormone (GnRH) (Dose/Dosage: one implant every 12 months).

HPV vaccine (Gardasil®) developed by Merck & co ltd is used in treatment of Prevention of HPV infection which targets Quadrivalent HPV recombinant vaccine (strains 6, 11, 16, 18); contains major capsid proteins from four HPV strains (Dose/Dosage: 0.5 ml for 6 months).

Human albumin (Albuminar®-5) developed by CSL Behring is used in treatment of Decreased production of albumin (hypoproteinaemia), increased loss of albumin (nephrotic syndrome), hypovolaemia, hyperbilirubinaemia (Dose/Dosage: varies as per patient).

Human chorionic gonadotropin (HCG) Ovidrel® developed by EMD Serono, Inc. is used in treatment of Stimulates ovarian follicle rupture and ovulation which targets recombinant human Chorionic Gonadotropin, r-hCG (Dose/Dosage: 250 µg one day following FSH).

Hyaluronidase (Amphadase®) developed by Amphastar Pharmaceuticals is used in treatment of adjuvant to increase the absorption and dispersion of injected drugs like anaesthetics (Dose/Dosage: 150 U).

Hyaluronidase (HYLENEX®) developed by Halozyme Therapeutics, Inc is used in treatment of adjuvant to increase the absorption and dispersion of injected drugs like anaesthetics prior to subcutaneous fluid which targets from human recombinant endoglycosidase (Dose/Dosage: 150 U).

Idursulfase (ELAPRASE®) developed by Shire Plc. is used in treatment of Hunter syndrome (Mucopolysaccharidosis II, MPS II) which targets hydrolytic lysosomal glycosaminoglycan (GAG)-specific enzyme (Dose/Dosage: 25 mg once every week).

Imiglucerase (CEREZYME®) developed by Genzyme Corporation is used in treatment of Type 1 Gaucher disease, anemia, thrombocytopenia, bone disease, hepatomegaly or splenomegaly which targets analogue of the human enzyme β-glucocerebrosidase (Dose/Dosage: 300 U once every 2 weeks).

IncobotulinumtoxinA (Xeomin®) developed by Merz Pharmaceuticals, LLC is used in treatment of cervical dystonia, Blepharospasm which targets acetylcholine release inhibitor and neuromuscular blocking agent (Dose/Dosage: 120 Units).

Interferon alfa-1 (INFERGEN®) developed by Amgen is used in treatment of chronic hepatitis C (Dose/Dosage: 15 mcg three times weekly for up to 48 weeks).

Interferon alfa-2a (Roferon-A®) developed by Hoffmann-La Roche Inc. is used in treatment of (Dose/Dosage: 3 MIU three times a week).

Interferon alfa-N3 (Alferon N®) developed by Hemispherx Biopharma, Inc. is used in treatment of *Condylomata acuminata* (genital warts caused by human papillomavirus) which targets non-recombinant human IFNα-n3 purified from pooled human leukocytes (Dose/Dosage: 0.05 mL (250,000 IU) per wart twice a week).

Interferon beta-1a (AVONEX®) developed by Biogen IDEC is used in treatment of Multiple sclerosis (Dose/Dosage: 30 mcg once a week).

Interferon beta-1a (Rebif®) developed by Serono Laboratories is used in treatment of Multiple sclerosis (Dose/Dosage: 44 mcg three times per week).

Interferon beta-1b (Betaseron®) developed by CHIRON Corporation is used in treatment of multiple sclerosis (Dose/Dosage: 0.25 mg every other day).

Interferon gamma-1b (ACTIMMUNE®) developed by Horizon Pharma USA, Inc. is used in treatment of chronic granulomatous disease, severe osteopetrosis (Dose/Dosage: 50 mcg three times weekly).

Interferon-α2b (INTRON® A) developed by Merck is used in treatment of Malignant Melanoma, Follicular Lymphoma, *Condylomata Acuminata*, AIDS-Related Kaposi's Sarcoma I (Dose/Dosage: 20 million IU/4 weeks).

Laronidase (ALDURAZYME®) developed by Genzyme enzyme is used in treatment of Hurler and Hurler-Scheie forms of Mucopolysaccharidosis I (MPS I), Scheie (Dose/Dosage: 29 mg once weekly).

Lepirudin (REFLUDAN®) developed by Hoechst Marion Roussel is used in treatment of Heparin induced thrombocytopaenia which is direct inhibitor of thrombin (Dose/Dosage: 7.5 mg).

Lxisenatide (ADLYXIN™) developed by sanofi-aventis is used in treatment of type 2 diabetes mellitus which targets glucagon-like peptide-1 (GLP-1) receptor agonist (Dose/Dosage: 20 mcg once daily).

Lutropin alfa (Luveris®) developed by EMD Serono, Inc. is used in treatment of increases estradiol secretion, Infertility with luteinizing hormone deficiency which targets recombinant human luteinizing hormone, r-hLH (Dose/Dosage: 150 IU).

Mecasermin (INCRELEX®) developed by Tercica, Inc is used in treatment of severe primary IGF-1 deficiency (5.3) or with growth hormone (GH) gene deletion (Dose/Dosage: 4 mg twice daily).

Mecasermin rinfabate (IPLEX™) developed by Insmed Incorporated is used in treatment of severe primary IGF-1 deficiency (Primary IGFD) or with growth hormone (GH) gene deletion which targets Recombinant binary protein complex of human insulin-like growth factor-1 (rhIGF-1) and human insulin-like growth factor-binding protein-3 (rhIGFBP-3) (Dose/Dosage: 100 mg once daily).

Metreleptin for injection (MYALEPT™) developed by Amylin Pharmaceuticals, is used in treatment of leptin deficiency in patients with congenital or acquired generalized lipodystrophy which targets leptin (Dose/Dosage: 10 mg/day once daily).

Nesiritide (NATRECOR®) developed by Scios Inc is used in treatment of acute decompensated congestive heart failure which targets Recombinant B-type natriuretic peptide (Dose/Dosage: 100 mcg).

Nulojix (Belatacept) developed by Bristol-Myers-Squib is used in treatment of graft survival.

Octreotide acetate (Sandostatin®) developed by Novartis is used in treatment of Acromegaly, symptomatic relief of VIP-secreting adenoma and metastatic carcinoid tumours which targets a cyclic octapeptide & potent somatostatin (Dose/Dosage: 300 mcg daily).

Oprelvekin (Neumega®) developed by Pfizer is used in treatment of Prevention of severe thrombocytopaenia, especially after myelosuppressive chemotherapy which targets Interleukin11 (Dose/Dosage: 2500 mcg once daily).

OspA (LYMErix™) developed by GlaxoSmithKline Beecham Biologicals is used in treatment of Lyme disease vaccination which targets Non-infectious lipoprotein on outer surface of *Borrelia burgdorferi* (Dose/Dosage: 30 mcg/0.5 mL).

Palifermin (Kepivance®) developed by Amgen is used in treatment of severe oral mucositis which targets Recombinant analogue of KGF (Dose/Dosage: 300 mcg per day for 3 consecutive days).

Pegaspargase (Oncaspar®) developed by Enzon Pharmaceuticals, Inc. is used in treatment of acute lymphoblastic leukemia (ALL) which targets asparagine specific enzyme (Dose/Dosage: 2,500 IU).

Pegdamase bovine (ADAGEN®) developed by Sigma-Tau Pharmaceuticals, Inc. is used in treatment of severe combined immunodeficiency disease (SCID), Metabolizes adenosine, prevents accumulation of adenosine which targets Adenosine deaminase (Dose/Dosage: 100 U per week).

Pegfilgrastim (NEULASTA®) developed by Amgen is used in treatment of Neutropenia/leukopenia which targets leukocyte growth factor (Dose/Dosage: 6 mg once per chemotherapy cycle).

Pegloticase (Krystexxa®) developed by Savient Pharmaceuticals, Inc. is used in treatment of chronic gout which targets uric acid (Dose/Dosage: 8 mg every two weeks).

Pegvisomant (Somavert®) developed by Pharmacia &Upjohn is used in treatment of Acromegaly which targets Recombinant human growth hormone conjugated to PEG; blocks the growth hormone receptor (Dose/Dosage: 10 mg/daily).

PEGylated interferon beta-1a (Plegridy™) developed by Biogen Idec is used in treatment of relapsing forms of multiple sclerosis (Dose/Dosage: 1000 mg/day).

Pooled immunoglobulins (OCTAGAM® 10%) developed by Octapharma is used in treatment of Primary immunodeficiencies, chronic immune thrombocytopenic purpura (ITP) as immunoglobulin preparation (Dose/Dosage: 50 mg daily).

Protein C Concentrate (Human) (CEPROTIN) developed by Baxter Healthcare Corporation is used in treatment of severe congenital Protein C deficiency, venous thrombosis and purpura fulminans which targets protein C inhibits coagulation factors Va and VIIIa (Dose/Dosage: 6000 IU).

Rasburicase (ELITEK™) developed by sanofi-aventis U.S. LLC is used in treatment of management of plasma uric acid in leukemia, lymphoma, solid tumor which targets recombinant urate-oxidase (Dose/Dosage: 10 mg).

Reteplase, recombinant RETAVASE® developed by Boehringer Mannheim Corporation, Inc. is used in treatment of acute myocardial infarction, ventricular function which targets Non-glycosylated deletion mutein of tissue plasminogen activator (tPA), containing the kringle 2 and the protease domains of human tPA (Dose/Dosage: 10+10 unit double-bolus injection).

Romiplostim (Nplate™/Nplate®) developed by Amgen is used in treatment of thrombocytopenia with chronic immune (idiopathic) thrombocytopenic purpura (ITP) which targets thrombopoietin receptor (Dose/Dosage: 500 mcg).

Sargramostim (Leukine®) developed by sanofi-aventis is used in treatment of Leukopaenia, myeloid reconstitution post-bone-marrow transplantation, HIV/AIDS which targets Recombinant GM-CSF (Dose/Dosage: 250 mcg/day).

Sebelipase alfa (KANUMA™) developed by Alexion is used in treatment of Lysosomal Acid Lipase (LAL) deficiency which targets hydrolytic lysosomal cholesteryl ester and triacylglycerol-specific enzyme (Dose/Dosage: 150 mg once weekly).

Serelaxin (Reasanz™) developed by Novartis is used in treatment of acute heart failure which targets recombinant form of relaxin-2 hormone (Dose/Dosage: 150 µg per day).

Somatropin (GENOTROPIN®) developed by Pharmacia & Upjohn is used in treatment of growth hormone survivors treated with somatropin in particular meningiomas in patients deficiency (GHD), Prader-Willi syndrome Turner syndrome, and Idiopathic Short Stature which targets recombinant human growth hormone (Dose/Dosage: 24 mg per week).

Streptokinase (Streptase®) developed by CSL Behring is used in treatment of Acute evolving transmural myocardial infarction, pulmonary embolism, deep vein thrombosis, arterial thrombosis or embolism, occlusion of arteriovenous cannula which converts plasminogen to plasmin (Dose/Dosage: 100,000 IU/hr for 72 hr).

Taliglucerase alfa (ELEYSO®) developed by Pfizer Inc is used in treatment of long-term enzyme replacement therapy (ERT) for adults with a confirmed diagnosis of Type 1 Gaucher disease which targets hydrolytic lysosomal glucocerebroside-specific (Dose/Dosage: 300 U every other week).

Tenecteplase recombinant (TNKase™/TNKase®) developed by Genentech, Inc is used in treatment of acute myocardial infarction which targets tissue plasminogen activator (tPA) recombinant (Dose/Dosage: 50 mg).

Teriparatide (FORTEO®) developed by Eli Lilly is used in treatment of postmenopausal osteoporosis which targets recombinant human parathyroid hormone (1-34), [rhPTH(1-34)] (Dose/Dosage: 20 mcg once a day).

Trenonacog alfa (IXINITY®) developed by Emergent BioSolutions/Cangene is used in treatment of Hemophilia B which targets Recombinant coagulation Factor IX (rFIX) (Dose/Dosage: 3750 IU).

UROKINASE (Abbokinase®) developed by Abbott Laboratories is used in treatment of pulmonary embolism which targets thrombolytic agent (Dose/Dosage: 220000 U).

Velaglucerase alfa (VPRIV™) developed by Shire Human Genetic Therapies. Inc is used in treatment of long-term enzyme replacement therapy (ERT) for pediatric and adult patients with type 1 Gaucher disease which targets hydrolytic lysosomal glucocerebroside-specific enzyme (Dose/Dosage: 300 U every other week).

Insulin degludec and liraglutide injection (XULTOPHY® 100/3.6) developed by Novo Nordisk is used in treatment of type 2 diabetes mellitus which targets combination of insulin degludec & liraglutide, a glucagon-like peptide 1 (GLP-1) (Dose/Dosage: 16 units once daily).

Insulin degludec injection (TRESIBA®) developed by Novo Nordisk is used in treatment of diabetes mellitus which targets human insulin (Dose/Dosage: FlexTouch pens).

Insulin Glargine (LY2963016) BASAGLAR™® developed by Eli Lilly and Company is used in treatment of type 1 diabetes mellitus and in adults with type 2 diabetes mellitus which targets human insulin (Dose/Dosage: 3 mL BASGLAR™ KwikPen™ (prefilled).

Insulin glargine injection U-300 TOUJEO® developed by sanofi-aventis is used in treatment of diabetes mellitus which targets human insulin (Dose/Dosage: as per metabolism).

Insulin glargine/lixisenatide fixed-ratio combination (iGlarLixi) developed by sanofi-aventis is used in treatment of TYPE 2 DIABETES MELLITUS which targets human insulin (Dose/Dosage: as per metabolism).

Insulin lispro injection, USP [rDNA origin] (HUMALOG®) developed by Eli Lilly is used in treatment of diabetes mellitus which targets human insulin (Dose/Dosage: 1 unit/mL).

Aspart (Novolog®) developed by Novo Nordisk is used for treating type 1 (insulin dependent) or type 2 (non-insulin dependent) diabetes in adults (Dose/Dosage: 1.0 units/kg/day=50 units).

Detemir (Levemir®) developed by Novo Nordisk Inc is used for treating type 1 (insulin dependent) or type 2 (non-insulin dependent) diabetes in adults. (Dose/Dosage: 0.77 U/kg=38.5 U).

Exenatide (BYETTA®) developed by Amylin Pharmaceuticals, Inc. and Eli Lilly is used for treating Type 2 diabetes resistant to treatment with metformin and a sulphonylurea (Dose/Dosage: 10 mcg twice daily).

Glargine (Lantus®), developed by Sanofi-Aventis pharmaceuticals is used for treating type 1 (insulin dependent) or type 2 (non-insulin dependent) diabetes in adults (Dose/Dosage: 0.2 Units/kg=10 U).

Glulisine (Apidra®) Sanofi-Aventis pharmaceuticals is used in treating type 1 (insulin dependent) or type 2 (non-insulin dependent) diabetes in adults (Dose/Dosage: 1 unit/kg/day=50 units).

Insulin (Humulin®, Novolin®) by Novo Nordisk (also marketed as Actraphane®, Insulatard®, Mixtard® and Protaphane® in EU by Genentech is used in treating Diabetes mellitus, diabetic ketoacidosis, hyperkalaemia (Dose/Dosage: 1 unit/kg/day=50 units).

Isophane NPH by Eli Lilly is used for treat Type 1 or Type 2 DM (Dose/Dosage: individualized).

Pramlintide acetate (Symlin®) developed by AstraZeneca Pharmaceuticals LP is used in Type 1 or Type 2 DM (Dose/Dosage: 120 mcg).

Lente Insulin (Humulin®-L, Novolin®-L) Eli Lilly and Company is used in Type 1 or Type 2 diabetes in adults (Dose/Dosage: individualized).

Insulin degludec and insulin aspart injection (RYZODEG® 70/30) Novo Nordisk is used for diabetes mellitus.

Lixisenatide (ADLYXIN™) is developed by Sanofi-Aventis for treating type 2 diabetes mellitus subcutaneously. (Dose/Dosage: 20 mcg once daily).

Example 30: FDA Approved Fusion Proteins

The present example describes known FDA-approved therapeutic proteins that may be used in low viscosity formulations described herein.

Fusion Protein therapeutics currently on the market that can be formulated with viscosity-reducing agents includes:

Abatacept (ORENCIA®) developed by Bristol-Myers Squibb is used in treatment of Rheumatoid Arthritis, Idiopathic Arthritis which targets T-cell co-stimulation modulator (Dose/Dosage: 1000 mcg).

Aflibercept (EYLEA®) developed by Regeneron Pharmaceuticals is used in treatment of Age-Related Macular Degeneration (AMD), Macular Edema Following Retinal Vein Occlusion (RVO), Diabetic Macular Edema (DME), •Diabetic Retinopathy (DR) (Dose/Dosage: 2 mg monthly).

Aldesleukin (PROLEUKIN®) developed by Chiron is used in treatment of Metastatic renal cell cancer, melanoma which targets Interleukin 2 (IL2), epidermal thymocyte activating factor (ETAF) (Dose/Dosage: 18.5 mg).

Alefacept (AMEVIVE®) developed by Biogen IDEC is used in treatment of chronic plaque psoriasis which targets lymphocyte antigen, CD2, and inhibits LFA-3/CD2 interaction (Dose/Dosage: 15 mg).

Antihemophilic Factor (recombinant Factor VIII) (ELOCTATE®) developed by Biogen Idec is used in treatment of Hemophilia A, control of bleeding (Dose/Dosage: 2500 IU every 4 days).

Antithymocyte globulin (rabbit) (Thymoglobulin) developed by Genzyme Corporation is used in treatment of Acute kidney transplant rejection, aplastic anemia by selective depletion of T cells (Dose/Dosage: 75 mg).

Belatacept (NULOJIX®) developed by Bristol-Myers Squibb is used in treatment of reduce organ rejection which targets T-cell co-stimulation (Dose/Dosage: 500 mg).

Coagulation Factor IX (Recombinant) (ALPROLIX™) developed by Biogen Idec is used in treatment of hemophilia B, reduce the frequency of bleeding (Dose/Dosage: 100 IU/dL).

Crotalidae polyvalent immune Fab (bovine) (Crofab®) developed by Protherics Inc is used in treatment of Crotalidae envenomation (Western diamondback, Eastern diamondback and Mojave rattlesnakes, and water moccasins) by targeting mixture of Fab fragments of IgG that bind and neutralize venom toxins of ten clinically important North American Crotalidae snakes (Dose/Dosage: 1.9 mg).

Enfuvirtide (Fuzeon®) developed by Roche is used in treatment of Adults and children (at least 6 years old) with advanced HIV infection which targets 36 amino-acid peptide that inhibits HIV entry into host cells by binding to the HIV envelope protein gp120/gp41 (Dose/Dosage: 100 mg).

Etanercept (ENBREL®) developed by Amgen Inc., Immunex is used in treatment of Rheumatoid Arthritis, Polyarticular Juvenile Idiopathic Arthritis, Psoriatic Arthritis, Ankylosing Spondylitis, Plaque Psoriasis which targets tumor necrosis factor (TNF) blocker. (Dose/Dosage: 50 mg once weekly).

Paclitaxel protein-bound (ABRAXANE®) developed by Abraxis Bioscience, Llc. is used in treatment of Metastatic breast cancer, non-small cell lung cancer (NSCLC), adenocarcinoma which targets a microtubule inhibitor (Dose/Dosage: 260 mg every 3 weeks).

Ziv-aflibercept (ZALTRAP®) developed by Sanofi Aventis is used in treatment of metastatic colorectal cancer (mCRC) (Dose/Dosage: 200 mg every 2 weeks).

Rilonacept (ARCALYST®) developed by Regeneron Pharmaceuticals is used for Cryopyrin-Associated Periodic Syndromes (CAPS), Familial Cold Autoinflammatory Syndrome (FCAS), Muckle-Wells Syndrome (MWS) (Dose/Dosage: 320 mg).

Example 31: Protein Therapeutics in Early-Stage and in Late-Stage Trials and Development The present example describes protein agent therapeutics currently undergoing testing at Early-stage and also Late-stage trials that may be used in low viscosity formulations described herein.

The progression of protein agent therapeutics from early-stage to late-stage clinical development and regulatory review are proceeding at a much rapid pace. Many therapeutic Proteins/mAbs have recently entered, or are entering, clinical trials. They can include protein agents currently administered via IV infusion, preferably those having a molecular weight greater than about 100 kDa, typically from about 140 kDa to about 180 kDa. They can also include such protein agents such as Albumin-conjugated drugs or peptides that are also entering clinical trials or have been approved by the FDA. They can also include such proteins agents as those having a molecular weight less than 100 kDa but have high viscosities at a therapeutic dose.

Protein therapeutics in Early-Stage and Late-Stage Trials and Development that can be formulated with viscosity-reducing agent(s) include: 3K3A-activated protein C (3K3A-APC) from The Scripps Research Institute, University of Southern California and ZZ Biotech; ABT-122 from Abbott Laboratories/AbbVie; ACE-031 (ACVR2B) from Acceleron Pharma, Inc; AGN-214868 (senrebotase) from Health Protection Agency Porton Down; Albumin-binding somatropin (Somapacitan) from Novo Nordisk; Alpha Galactosidase (GALAZYME-A) from Intra Lab; Ambrx MS from Merck Serono; AMI MultiStem (PF-05285401) from Athersys; Andexanet alfa from Portola Pharmaceuticals, Inc; Apcitide (Acutect; AcuTect; P 280; Tc 99m P 280; Technetium Tc 99m apcitide; Technetium Tc 99m P280) from Bayer HealthCare Pharmaceuticals; AURIMUNE (CYT 6091) from CytImmune Sciences; BAY 86-6150 from Bayer AG; Damoctocog alfa pegol (BAY 94-9027) from Bayer AG; BMN 270 from BioMarin Pharmaceutical; BXL-1H5 (GBR 900) from Glenmark Pharmaceuticals S.A.; Catridecacog (NN1841) from Novo Nordisk; Cerebroside sulfatase (HGT-1110) from Shire and Zymenex A/S; Cerliponase alfa (BMN 190; Brineura) from BioMarin Pharmaceutical; Cimaglermin alfa (Recombinant human glial growth factor-2 (rhGGF 2)) from Acorda Therapeutics; Condoliase from Seikagaku Corporation; Corifollitropin alfa from Merck KGaA; Cyclic pyranopterin monophosphate from Alexion Pharmaceuticals; Damoctocog alfa pegol (BAY-949027; peg rFVIII; PEG rFVIII mutein; PEGylated B-Domain-Delted Recombinant rFVIII; PEGylated BDD-rFVIII; rFVIII glycopegylated) from Bayer HealthCare Pharmaceuticals; Eflapegrastim (SPI-2012) from Hanmi Pharmaceuticals Co; Entolimod (CBLB 502) from Cleveland BioLabs; Exenatide-XTEN (VRS-859) from Versartis; Factor VIII from CSL Behring; Factor Xa variant (IL 16)(PF 5230907) from Pfizer, Inc; FGF-18 (sprifermin) from Merck Serono, Molecular Therapeutics, Nordic Bioscience and Pfizer; fibroblast growth factor-1 from CardioVascular BioTherapeutics Inc.; Glucagon-like peptides (GLP2-2G-XTEN) from Amunix, Inc; Glucagon-like peptides (NN 9927 and NN 9928) from Novo Nordisk; Sermorelin (alternative names: Geref; Gerel; GRF 1-29; GRF(1-29)NH2; Groliberin; Growth hormone releasing factor-(1-29)amide; Human growth hormone releasing factor; human somatoliberin-(1-29) amide; Somatoliberin-(1-29) amide) from Salk Institute; GSK2586881 from Apeiron Biologics and GlaxoSmithKline; GZ402666 (alternative names: 2nd generation aglucosidase-alpha; neo rhGAA; Neo-recombinant human acid alpha-glucosidase; Neo-rhGAA; Neo-rhGAA enzyme therapy; NeoGAA) from Sanofi Genzyme and Genzyme Corporation; Indium-111-octreotide (OctreoScan) from Mallinckrodt Pharmaceuticals; Insulin lispro from Sanofi; Insulins; Pancreatic hormones (Insulin 338) from Novo Nordisk; interferon alpha-2b infusion from Medtronic; Interleukin 12 stimulant (NHS-IL 12) from National Cancer Institute (USA), Merck Serono; IRX-2 from IRX Therapeutics, Inc; KUR-211 from Baxter; LA-EP2006 (pegfilgrastim biosimilar) from Novartis AG;

Lamazyme from Zymenex; Lesinidase alfa (SBC-103) from Alexion Pharmaceuticals; Liraglutide (NN9211, LATIN TID; NN 2211; NN 9211; NN-8022; NNC 90-1170; Saxenda; Victoza) from Novo Nordisk; Long-acting basal insulin analogue (Insulin 287) from Novo Nordisk; Long-acting Erythropoietin (EPO) (HM10760A) from Hanmi Pharmaceutical Company Limited; long-acting FGF21 mimetic (PF-05231023) from Pfizer, Inc; Long-acting GLP-1 analogue (NN 9926) from Novo Nordisk; MAGEA-3-protein-modulators (MAGE A3 TCR) from Kite Pharma and National Cancer Institute (USA); Marzeptacog alfa (PF-05280602) from Catalyst Biosciences; Midostaurin (alternative names: 4-N-benzoyl staurosporine; Benzoylstaurosporine; CGP 41251; N-benzoyl-staurosporine; PKC412; PKC412A) from Novartis; MK-1293 from Merck; Turoctocog alfa pegol (alternative names: Long acting recombinant factor VIII—Novo Nordisk; N8-GP; N8-GP rFVIII; NN-7088; NNC-0129-0000-1003; PEG turoctocog alfa; Pegylated turoctocog alfa; Recombinant factor VIII long acting—Novo Nordisk; rFVIII glycopegylated—Novo Nordisk) from Novo Nordisk; NEUBLASTIN from Biogen and NsGene; Nonacog beta pegol (NN7999) from Novo Nordisk; Notch-3 receptor antagonists (PF 6650808) from Pfizer; olipudase alfa (GZ402665) from Sanofi; Pegapamodutide (LY2944876) from Eli Lilly; Peginterferon beta (AZ01) from Allozyne; PEGUNIGALSIDASE ALFA (PRX-102) from Protalix Biotherapeutics; Peptide vaccines (ATX MS 1467) from Apitope Technology and Merck Serono; PF-04856884 from Pfizer; PRAME from GlaxoSmithKline; PREMIPLEX (Mecasermin rinfabate) from Shire; Recombinant factor VIII, Octocog alfa (Helixate, Kogenate) from Bayer; Recombinant human bone morphogenic protein 7 (rhBMP7) (Osteogenic protein 1) from Olympus Biotech Corporation; recombinant human C1 esterase inhibitor from Pharming Group and Santarus Inc; Recombinant human serum albumin (RU-101) from R-Tech Ueno, Ltd.; Recombinant human Acetylcholinesterase (PRX-105) from Protalix BioTherapeutics; Recombinant-lecithin-cholesterol-acyltransferase (MEDI 6012) from AstraZeneca and MedImmune; insulin (rHuPH20) from Halozyme, Inc; RNA inhibitors (QBI 139) from Quintessence Biosciences; Secretin (ChiRhoStim (human peptide), SecreFlo (porcine peptide)) from ChiRhoClin; Semaglutide (NN9535) from Novo Nordisk; Semaglutide oral (NN-9924; NNC0113-0217) from Novo Nordisk; Serum amyloid P (PRM 151) from Promedior; Somatropin biosimilar from LG Life Sciences LTD; Synairgen plc AZD9412 from AstraZeneca; Tecemotide (EMD-531444, ONO-7165) from Biomira; Thrombolytics (TS 01) from Thrombotargets Corporation; Thyroid stimulating hormone (TSH), thyrotropin from Genzyme Corporation; Turoctocog alfa (NN-7008) from Novo Nordisk; Type 1 tumour necrosis factor receptor antagonists (GSK 1995057) from GlaxoSmithKline; Vanutide cridificar ACC-001 (PF-05236806) from JANSSEN Alzheimer Immunotherapy and Pfizer; VEN100 from Ventria Bioscience; Vibriolysin from W.R. Grace; Vosoritide (BMN-111) from BioMarin Pharmaceutical; WTI (Galinpepimut-S) from GlaxoSmithKline; Yeast-derived microvesicles containing recombinant Tissue Factor (TT 173) from Thrombotargets Corporation; Soluble complement receptor 1 (CDX-1135) from Celldex; Interleukin-7—Revimmune SAS (alternative names: CYT 107; Glycosylated recombinant human interleukin-7—Cytheris; IL-7; Recombinant human interleukin-7—Cytheris; rhIL-7; Second-generation CYT 99 007) from Cytheris.

Example 32: Fusion Protein Therapeutics in Early-Stage and in Late-Stage Trials and Development The present example describes fusion protein therapeutics currently undergoing testing at Early-stage and also Late-stage trials that may be used in low viscosity formulations described herein.

Fusion protein therapeutics in Early-Stage and Late-Stage Trials and Development that can be formulated with viscosity-reducing agent(s) include: Alpha-N-acetyglucosaminidase-insulin-like-growth-factor-2 fusion protein (BMN 250) from BioMarin Pharmaceutical; ALT 801 from Altor BioScience Corporation; Atacicept from EMD Serono, Merck Serono and ZymoGenetics; BA-210 from BioAxone Biosciences, Inc; Benegrastim from Generon (Shanghai) Corporation; Dalantercept from Acceleron Pharma; Dekavil (F8 IL10) from Pfizer and Philogen; FP 1039 from Five Prime Therapeutics; Glucagon-like peptides (PF 4856883) from Pfizer; Immunoglobulin Fc fragments, Fzd8-Fc (Ipafricept, OMP 54F28) from OncoMed and Bayer Pharma AG; Recombinant fusion proteins (ALXN 1102) from Alexion Pharmaceuticals; Recombinant Factor X (CSL 689) from CSL Behring; SL 401 from Stemline Therapeutics; Somavaratan (VRS-317, Human growth hormone-XTEN) from Versartis and Amunix; Sotatercept (ACE-011) from Celgene Corporation; trebananib (AMG 386) from Amgen; Vasomera (PB 1046) from PhaseBio Pharmaceuticals; Antihemophilic Factor (recombinant Factor VIII) from Biogen Idec.

Example 33: Antibody Therapeutics Currently on the Market

The present example describes antibody therapeutics currently available on the market that may be used in low viscosity formulations described herein.

Antibody therapeutics currently on the market that can be formulated with viscosity-reducing agents include Abciximab, REOPRO®; Adalimumab, HUMIRA® (Pfizer), ABP501 (Amgen), GP2017 (Novartis); Ado trastuzumab emtansine, KADCYLA™; Alemtuzumab, CAMPATH®; Alemtuzumab, LEMTRADA™; Alirocumab, PRALUENT®; Atezolizumab, TECENTRIQ® (Genetech), RG7446 (Roche); Basiliximab, SIMULECT®; Belimumab, BENLYSTA®; Bevacizumab, AVASTIN® (Roche), ABP 215 (Amgen); Bezlotoxumab, ZINPLAVA™; Blinatumomab, BLINCYTO®; Brentuximab vedotin, ADCETRIS; Canakinumab, ILARIS®; Capromab pendetide, PROSTASCINT® Kit; Certolizumab pegol, CIMZIA®; Cetuximab, ERBITUX®; Daclizumab, ZINBRYTA™, ZENAPAX®; Daratumumab, DARZALEX®; Denosumab, PROLIA®; Denosumab, XGEVA®; Dinutuximab, UNITUXIN; Eculizumab, SOLIRIS®; Efalizumab, RAPTIVA®; Elotuzumab, EMPLICITI™; Evolocumab, REPATHA®; Gemtuzumab ozogamicin, MYLOTARG; Golimumab, SIMPONI®; Ibritumomab tiuxetan, ZEVALIN®; Idarucizumab, PRAXBIND; Infliximab, REMICADE® (Pfizer), ABP 710 (Amgen), FLIXABI® (Biogen); Ipilimumab, YERVOY®; Itolizumab, ALZUMAB™; Ixekizumab, TALTZ™; Mepolizumab, NUCALA®; Muromonab, Orthoclone OKT3®; Natalizumab, TYSABRI®; Necitumumab, PORTRAZZA™; Nimotuzumab, THERACIM®; Nivolumab, OPDIVO®; Nofetumomab, VERLUMA® (iagnostic); Obiltoxaximab, ANTHIM®; Obinutuzumab, GAZYVA® (Genentech), GA101 (Roche); Ofatumumab, ARZERRA®; Olaratumab, LARTRUVO™; Omalizumab, XOLAIR®;

Palivizumab, SYNAGIS®; Panitumumab, VECTIBIX®; Pembrolizumab, KEYTRUDA®; Pertuzumab, PERJETA® (Genentech), RG1273 (Roche); Ramucirumab, CYRAMZA®; Ranibizumab, LUCENTIS® (Genentech), RG3645 (Roche) & Novartis; Raxibacumab, ABTHRAX™; Reslizumab, CINQAIR®; Rituximab, RITUXAN® (Pfizer), ABP 798 (Amgen), MabThera (Roche), (Genetech), GP2013 (Novartis); Secukinumab, COSENTYX®; Siltuximab, SYLVANT™; Tocilizumab, ACTEMRA® (Roche & Genentech); Tositumomab, BEXXAR®; Trastuzumab, HERCEPTIN®(Genentech), ABP 980 (Amgen), HERTRAZ® (mylan), CANMAB™ (Biocon); Ustekinumab, STELARA®; Vedolizumab, ENTYVIO®.

Example 34: Antibody Therapeutics Currently on the Market that can be Formulated with Viscosity-Reducing Agent(s) Include The present example describes antibody therapeutics currently available on the market that may be used in low viscosity formulations described herein.

Abciximab (REOPRO®) developed by Eli lilly is used in treatment of cardiac ischemic complications, percutaneous coronary intervention by targeting glycoprotein (GP) IIb/IIIa receptor of human platelets (Dose/Dosage: 0.25 mg/kg).

Abciximab (REOPRO®) is a Fab fragment of the chimeric human-murine monoclonal antibody 7E3. Abciximab binds to the glycoprotein (GP) IIb/IIIa receptor of human platelets and inhibits platelet aggregation by preventing the binding of fibrinogen, von Willebrand factor, and other adhesive molecules. It also binds to vitronectin ($\alpha v \beta 3$) receptor. Abciximab is administered via IV infusion, first in a bolus of 0.25 mg/kg and followed by continuous IV infusion of 0.125 mcg/kg/minute for 12 hours.

Adalimumab (HUMIRA®) developed by AbbVie is used in treatment of Rheumatoid Arthritis (RA), Juvenile Idiopathic Arthritis (JIA), Psoriatic Arthritis (PsA), Ankylosing Spondylitis (AS), Crohn's Disease (CD), Ulcerative Colitis (UC) Plaque Psoriasis (Ps) by inhibiting TNF-$\alpha$ (Dose/Dosage: 40 mg every other week).

Ado trastuzumab emtansine (KADCYLA™) developed by Genentech is used in treatment of breast & gastric cancer (Dose/Dosage: 3.6 mg/kg).

Alemtuzumab (CAMPATH®) developed by BayerAG is used in treatment of B-CLL, NHL by targeting CD52 (Dose/Dosage: 3 mg).

Alemtuzumab (CAMPATH®, MABCAMPATH®, or CAMPATH-1H® and LEMTRADA®) is a mAb used in the treatment of chronic lymphocytic leukemia (CLL), cutaneous T-cell lymphoma (CTCL), and T-cell lymphoma: also for treatment of some autoimmune diseases, such as multiple sclerosis. It is administered in daily IV infusions of 30 mg for patients with B-cell chronic lymphocytic leukemia.

Alemtuzumab (LEMTRADA™) developed by Sanofi-Aventis is used in treatment of relapsing forms of multiple sclerosis by targeting CD52 (Dose/Dosage: 12 mg/day).

Alirocumab (PRALUENT®) developed by Regeneron Pharmaceuticals is used in to lower LDL cholesterol targeting PCSK9 (Dose/Dosage: 150 mg every 2 weeks).

Atezolizumab (TECENTRIQ®) developed by Roche is used in treatment of urothelial carcinoma & solid tumors by targeting PD-L1 (Dose/Dosage: 1200 mg for 3 weeks).

Basiliximab (SIMULECT®) developed by Novartis is used in reversal of transplantation rejection {Dose/Dosage: 2 doses of 20 mg each (before & after transplantation)}.

Belimumab (BENLYSTA®) developed by Human Genome Sciences Inc. used in treatment of systemic lupus erythematosus by targeting B-lymphocyte stimulator (BLyS) (Dose/Dosage: 10 mg/kg for 2 weeks).

Belimumab (BENLYSTA®) is a human mAb which inhibits B-cell activating factor (BAFF) used for treatment of systemic lupus erythematosus. Belimumab is currently administered to lupus patients by IV infusion at a 10 mg/kg dosage.

Bevacizumab (AVASTIN®) developed by Genentech is used in treatment of Metastatic colorectal cancer, Non-squamous non-small cell lung cancer, Metastatic breast cancer by inhibiting vascular endothelial growth factor-specific angiogenesis (Dose/Dosage: 15 mg/kg every 2 weeks).

Bevacizumab, a humanized mAb that inhibits vascular endothelial growth factor A (VEGF-A), acts as an anti-angiogenic agent. It is marketed under the trade name AVASTIN® by Genentech, Inc. ("Genentech") and F. Hoffmann-La Roche, LTD ("Roche"). It is licensed to treat various cancers, including colorectal, lung, breast, glioblastoma, recurrent glioblastoma multiforme, metastatic renal cell carcinoma, kidney and ovarian. AVASTIN® is given as an IV infusion every three weeks at the dose of either 15 mg/kg or 7.5 mg/kg. Bevacizumab is described in U.S. Pat. No. 6,054,297. Bevacizumab includes the active agent in products marketed under the trade name AVASTIN® and biosimilar products thereof. Biosimilars of AVASTIN® can include those currently being developed by Amgen, Actavis, AlphaMab, and Pfizer, Inc ("Pfizer"). Biosimilars of AVASTIN® can include the biosimilar known as BCD-021 produced by Biocad.

Bezlotoxumab (ZINPLAVA™) developed by Merck is used in treatment of *Clostridium difficile* infection which binds to *Clostridium difficile* toxin B (Dose/Dosage: 10 mg/kg).

Blinatumomab (BLINCYTO®) developed by Amgen is used in treatment of Philadelphia chromosome-negative relapsed B-ALL by targeting CD19-directed CD3 T-cell (Dose/Dosage: 28 mcg/day).

Brentuximab vedotin (ADCETRIS®) developed by Seattle Genetics, Inc is used in treatment of Hodgkin lymphoma by targeting CD30 (Dose/Dosage: 1.8 mg/kg).

Brentuximab vedotin (ADCETRIS®) is an antibody-drug conjugate directed to the protein CD30, expressed in classical Hodgkin's lymphoma and systemic anaplastic large cell lymphoma. It is administered by IV infusion of about 1.8 mg/kg.

Catumaxomab (Proximium®) developed by Viventia and (Removab) by Fresenius Biotech and Trion Pharma is used in the treatment of head and neck cancer (150 µg on 4th dose).

Canakinumab (ILARIS®) developed by Novartis Pharmaceutical Corporation is used in treatment of hereditary periodic fevers & prevention of cardiovascular event by targeting interleukin-1$\beta$ (Dose/Dosage: 150 mg).

Capromab pendetide (PROSTASCINT® Kit) developed by Cytogen Corporation, is used in treatment of distant Metastases by targeting Prostate Specific Membrane Antigen (PSMA) (Dose/Dosage: 0.5 mg radiolabeled with 5 mCi of Indium in 111 chlorides).

Certolizumab pegol (CIMZIA®) developed by UCB company is used in treatment of Crohn's disease, rheumatoid arthritis by targeting TNF (Dose/Dosage: 400 mg).

Certolizumab pegol (CIMZIA®) is a recombinant, humanized antibody Fab' fragment, with specificity for human tumor necrosis factor alpha (TNF$\alpha$), conjugated to an approximately 40 kDa polyethylene glycol (PEG2MAL40K).

Cetuximab (ERBITUX®) developed by Sanofi-Aventis is used in treatment of EGFR-expressing, metastatic colorectal carcinoma (Dose/Dosage: 400 mg).

Cetuximab is an epidermal growth factor receptor (EGFR) inhibitor used for the treatment of metastatic colorectal cancer and squamous cell carcinoma of the head and neck cancer. Cetuximab is marketed for IV use only under the trade name ERBITUX® by Bristol-Myers Squibb Company, Eli Lilly and Company, and Merck KGaA. ERBITUX® is produced in mammalian (murine myeloma) cell culture. Each single-use, 50-mL vial of ERBITUX® contains 100 mg of cetuximab at a concentration of 2 mg/mL.

Cetuximab includes antibodies described in U.S. Pat. No. 6,217,866. Cetuximab includes the active agent in products marketed under the trade name ERBITUX® and biosimilar products thereof. Biosimilars of ERBITUX® can include those currently being developed by Amgen, AlphaMab Co., Ltd. ("AlphaMab"), and Actavis plc ("Actavis").

Daclizumabb (ZINBRYTA™) developed by Biogen and AbbVie and (ZENPAX®) developed by Roche is used in treatment of relapsing multiple sclerosis (RMS) (Dose/Dosage: 150 mg once in a month).

Daclizumab (ZENAPAX®) is a humanized anti-CD25 mAb and is used to prevent rejection in organ transplantation, especially in kidney transplants and also under investigation for the treatment of multiple sclerosis. Daclizumab is administered by IV infusion of 1 mg/kg. Daclizumab High-Yield Process (DAC HYP; BIIB019; Biogen Idec ("Biogen") and AbbVie, Inc. ("AbbVie")) is also under investigation as a 150 mg, once-monthly subcutaneous injection to treat relapsing, and remitting multiple-sclerosis.

Daratumumab (DARZALEX®) developed by Janssen Biotech is used in treatment of CD38-directed for multiple myeloma (Dose/Dosage: 16 mg/kg).

Denosumab (PROLIA®) developed by Amgen is used in treatment for postmenopausal women with osteoporosis by targeting RANK ligand (RANKL) (Dose/Dosage: 60 mg every 6 months).

Denosumab (XGEVA®) developed by Amgen is used in treatment of solid tumors of bone by targeting RANK ligand (RANKL) (Dose/Dosage: 120 mg every 4 weeks).

Denosumab (PROLIA® and XGEVA®) is a human mAb and the first RANKL inhibitor-approved for use in post-menopausal women with risk of osteoporosis and patients with bone metastases from solid tumors.

Dinutuximab (UNITUXIN) developed by United Therapeutics Corporation is used in treatment of neuroblastoma by targeting GD2 (Dose/Dosage: 17.5 mg/day).

Eculizumab (SOLIRIS®) developed by Alexion Pharmaceuticals is used in treatment of paroxysmal nocturnal hemoglobinuria (PNH), atypical hemolytic uremic syndrome (aHUS), thrombotic microangiopathy (TMA) by targeting complement (Dose/Dosage: 900 mg for PNH; 1200 mg for aHUS).

Eculizumab (SOLIRIS®) is a humanized mAb approved for the treatment of rare blood diseases, such as paroxysmal nocturnal hemoglobinuria and atypical hemolytic uremic syndrome. It is administered by IV infusion in the amount of about 600 mg to about 1,200 mg.

Efalizumab (RAPTIVA®) developed by Genentech/Merck Serono is used in treatment of immunosuppressive, plaque psoriasis (Dose/Dosage: 1 mg/kg weekly).

Elotuzumab (EMPLICITI™) developed by Bristol-Myers Squibb and AbbVie is used in treatment of multiple myeloma (Dose/Dosage: 10 mg/kg=500 mg with lenalidomide & dexamethasone).

Evolocumab (REPATHA®) developed by Amgen is used in treatment of HeFH, CVD, reducing of low density lipoprotein cholesterol (LDL-C) by targeting PCSK9 (proprotein convertase subtilisin kexin type 9) (Dose/Dosage: 420 mg monthly).

Gemtuzumab ozogamicin (MYLOTARG®) developed by Wyeth Pharmaceuticals is used in treatment of acute myelogenous leukemia (AML) (Dose/Dosage: 9 mg).

Golimumab (SIMPONI®) developed by Janssen Biotech, Inc. is used in treatment of Rheumatoid Arthritis, Psoriatic Aithritis, Ankylosing Spondylitis (Dose/Dosage: 50 mg).

Ibritumomab tiuxetan (ZEVALIN®) developed by Biogen Idec is used in treatment of relapsed & untreated follicular NHL (Dose/Dosage: 0.4 mCi/Kg or 14.8 MBq per kg).

Idarucizumab (PRAXBIND®) developed by Boehringer Ingelheim Pharmaceuticals, Inc. is used in surgery, life-threatening or uncontrolled bleeding (Dose/Dosage: 5 g).

Infliximab (REMICADE®) developed by Janssen Biotech, Inc. and its biosimilar drugs (FLIXABI®) developed by Biogen, (Inflectra) by Celltrion, is used in treatment of rheumatoid arthritis, adult ulcerative colitis, plaque psoriasis, psoriatic arthritis, ankylosing spondylitis, adult & pediatric Crohn's disease (Dose/Dosage: 5 mg/kg).

Infliximab is a mAb against tumor necrosis factor alpha (TNF-α) used to treat autoimmune diseases. Infliximab neutralizes the biological activity of TNFα by binding with high affinity to the soluble and transmembrane forms of TNFα and inhibits binding of TNFα with its receptors. It is marketed under the trade name REMICADE® by Janssen Global Services, LLC ("Janssen") in the U.S., Mitsubishi Tanabe Pharma in Japan, Xian Janssen in China, and Merck & Co ("Merck"); elsewhere. In some embodiments, the formulations contain a biosimilar of REMICADE®, such as REMSIMA™ or INFLECTRA™. Both REMSIMA™, developed by Celltrion, Inc. ("Celltrion"), and INFLECTRA™, developed by Hospira Inc., UK. Infliximab is currently administered via IV infusion at doses ranging from about 3 mg/kg to about 10 mg/kg.

Ipilimumab (YERVOY®) developed by Bristol-Myers Squibb is used in treatment of metastatic melanoma (Dose/Dosage: 10 mg/kg for 12 weeks).

Ipilimumab (YERVOY®) is a human mAb used for the treatment of melanoma and non-small cell lung carcinoma (NSCLC), small cell lung cancer (SCLC), and metastatic hormone-refractory prostate cancer. Ipilimumab is currently administered by IV infusion of 3 mg/kg.

Itolizumab (ALZUMAB™) developed by Biocon is used in treatment of reduce pro-inflammatory cytokines & T cell infiltration at sites of inflammation (Dose/Dosage: 1.6 mg/Kg).

Itolizumab (ALZUMAB®) is a humanized IgG1 mAb used for moderate to severe psoriasis.

Ixekizumab (TALTZ™) developed by Eli lilly is used in treatment of plaque psoriasis targeting interleukin-17A (Dose/Dosage: 160 mg).

Mepolizumab (NUCALA®) developed by GlaxoSmithKline is used in treatment of asthma targeting interleukin-5 (Dose/Dosage: 100 mg once every 4 week).

Muromonab (Orthoclone OKT3®) developed by Johnson & Johnson is used in reversal of graft rejection by targeting CD3 (Dose/Dosage: 5 mg/day).

Natalizumab (TYSABRI®) developed by Biogen Idec/Elan Corporation is used in Acute ischemic stroke, Multiple Sclerosis (MS), Crohn's Disease (CD) by targeting α4-integrin (Dose/Dosage: 300 mg every 4 weeks).

Natalizumab, a humanized mAb against the cell adhesion molecule α4-integrin, is used in the treatment of multiple sclerosis and Crohn's disease. Previously marketed under the trade name ANTEGREN®, natalizumab is currently co-marketed as TYSABRI® by Biogen Idec ("Biogen") and Elan Corp. ("Elan"). Each dose contains 300 mg natalizumab. Natalizumab includes antibodies described in U.S. Pat. Nos. 5,840,299, 6,033,665, 6,602,503, 5,168,062, 5,385,839, and 5,730,978.

Necitumumab (PORTRAZZA™) developed by Eli Lilly is used in metastatic squamous non-small cell lung cancer by targeting epidermal growth factor receptor (EGFR) (Dose/Dosage: 800 mg).

Nimotuzumab (THERACIM™) developed by Center of Molecular Immunology is used in treatment of anaplastic astrocytoma, Brain, nasopharyngeal, esophageal cancer, Glioblastoma, Glioma (Dose/Dosage: 200 mg).

Nimotuzumab (THERACIM™, BIOMAB EGFR®, THERALOC®, CIMAher®) is a humanized mAb with a molecular weight of about 151 kDa used to treat squamous cell carcinomas of the head and neck, recurrent or refractory high-grade malignant glioma, anaplastic astrocytomas, glioblastomas, and diffuse intrinsic pontine glioma. Nimotuzumab is typically administered by IV infusion of about 200 mg weekly.

Nivolumab (OPDIVO®) developed by Bristol-Myers Squibb is used in treatment of Metastatic Melanoma, Non-Small Cell Lung Cancer, Renal Cell Carcinoma, Classical Hodgkin Lymphoma (Dose/Dosage: 240 mg every 2 weeks).

Nofetumomab (VERLUMA®, diagnostic) developed by Boehringer Ingelheim, NeoRx is used in treatment of cancer (Dose/Dosage: 10 mg).

Obiltoxaximab (ANTHIM®) developed by Elusys Therapeutics, Inc. is used as protective antigen of *Bacillus anthracis* (Dose/Dosage: 32 mg/kg).

Obinutuzumab (GAZYVA®) developed by Genentech is used in treatment of non-Hodgkin's lymphoma, lupus, Chronic Lymphocytic Leukemia (Dose/Dosage: 1000 mg).

Obinutuzumab (GAZYVA®) is a humanized anti-CD20 mAb approved for treatment of chronic lymphocytic leukemia. Dosages of about 1,000 mg are being administered via IV infusion.

Ofatumumab (ARZERRA®) developed by Norvartis Pharmaceutical Corporation is used in treatment of non-Hodgkin's lymphoma, Chronic Lymphocytic Leukemia, Relapsing multiple sclerosis (Dose/Dosage: 2000 mg every 4 weeks).

Olaratumab (LARTRUVO™) developed by Eli Lilly is used as anti-PDGFR-α for soft tissue sarcoma (Dose/Dosage: 15 mg/kg).

Ofatumumab (ARZERRA®) is a human anti-CD20 mAb which appears to inhibit early-stage B lymphocyte activation. Ofatumumab is used for treating chronic lymphocytic leukemia and has also shown potential in treating Follicular non-Hodgkin's lymphoma, Diffuse large B cell lymphoma, rheumatoid arthritis, and relapsing remitting multiple sclerosis. It is currently administered by IV infusion at an initial dose of 300 mg, followed by weekly infusions of 2,000 mg.

Omalizumab (XOLAIR®) developed by Genentech/Novartis is used in treatment of asthma, chronic idiopathic urticaria, and acute bronchospasm or status asthmatics (Dose/Dosage: 375 mg every 2-4 weeks).

Palivizumab (SYNAGIS®) developed by MedImmune is used for prevention of respiratory syncytial virus (RSV) disease (Dose/Dosage: 15 mg/kg).

Palivizumab (SYNAGIS®) is a humanized mAb directed against an epitope in the A antigenic site of the F protein of respiratory syncytial virus. Palivizumab is dosed once a month via IM injection of 15 mg/kg.

Panitumumab (VECTIBIX®) developed by Amgen is used in treatment of metastatic colorectal carcinoma targeting epidermal growth factor receptor (Dose/Dosage: 6 mg/kg).

Panitumumab (VECTIBIX®) is a fully human mAb for treatment of EGFR-expressing metastatic cancer with disease progression. VECTIBIX® is administered at a dosage of 6 mg/kg every 14 days as an intravenous infusion. The term "panitumumab" includes monoclonal antibodies described in U.S. Pat. No. 6,235,883. The term "panitumumab" includes the active agent in biosimilar VECTIBIX® products, including biosimilar VECTIBIX® being developed by BioXpress, SA ("BioXpress").

Pembrolizumab (KEYTRUDA®) developed by Merck is used in treatment of metastatic melanoma (Dose/Dosage: 200 mg every 3 weeks).

Pertuzumab (PERJETA®) developed by Genentech is used in treatment of HER2-positive breast cancer (Dose/Dosage: 840 mg every 3 weeks, thereafter 420 mg).

Pertuzumab (PERJETA®) is a mAb that inhibits HER2 dimerization and is used for the treatment of HER2-positive metastatic breast cancer in 2012. The currently recommended dosage of Pertuzumab is 420 mg to 840 mg by IV infusion.

Ramucirumab (CYRAMZA®) developed by Eli Lilly is used in treatment of adenocarcinoma, non-small cell lung cancer, colorectal cancer (Dose/Dosage: 10 mg/kg every 2 weeks).

Ranibizumab (LUCENTIS®) developed by Genentech is used in treatment of Age-Related Macular Degeneration (AMD), Macular Edema, Retinal Vein Occlusion (RVO), Diabetic Macular Edema (DME), Choroidal neovascularization, retinopathy of prematurity (Dose/Dosage: 0.05 mg once a month).

Raxibacumab (Abthrax™) developed by GlaxoSmithKline is used in inhalational anthrax due to *Bacillus anthracis* (Dose/Dosage: 80 mg/kg).

Raxibacumab (Abthrax™) is a human mAb intended for the prophylaxis and treatment of inhaled anthrax. It is currently administered by IV infusion. The suggested dosage in adults and children over 50 kg is 40 mg/kg.

Reslizumab (CINQAIR®) developed by Teva Pharmaceuticals, LLC is used in severe asthma attacks (exacerbations) (Dose/Dosage: 3 mg/kg).

Rituximab (RITUXAN®) developed by Genentech and their biosimilars (Reditux) Dr. Reddy's Laboratories and (MabThera®) Biogen Idec is used in treatment of Non-Hodgkin's Lymphoma (NHL), CLL, RA, Granulomatosis with Polyangiitis (GPA) (Dose/Dosage: 1000 mg on day 1 & day 15).

Rituximab (RITUXAN®, MABTHERA®) is a chimeric anti-CD20 mAb used to treat a variety of diseases characterized by excessive numbers of B cells, overactive B cells, or dysfunctional B cells. Rituximab is used to treat cancers of the white blood system, such as leukemias and lymphomas, including Hodgkin's lymphoma and its lymphocyte-predominant subtype. It has been shown to be an effective rheumatoid arthritis treatment. Rituximab is widely used off-label to treat difficult cases of multiple sclerosis, systemic lupus erythematosus, and autoimmune anemias. RITUXAN® is typically administered by IV infusion of about 375 mg/m2. Rituximab includes mAbs described in U.S. Pat. No. 5,736,137 and biosimilars thereof.

Secukinumab (COSENTYX®) developed by Novartis Pharmaceutical Corporation is used as Anti-interleukin-17 (Dose/Dosage: 150 mg).

Siltuximab (SYLVANT™) developed by Janssen Biotech, Inc is used in treatment of multicentric Castleman's disease (MCD) (Dose/Dosage: 11 mg/kg).

Tocilizumab (ACTEMRA®) developed by Genentech is used in treatment of Rheumatoid arthritis, Juvenile Idiopathic Arthritis (JIA) (Dose/Dosage: 8 mg/kg every 4 weeks).

Tocilizumab (ACTEMRA®) is a humanized mAb against the interleukin-6 receptor. It is an immunosuppressive drug, mainly for the treatment of rheumatoid arthritis (RA) and systemic juvenile idiopathic arthritis, a severe form of RA in children. Tocilizumab is commonly administered by IV infusion in doses of about 6 mg/kg to about 8 mg/kg.

Tositumomab (BEXXAR®) developed Corixa Corporation is used in treatment of follicular or transformed non-Hodgkin's lymphoma (Dose/Dosage: dosimetric dose: 450 mg & 5 mCi I-131 and 35 mg protein).

Tositumomab (BEXXAR®) is a mAb for the treatment of follicular lymphoma. It is an IgG2a anti-CD20 mAb. BEXXAR® is currently administered at a dose of 450 mg via IV infusion.

Trastuzumab (HERCEPTIN®) developed by Genentech and its biosimilars (HERTRAZ™) by Mylan and (CANMAB™) by Biocon is used in treatment of HER2 overexpressing breast cancer & gastric or gastro esophageal junction adenocarcinoma (Dose/Dosage: 8 mg/kg every 3 weeks).

Trastuzumab is a mAb that interferes with the HER2/neu receptor. Trastuzumab is mainly used to treat certain breast cancers. The HER2 gene is amplified in 20-30% of early-stage breast cancers, which makes it overexpress epidermal growth factor (EGF) receptors in the cell membrane. Trastuzumab is generally administered as a maintenance therapy for patients with HER2-positive breast cancer, typically for one year post-chemotherapy. Trastuzumab is marketed under the trade name HERCEPTIN® by Genentech, Inc. HERCEPTIN® is currently administered via IV infusion as often as weekly and at a dosage ranging from about 2 mg/kg to about 8 mg/kg. Trastuzumab is described in U.S. Pat. No. 5,821,337. The term "trastuzumab" includes the active agent in biosimilar HERCEPTIN® products marketed under the trade names HERTRAZ™ by Mylan, Inc. ("Mylan") and CANMAB™ by Biocon, Ltd. ("Biocon") and. Trastuzumab can include the active agent in biosimilar HERCEPTIN® products being developed by Amgen and by PlantForm Corporation, Canada.

Ustekinumab (STELARA®) developed by Janssen Biotech Inc. is used in treatment of plaque psoriasis (Ps), psoriatic arthritis, and Crohn's disease (CD) (Dose/Dosage: for Ps & PsA: 45 mg every 4 weeks, for CD: 520 mg).

Vedolizumab (ENTYVIO®) developed by Takeda Pharmaceutical Company Ltd. is used in treatment of Ulcerative Colitis, Crohn's Disease (Dose/Dosage: 300 mg).

Other antibody therapeutics that can be formulated with viscosity-reducing agents include CT-P6 from Celltrion, Inc. (Celltrion).

Example 35: Antibody Therapeutics in Early-Stage and in Late-Stage Trials and Development The present example describes antibody therapeutics currently undergoing testing at Early-stage and also Late-stage trials that may be used in low viscosity formulations described herein.

Antibody therapeutics in Early-Stage and Late-Stage Trials and Development that can be formulated with viscosity-reducing agent(s) include: November-7, November-8 from Morphosys AG & Novartis; CHR-1201 (alternative name: GBR600) from Glenmark Pharmaceuticals S.A.; 3F8, 8H9 from United Therapeutics corporation; AAB 003, PF-05236812 and PF-5236812 from JANSSEN Alzheimer Immunotherapy and Pfizer; Abagovomab from Menarini; AbGn 7 from AbGenomics Corporation; Abituzumab from Merck Senero; Abrilumab (alternative name: AMG 181) from Amgen; ABT 981 from Abbott Laboratories, AbbVie; Actimab A M195 (alternative names: 225Ac-HuM-195; 225Ac-lintuzumab; AC225 MOAB M195; Ac225 monoclonal antibody M195; Lintuzumab Ac-225; Actimab-M; Actinium-225 (225Ac)-Lintuzumab; Actinium-225-labelled HuM195; HuM195-Ac-225; Lintuzumab-Ac225; SMART actinium-225-M-195) from Actinium Pharmaceuticals; Actoxumab (alternative names: 3D8; Bezlotoxumab; CDA-1/CDA-2; CDA 1; GS-CDA-1/MDX-1388; MBL-CDA1/MBL-CDB 1; MDX 066; MDX-066+MDX-1388; MDX-066/MDX-1388; MK-3415+MK-6072; MK-3415/MK-6072; MK-3415A) from Merck & Co; Adecatumumab (alternative names: Anti-EpCAM mAb MT201; Human anti-EpCAM monoclonal antibody MT201; Monoclonal antibody MT201; MT 201; MT201 antibody) from Amgen; Merck Serono; Aducanumab (alternative names: BART; BIIB 037; NI-10) from Biogen; Afasevikumab (Alternative name: MCAF-5352A, NI-1401, RG 7624) from NovImmune and Genentech; Afelimomab from Abbott GmbH & Co. KG; AGS 16C3F (AGS-16M8F) from Agensys; AGS-009 (NNC 0152-0000-0001) from Argos Therapeutics Inc; Alacizumab pegol (alternative names CDP-791, g165 DFM-PEG) from Celltech, UCB; Clazakizumab (alternative names ALD 518; ALD518-003; BMS-645429; BMS-945429) from Alder Biopharmaceuticals; ALT-836 (alternative names cH36; Sunol-cH36; TNX 832) from Altor BioScience Corporation; ALX 0141 (alternative name EDP-406), ALX 0171, ALX-0761 and ALX-0962 from Ablynx; ALXN 1007 from Alexion Pharmaceuticals; Amatuximab (alternative name: MORAb-009; MORAB-009-006) from Eisai Co Ltd; Morphotek; AMG 557, AMG 595, AMG 595, AMG 780, AMG 820, AMG 827, patritumab (AMG 888), AMG167 and AMG 172 from Amgen; Anatumomab mafenatox (alternative names ABR 214936; PNU 214936; TTS CD2) from Active Biotech; Anetumab ravtansine (alternative names BAY 94-9343; BAY-94-9343; BAY-94-9343-SPDB-DM4) from Bayer HealthCare; Anifrolumab (MEDI-546) from Medarex and MedImmune; Anrukinzumab from Pfizer and Wyeth; Anti-IL-21 (NN8828) from Novo Nordisk A/S; APN301 (hu14. 18-IL2) from APEIRON Biologics AG; Apolizumab (alternative Hu1D10; Remitogen; SMART 1D 10 antibody) from PDL BioPharma; Arcitumomab from Immunomedics; Ascrinvacumab from Pfizer; Aselizumab (alternative names: Anti-L-selectin monoclonal antibody DREG 200—PDL BioPharma; Anti-L-selectin monoclonal antibody DREG 55; Aselizumab; BNP 001; DREG 200—PDL BioPharma; DREG 55; hDREG-200—PDL BioPharma; hDREG-55; Hu DREG 55; SMART anti-L-selectin antibodies) from PDL BioPharma; ASG-5ME Agensys and Seattle Genetics; ATI 355 from Novartis; anti-thrombin gamma (KW-3357) Kyowa; Atinumab (alternative names: 1226761-65-4; ATI355; RTN4; reticulon 4; reticulon-4; ASY; KIAA0886) from Creative Biolabs; Atorolimumab from Creative Biolabs; AV-203 from AVEO; Avelumab from Merck KGaA; AVX 701 and AVX 901 from AlphaVax and Duke University Medical Center; BAN2401 from Biogen Idec/Eisai Co. LTD; Bapineuzumab from Pfizer; Johnson &

Johnson; Bavituximab (PGN401) from University of Texas Southwestern Medical Center at Dallas, (U.S. Pat. No. 6,300,308), (U.S. Pat. Nos. 6,406,693 and 6,312,694); BAY2010112 (AMG 212) from Amgen; Bectumomab (LymphoScan™) from Immunomedics; Begelomab from Adienne; Benralizumab from Big Pharma, AstraZeneca, Teva and GlaxoSmithKline; Bertilimumab from Cambridge Antibody Technology & IMMUNE Pharmaceuticals; Besilesomab (Scintimun™) from Bayer Schering Pharma A. & CIS bio international; BHQ880 from Novartis; BI 1034020 from Ablynx and Boehringer Ingelheim Pharmaceuticals; BI 505 from BioInvent International; Biciromab (FibriScint™) from Centocor; BIIB 059 from Biogen; BIIB022 from Biogen; BIIB023 from Biogen; Bimagrumab (BYM338) from Novartis; Bimekizumab (CDP-4940; UCB-4940) from UCB; Bivatuzumab (KHK4083) from Kyowa Hakko Kirin; Bivatuzumab mertansine from Boehringer Ingelheim & ImmunoGen; BIW 8962 from Kyowa Hakko Kirin & Kyowa Hakko Kirin Korea; Bleselumab (ASKP 1240) from Astellas Pharma & Kyowa Hakko Kirin; Blontuvetmab (Blontress) from Aratana Pharmaceuticals; Blosozumab from Eli Lilly and Company; BMS 962476 from Adnexus Therapeutics & Bristol-Myers Squibb; Bococizumab from & Pfizer; Brazikumab (AMG 139) from Amgen and AstraZeneca; Briakinumab from Abbott Laboratories; Brodalumab from LEO Pharma; Brolucizumab from Alcon Laboratories; Brontictuzumab from OncoMed Pharmaceuticals; Burosumab from Ultragenyx; BVX 20 from Biocon and Vaccinex; Cabiralizumab from Bristol-Myers Squibb; Cantuzumab mertansine (alternative names: C-242 DM1; C-242 May; C242 maytansinoid conjugate; huC242 maytansinoid conjugate; huC242-DM1; Monoclonal antibody C-242 DM1 conjugate; Monoclonal antibody C-242 May conjugate; Monoclonal antibody huC242-May conjugate; SB-408075) from ImmunoGen; Cantuzumab ravtansine from ImmunoGen; Caplacizumab from Ablynx NV; Carlumab from Johnson & Johnson; Carotuximab from TRACON Pharmaceuticals; Coltuximab ravtansine (alternative names: SAR3419; Anti-CD19-DM4 immunoconjugate SAR3419; huB4-DM4; Maytansin-loaded anti-CD19 mAb) from ImmunoGen; cBR96-doxorubicin immunoconjugate from Seattle Genetics; Dapirolizumab pegol (alternative names: Anti-CD40L Fab; Anti-CD40L Fab-PEG; CD40L—Fab; CDP-7657; Pegylated anti-CD40L antibody) from Biogen; UCB; CDX-0401 from Celldex Therapeutics; Cedelizumab from Ortho-McNeil; Cergutuzumab amunaleukin from Roche; Ch. 14.18 mab from United Therapeutics; Citatuzumab bogatox from Viventia Biotech; Cixutumumab from ImClone Systems Inc. and Eli Lilly; Claudiximab (IMAB362) from Ganymed Pharmaceuticals AG; Clazakizumab (alternavtive names: ALD 518; ALD518-003; BMS-645429; BMS-945429) from Alder Biopharmaceuticals; Clenoliximab (alternavtive names: Anti-CD4 monoclonal antibody IDEC 151; IDEC 151; Lenoliximab; PRIMATIZED anti-CD4 antibody IDEC 151; SB 217969) from Biogen Idec; Clivatuzumab tetraxetan (alternavtive names: hPAM4-Cide) from Immunomedics, Inc; CNTO 5 from MorphoSys and Janssen Biotech; CNTO 5825 from Centocor Ortho Biotech and Janssen Biotech; CNTO3157 from Janssen Biotech; CNTO6785 from Janssen Biotech; Codrituzumab (alternavtive names: GC-33; RG 7686; RO 5137382) from Chugai Pharmaceutical and Roche; Coltuximab ravtansine from ImmunoGen, Inc; Conatumumab from Amgen Inc; concizumab from Novo Nordisk; Clenoliximab (alternavtive names: CR6261; Anti-CD4 monoclonal antibody IDEC 151; IDEC 151; Lenoliximab; PRIMATIZED anti-CD4 antibody IDEC 151; SB 217969) from Biogen Idec; Crenezumab from Genentech; crizanlizumab (Novartis SEG101) from Novartis and Selexys Pharmaceuticals; Crotedumab from Regeneron Pharmaceuticals; CT-P19, CT-P24, CT-P25 and CT-P26 from Celltrion; Dacetuzumab from Seattle Genetics, Inc; Dalotuzumab from Merck & Co., Inc.; Dapirolizumab pegol from Biogen Idec; UCB; Dectrekumab (QAX-576 and VAK 694) from Novartis; DEDN6526A (DEDN-6526A; RG7636) from Genentech; Demcizumab and Denintuzumab mafodotin from Seattle Genetics, Inc.; Depatuxizumab mafodotin from AbbVie; Derlotuximab Biotin from Peregrine Pharmaceuticals, Inc.; Detumomab from Creative Biolabs; DFRF4539A from Genentech, Inc.; DI17E6 from EMD Serono Inc, Diridavumab (alternative names: CR-6261; JNJ-54235025; mAb CR6261; Monoclonal antibody CR6261) from Johnson & Johnson; DKN 01 (LY-2812176) from Eli Lilly, Leap Therapeutics; Domagrozumab from Pfizer; Drozitumab from Genentech; Duligotuzumab (alternative names: Anti-HER3/EGFR DAF; MEHD-7945A; RG 7597; RO-5541078) from Genentech; Dupilumab from Regeneron Pharmaceuticals; Durvalumab from MedImmune; Dusigitumab from MedImmune; Ecromeximab from Kyowa Hakko Kogyo Co/Life Science Pharmaceuticals; Edobacomab (E5; Promune-ES; Xomen-E5) from XOMA Corporation; Edrecolomab (alternative names: 1083 17-1A; 17-1A; Adjuqual; C-1; CO17-1A; M-17-1A; Monoclonal antibody 17-1A; Panorex) from Ajinomoto and Centocor; Efungumab (Mycograb) from NeuTec Pharma; Eldelumab from Bristol-Myers Squibb; Elgemtumab (LJM-716; November-6) from MorphoSys and Novartis; Elsilimomab from OPi; Emactuzumab from Genentech and Roche; Emibetuzumab from Eli Lilly & Company; Emicizumab from Chugai; Enavatuzumab from Facet Biotech Corp.; Enfortumab vedotin from Seattle Genetics Inc.; Enlimomab pegol from Boehringer Ingelheim Pharmaceuticals; Enoblituzumab (MGA271) from MacroGenics, Inc; Enoticumab from Regeneron Pharmaceuticals; sanofi-aventis; Ensituximab (NEO-101; NEO-102; NPC-1C) from Neogenix Oncology; Epratuzumab (alternative names: AMG 412; Epratucyn; hCD22; Humanised monoclonal antibody LL2; Humanized anti-CD22 monoclonal antibody IgG1; IMMU 103; IMMU LL2; LymphoCide) from Immunomedics, Erenumab (AMG 334) from Amgen Novartis; Erlizumab from Genentech; Ertumaxomab (alternative names: Anti-CD3× anti-HER-2/neu; Rexomab®; Rexomun) from TRION Pharma; Etaracizumab (Abegrin™) from MedImmune; Etrolizumab from Genentech; Evinacumab from Regeneron Pharmaceuticals, Inc.; Exbivirumab (alternative names: HBV-AB17; HBV-AB19; HBV-XTL; Hepatitis B MAb-XTL; Human anti-HBV-XTL; libivirumab; Monoclonal antibody HBV-XTL; XTL-001; HepeX B) from XTL Biopharmaceuticals; Yeda; F 598 (SAR279356) from Alopexx Pharmaceuticals; Fanolesomab (NeutroSpec™) from Palatin Technologies; Farletuzumab from Morphotek, Inc.; Fasinumab (REGN475) from Regeneron Pharmaceuticals; FB 301 from Cytovance Biologics; Fountain BioPharma; FBTA 05 (Bi20; FBTA05; Lymphomun) from TRION Pharma; Felvizumab (alternative names: HuRSV19VHFNS/VK; RSHZ19; RSV monoclonal antibody; SB 209763) from Scotgen; Ferroportin & Hepcidin mab from Eli Lilly And Company; Fezakinumab (ILV-094; PF-5212367) from Wyeth, Pfizer; FG-3019 from FibroGen, Inc.; Ficlatuzumab (AV-299) from AVEO and Biodesix, Inc.; Figitumumab (CP-751871) from Pfizer; Firivumab (Cell-trion. Inc; Flanvotumab (20D7; 20D7S; IMC 20D7S) from Eli Lilly; Fletikumab from ZymoGenetics and Novo Nordisk; Flu mAB (CR6261) from Janssen & NIH; Fontolizumab from PDL BioPharma; Foralumab from NovImmune SA and Tiziana Life Sciences; Foravirumab from Sanofi/Crucell; Fresolimumab from Sanofi-Aventis; Fresolimumab from Genzyme & Sanofi; Fulranumab from Johnson & Johnson; Futuximab from Symphogen; Galcanezumab (LY2951742) from Eli Lilly & Co.; Galiximab from Biogen Idec; Ganitumab from Amgen; Gantenerumab from Chugai Pharmaceutical Co., Ltd. and Hoffmann-La Roche; Gavilimomab (ABX-CBL) from Abgenix; Gemtuzumab (Mylotarg™) from Pfizer; Gevokizumab from XOMA Corporation; Girentuximab (Rencarex™) from Wilex AG; Glembatumumab (alternative names: CDX-011; CR 011 ADC; CR 011-vcMMAE; CR011; Glemba; Glembatumumab vedotin; GV) from Celldex Therapeutics Inc; Gomiliximab from IDEC Pharmaceuticals Corporation; GS 5745 from Gilead Sciences, Kyowa Hakko Kirin; GSK 1070806 from GlaxoSmithKline; GSK 2398852 from Pentraxin Therapeutics, GSK; GSK 2618960 from GlaxoSmithKline; GSK 2862277 from GlaxoSmithKline; Guselkumab (CNTO-1959) from Janssen; HuL2G7 from Galaxy Biotech LLC; Ibalizumab from Genentech; Icrucumab (IMC-18F1) from ImClone Systems Inc.; Imalumab (BAY 79-4620) from Baxalta and Shire; IMC CS4 (IMCCS4; LY-3022855) from AstraZeneca, Eli Lilly and ImClone Systems; IMC TR1 (LY3022859) from ImClone Systems and Eli Lilly; Imciromab (Myoscint™) from Centocor; Imgatuzumab from Genentech/Roche; IMGN529 from ImmunoGen Inc; Inclacumab from Genentech/Roche; Indatuximab ravtansine from Biotest AG; Indusatumab vedotin from Takeda Oncology; Inebilizumab from MedImmune, LLC; Inolimomab from Orphan Pharma International; Inotuzumab ozogamicin from Pfizer and UCB; Intetumumab from Centocor, Inc.; Iomab-B from Actinium Pharmaceuticals; Iratumumab from Medarex, Inc.; Isatuximab (SAR-650984) from Sanofi-Aventis; istiratumab (MM-141) from Merrimack; J 591 Lu-177 from BZL Biologics LLC; KB 004 from KaloBios Pharmaceuticals; KD 247 from Kaketsuken; Keliximab from Biogen IDEC Pharmaceuticals, SKB; KHK6640 from Kyowa Hakko Kirin, Immunas Pharma; Labetuzumab (CEA-Cide) from Immunomedics, Inc.; Lambrolizumab (alternative names: Anti-PD-1 monoclonal antibody—Merck; Humanised monoclonal IgG4 antibody against PD-1—Merck; Keytruda; Pembrolizumab; MK-3475; SCH-900475) from Merck & Co; lampalizumab from Roche; Lanadelumab from Dyax Corp; Landogrozumab (LY-2495655) from Eli Lilly & Co.; Laprituximab emtansine from ImmunoGen; Lebrikizumab from Genentech; Lemalesomab from Creative Biolabs; Lendalizumab from Alexion Pharmaceuticals; Lenzilumab from KaloBios Pharmaceuticals Inc.; Lerdelimumab (CAT-152) from Cambridge Antibody Technology; Lexatumumab from HGS through a collaboration with Cambridge Antibody Technology; LFG316/Tesidolumab from Morphosys AG & Novartis AG; Libivirumab from XTL Biopharmaceuticals; Yeda; Lifastuzumab vedotin from Genentech/Roche; Ligelizumab from Novartis Pharma AG; Lilotomab satetraxetan from Nordic Nanovector; Lintuzumab (HuM195/rGel) from Seattle Genetics, Lirilumab from Bristol-Myers Squibb; Lodelcizumab from Novartis; Lokivetmab from Zoetis; Lorvotuzumab mertansine from Bristol-Myers Squibb; Lucatumumab from Novartis Pharmaceuticals Corp.; Lulizumab pegol from Bristol-Myers Squibb; Lumiliximab (alternative name IDEC-152, P5E8) from Biogen IDEC Pharmaceutical; Lumretuzumab from Genentech/Roche; LY 2928057, LY 3016859, LY2382770, LY2812176 and LY3015014 from Eli Lilly; MabVax/SKCC from MabVax Therapeutics; MAdCAM Mab (SHP 647) from Pfizer; Mapatumumab from Cambridge Antibody Technology (CAT) and Human Genome Sciences, Inc. (HGS); Margetuximab from Merck, MacroGenics, Inc.; Maslimomab from Creative Biolabs; Matuzumab from Merck Serono and Takeda Pharmaceutical; Mavrilimumab from Zenyth Therapeutics, MedImmune; MB-003 (alternative name: c13C6, h13F6 and c6D8) from National Microbiology Laboratory; MBL-HCV1 from MassBiologics; MCS110 from Novartis; MEDI 0639, MEDI 1814, MEDI 3617, MEDI 4212, MEDI 4893, MEDI 4920, MEDI 5117, MEDI 547, MEDI 565 (AMG-211 from Amgen), MEDI-570, MEDI 6469, MEDI 7814, MEDI 8897, MEDI 8968, MEDI-0680/AMP 514, MEDI-573 and MEDI-575 from MedImmune; Metelimumab from Genzyme; MFGR 1877S from Genentech and Roche; MHAA 4549A/MHAA-4549A; RG 7745 from Roche; Milatuzumab from Immunomedics, Inc; Minretumomab (CC49) from Creative Biolabs; MINT 1526A from Genentech; Mirvetuximab soravtansine (IMGN853; IMGN-853; M9346A-sulfo-SPDB-DM4) from ImmunoGen; Mitumomab (Anti-idiotype cancer vaccine—ImClone Systems/Merck KGaA; BEC-2; IMC-BEC2; LuVax; MelVax; Monoclonal antibody BEC-2) from ImClone Systems; MM 111, MM-121, MM-131, MM-151, MM-302 and MM-310 from Merrimack Pharmaceuticals, Inc; Mogamulizumab from Amgen; Monalizumab (Anti-NKG2A; IPH-2201; NN-8765; NNC 0141-0000-0100) from Innate Pharma and Novo Nordisk; MOR103 from Morphosys AG & GSK; Morolimumab from Creative Biolabs; Motavizumab (Numax) from MedImmune; Moxetumomab pasudotox from AstraZeneca and MedImmune; Nacolomab tafenatox (C242 Fab-SEA; LS 4565; PNU 214565; PNV 214565) from Pharmacia Corporation; Namilumab from Takeda Pharmaceuticals International GmbH; Naptumomab estafenatox (ABR-217620, ANYARA, TTS CD3) from Active Biotech AB; Naratuximab emtansine from ImmunoGen; Narnatumab from ImClone Systems; Navicixizumab (OMP-305B83) from OncoMed Pharmaceuticals; Navivumab (CT-P27═CT-P22+CT-P23) from Celltrion; Nebacumab from Centocor; Neihulizumab (AbGn-168H) from AbGenomics International Inc; Nemolizumab (CIM331) from Roche; Nerelimomab from Chiron Corporation, Celltech Group; Nesvacumab from Regeneron Pharmaceuticals; NN8209 & NN8210 from Argos Therapeutics Inc, Novo Nordisk; NN8555 from Janssen Biotech and Novo Nordisk; nofetumomab merpentan from Poniard Pharmaceuticals; Ocaratuzumab from Hoffmann-La Roche's subsidiary Genentech; Ocrelizumab from Roche; Odulimomab (afolimomab. ANTILFA®) from Pasteur-Merieux; Olokizumab from R-Pharm and UCB; Onartuzumab from Genentech, Inc; onclacumab from Creative Biolabs; Ontuxizumab from Morphotek and Ludwig Institute for Cancer Research; Opicinumab (BIIB033) from Biogen; Oportuzumab monatox (Proxinium; VB-4847; VB-845; VB4-845; Vicinium) from Eleven Biotherapeutics and Viventia Biotechnologies; Oregovomab (CA125) from AltaRex Corp.; Oregovomab (CA125) from AltaRex Corp. and Quest Pharmatech; Orticumab (BI-204; MLDL 1278A; RG 7418) from BioInvent International and Genentech; Otelixizumab from Abbott Laboratories, Otlertuzumab from Emergent BioSolutions; Oxelumab from Genentech/Roche; Ozanezumab (GSK1223249) from GlaxoSmithKline; Ozoralizumab from Pfizer Inc and Ablynx NV; Pagibaximab (A110; BSYX-A110; HU 96110) from Biosynexus; Pamrevlumab from FibroGen; Pankomab (GlycoOptimised IgG1 antibody—Glycotope; GT-MAB 2.5-GEX; Anti-TA-MUCI monoclonal antibody—Glycotope; PankoMab-GEX) from Glycotope; Panobacumab (AERUMAB 11; AR 101 (anti-Pa mAb); AR-101) from Aridis Pharmaceuticals; Parsatuzumab from Genentech/Roche; Pascolizumab (Anti-IL-4 monoclonal antibody—GlaxoSmithKline; Anti-IL-4 monoclonal antibody—Protein Design Labs; Anti-interleukin-4 monoclonal antibody—GlaxoSmithKline; Anti-interleukin-4 monoclonal antibody—Protein Design Labs; SB 240683) from GlaxoSmithKline; Pasotuxizumab from Micromet Inc, Amgen and Bayer HealthCare Pharmaceuticals; Pateclizumab from Genentech/Roche; Patritumab (AMG-888; U3-1287) from Amgen; U3 Pharma; Pemtumomab (R 1549; Monoclonal antibody HMFG1 yttrium 90 labelled; Pemtumomab; R1549; Theragyn; Yttrium 90 labelled monoclonal antibody HMFG1) from Cancer Research UK; Perakizumab from Genentech/Roche; Pexelizumab (5G1.1-SC; Anti-CS monoclonal antibody 5G1.1-SC; h5G1.1-scFV; Monoclonal antibody 5G1.1-SC; Short-acting monoclonal antibody 5G1.1) from Stanford University; PF-04605412 from Pfizer; Pidilizumab (CT-011; MDV 9300) from CureTech; Pinatuzumab vedotin from Genentech; PINTA 745 from Amgen; Pintumomab from Creative Biolabs; Placulumab from Teva Pharmaceutical Industries, Inc; Plozalizumab from Takeda Pharmaceuticals International Co; Pogalizumab from Roche/Genentech Inc; Polatuzumab vedotin from Genentech/Roche; Ponezuma from Pfizer; ponezumab from Pfizer and Rinat Neuroscience; Prezalizumab from Creative Biolabs; Priliximab from Centocor; Pritoxaximab (TAB-896) from Creative Biolabs; Pritumumab (ACA 11; CLN-IgG; CLNH 11; Monoclonal antibody ACA 11) from Nascent Biotech; PRO 140 from Cytodyn Inc; PSMA ADC from Peregrine Pharmaceuticals; Quilizumab from Genentech; Rabies mAB from Janssen and Sanofi; Racotumomab (Vaxira) from Center of Molecular Immunology; Radretumab from Philogen; Rafivirumab (CR57) from Crucell; Ralpancizumab from Pfizer; Raxibacumab from GlaxoSmithKline; Refanezumab from GlaxoSmithKline; Regavirumab from Teijin; REGN 1154 from Regeneron Pharmaceuticals and Sanofi; REGN 1400 from Regeneron Pharmaceuticals; REGN 1908 1909 from Regeneron Pharmaceuticals; REGN 2009 from Regeneron Pharmaceuticals; REGN 728 from Regeneron Pharmaceuticals; REGN 846 from Regeneron Pharmaceuticals; Reslizumab (Cinqair (US), Cinqaero (EU)) from Teva Pharmaceuticals; AMG 282 (RG 6149) from Amgen; RG 7212 from Roche; RG 7356 from Chugai Biopharmaceuticals and Roche; RG 7600 from Genentech; RG 7636 (DEDN-6526A) from Genentech; RG 7652 from Genentech and Roche; RG 7716 from Roche; RG 7841 from Genentech; RG 7882 (D-4064A; DMUC 4064A) from Genentech; Rilotumumab from Amgen and Astellas Pharma; rinucumab (REGN2176-3) from Regeneron Pharmaceuticals; Risankizumab (ABBV 066; BI-655066) from AbbVie; Boehringer Ingelheim; RN-307 from Labrys Biologics Inc.; RN6G/PF-04382923 from Pfizer; Robatumumab from KaloBios Pharmaceuticals; Roledumab from Merck & Co; Schering-Plough; Romosozumab (AMG 785) from Amgen; Rontalizumab from Chugai Pharmaceutical, Genentech; Rovalpituzumab tesirine from LFB Biotechnologies; Rovelizumab (LeukArrest; Hu23FG2) from Icos; Ruplizumab from AbbVie; Sacituzumab govitecan from Biogen; Samalizumab (ALXN 6000) from Alexion Pharmaceuticals; SAN 300 from Biogen Idec, Salix Pharmaceuticals; Sapelizumab from Alexion Pharmaceuticals; The Leukemia & Lymphoma Society; SAR 156597 from sanofi-aventis; SAR 228810 from Sanofi; SAR 252067 from Kyowa Hakko Kirin and Sanofi; SAR 566658 from ImmunoGen and Sanofi; SAR 113244 from Sanofi; SAR153191 REGN88 from Sanofi and Regeneron; Sarilumab from Sanofi and Regeneron Pharmaceuticals, Inc; Satumomab pendetide (CYT 103; Indium 111In-satumomab pendetide; OncoScint CR/OV; OncoScint CR103; OncoScint OV103) from Cytogen Corporation; seribantumab (SAR256212) from Merrimack; Setoxaximab from Chugai Pharmaceutical; Sevirumab from Novartis; SGN-CD70A from Seattle Genetics; SGN-LIV1A from Seattle Genetic; Sibrotuzumab from Novartis; Sifalimumab from MedImmune; Simtuzumab (GS 6624) from Gilead; Siplizumab from Boehringer Ingelheim; Sirukumab (CNTO-136) from Johnson & Johnson; Sofituzumab vedotin (RG7458) from Genentech; Solanezumab from Eli Lilly; Solitomab (AMG 110) from Amgen; Sonepcizumab (ASONEP; iSONEP; LT-1009; Sonepcizumab/LT1009; Sphingomab™) from Lpath and Pfizer; Sontuzumab from Lpath and Pfizer; Stamulumab (Anti-GDF-8 antibody; Anti-myostatin antibody; MYO 29; MYO-029) from Wyeth; STX-100 (BG-00011; STX-100) from Biogen; Sulesomab (LeukoScan) from Immunomedics; Suptavumab (REGN-2222; SAR-438584) from Regeneron Pharmaceuticals and sanofi; Suvizumab from Creative Biolabs; Tabalumab from Eli Lilly and Company; Tacatuzumab tetraxetan (AFP-Cide) from Immunomedics Inc.; Tadocizumab from Wyeth Pharmaceuticals; Talizumab from Houston-based Tanox; TALL-104 (ABIO-0501) from Abiogen Pharma; Tamtuvetmab from Yamanochi Pharma America, Inc; Tanezumab from Pfizer and Eli Lilly; Taplitumomab paptox (Tactress) from Aratana Therapeutics; Tarextumab from OncoMed and GlaxoSmithKline; TCN 202 from Theraclone Sciences; TCN-032 from Theraclone Sciences; Tefibazumab from University of Minnesota; Telimomab aritox from Inhibitex; Tenatumomab from Sigma-Tau; Teneliximab from Creative Biolabs; Teplizumab from MacroGenics, Inc/Eli Lilly; Teprotumumab from Genmab and Roche; Tetulomab from Norwegian company Nordic Nanovector ASA; Tezepelumab (AMG 157) from Amgen; AstraZeneca; MedImmune; TF2 (DOCK-AND-LOCK™, or DNL™) from Immunomedics, Inc.; TGN1412 (Anti-CD28 monoclonal antibody—TeGenero; CD28-SuperMAB™; TGN-1412) from TeGenero; Thravixa (AVP 21D9) from Avanir Pharmaceuticals; Emergent BioSolutions; Ticilimumab (tremelimumab) from pfizer/MedImmune; Tigatuzumab from Daiichi Sankyo Company; Tildrakizumab from Merck; Timolumab from TeGenero Immuno Therapeutics; Tisotumab vedotin from Genmab; TOL 101 from Tolera Therapeutics, Inc.; Toralizumab from IDEC Pharmaceuticals Corporation; Tosatoxumab from Biotie Therapies Corp; Tovetumab (Anti-PDGFRa MAb—MedImmune; MEDI-575) from MedImmune; Tralokinumab from MedImmune, Astrazeneca; TRBS07 from MedImmune; TRC 105 from TRACON Pharmaceuticals, Inc; Tregalizumab (BT-061) from Biotest AG, abbVie; Trevogrumab (REGN-1033; SAR-391786) from Regeneron Pharmaceuticals and Sanofi; Trevogrumab/REGN-1033; SAR-391786 from Regeneron Pharmaceuticals; Tucotuzumab celmoleukin (EMD-273066; huKS-IL2; KS-IL2; KS-interleukin-2) from EMD Lexigen and Merck KGaA; Tuvirumab (Hepatitis-B-MAb; Human anti-Hep B; OST 577; Ostavir; Ostavir human anti-hepatitis B antibody) from Novartis; U3 1565 from Amgen, U3 Pharma and Daiichi Sankyo Company; UB-421 from United Biomedical Inc; Ublituximab (1303; EMAB-6; LFB-R603; R603; TG-1101; TG-1303; TGTX-1101; Utuxin) from LFB Biotechnologies and TG Therapeutics Inc; ublituximab from TG Therapeutics Inc; Ulocuplumab from Bristol-Myers Squibb; Urelumab (BMS-663513) from Bristol-Myers Squibb; Urtoxazumab (Anti-verotoxin of 0-157; TMA-15) from Teijin Pharma; Utomilumab from Pfizer; Vadastuximab talirine from Seattle Genetics; Vandortuzumab vedotin (Anti-STEAP1-vc-MMAE; DSTP-3086S; RG-7450) from Genentech; vanticumab from OncoMed Pharmaceuticals Inc; Vanucizumab from Genentech/Roche; Vapaliximab from EMD Lexigen; Merck KGaA; Varlilumab from Celldex Therapeutics; Vatelizumab (GBR 500, SAR 339658) from Glenmark Pharmaceuticals S.A. and Sanofi; VB4-845 from Viventia Bio, Inc; Veltuzumab from BioTie Therapies; Vepalimomab from Immunomedics, Inc; Vesencumab from BioTie Therapies; VGX 100 from Vegenics, Ceres Oncology; Opthea; Visilizumab (Nuvion) from PDL BioPharma Inc.; Vobarilizumab (ALX-0061) from Ablynx; Volociximab (M200) from Abbott Biotherapeutics Corp; Biogen Idec; National Cancer Institute (USA); OphthoTech Corporation; PDL BioPharma, AbbVie; vorsetuzumab mafodotin from Seattle Genetics; Votumumab (HumaSPECT®) from Organon Teknika; VX 15 from Teva Pharmaceutical Industries; Vaccinex; Xentuzumab (BI 836845) from Boehringer Ingelheim; XmAb 5871XmAb 7195 and XmAb®2513 from Xencor; AMG 729 from Amgen; XmAb5574 (MOR00208, MOR208, anti-CD19 MAb XmAb5574; anti-CD19 MoAb XmAb5574; MOR-00208; MOR-208; XENP-5574) from MorphoSys and Xencor; XOMA 213 (LFA102) from Novartis; XOMA; XOMA 3AB from XOMA and National Institute for Allergy and Infectious Diseases; Zalutumumab (HuMax-EGFr) from Genmab; Zanolimumab from Genmab; Zatuximab from Creative Biolabs; ziralimumab from Creative Biolabs; ZMAb (mixture of three mouse mAbs: m1H3, m2G4 and m4G7) from National Microbiology Laboratory; Zmapp (c13C6 from MB-003 and two chimeric mAbs from ZMAb, c2G4 and c4G7) from National Microbiology Laboratory and Mapp Biopharmaceutical, Inc; Zolimomab aritox (Anti-CD5 monoclonal antibody-ricin-chain-A conjugate; Anti-CD5 ricin A chain immunotoxin; CD5 Plus; CD5+; Muromonab; Orthozyme CD5 Plus; Xomazyme CD5 Plus; XZ-CD5) from Ortho-McNeil and XOMA; anti-CD8 mAb (Cytolin®) from CytoDyn, Inc; 131I-chTNT-1/B (Cotara®) from Peregrine Pharmaceuticals; PD 360324 (formerly PD-360324) from Pfizer; GBR 830 from Glenmark Pharmaceuticals S.A.; Dorlimomab aritox from Medarex/Houston Biotechnolgy.

Biosimilars that are not approved are Adalimumab [ABP501 (Amgen), GP2017 (Novartis)], Atezolizumab [RG7446 (Roche)], Bevacizumab [ABP 215 (Amgen)], Evolucumab [AMG 145 (Amgen)] Infliximab [TNFmab (LGLS), CT-P13 (Celltrion), ABP 710 (Amgen)], Obinutuzumab [GA101 (Roche)], Rituximab [ABP 798 (Amgen), GP2013 (Novartis), TL011 (Teva/Lonza)], Trastuzumab [ABP 980 (Amgen)].

Example 36: List of mAbs Currently on the Market Along with Dose and Volume for Intravenous Infusion or Subcutaneous Delivery The present example describes monoclonal antibodies (mAbs) that are currently available on the market along with known dose and volume information for intravenous or subcutaneous administration that may be used in low viscosity formulations described herein.

| mAb name (subcutaneous) | Trade name | Dose (mg) | Volume (mL) |
|---|---|---|---|
| Evolocumab | Repatha ® | 420 | 3.5 |
| Secukinumab | Cosentyx ™ | 300 | 2 |
| Certolizumab pegol | Cimzia ® | 400 | 2 |
| Tocilizumab | ACTEMRA ® (Roche & Genentech) | 162 | 0.9 |

-continued

| mAb name (subcutaneous) | Trade name | Dose (mg) | Volume (mL) |
|---|---|---|---|
| Ixekizumab | TALTZ ™ | 160 | 2 |
| Omalizumab | Xolair ® | 150 | 1.2 |
| Canakinumab | Ilaris ® | 150 | 1 |
| Alirocumab | Praluent ® | 150 | 1 |
| Daclizumab | ZINBRYTA ™, ZENAPAX ® | 150 | 1 |
| Denosumab | XGEVA ® | 120 | 1.7 |
| Denosumab | Prolia ® | 120 | 1.7 |
| Mepolizumab | Nucala ® | 100 | 1.2 |
| Ustekinumab | Stelara ® | 90 | 1 |
| Golimumab | Simponi ® | 50 | 0.5 |
| Adalimumab | HUMIRA ® (Pfizer), ABP501 (Amgen), GP2017 (Novartis) | 40 | 0.8 |
| Idarucizumab | Praxbind | 2500 | 50 |
| Raxibacumab | ABTHRAX | 1700 | 34 |
| Atezolizumab | TECENTRIQ ™ (Genetech), RG7446 (Roche) | 1200 | 20 |
| Ofatumumab | Arzerra ™ | 1000 | 50 |
| Obinutuzumab | GAZYVA ® (Genentech), GA101 (Roche) | 1000 | 40 |
| Bezlotoxumab | ZINPLAVA ™ | 1,000 | 40 |
| Necitumumab | Portrazza ™ | 800 | 50 |
| Obiltoxaximab | ANTRIM ® | 600 | 6 |
| Olaratumab | Lartruvo ™ | 500 | 50 |
| Rituximab | RITUXAN ® (Pfizer), ABP 798 (Amgen), MabThera (Roche), (Genetech), GP2013 (Novartis) | 500 | 50 |
| Tositumomab | Bexxar ® | 450 | 50 |
| Trastuzumab | HERCEPTIN ® (Genentech), ABP 980 (Amgen), HERTRAZ ™ (mylan), CANMAB ™ (Biocon) | 440 | 20 |
| Pertuzumab | PERJETA ® (Genentech), RG1273 (Roche) | 420 | 14 |
| Tocilizumab | ACTEMRA ® (Roche & Genentech) | 400 | 20 |
| Bevacizumab | AVASTIN ® (Roche), ABP 215 (Amgen), | 400 | 16 |
| Daratumumab | Darzalex ® | 400 | 20 |
| Elotuzumab | EMPLICIT ™ | 400 | 17 |
| Siltuximab | SYLVANT ™ | 400 | 20 |
| Panitumumab | Vectibix ® | 400 | 20 |
| Vedolizumab | Entyvio ® | 300 | 20 |
| Eculizumab | Soliris ® | 300 | 30 |
| Natalizumab | TYSABRI ® | 300 | 15 |
| Cetuximab | ERBITUX ® | 200 | 100 |
| Ipilimumab | YERVOY ® | 200 | 40 |
| Ustekinumab | Stelara ® | 130 | 26 |
| Reslizumab | CINQAIR ® | 100 | 10 |
| Pembrolizumab | KEYTRUDA ® | 100 | 4 |
| Nivolumab | OPDIVO ® | 100 | 10 |
| Infliximab | REMICADE ® (Pfizer), ABP 710 (Amgen), FLIXABI ® (Biogen) | 100 | 20 |

Exemplary molecular targets for antibodies described herein may, for example, be antibodies directed against a particular predetermined antigen. In a specific aspect, the antigen is IgE (e.g., rhuMAbE-25, rhuMAbE-26 and rhuMAbE-27 described in WO 99/01556). Alternatively, the antigen may include: the CD proteins CD3, CD4, CD8, CD19, CD20 and CD34; members of the HER receptor family such as EGF receptor, HER2, HER3 or HER4 receptor; cell adhesion molecules such as LFA-1, Mol, pi 50,95, VLA-4, ICAM-1, NCAM and $\alpha v/\beta 3$ integrin including the $\alpha$- and $\beta$-subunits thereof (e.g., anti-CD11a, anti-CD18 or anti-CD11b antibodies); growth factors such as VEGF: blood group antigens; flk2/flt3 receptor: obesity (OB) receptor; and protein C.

Example 37: Preferred mAbs

The present example describes monoclonal antibodies (mAbs) that may be used in low viscosity formulations described herein.

Preferred mAbs for use with the invention herein include Idarucizumab (Praxbind®); Raxibacumab (ABTHRAX®); Atezolizumab (TECENTRIQ™, RG7446 (Roche)); Ofatumumab (Arzerra™); Obinutuzumab (GAZYVA®, GA101 (Roche)); Bezlotoxumab (ZINPLAVA™); Necitumumab (Portrazza™); Obiltoxaximab (ANTHIM®); Olaratumab (Lartruvo™); Rituximab (RITUXAN®, ABP 798 (Amgen), MabThera™, GP2013 (Novartis)); Tositumomab (Bexxar®); Trastuzumab (HERCEPTIN®, ABP 980 (Amgen), HERTRAZ™, CANMAB™); Pertuzumab (PERJETA®, RG1273 (Roche)); Tocilizumab (ACTEMRA®); Bevacizumab (AVASTIN®, ABP 215 (Amgen)); Daratumumab (Darzalex®); Elotuzumab (EMPLICITI™); Siltuximab (SYLVANT™); Panitumumab (Vectibix®); Vedolizumab (Entyvio®); Eculizumab (Soliris®); Natalizumab (TYSABRI®); Cetuximab (ERBITUX®); Ipilimumab (YERVOY®); Ustekinumab (Stelara®); Reslizumab (CINQAIR®); Pembrolizumab (KEYTRUDA®); Nivolumab (OPDIVO®); Infliximab (REMICADE®, ABP 710 (Amgen), FLIXABI®); Abciximab (ReoPro®); Evolocumab (Repatha®); Secukinumab (Cosentyx™); Certolizumab pegol (Cimzia®); Tocilizumab (ACTEMRA®); Ixekizumab (TALTZ™); Omalizumab (Xolair®); Canakinumab (Ilaris®); Alirocumab (Praluent™); Daclizumab (ZINBRYTA™, ZENAPAX®); Denosumab (XGEVA®); Denosumab (Prolia®); Mepolizumab (Nucala®); Ustekinumab (Stelara®); Golimumab (Simponi®); Adalimumab (HUMIRA®, ABP501 (Amgen), GP2017 (Novartis)); Ramucirumab (CYRAMZA®); Ranibizumab (LUCENTIS®, RG3645 (Roche & Novartis)); Efalizumab (Raptiva®); Palivizumab (Synagis®) and biosimilars thereof.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. An antibody agent formulation comprising:
   (i) one or more antibody agents at a concentration between about 10 mg/mL and about 300 mg/mL; and
   (ii) one or more viscosity-reducing agents, wherein the one or more viscosity reducing agents comprise:
      (a) a combination of nicotinic acid (acid form) present at a concentration of about 122 mM and tryptophan present at a concentration between about 5 mM and about 100 mM; or
      (b) caffeine citrate, present at a concentration between about 5 mM and about 100 mM;
   wherein the formulation has a viscosity between about 1 cP and about 100 cP when measured at 25° C., using a cone and plate viscometer.

2. The formulation of claim 1, wherein the antibody agents comprise a monoclonal antibody or fragment thereof.

3. The formulation of claim 1, wherein the antibody agents comprise an antibody agent having a molecular weight of between about 25 kDa and about 1000 kDa.

4. The formulation of claim 1, wherein the antibody agents comprise an antibody agent having a molecular weight between about 120 kDa and about 250 kDa.

5. The formulation of claim 1, wherein the concentration of the antibody agents is between about 150 mg/ml and about 300 mg/mL.

6. The formulation of claim 1, wherein the formulation includes a phosphate buffer or histidine buffer.

7. The formulation of claim 6, wherein the buffering agent of the phosphate buffer or histidine buffer is at a concentration between about 1 mM and about 50 mM.

8. The formulation of claim 6, wherein the buffering agent of the phosphate buffer or histidine buffer is at a concentration between about 10 mM and about 50 mM.

9. The formulation of claim 1, wherein the formulation has a pH between about 4.0 and about 8.0.

10. The formulation of claim 1, wherein the formulation further comprises an excipient or additive selected from a group consisting of aggregation-reducing agents, sugars or sugar alcohols, polysaccharides, stabilizers, hyaluronidase, buffering agents, preservatives, carriers, antioxidants, chelating agents, natural or synthetic polymers, cryoprotectants, lyoprotectants, surfactants, bulking agents, acidifying agents, ingredients to reduce injection site discomfort, antifoaming agents, alkalizing agents, vehicles, aggregation inhibitors, solubilizing agents, tonicity modifiers, stabilizing agents, and combinations thereof.

11. The formulation of claim 1, wherein the formulation further comprises one or more aggregation-reducing agents selected from the group consisting of nicotinic acid, caffeine citrate, caffeine nicotinate, caffeine, octyl-β-D-glucopyranoside, and n-dodecyl-β-D-maltoside and optionally in combination with one or more of arginine, tryptophan, histidine, proline, cysteine, methionine, β-alanine, Potassium Glutamate, Arginine Ethylester, lysine, aspartic acid, glutamic acid, glycine, DTPA (diethylenetriaminepentaacetic acid), EGTA (aminopolycarboxylic acid), EDTA (Ethylenediaminetetraacetic acid), hydroxy propyl beta (HP-Beta) cyclodextrins, hydroxy propyl gamma (HP-Gamma) cyclodextrins, sulfo-butyl ether (SBE) cyclodextrins, TMAO (trimethylamine N-oxide), trehalose, ethylene glycol, betaine, xylitol, sorbitol, 6-(N-(7-nitrobenz-2-oxa-1,3-diazol-4-yl)amino)hexanoic acid (NBD-X), methyl acetyl phosphate (MAP), citraconic anhydride, pyrophosphate, and citrate.

12. The formulation of claim 1, wherein the formulation further comprises one or more tonicity modifiers selected from the group consisting of arginine, cysteine, histidine, glycine, alkali salts such as sodium chloride, potassium chloride, sodium citrate, saccharides such as sucrose, glucose, dextrose, glycerin, mannitol, and combinations thereof.

13. The formulation of claim 1, wherein the formulation further comprises one or more antioxidants selected from the group consisting of glycine, lysine, EDTA, DTPA, sorbitol, mannitol, ascorbic acid, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, sodium thiosulfate, sulfur dioxide, tocopherol, and combinations thereof.

14. The formulation of claim 1, wherein the formulation further comprises one or more lyoprotectants selected from the group consisting of sucrose, lactose, trehalose, dextran, erythritol, arabitol, xylitol, sorbitol, maltose, lactulose, maltulose, glucitol, maltitol, lactitol, isomaltulose and mannitol; amino acids, such as arginine or histidine or proline or glycine; lyotropic salts, such as magnesium sulfate; polyols, such as propylene glycol, glycerol, poly(ethylene glycol), or polypropylene glycol); gelatin, dextrins, modified starch, carboxymethyl cellulose, and combinations thereof.

15. The formulation of claim 1, wherein the viscosity of the formulation is reduced relative to the viscosity of an otherwise identical control lacking the viscosity reducing agents, where the formulation has a viscosity that is between about 10% and about 90% less than that of the control, between about 10% and about 50% less than the control, or between about 10% and about 30% less than the control.

16. The formulation of claim 1, wherein the formulation is in aqueous liquid form.

17. The formulation of claim 1, wherein the formulation is in non-aqueous liquid form.

18. The formulation of claim 1, wherein the formulation is in a liquid form that is a mixture of aqueous and non-aqueous liquids.

19. The formulation of claim 1, wherein the formulation is in lyophilized form, crystallized form, amorphous form, or suspension form.

\* \* \* \* \*